US008927701B2

(12) United States Patent
Lina et al.

(10) Patent No.: US 8,927,701 B2
(45) Date of Patent: Jan. 6, 2015

(54) HPIV-2 VARIANTS AND THEIR MEDICAL APPLICATIONS

(75) Inventors: Bruno Lina, Lyons (FR); Olivier Terrier, Lyons (FR); Danielle Françoise Thouvenot, Saint Priest (FR)

(73) Assignees: Centre National de la Recherche Scientifique, Paris (FR); Les Hospices Civils de Lyon, Lyons (FR)

( * ) Notice: Subject to any disclaimer, the term of this patent is extended or adjusted under 35 U.S.C. 154(b) by 1185 days.

(21) Appl. No.: 12/669,607

(22) PCT Filed: Jul. 18, 2008

(86) PCT No.: PCT/FR2008/001067
§ 371 (c)(1),
(2), (4) Date: Jul. 21, 2010

(87) PCT Pub. No.: WO2009/037402
PCT Pub. Date: Mar. 26, 2009

(65) Prior Publication Data
US 2011/0077170 A1 Mar. 31, 2011

(30) Foreign Application Priority Data
Jul. 19, 2007 (FR) .................................. 07 05235

(51) Int. Cl.
C07H 21/04 (2006.01)
C12Q 1/70 (2006.01)
C12N 7/00 (2006.01)

(52) U.S. Cl.
CPC *C12Q 1/701* (2013.01); *C12N 7/00* (2013.01); C12N 2760/18621 (2013.01)
USPC .................... 536/23.72; 536/23.1; 536/24.32; 536/24.33; 435/5

(58) Field of Classification Search
None
See application file for complete search history.

(56) References Cited

U.S. PATENT DOCUMENTS 7,250,171 B1 * 7/2007 Tao et al. .................... 424/211.1

FOREIGN PATENT DOCUMENTS

EP 1 327 691 A 7/2003

OTHER PUBLICATIONS

UNIPROT sequence result database # A4Z4H4 from IDS dated May 29, 2007.*
Human parainfluenza virus 2 strain V98, complete genome, GenBank: AF533011.1, dated 2002.*
Human parainfluenza virus 2 strain GREER, complete genome, GenBank: AF533012.1, dated 2002.*
Result 1 for SEQ ID# 87, date 2001.*
Non Patent Literature: accession No. DQ072586 on p. 81 line 14, 2007.
Non Patent Literature: accession No. DQ072587 on p. 86 line 44, 2007.
Non Patent Literature: accession No. DQ072588 on p. 92 line 18, 2007.
Non Patent Literature: accession No. DQ072589 on p. 97 line 42, 2007.
Non Patent Literature: accession No. DQ072590 on p. 103 line 17, 2007.
Database UniProt [Online], May 29, 2007, "Fusion glycoprotein FO." XP002472207.
Database UniProt [Online], May 29, 2007, "Hemagglutinin-neuraminidase.", XP002472208.
Database UnlProt [Online], May 29, 2007, "Fusion glycoprotein FO.", XP002472209.
Database UniProt [Online], May 29, 2007, "Hemagglutinin-neuraminidase.", XP002472210.
Database UniProt [Online], May 29, 2007, "Hemagglutinin-neuraminidase.", XP002472211.
Database UniProt [Online], May 29, 2007, "Hemagglutinin-neuraminidase.", XP002472212.
Database UniProt [Online], May 29, 2007, "Fusion glycoprotein FO.", XP002472213.
Database UniProt [Online], May 29, 2007,"Hemagglutinin-neuraminidase.", XP002472214.
Aguilar Jose C et al: "Detection and identification of human parainfluenza viruses 1, 2, 3, and 4in clinical samples of pediatric patients by multiplex reverse transcription-PCR", Journal of Clinical Microbiology, Mar. 2000, pp. 1191-1195, vol. 38, No. 3., XP002472202.
Ray R et al: "Distinct Hemagglutinin and Neuraminidase Epitopes Involved in Antigenic Variation of Recent Human Parainfluenza Virus Type 2 Isolates", Jun. 1, 1992, pp. 107-113, vol. 24, No. 1, Virus Research, Amsterdam, NL, XP000647388.
Skiadopo

(56) References Cited

OTHER PUBLICATIONS

Fan J et al: "Rapid Simultaneous Diagnosis of Infections With Respiratory Syncytial Viruses A and B, Influenza Viruses A and B, and Human Parainfluenza Virus Types 1, 2, and 3 by Multiplex Quantitative Reverse Transcription-Polymerase Chain Reaction-Enzyme Hybridizati", Clinical Infectious Diseases, 1998, pp. 1397-1402, vol. 26, The University of Chicago Press, Chicago, IL, US, XP009022813.

Terrier 0 et al: "Characterization of naturally occurring parainfluenza virus type 2 (hPIV-2) variants", Journal of Clinical Virology, Sep. 1, 2008, pp. 86-92, vol. 43, No. 1, Elsevier, Amsterdam, NL, XP024098939.

Korimbocus Jehanara et al: DNA Probe Array for the Simultaneous Identification of Herpesviruses, Enteroviruses, and Flaviviruses, Journal of Clinical Microbiology, Aug. 2005, pp. 3779-3787, vol. 43, No. 8, American Society for Microbiology.

Combet Christophe et al: Gen03D: automatic comparative molecular modelling of protein, Applications Note, 2002, pp. 213-214, vol. 18, No. 1, Oxford University Press.

Combet Christophe et al: Network Protein Sequence Analysis, TIBS, 2000, pp. 147-150, Elsevier Science Ltd.

Singh Mona et al: LearnCoil-VMF: Computational Evidence for Coiled-coil-like Motifs in Many Viral Membrane-fusion Proteins, Journal of Molecular Biology, 1999, pp. 1031-1041, Academic Press.

Numazaki Yoshio et al: A Variant of Parainfluenza Type 2 Virus, Proceedings of the Society for Experimental Biology and Medicine, 1968, pp. 992-996.

Horvath Curt et al: Studies on the Fusion Peptide of a Paramyxovirus Fusion Glycoprotein: Roles of Conserved Residues in Cell Fusion, Journal or Virology, 1992, pp. 2443-2455, vol. 66, No. 4, American Society for Microbiology.

Sergel Theresa et al: Mutations in the Fusion Peptide and Adjacent Heptad Repeat Inhibit Folding or Activity of the Newcastle, Journal of Virology, Sep. 2001, pp. 7934-7943, vol. 75, No. 17, American Society for Microbiology.

French Search Report in Corresponding Application No. FA 698914/ FR 0705235 Dated Mar. 18, 2008.

International Search Report in Corresponding Application No. PCT/ FR2008/001067 Dated Mar. 23, 2009.

Terrier, O., "Human parainfluenza virus 2 isolate PIV-2:LYON/ 18620/2001 fusion prof hemagglutinin-neuraminidase (HN) genes, complete cds", Genbank: DQ072586.1.

* cited by examiner

- N - terminal
- C - terminal
- Catalytic site

S316

HN protein of HPIV-2 Greer isolate

New glycosylation site N316

HN protein of HPIV-2 variants of the invention

FIGURE 1

|  |  | 107 | 126 |  |
|---|---|---|---|---|
|  | SV5 | FAGVVIGLAALGVATAAQVT | SEQ ID NO : 15 |
|  | 18620 | FAGVVIGLAALGVATAAQIT | SEQ ID NO : 16 |
| HPIV-2 variants of the invention | 20283 | FAGVVIGLAALGVATAAQIT | SEQ ID NO : 17 |
|  | 20435 | FAGVVIGLAALGVATAAQIT | SEQ ID NO : 18 |
|  | 26056 | FAGVVIGLAALGVATAAQIT | SEQ ID NO : 19 |
|  | 26632 | FAGVVIGLAALGVATAAQIT | SEQ ID NO : 20 |
|  | Greer | FAGVVVGLAALGVATAAQIT | SEQ ID NO : 21 |
|  |  | ***** .*********** .* |  |

FIGURE 2

Alignment of CDS of F

```
Greer   ATGCATCACCTGCATCCAATGATAGTATGCATCTTTGTTATGTACACTGGAATTGTAGGT  60
18620   ATGCATCACCTGCATCCAATGATAGTATGCATCTTTGTTATGTACACTGGAATTGTAGGT
20283   ATGCATCACCCGCATCAATGATAGTATGCATCTTTGTTATGTACACTGGAATTGTAGGT
20435   ATGCATCACCTGCATCCAATGATAGTATGCATCTTTGTTATGTACACTGGAATTGTAGGT
26056   ATGCATCACCTGCATCCAATGATAGTATGCATCTTTGTTATGTACACTGGAATTGTAGGT
26632   ATGCATCACCTGCATCCAATGATAGTATGCATCTTTGTTATGTACACTGGAATTGTAGGT
        ********  ** ***************  ********************* ******

Greer   TCAGATGCCATTGCTGGAGATCAACTACTTAATATAGGGGTCATTCAATCAAAGATAAGA  120
18620   TCAGATGCCATTGCTGGAGATCAACTCCTCAATGTAGGGGTCATTCAATCAAAGATAAGA
20283   TCAGATGCCATTGCTGGAGATCAACTCCTCAATGTAGGGGTCATTCAATCAAAGATAAGA
20435   TCAGATGCCATTGCTGGAGATCAACTCCTCAATGTAGGGGTCATTCAATCAAAGATAAGA
26056   TCAGATGCCATTGCTGGAGATCAACTCCTCAATGTAGGGGTCATTCAATCAAAGATAAGA
26632   TCAGATGCCATTGCTGGAGATCAACTCCTCAATGTAGGGGTCATTCAATCAAAGATAAGA
        *************************  **  *** ************************

Greer   TCACTCATGTACTATACTGATGGTGGTGCTAGCTTTATTGTTGTAAAATTGCTACCTAAT  180
18620   TCACTCATGTACTACACTGATGGTGGCGCTAGCTTTATTGTTGTAAAATTACTACCAAAT
20283   TCACTCATGTACTACACTGATGGTGGCGCTAGCTTTATTGTTGTAAAATTACTACCCAAT
20435   TCACTCATGTACTACACTGATGGTGGCGCTAGCTTTATTGTTGTAAAATTACTACCAAAT
26056   TCACTCATGTACTACACTGATGGTGGCGCTAGCTTTATTGTTGTAAAATTACTACCAAAT
26632   TCACTCATGTACTACACTGATGGTGGCGCTAGCTTTATTGTTGTAAAATTACTACCAAAT
        **************  ********** ***************  ****** *****  **

Greer   CTTCCCCCAAGCAATGGAACATGCAACATCACCAGTCTAGATGCATATAATGTTACCCTA  240
18620   CTTCCCCCAAGCAATGGAACATGCAACATCACCAGTCTAGATGCATATAATGTTACCCTA
20283   CTTCCCCCAAGCAATGGAACATGCAACATCACCAGTCTAGATGCATATAATGTTACCCTA
20435   CTTCCCCCAAGCAATGGAACATGCAACATCACCAGTCTAGATGCATATAATGTTACCCTA
26056   CTTCCCCCAAGCAATGGAACATGCAACATCACCAGTCTAGATGCATATAATGTTACCCTA
26632   CTTCCCCCAAGCAATGGAACATGCAACATCACCAGTCTAGATGCATATAATGTTACCCTA
        ************************************************************

Greer   TTTAAGTTACTAACACCCCTGATTGAGAACCTGAGCAAAATTTCCACTGTTACAGATACC  300
18620   TTTAAGTTGCTAACGCCCCTGATTGAGAACCTGAGCAAAATTTCTGCTGTTACAGATACC
20283   TTTAAGTTGCTAACGCCCCTGATTGAGAACCTGAGCAAAATTTCTGCTGTTACAGATACC
20435   TTTAAGTTGCTAACGCCCCTGATTGAGAACCTGAGCAAAATTTCTGCTGTTACAGATACC
26056   TTTAAGTTGCTAACACCCCTGATTGAGAACCTGAGCAAAATTTCCGCTGTTACAGATACC
26632   TTTAAGTTGCTAACGCCCCTGATTGAGAACCTGAGCAAAATTTCTGCTGTTACAGATACC
        ******** *****  ********************** ****   **************

Greer   AAAACCCGCCAAGAACGATTTGCAGGAGTAGTTGTTGGACTTGCTGCATTAGGAGTAGCC  360
18620   AAACCCCGCCGAGAACGATTTGCAGGAGTCGTTATTGGGCTTGCTGCACTAGGAGTAGCT
20283   AAACCCCGCCGAGAACGATTTGCAGGAGTCGTTATTGGGCTTGCTGCACTAGGAGTAGCT
20435   AAACCCCGCCGAGAACGATTTGCAGGAGTCGTTATTGGGCTTGCTGCACTAGGAGTAGCT
26056   AAACCCCGCCGAGAACGATTTGCAGGGGTCGTTATTGGGCTTGCTGCACTAGGAGTAGCT
26632   AAACCCCGCCGAGAACGATTTGCAGGAGTCGTTATTGGGCTTGCTGCACTAGGAGTAGCT
        ***  ****** *****************  ***  ***  ********* *********

Greer   ACAGCCGCACAAATAACTGCAGCTGTAGCAATAGTGAAACCTAATGCAAATGCTGCTGCG  420
18620   ACAGCTGCACAAATAACCGCAGCTGTAGCAATAGTAAAAGCCAATGCAAATGCTGCTGCG
20283   ACAGCTGCACAAATAACCGCAGCTGTAGCAATAGTAAAAGCCAATGCAAATGCTGCTGCG
20435   ACAGCTGCACAAATAACCGCAGCTGTAGCAATAGTAAAAGCCAATGCAAATGCTGCTGCG
26056   ACAGCCGCACAAATAACCGCAGCTGTAGCAATAGTGAAAGCCAATGCAAATGCTGCTGCG
26632   ACAGCTGCACAAATAACCGCAGCTGTAGCAATAGTAAAAGCCAATGCAAATGCTGCTGCG
        *****  ********** *****************  ****  *****************
```

FIGURE 5

```
Greer    ATAAACAATCTTGCATCTTCAATTCAATCCACCAACAAGGCAGTATCCGATGTGATAGAT 480
18620    ATAAACAATCTTGCATCTTCAATTCAATCCACCAACAAGGCAGTATCCGATGTGATAACT
20283    ATAAACAATCTTGCATCTTCAATTCAATCCACCAACAAGGCAGTATCCGATGTGATAACT
20435    ATAAACAATCTTGCATCTTCAATTCAATCCACCAACAAGGCAGTATCCGATGTGATAACT
26056    ATAAACAATCTTGCATCTTCAATTCAATCCACCAACAAGGCAGTATCCGATGTGATAACT
26632    ATAAACAATCTTGCATCTTCAATTCAATCCACCAACAAGGCAGTATCCGATGTGATAACT
         *********************************************************  *

Greer    GCATCAAGAACAATTGCAACCGCAGTTCAAGCAATTCAGGATCGCATCAATGGAGCTATT 540
18620    GCATCAAGAACAATTGCAACCGCAGTTCAAGCAATTCAGGATCGCATCAATGGAGCTATT
20283    GCATCAAGAACAATTGCAACCGCAGTTCAAGCAATTCAGGATCGCATCAATGGAGCTATT
20435    GCATCAAGAACAATTGCAACCGCAGTTCAAGCAATTCAGGATCGCATCAATGGAGCTATT
26056    GCATCAAGAACAATTGCAACCGCAGTTCAAGCAATTCAGGATCGCATCAATGGAGCCATT
26632    GCATCAAGAACAATTGCAACCGCAGTTCAAGCAATTCAGGATCGCATCAATGGAGCCATT
         ********************************************************  ***

Greer    GTTAATGGGATAACATCTGCATCATGCCGTGCCCATGATGCACTCATTGGGTCAATATTA 600
18620    GTTAATGGGATAACATCTGCATCATGCCGTGCCCATGATGCACTAATTGGGTCAATATTA
20283    GTTAATGGGATAACATCTGCATCATGCCGTGCCCATGATGCACTAATTGGGTCAATATTA
20435    GTTAATGGGATAACATCTGCATCATGCCGTGCCCATGATGCACTAATTGGGTCAATATTA
26056    GTCAACGGGATAACATCTGCATCATGCCGTGCCCATGATGCACTAATTGGGTCAATATTA
26632    GTCAACGGGATAACATCTGCATCATGCCGTGCCCATGATGCACTAATTGGGTCAATATTA
         ** ** ***************************************  *************

Greer    AATCTTTATCTCACTGAGCTTACCACAATATTTCATAATCAAATAACAAACCCTGCGCTG 660
18620    AATTTGTATCTCACTGAGCTTACTACAATATTTCATAATCAAATAACAAACCCTGCGCTG
20283    AATTTGTATCTCACTGAGCTTACTACAATATTTCATAATCAAATAACAAACCCTGCGCTG
20435    AATTTGTATCTCACTGAGCTTACTACAATATTTCATAATCAAATAACAAACCCTGCGCTG
26056    AATTTGTATCTCACTGAGCTTACTACAATATTTCATAATCAAATAACAAACCCTGCGCTG
26632    AATTTGTATCTCACTGAGCTTACTACAATATTTCATAATCAAATAACAAACCCTGCGCTG
         *** * ***************** ************************************

Greer    ACACCACTCTCCATCCAAGCTTTAAGAATCCTCCTCGGTAGCACCTTGCCAATTGTCATT 720
18620    ACACCACTTTCCATCCAAGCTTTAAGAATCCTCCTCGGTAGCACCTTGCCAATTGTCATT
20283    ACACCACTTTCCATCCAAGCTTTAAGAATCCTCCTCGGTAGCACCTTGCCAATTGTCATT
20435    ACACCACTTTCCATCCAAGCTTTAAGAATCCTCCTCGGTAGCACCTTGCCAATTGTCATT
26056    ACACCACTTTCCATCCAAGCTTTAAGAATCCTCCTCGGTAGCACCTTGCCAATTGTCATT
26632    ACACCACTTTCCATCCAAGCTTTAAGAATCCTCCTCGGTAGCACCTTGCCAATTGTCATT
         ******** ***************************************************

Greer    GAGTCCAAACTCAACACAAACTTCAACACAGCAGAGCTGCTCAGTTCCGGACTGTTAACT 780
18620    GAATCCAAACTCAACACAAAACTCAACACAGCAGAGCTGCTCAGTTCCGGACTGTTAACT
20283    GAATCCAAACTCAACACAAAACTCAACACAGCAGAGCTGCTCAGTTCCGGACTGTTAACT
20435    GAATCCAAACTCAACACAAAACTCAACACAGCAGAGCTGCTCAGTTCCGGACTGTTAACT
26056    GAATCCAAGCTCAACACAAAACTCAACACAGCAGAGTTACTCAGTTCCGGACTGTTAACT
26632    GAATCCAAACTCAACACAAAACTCAACACAGCAGAGCTGCTCAGTTCCGGACTGTTAACT
         ** *****  *********  ***************  * ********************

Greer    GGTCAAATAATTTCCATTTCCCCAATGTACATGCAAATGCTAATTCAAATCAATGTTCCG 840
18620    GGTCAAATAATTTCCATTTCCCCAATGTACATGCAAATGCTAATTCAAATCAATGTTCCG
20283    GGTCAAATAATTTCCATTTCCCCAATGTACATGCAAATGCTAATTCAAATCAATGTTCCG
20435    GGTCAAATAATTTCCATTTCCCCAATGTACATGCAAATGCTAATTCAAATCAATGTTCCG
26056    GGTCAAATAATTTCCATTTCCCCAATGTACATGCAAATGCTAATTCAAATCAATGTTCCG
26632    GGTCAAATAATTTCCATTTCCCCAATGTACATGCAAATGCTAATTCAAATCAATGTTCCG
         ************************************************************

Greer    ACATTTATAATGCAACCCGGTGCGAAGGTAATTGATCTAATTGCTATCTCGGCAAACCAT 900
18620    ACATTTATAATGCAACCCGGTGCGAAGGTAATTGATCTAATTGCTATCTCTGCAAACCAT
20283    ACATTTATAATGCAACCCGGTGCGAAGGTAATTGATCTAATTGCTATCTCTGCAAACCAT
20435    ACATTTATAATGCAACCCGGTGCGAAGGTAATTGATCTAATTGCTATCTCTGCAAACCAT
26056    ACATTTATAATGCAACCCGGTGCGAAGGTAATTGATCTAATTGCTATCTCTGCAAACCAT
26632    ACATTTATAATGCAACCCGGTGCGAAGGTAATTGATCTAATTGCTATCTCTGCAAACCAT
         ************************************************* **********
```

FIGURE 5 cont'd

```
Greer   AAATTGCAAGAAGTGGTTGTACAAGTTCCGAATAGGATTCTAGAGTATGCAAATGAACTA  960
18620   AAATTACAAGAAGTAGTTGTACAAGTTCCTAATAGAATTCTAGAATACGCAAATGAACTA
20283   AAATTACAAGAAGTAGTTGTACAAGTTCCTAATAGAATTCTAGAATACGCAAATGAACTA
20435   AAATTACAAGAAGTAGTTGTACAAGTTCCTAATAGAATTCTAGAATACGCAAATGAACTA
26056   AAATTACAAGAAGTAGTTGTACAAGTTCCTAATAGAATTCTAGAGTATGCAAATGAACTA
26632   AAATTGCAAGAAGTAGTTGTACAAGTTCCTAATAGAATTCTAGAATACGCAAATGAACTA
        ****  ******** ***** ********  ******* ******  ** **********

Greer   CAAAATTACCCAGCCAATGACTGTGTCGTGACACCGAACTCTGTATTTTGTAGATACAAT 1020
18620   CAAAACTACCCAGCCAATGATTGTGTCGTGACACCAAACTCTGTATTTTGTAGATACAAT
20283   CAAAACTACCCAGCCAATGATTGTGTCGTGACACCAAACTCTGTATTTTGTAGATACAAT
20435   CAAAACTACCCAGCCAATGATTGTGTCGTGACACCAAACTCTGTATTTTGTAGATACAAT
26056   CAAAACTACCCAGCCAATGATTGTGTCGTGACACCAAACTCTGTATTTTGTAGATACAAT
26632   CAAAACTACCCAGCCAATGATTGTGTCGTGACACCAAACTCTGTATTTTGTAGATACAAT
        ***** ************** ************* ************************

Greer   GAGGGTTCCCCTATCCCTGAATCACAATATCAATGCTTGAGGGGGAATCTTAATTCTTGC 1080
18620   GAGGGTTCCCCGATCCCTGAATCACAATATCAATGCTTAAGGGGGAATCTTAATTCTTGC
20283   GAGGGTTCCCCGATCCCTGAATCACAATATCAATGCTTAAGGGGGAATCTTAATTCTTGC
20435   GAGGGTTCCCCGATCCCTGAATCACAATATCAATGCTTAAGGGGGAATCTTAATTCTTGC
26056   GAGGGTTCCCCGATCCCTGAATCACAATATCAATGCTTAAGGGGGAATCTTAATTCTTGC
26632   GAGGGTTCCCCGATCCCTGAATCACAATATCAATGCTTAAGGGGGAATCTTAATTCTTGC
        ***********  ************************ **********************

Greer   ACTTTTACCCCTATTATCGGGAACTTTCTTAAGCGATTCGCATTTGCTAATGGTGTGCTC 1140
18620   ACTTTTACCCCTATTATCGGGAACTTTCTCAAGCGATTCGCATTTGCCAATGGTGTGCTC
20283   ACTTTTACCCCTATTATCGGGAACTTTCTCAAGCGATTCGCATTTGCCAATGGTGTGCTC
20435   ACTTTTACCCCTATTATCGGGAACTTTCTCAAGCGATTCGCATTTGCCAATGGTGTGCTC
26056   ACTTTTACCCCTATTATCGGAAACTTTCTCAAGCGATTCGCATTTGCCAATGGTGTGCTC
26632   ACTTTTACCCCTATTATCGGGAACTTTCTCAAGCGATTCGCATTTGCCAATGGTGTGCTC
        ******************** ******* *****************  ************

Greer   TATGCCAACTGCAAATCTTTGCTATGTAGGTGTGCCGACCCCCCCCATGTTGTATCCCAG 1200
18620   TATGCCAACTGCAAATCTTTGCTATGTAAGTGTGCCGACCCTCCCCATGTTGTGTCTCAA
20283   TATGCCAACTGCAAATCTTTGCTATGTAAGTGTGCCGACCCTCCCCATGTTGTGTCTCAA
20435   TATGCCAACTGCAAATCTTTGCTATGTAAGTGTGCCGACCCTCCCCATGTTGTGTCTCAA
26056   TATGCCAACTGCAAATCTTTGCTATGTAAGTGTGCCGACCCTCCCCATGTTGTGTCTCAA
26632   TATGCCAACTGCAAATCTTTGCTATGTAAGTGTGCCGACCCTCCCCATGTTGTGTCTCAA
        ***************************  ***********  *********** ** **

Greer   GATGATACCCAAGGCATCAGCATAATTGATATTAAGAGATGCTCTGAGATGATGCTTGAC 1260
18620   GATGACACCAAGGCATCAGCATAATTGATATTAAGAGGTGCTCTGAGATGATGCTTGAC
20283   GATGACAACCAAGGCATCAGCATAATTGATATTAAGAGATGCTCTGAGATGATGCTTGAC
20435   GATGACACCAAGGCATCAGCATAATTGATATTAAGAGATGCTCTGAGATGATGCTTGAC
26056   GATGCACCCAAGGCATCAGCATAATTGATATTAAGAGGTGCTCTGAGATGATGCTTGAC
26632   GATGACACCAAGGCATCAGCATAATTGATATTAAGAGGTGCTCTGAGATGATGCTTGAC
        ****     *************************** **********************

Greer   ACTTTTTCATTTAGGATCACATCTACTTTCAATGCTACGTACGTGACAGACTTCTCAATG 1320
18620   ACTTTTTCATTTAGGATCACATCTACATTCAATGCTACATACGTGACAGACTTCTCAATG
20283   ACTTTTTCATTTAGGATCACATCTACATTCAATGCTACATACGTGACAGACTTCTCAATG
20435   ACTTTTTCATTTAGGATCACATCTACATTCAATGCTACATACGTGACAGACTTCTCAATG
26056   ACTTTTTCATTTAGGATCACATCTACATTCAATGCTACATACGTGACAGACTTCTCAATG
26632   ACTTTTTCATTTAGGATCACATCTACATTCAATGCTACATACGTGACAGACTTCTCAATG
        **************************  **********  *******************

Greer   ATTAATGCAAATATTGTACATCTAAGTCCTCTAGACTTGTCAAATCAAATCAATTCAATA 1380
18620   ATTAATGCAAATATTGTACATCTAAGTCCTCTAGACTTGTCAAATCAAATTAATTCAATA
20283   ATTAATGCAAATATTGTACATCTAAGTCCTCTAGACTTGTCAAATCAAATCAATTCAATA
20435   ATTAATGCAAATATTGTACATCTAAGTCCTCTAGACTTGTCAAATCAAATCAATTCAATA
26056   ATTAATGCAAATATTGTACATCTAAGTCCTCTAGACTTGTCAAATCAAATCAATTCAATA
26632   ATTAATGCAAATATTGTACATCTAAGTCCTCTAGACTTGTCAAATCAAATCAATTCAATA
        ************************** *********************  **********
```

FIGURE 5 cont'd

```
Greer   AACAAATCTCTTAAAAGTGCTGAGGATTGGATTGCAGATAGCAACTTCTTTGCTAATCAA 1446
18620   AACAAATCTCTTAAAAGTGCTCAAGATTGGATTGCAGATAGCAACTTCTTTGCTAATCAA
20283   AACAAATCTCTTAAAAGTGCTGAGGATTGGATTGCAGATAGCAACTTCTTTGCTAATCAA
20435   AACAAATCTCTTAAAAGTGCTGAGGATTGGATTGCAGATAGCAACTTCTTCGCTAATCAA
26056   AACAAATCTCTTAAAAGTGCTGAGGATTGGATTGCAGATAGCAACTTCTTTGCTAATCAA
26632   AACAAATCTCTTAAAAGTGCTGAGGATTGGATTGCAGATAGCAACTTCTTCGCTAATCAA
        *********************** **** ******** ***************** *********

Greer   GCCAGGACAGCCAAGACACTTTATTCACTAAGTGCAATAGCATTAATACTATCAGTGATT 1500
18620   GCCAGAACAGCCAAGACACTTTATTCACTAAGTGCAATAGCATTAATACTATCAGTGATT
20283   GCCAGAACAGCCAAGACACTTTATTCACTAAGTGCAATAGCATTAATACTATCAGTGATT
20435   GCCAGAACAGCCAAGACACTTTATTCACTAAGTGCAATAGCATTAATACTATCAGTGATT
26056   GCCAGAACAGCCAAGACACTTTATTCACTAAGTGCAATAGCATTAATACTATCAGTGATT
26632   GCCAGAACAGCCAAGACACTTTATTCACTAAGTGCAATAGCATTAATACTATCAGTGATT
        ***** ******************************************************

Greer   ACTTTGGTTGTCGTGGGATTGCTGATTGCCTACATCATCAAGCTGGTTTCTCAAATCCAT 1560
18620   ACTTTGGTTGTTGTGGGATTGCTGATTGCCTACATCATCAAGCTGGTTTCTCAAATCCAT
20283   ACTTTGGTTGTTGTGGGATTGCTGATTGCCTACATCATCAAGCTGATTTCTCAAATCCAT
20435   ACTTTGGTTGTTGTGGGATTGCTGATTGCCTACATCATCAAGCTGATTTCTCAAATCCAT
26056   ACTTTGGTTGTCGTGGGATTGCTGATTGCCTACATCATCAAGCTGGTTTCTCAAATCCAT
26632   ACTTTGGTTGTTGTGGGATTGCTGATTGCCTACATCATCAAGCTGGTTTCTCAAATCCAT
        *********** ******************************** ***************

Greer   CAATTCAGATCGCTAGCTGCTACAACAATGTTCCACAGGGAAAATCCTGCCTTCTTTTCC 1620
18620   CAATTCAGAGCACTAGCTGCTACAACAATGTTCCACAGGGAGAATCCTGCCGTCTTTTCC
20283   CAATTCAGAGCACTAGCTGCTACAACAATGTTCCACAGGGAGAATCCTGCCGTCTTTTCC
20435   CAATTCAGAGCACTAGCTGCTACAACAATGTTCCACAGGGAGAATCCTGCCGTCTTTTCC
26056   CAATTCAGAGCACTAGCTGCTACAACAATGTTCCACAGGGAGAATCCTGCCGTCTTTTCC
26632   CAATTCAGAGCACTAGCTGCTACAACAATGTTCCACAGGGAGAATCCTGCCGTCTTTTCC
        ********* * ***************************** ********* ********

Greer   AAGAATAACCATGGAAACATATATGGGATATCTTAA 1656
18620   AAGAACAATCATGGAAACATATATGGGATATCTTAA
20283   AAGAACAATCATGGAAACATATATGGGATATCTTAA
20435   AAGAACAATCATGGAAACATATATGGGATATCTTAA
26056   AAGAACAATCATGGAAACATATATGGGATATCTTAA
26632   AAGAACAATCATGGAAACATATATGGGATATCTTAA
        ***** ** ***************************
```

FIGURE 5 cont'd

Alignment of CDS of HN

```
Greer   ATGGAAGATTACAGCAATCTATCTCTTAAATCAATTCCTAAAAGGACATGTAGAATCATT   60
18620   ATGGAAGATTACAGCAATCTATCTCTTAAATCAATTCCTAAAAGGACATGTAGAATCATT
20283   ATGGAAGATTACAGCAATCTATCTCTTAAATCAATTCCTAAAAGGACATGTAGAATCATT
20435   ATGGAAGATTACAGCAATCTATCTCTTAAATCAATTCCTAAAAGGACATGTAGAATCATT
26056   ATGGAAGATTACAGCAATCTATCTCTTAAATCAATTCCTAAAAGGACATGTAGAATCATT
        ************************************************************

Greer   TTCCGAACTGCCACAATTCTTGGAATATGCACATTGATTGTTCTATGTTCAAGTATTCTT   120
18620   TTCCGAACTGCCACAATTCTTGGCATATGCACATTAATTGTGCTATGTTCAAGTATTCTT
20283   TTCCGAACTGCCACAATTCTTGGCATATGCACATTAATTGTGCTATGTTCAAGTATTCTT
20435   TTCCGAACTGCCACAATTCTTGGCATATGCACATTAATTGTGCTATGTTCAAGTATTCTT
26056   TTCCGAACTGCCACAATTCTTGGCATATGCACATTAATTGTGCTATGTTCAAGTATTCTT
        ***********************  ********** **** * ****************

Greer   CATGAGATAATTCATCTTGATGTTTCCTCTGGTCTCATGGATTCCGATGATTCACAGCAA   180
18620   CATGAGATAATTCATCTTGATGTTTCCTCTGATCTTATGAATTCTGATGAGTCACAGCAA
20283   CATGAGATAATTCATCTTGATGTTTCCTCTGGTCTTATGAATTCTGATGAGTCACAGCAA
20435   CATGAGATAATTCATCTTGATGTTTCCTCTGGTCTTATGAATTCTGATGAGTCACAGCAA
26056   CATGAGATAATTCATCTTGATGTTTCCTCTGGTCTTATGAATTCTGATGAGTCACAGCAA
        ******************************  ** *** *** ***** *********

Greer   GGCATTATTCAGCCTATTATAGAATCATTAAAATCATTAATTGCTTTGGCTAACCAGATT   240
18620   GGCATTATCCAGCCTATCATAGAATCATTAAAATCATTGATTGCTTTGGCCAACCAGATT
20283   GGCATTATCCAGCCTATCATAGAATCATTAAAATCATTGATTGCTTTGGCCAACCAGATT
20435   GGCATTATCCAGCCTATCATAGAATCATTAAAATCATTGATTGCTTTGGCCAACCAGATT
26056   GGCATCATTCAGCCTATCATAGAATCATTAAAATCATTGATTGCTTTGGCCAACCAGATT
        ***** ** ******** ******************** *********** ********

Greer   CTGTACAATGTTGCAATAATAATTCCTCTTAAAATTGACAGTATCGAGACTGTAATATTC   300
18620   CTATATAATGTTGCAATAGTAATTCCTCTTAAAATTGACAGTATCGAAACTGTAATACTC
20283   CTATATAATGTTGCAATAGTAATTCCTCTTAAAATTGACAGTATCGAAACTGTAATACTC
20435   CTATATAATGTTGCAATAATAATTCCTCTTAAAATTGACAGTATCGAAACTGTAATACTC
26056   CTATATAATGTTGCAATAATAATTCCTCTTAAAATTGACAGTATCGAAACTGTAATACTC
        ** ** ************ ***************************  ********* **

Greer   TCTGCTTTAAAGGATATGCATACTGGGAGCATGTCCACACCAACTGTACACCCGGAAAT   360
18620   TCTGCTTTAAAAGATATGCACACCGGGAGTATGTCCAATGCCAACTGCACGCCAGGAAAT
20283   TCTGCTTTAAAAGATATGCACACCGGGAGTATGTCCAATGCCAACTGCACGCCAGGAAAT
20435   TCTGCTTTAAAAGATATGCACACCGGGAGTATGTCCAATGCCAACTGCACGCCAGGAAAT
26056   TCTGCTTTAAAAGATATGCACACCGGGAGTATGTCCAATGCCAACTGCACGCCAGGAAAT
        *********** ******** ** ***** *******   ******* ** ** ******

Greer   CTGCTTCTGCATGATGCAGCGTACATCAATGGAATAAACAAATTCCTTGTACTTAAATCA   420
18620   CTACTTCTGCATGATGCAGCATACATCAATGGAATAAACAAATTCCTTGTACTTGAATCA
20283   CTACTTCTGCATGATGCAGCATACATCAATGGAATAAACAAATTCCTTGTACTTGAATCA
20435   CTACTTCTGCATGATGCAGCATACATCAATGGAATAAACAAATTCCTTGTACTTGAATCA
26056   TTGCTTCTGCATGATGCAGCATACATCAATGGAATAAACAAATTCCTTGTACTTGAATCA
        *  ***************** ********************************  ****

Greer   TACAATGGGACGCCTAAATATGGACCTCTCCTAAATATTCCCAGCTTTATCCCCTCAGCA   480
18620   TACAATGGGACGCCTAAATATGGACCTCTCCTAAATATACCCAGCTTTATCCCCTCAGCA
20283   TACAATGGGACGCCTAAATATGGACCTCTCCTAAATATACCCAGCTTTATCCCCTCAGCA
20435   TACAATGGGACGCCTAAATATGGACCTCTCCTAAATATACCCAGCTTTATCCCCTCAGCA
26056   TACAATGGGACGCCTAAATATGGACCTCTCCTAAATATACCCAGCTTTATCCCCTCAGCA
        ************************************** *********************

Greer   ACATCTCCCAACGGGTGCACTAGAATACCATCATTTTCACTCATTAAGACCCATTGGTGT   540
18620   ACATCTCCCCATGGTGTACTAGAATACCATCATTTTCACTCATCAAGACCCATTGGTGT
20283   ACATCTCCCCATGGGTGTACTAGAATACCATCATTTTCACTCATCAAGACCCATTGGTGT
20435   ACATCTCCCCATGGGTGTACTAGAATACCATCATTTTCACTCATCAAGACCCATTGGTGT
26056   ACATCTCCCAATGGGTGTACTAGAATACCATCATTTTCACTCATCAAGACCCATTGGTGT
        *********  * ** *********************** ** *****************
```

FIGURE 6

```
Greer   TACACTCACAATGTAATGCTTGGAGATTGCCTCGATTTCACGACATCTAATCAGTATTTA 600
18620   TACACTCACAATGTAATACTTGGAGATTGTCTTGATTTCACGGCATCTAACCAGTATTTA
20283   TACACTCACAATGTAATACTTGGAGATTGTGTCTTGATTTCACAGCATCTAACCAGTATTA
20435   TACACTCACAATGTAATACTTGGAGATTGTCTTGATTTCACAGCATCTGACCAGTATTTA
26056   TACACTCACAATGTAATACTTGGAGATTGTCTTGATTTCACAGCATCTAACCAGTATTTA
        ******************  ********* **  ********    *****  *  *********

Greer   GCAATGGGGATAATACAACAATCTGCTGCAGCATTTCCAATCTTCAGGACTATGAAAACC 660
18620   TCAATGGGGATAATACAACAATCTGCTGCAGGGTTTCCAATTTTCAGGACTATGAAAACC
20283   TCAATGGGGATAATACAACAATCTGCTGCAGCATTTCCNTTTTTCAGGACTATGAAAACC
20435   TCAATGGGGATAATACAACAATCTGCTGCAGGGTTTCCAATTTTCAGGCTATGAAAACC
26056   TCAATGGGGATAATACAACAATCTGCTGCAGGGTTTCCAATTTTCAGGACTATGAAAACC
         **********************         ******  * *****************

Greer   ATTTACCTAAGTGATGGAATCAATCGCAAAAGCTGTTCAGTCACTGCTATACCAGGAGGT 720
18620   ATTTACCTAAGTGATGGAATCAATCGCAAAAGCTGTTCAGTCACTGCTATACCAGGAGGT
20283   ATTTACCTAAGTGATGGAATCAATCGCAAAAGCTGTTCAGTCACTGCTATACCAGGAGGT
20435   ATTTACCTAAGTGATGGAATCAATCGCAAAAGCTGTTCAGTCACTGCTATACCAGGAGGT
26056   ATTTACCTAAGTGATGGAATCAATCGCAAAAGCTGTTCAGTCACTGCTATACCAGGAGGT
        ************************************************************

Greer   TGTGTCTTGTATTGCTATGTAGCTACAAGATCTGAGAAAGAAGATTATGCCACAACTGAT 780
18620   TGTGTCTTGTATTGCTATGTAGCTACAAGGTCTGAAAAAGAAGATTATGCCACGACTGAT
20283   TGTGTCTTGTATTGCTATGTAGCTACAAGGTCTGAAAAAGAAGATTATGCCACGACTGAT
20435   TGTGTCTTGTATTGCTATGTAGCTACAAGGTCTGAAAAAGAAGATTATGCCACGACTGAT
26056   TGTGTCTTGTATTGCTATGTAGCTACAAGGTCTGAAAAAGAAGATTATGCCACGACTGAT
        *****************************  *****  **************** *****

Greer   CTAGCTGAACTGAGACTTGCTTTCTATTATTATAATGATACCTTTATTGAAAGAGTCATA 840
18620   CTAGCTGAACTGAGACTTGCCTTCTATTATTATAATGATACCTTTATTGAAAGAGTCATA
20283   CTAGCTGAATTGAGACTTGCCTTCTATTATTATAATGATACCTTTATTGAAAGAGTCATA
20435   CTAGCTGAATTGAGACTTGCCTTCTATTATTATAATGATACCTTTATTGAAAGAGTCATA
26056   CTAGCTGAACTGAGACTTGCTTTCTATTATTATAATGATACCTTTATTGAAAGAGTCATA
        *********  ********* ****************************************

Greer   TCTCTTCCAAATACAACAGGGCAATGGGCCACAATCAATCCTGCAGTTGGAAGCGGGATC 900
18620   TCTCTTCCAAATACAACAGGGCAGTGGGCCACAATCAACCCTGCAGTCGGAAGCGGGATC
20283   TCTCTTCCAAATACAACAGGGCAGTGGGCCACAATCAACCCTGCAGTCGGAAGCGGGATC
20435   TCTCTTCCAAATACAACAGGGCAGTGGGCCACAATCAACCCTGCAGTCGGAAGCGGGATC
26056   TCTCTTCCAAATACAACAGGGCAGTGGGCCACAATCAACCCTGCAGTTGGAAGCGGGATC
        ***********************.*************  ******* *************

Greer   TATCATCTAGGCTTTATCTTATTTCCTGTATATGGTGGTCTCATAAGTGGGACTCCTTCC 960
18620   TATCATCTAGGCTTTATCTTATTTCCTGTATATGGTGGTCTCATAAATGGGACTACTTCT
20283   TATCATCTAGGCTTTATCTTATTTCCTGTATATGGTGGTCTCATAAATGGGACTACTTCT
20435   TATCATCTAGGCTTTATCTTATTTCCTGTATATGGTGGTCTCATAAATGGGACTACTTCT
26056   TATCATCTAGGCTTTATCTTATTTCCTGTATATGGTGGTCTCATAAATGGGACTACTTCT
        **********************************************  ******  ****

Greer   TACAACAAGCAGTCCTCACGCTATTTTATCCCAAAACATCCCAACATAACCTGTGCCGGT 1020
18620   TACAATGAGCACTCCTCACGCTATTTTATCCCAAAACATCCCAACATAACTTGTGCCGGT
20283   TACAATGAGCAGTCCTCACGCTATTTTATCCCAAAACATCCCAACATAACTTGTGCCGGT
20435   TACAATGAGCAGTCCTCACGCTATTTTATCCCAAAACATCCCAACATAACTTGTGCCGGT
26056   TACAATGAGCAGTCCTCACGCTATTTTATCCCAAAACATCCCAACATAACTTGTGCCGGT
        *****  ****  ************************************** *********

Greer   AACTCCAGCGAACAGGCTGCAGCAGCACGGAGTTCCTATCTAATCCGTTATCACTCAAAC 1080
18620   AACTCCAGCAAACAGGCTGCAATAGCACGGAGTTCCTATGTCATCCGTTATCACTCAAAC
20283   AACTCCAGCAAACAGGCTGCAATAGCACGGAGTTCCTATGTCATCCGTTATCACTCAAAC
20435   AACTCCAGCAAACAGGCTGCAATAGCACGGAGTTCCTATGTCATCCGTTATCACTCAAAC
26056   AACTCCAGCAAACAGGCTGCAATAGCACGGAGTTCTTATGTCATCCGTTATCACTCAAAC
        *********  ********** ************ ***    ******************
```

```
Greer   ACTCAAAGATTTATTGTTTGATAATAATTGAAATGGGCTCATCTCTTTTAGGGGAGTTC 1680
18620   ACCCAAAAATTTATTGTTTAATAATAATTGAAATGGGCTCATCTCTTTTAGGGGAGTTC
20283   ACCCAAAAAATTTATTGTTTAATAATAATTGAAATGGGCTCATCTCTTTTAGGGGAGTTC
20435   ACCCAAAAAATTTATTGTTTAATAATAATTGAAATGGGCTCATCTCTTTTAGGGGAGTTC
26056   AACCAAAAAATTTATTGTTTAATAATAATTGAAATGGGCTCATCTCTTTTAGGGGAGTTC
        *  ****  ******** *****************************************

Greer   CAAATAATACCATTTCTAAGGGAACTAATACCTTAA 1716
18620   CAAATAATACCATTTTTAAGGGAACTAATGCTTTAA
20283   CAAATAATACCATTTTTAAGGGAACTAATGCTTTAA
20435   CAAATAATACCATTTTTAAGGGAACTAATGCTTTAA
26056   CAAATAATACCATTTTTAAGGGAACTAATGCTTTAA
        **************  ***********  * ****
```

FIGURE 6 cont'd

Alignments of F proteins

```
isolat18620F      MEHLHPMIVCIFVMYTGIVGSDAIAGDQLLNVGVIQSKIRSLMYYTDGGASFIVVKLLPN 60
isolat26632F      MEHLHPMIVCIFVMYTGIVGSDAIAGDQLLNVGVIQSKIRSLMYYTDGGASFIVVKLLPN 60
isolat20283F      MEHPHPMIVCIFVMYTGIVGSDAIAGDQLLNVGVIQSKIRSLMYYTDGGASFIVVKLLPN 60
isolat20435F      MEHLHPMIVCIFVMYTGIVGSDAIAGDQLLNVGVIQSKIRSLMYYTDGGASFIVVKLLPN 60
isolat26056F      MEHLHPMIVCIFVMYTGIVGSDAIAGDQLLNVGVIQSKIRSLMYYTDGGASFIVVKLLPN 60
isolatGreerF      MEHLHPNIVCIFVMYTGIVGSDAIAGDQLLNIGVIQSKIRSLMYYTDGGASFIVVKLLPN 60
                  *** ***************************:**************************** isolat18620F      LPPSNGTCNITSLDAYNVTLFKLLTPLIENLSKISAVTDTKPRRERFAGVVIGLAALGVA 120
isolat26632F      LPPSNGTCNITSLDAYNVTLFKLLTPLIENLSKISAVTDTKPRRERFAGVVIGLAALGVA 120
isolat20283F      LPPSNGTCNITSLDAYNVTLFKLLTPLIENLSKISAVTDTKPRRERFAGVVIGLAALGVA 120
isolat20435F      LPPSNGTCNITSLDAYNVTLFKLLTPLIENLSKISAVTDTKPRRERFAGVVIGLAALGVA 120
isolat26056F      LPPSNGTCNITSLDAYNVTLFKLLTPLIENLSKISAVTDTKPRRERFAGVVIGLAALGVA 120
isolatGreerF      LPPSNGTCNITSLDAYNVTLFKLLTPLIENLSKISTVTDTKTRQKRFAGVVVGLAALGVA 120
                  ***********************************:*****.*::******:******** isolat18620F      TAAQITAAVAIVKANANAAAINNLASSIQSTNKAVSDVITASRTIATAVQAIQDRINGAI 180
isolat26632F      TAAQITAAVAIVKANANAAAINNLASSIQSTNKAVSDVITASRTIATAVQAIQDRINGAI 180
isolat20283F      TAAQITAAVAIVKANANAAAINNLASSIQSTNKAVSDVITASRTIATAVQAIQDRINGAI 180
isolat20435F      TAAQITAAVAIVKANANAAAINNLASSIQSTNKAVSDVITASRTIATAVQAIQDRINGAI 180
isolat26056F      TAAQITAAVAIVKANANAAAINNLASSIQSTNKAVSDVITASRTIATAVQAIQDRINGAI 180
isolatGreerF      TAAQITAAVAIVKANANAAAINNLASSIQSTNKAVSDVIDASRTIATAVQAIQDRINGAI 180
                  *************************************** ******************** isolat18620F      VNGITSASCRAHDALIGSILNLYLTELTTIFHNQITNPALTPLSIQALRILLGSTLPIVI 240
isolat26632F      VNGITSASCRAHDALIGSILNLYLTELTTIFHNQITNPALTPLSIQALRILLGSTLPIVI 240
isolat20283F      VNGITSASCRAHDALIGSILNLYLTELTTIFHNQITNPALTPLSIQALRILLGSTLPIVI 240
isolat20435F      VNGITSASCRAHDALIGSILNLYLTELTTIFHNQITNPALTPLSIQALRILLGSTLPIVI 240
isolat26056F      VNGITSASCRAHDALIGSILNLYLTELTTIFHNQITNPALTPLSIQALRILLGSTLPIVI 240
isolatGreerF      VNGITSASCRAHDALIGSILNLYLTELTTIFHNQITNPALTPLSIQALRILLGSTLPIVI 240
                  ************************************************************
```

FIGURE 7

(Key: isolat = isolate)

FIGURE 7 cont'd (Key: isolat = isolate)

```
isolat186620F  ARTAKTLYSLSAIALILSVITLVVVGLLIAYIIKLVSQIHQFRALAATTMFHREMPAVFS 540
isolat266320F  ARTAKTLYSLSAIALILSVITLVVVGLLIAYIIKLVSQIHQFRALAATTMFHREMPAVFS 540
isolat202835F  ARTAKTLYSLSAIALILSVITLVVVGLLIAYIIKLVSQIHQFRALAATTMFHREMPAVFS 540
isolat204352F  ARTAKTLYSLSAIALILSVITLVVVGLLIAYIIKLVSQIHQFRALAATTMFHREMPAVFS 540
isolat260562F  ARTAKTLYSLSAIALILSVITLVVVGLLIAYIIKLVSQIHQFRALAATTMFHREMPAVFS 540
isolatGreerF   ARTAKTLYSLSAIALILSVITLVVVGLLIAYIIKLVSQHQFRSLAATTMFHREMPAFFS 540
               *******************************:*:****** isolat186620F  KRNHGMIYGIS 551
isolat266320F  KRNHGMIYGIS 551
isolat202835F  KRNHGMIYGIS 551
isolat204352F  KRNHGMIYGIS 551
isolat260562F  KRNHGMIYGIS 551
isolatGreerF   KRNHGMIYGIS 551
               ***********
```

FIGURE 7 cont'd (Key: isolat = isolate)

Alignment of HN proteins

```
isolat18620HN    MEDYSNLSLKSIPKRTCRIIFRTATILGICTLIVLCSSILHEIIHLDVSSDLMNSDESQQ 60
isolat20283HN    MEDYSNLSLKSIPKRTCRIIFRTATILGICTLIVLCSSILHEIIHLDVSSGLMNSDESQQ 60
isolat20435HN    MEDYSNLSLKSIPKRTCRIIFRTATILGICTLIVLCSSILHEIIHLDVSSGLMNSDESQQ 60
isolat26056HN    MEDYSNLSLKSIPKRTCRIIFRTATILGICTLIVLCSSILHEIIHLDVSSGLMDSDESQQ 60
isolatGreerHN    MEDYSNLSLKSIPKRTCRIIFRTATILGICTLIVLCSSILHEIIHLDVSSGLMDSDDSQQ 60
                 **************************************************,**:**:*** isolat18620HN    GIIQPIIESLKSLIALANQILYNVAIVIPLKIDSIETVILSALKDMHTGSMSNANCTPGN 120
isolat20283HN    GIIQPIIESLKSLIALANQILYNVAIVIPLKIDSIETVILSALKDMHTGSMSNANCTPGN 120
isolat20435HN    GIIQPIIESLKSLIALANQILYNVAILIPLKIDSIETVILSALKDMHTGSMSNANCTPGN 120
isolat26056HN    GIIQPIIESLKSLIALANQILYNVAIIIPLKIDSIETVILSALKDMHTGSMSNANCTPGN 120
isolatGreerHN    GIIQPIIESLKSLIALANQILYNVAIIIPLKIDSIETVIFSALKDMHTGSMSNYNCTPGN 120
                 **************************:*************:************:****** isolat18620HN    LLLHDAAYINGINKFLVLESYNGTPKYGPLLNIPSFIPSATSPHGCTRIPSFSLIRTHWC 180
isolat20283HN    LLLHDAAYINGINKFLVLESYNGTPKYGPLLNIPSFIPSATSPHGCTRIPSFSLIKTHWC 180
isolat20435HN    LLLHDAAYINGINKFLVLESYNGTPKYGPLLNIPSFIPSATSPHGCTRIPSFSLIKTHWC 180
isolat26056HN    LLLHDAAYINGINKFLVPESYNGTPKYGPLLNIPSFIPSATSPNGCTRIPSFSLIKTHWC 180
isolatGreerHN    LLLHDAAYINGINKFLVLKSYNGTPKYGPLLNIPSFIPSATSPNGCTRIPSFSLIKTHWC 180
                 ***************** :************************:***********:**** isolat18620HN    YTHNVILGDCLDFTASMQYLSMGIIQQSAAGFPIFRTMKTIYLSDGINRKSCSVTAIPGG 240
isolat20283HN    YTHNVILGDCLDFTASMQYLSMGIIQQSAAAFPFFRTMKTIYLSDGINRKSCSVTAIPGG 240
isolat20435HN    YTHNVILGDCLDFTASDQYLSMGIIQQSAAGFPIFRTMKTIYLSDGINRKSCSVTAIPGG 240
isolat26056HN    YTHNVILGDCLDFTASMQYLSMGIIQQSAAGFPIFRTMKTIYLSDGINRKSCSVTAIPGG 240
isolatGreerHN    YTHNVMLGDCLDFTTSMQYLAMGIIQQSAAAFPIFRTMKTIYLSDGINRKSCSVTAIPGG 240
                 *****:********:*:***:*********.**:************************** isolat18620HN    CVLYCYVATRSEKEDYATTDLAELRLAFYYYNDTFIERVISLPNTTGQWATINPAVGSGI 300
isolat20283HN    CVLYCYVATRSEKEDYATTDLAELRLAFYYYNDTFIERVISLPNTTGQWATINPAVGSGI 300
isolat20435HN    CVLYCYVATRSEKEDYATTDLAELRLAFYYYNDTFIERVISLPNTTGQWATINPAVGSGI 300
isolat26056HN    CVLYCYVATRSEKEDYATTDLAELRLAFYYYNDTFIERVISLPNTTGQWATINPAVGSGI 300
isolatGreerHN    CVLYCYVATRSEKEDYATTDLAELRLAFYYYNDTFIERVISLPNTTGQWATINPAVGSGI 300
                 ************************************************************
```

FIGURE 8

(Key: isolat = isolate)

FIGURE 8 cont'd

HPIV-2 VARIANTS AND THEIR MEDICAL APPLICATIONS

TECHNICAL FIELD OF THE INVENTION

The present application relates to human parainfluenza virus type 2 (HPIV-2) variants and to their medical applications, more particularly to their diagnostic applications.

BACKGROUND OF THE INVENTION

In the Paramyxoviridae family, human parainfluenza viruses (HPIV) are RNA viruses included in two genuses of the Paramyxovirinae sub-family:

Respirovirus for type 1 and 3 parainfluenza viruses (HPIV-1, -3);

Rubulavirus for type 2 and 4 parainfluenza viruses (HPIV-2, -4).

HPIVs are envelope viruses. Their genome is approximately 15 kilobases long, constituted by single strand negative polarity RNA. The genome codes for six principal proteins.

The genes NP, P and L respectively code for the nucleoprotein, the phosphoprotein and the polymerase (L stands for large polymerase complex). These three proteins along with the viral RNA form the nucleocapsid (or holonucleocapsid). With the RNA, the nucleoprotein forms a support for the phosphoprotein and the polymerase, allowing transcription and eventually replication of the genome.

The F and HN genes respectively code for the fusion F protein and the haemagglutinin-neuraminidase (HN) protein, which are the two envelope proteins of the viruses and which participate in the mechanism by which the virus enters the host cell.

The HN protein is responsible for attachment of the virus to the cell, by binding itself to cellular sialic acids. Once the virus is attached, the fusion F protein is activated, inserts one of its domains into the cell membrane and then the mechanisms which draw the two membranes together and fuse them are triggered.

HPIVs which have been described in the prior art include various HPIV-2 viruses.

The reference HPIV-2 isolate is the Greer isolate which was isolated from a patient in 1955.

Diagnostic means, which include detecting HPIV-2, are all currently designed using the structure of this reference isolate.

As an example, detecting HPIV-2 in the context of a hospital is currently carried out by isolation in cell culture (on a LLC-MK2 sensitive system) or by immunofluorescence and immunocapture ELISA. The antibodies employed in those techniques were obtained from the HPIV-2 Greer strain.

The inventors have now shown that there is in fact an entire family of HPIV-2 viruses which are sufficiently different from the Greer isolate, and more particularly Greer, Toshiba and V98 isolates, not to be recognized by anti-envelope protein antibodies which are normally used in the prior art to detect HPIV-2.

Similarly, the prior art proposes several techniques for detecting HPIV-2 by PCR, but the primer design is based on the sequence for the Greer isolate, without allowing for the fact that, as the present inventors have shown, there exists an entire family of HPIV-2 viruses which are different from the Greer isolate, and more particularly from Greer, Toshiba and V98 isolates.

SUMMARY OF THE INVENTION

The inventors have identified a novel variant phylogenetic group of HPIV-2 and a novel variant phylogenetic sub group of HPIV-2.

The application pertains to HPIV-2 viruses which form part of this novel variant phylogenetic group, and to HPIV-2 viruses which form part of this novel variant phylogenetic sub group of HPIV-2.

The variant phylogenetic group of the invention is a HPIV-2 virus group which in particular does not include Greer, Toshiba and V98 isolates.

The variant phylogenetic sub group of the invention is a HPIV-2 virus group which in particular does not include Greer, Toshiba and V98 isolates and which also does not include the V94 isolate.

Five isolates forming part of this group and also of this sub-group have been deposited with the CNCM under the auspices of the Treaty of Budapest.

The application relates to proteins, more particularly to envelope proteins of viruses from the variant phylogenetic group or sub-group of the invention, in particular to the F and HN proteins of these viruses, and to fragments of said proteins.

The application also pertains to nucleic acids coding for these proteins or protein fragments.

The application also pertains to means for detecting, more particularly for diagnosing, HPIV-2.

The application pertains to particular nucleotide regions of the virus of the HPIV-2 group or sub-group of the invention, which are sufficiently specific to them to allow their detection, preferably their specific detection, with respect to the Greer isolate, and more particularly with respect to Greer and V98 isolates.

The application thus pertains to nucleotide regions which have been specifically selected for the construction and the production of real time PCR systems, comprising at least one pair of primers and a probe, as well as to nucleotide regions which have been specifically selected for the construction and the production of probes which are specially adapted for use on a chip.

The application also pertains to these primers, these probes and to chips comprising at least one probe of the invention.

Further, the application pertains to kits and compositions comprising at least one specific region and/or at least one primer and/or at least one probe of the invention.

The application also pertains to antibodies directed against an envelope protein of at least one of the viruses from the variant phylogenetic group or sub-group of the invention, and to hybridomas producing said antibodies.

BRIEF DESCRIPTION OF THE FIGURES

The application makes reference to the following figures:

FIG. 1: Three-dimensional model of ectodomains of the HN protein of the prototype HPIV-2 Greer isolate of the prior art (left hand model) and of an isolate of the invention, for example the HPIV-2 isolate 18620 (right hand model).

This Figure illustrates the fact that the isolates of the invention have one HN protein which is different to that of the HPIV-2 Greer isolate, in particular as regards the glycosylation sites. As can be seen in the Figure, the isolates of the invention in particular include a S316N mutation which creates a glycosylation site which does not have the HN protein from the HPIV-2 Greer isolate.

FIG. 2: Alignment of amino acid sequences for the fusion peptide (FP: fragment 107-126 of the fusion protein F) of:

five HPIV-2 isolates of the invention (human parainfluenza virus type 2; isolates 18620, 20283, 20435, 26056, 26632); against those of the prior art HPIV-2 Greer isolate (human parainfluenza virus type 2) and the SV5 virus (simian parainfluenza virus type 5).

Figure 3:
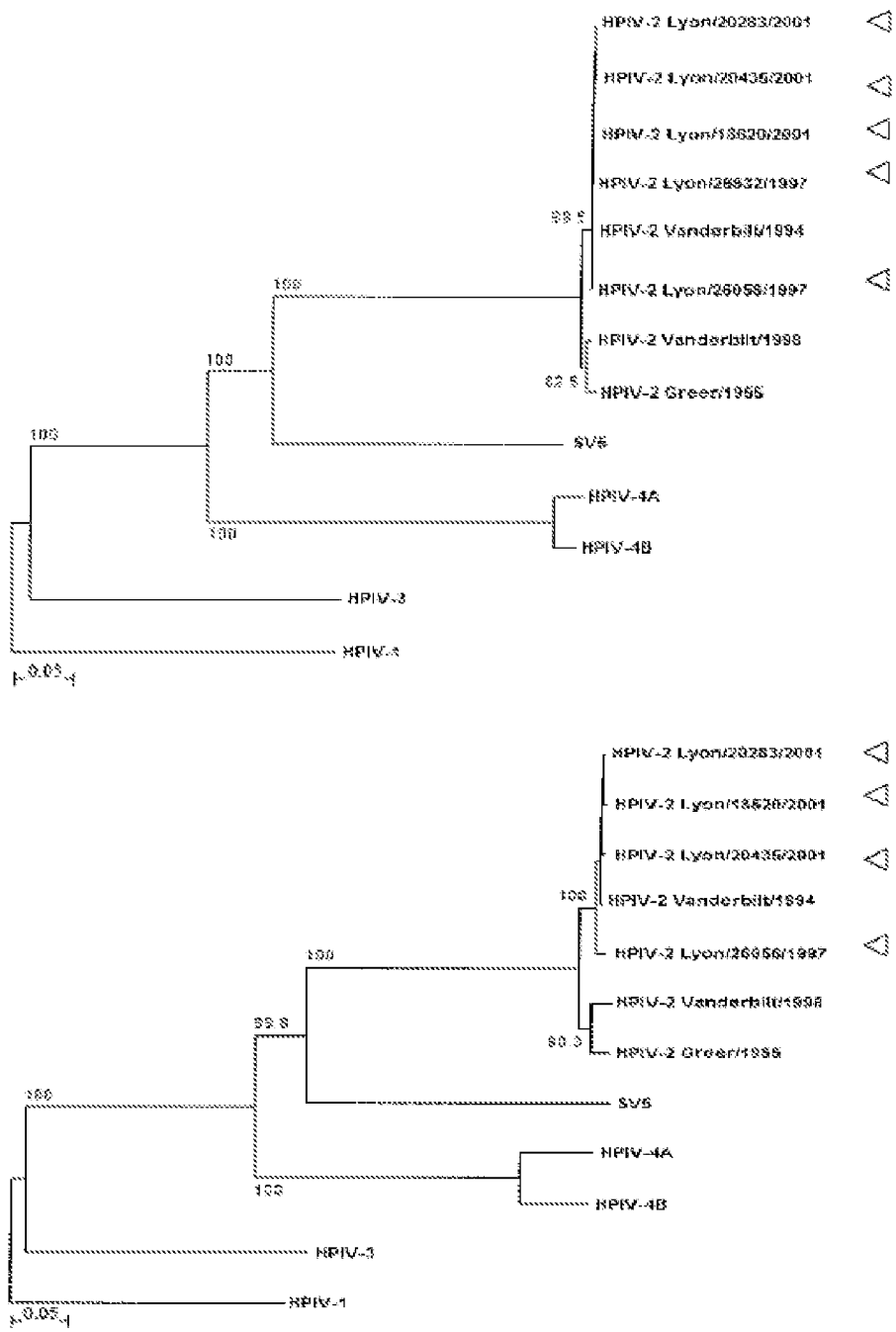

FIG. 3: Phylogenetic analysis of F proteins (top tree) and HN proteins (bottom tree) of the following isolates:

five HPIV-2 isolates of the invention (isolate HPIV-2 Lyon/ 20283/2001=isolate 20283; isolate HPIV-2 Lyon/ 20435/2001=isolate 20435; isolate HPIV-2 Lyon/ 18620/2001=isolate 18620; isolate HPIV-2 Lyon/ 26632/1997=isolate 26632; isolate HPIV-2 Lyon/ 26056/1997=isolate 26056);

isolate HPIV-2 Vanderbilt/1994 (=isolate HPIV-2 V94);
isolate HPIV-2 Vanderbilt/1998 (=isolate HPIV-2 V98);
isolate HPIV-2 Greer/1955 (=isolate HIPV-2 Greer);
virus SV5 (simian parainfluenza virus type 5);
HPIV-4A;
HPIV-4B;
HPIV-3; and
HPIV-1.

The sequences determined by the inventors are indicated by an arrow (isolates 20283, 20435, 18620, 26632, 26056).

The other sequences were obtained from the Genbank database (http///www.ncbi.nlm.nih.gov).

The phylogenetic trees were constructed using the neighbour-joining method. The scale indicates the number of amino acid substitutions per site, and the length of the horizontal branches is proportional to the indicated scale. The reliability of the branches was evaluated using the "bootstrap" method (1000 replications) and the percentages resulting from this procedure are indicated.

Figure 4:
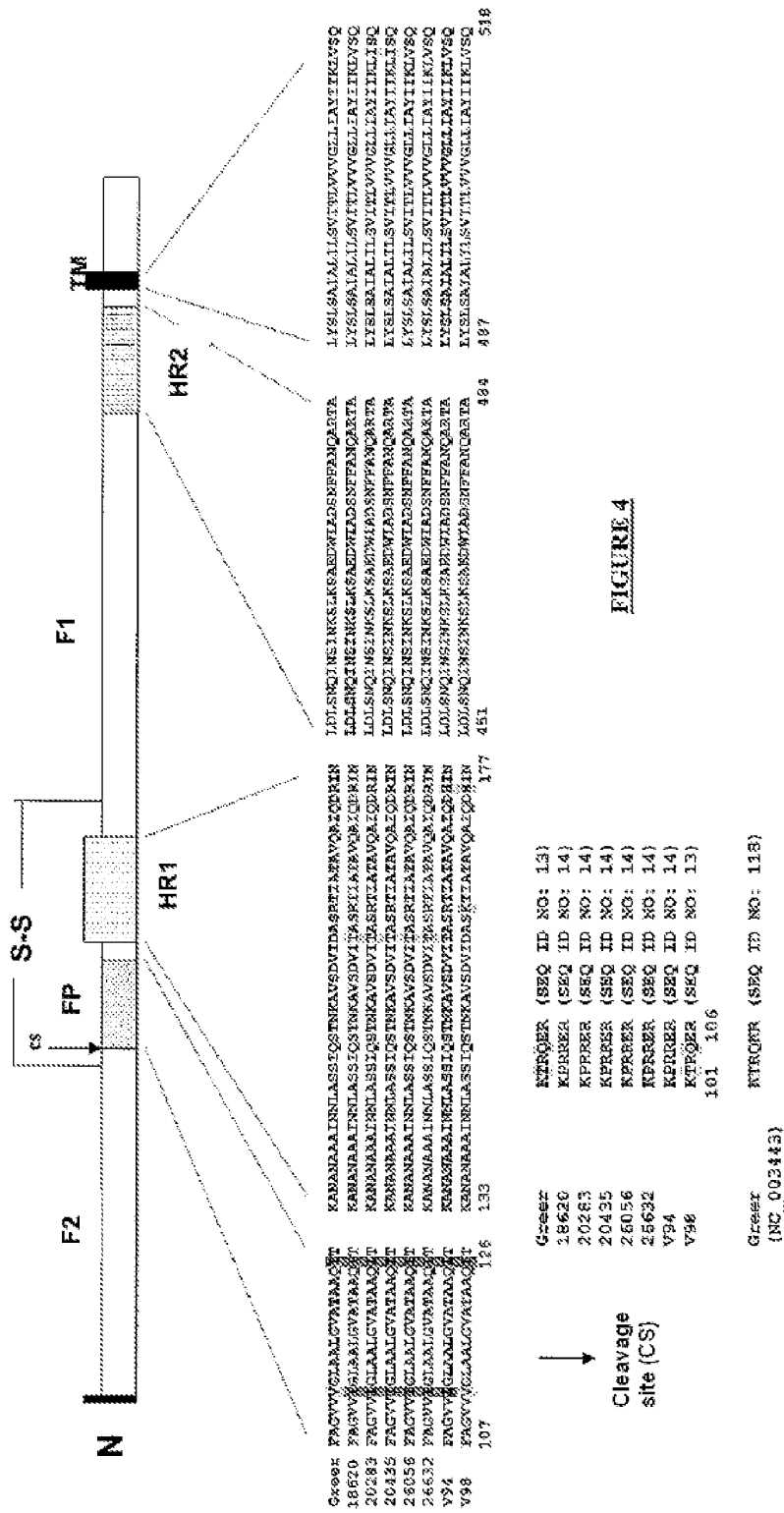

FIG. 4: Diagrammatic representation of structural domains of the F protein of HPIV-2, and presentation of the alignment of the amino acid sequences for the F Protein For five HPIV-2 isolates of the invention (isolates 18620, 20283, 20435, 26056, 26632), for the HPIV-2 Greer isolate and for the HPIV-2 isolates V94 and V98 (Vanderbilt/1994 and Vanderbilt/1998, respectively).

This figure illustrates the fact that certain amino acids of the F protein of the isolates of the invention are different from those observed in the other HPIV-2 isolates (Greer, V94 and V98 isolates). As an example, it may be seen that:

the F protein from isolates of the invention differ from that of the Greer isolate in particular because of the following sequence elements:

the sequence for the cleavage site (CS), which is KPRRER (SEQ ID NO: 14), instead of the sequence KTRQER (SEQ ID NO: 13) observed in the Greer isolate as sequenced by the inventors (mutations T102P and Q104R), and instead of the sequence KTRQRK (SEQ ID NO: 118) as appears in the Greer sequence available on the NCBI database (NLM, National Library of Medicine) with accession number NC_003443 (same mutations, T102P and Q104R);

the sequence for the fusion peptide (FP) which has the amino acid I in position 112 instead of the amino acid V (mutation V112I);

the sequence for the domain HR1 of the polypeptide F1, which has the amino acid T in position 160, instead of the amino acid D (mutation D160T);

the F protein of the isolates of the invention differs from that of the V98 isolate in particular because of the same sequence elements as those observed with respect to the Greer isolate (mutations T102P, Q104R in the CS; mutation V112I in the FP; mutation D160T in the HR1), as well as by the fact that at the sequence for the HR1 domain of the polypeptide F1, the isolates of the invention have:

the amino acid R in position 163, instead of the amino acid K (mutation K163R), and the amino acid R in position 175, instead of the amino acid H (mutation H175R);

the F protein of isolates of the invention differs from that of the V94 isolate in particular in the sequence for the HR1 domain of the polypeptide F1 which, in the isolates of the invention, has the amino acid R in position 175 instead of the amino acid H (mutation H175R).

It will also be seen that certain isolates of the invention have other mutations, especially in the transmembrane domain (TM) of the F protein. As an example, the isolates 20283 and 20435 of the invention are different from the isolates 18620, 26056 and 26632 of the invention, but also from the Greer, V94 and V98 isolates, in that their transmembrane domain has the amino acid I in position 516 instead of the amino acid V (mutation V516I).

The positions of the amino acids here are calculated with respect to the sequence for the F protein.

More particularly, FIG. 4 describes the sequences for the cleavage sites (CS), the fusion peptides (FP) of the HR1, HR2 and TM domains of each of the five HPIV-2 isolates of the invention (sequences 101-106, 107-126, 133-177, 451-484 and 487-518, respectively), aligned on the respective sequences for the Greer, V94 and V98 isolates.

The corresponding coding sequences may be deduced by the skilled person by following the universal genetic code and allowing for degeneracy of the code.

TM=transmembrane portion

It will be observed that, compared with the Greer, V98 and V94 isolates, the five particular isolates of the invention are characterized in that they have at the same time:

an amino acid other than D in position 160 (region HR1), preferably the amino acid T in position 160 (mutation D160T compared with Greer and V98 isolates); and an amino acid other than H in position 175 (region HR1), preferably the amino acid R in position 175 (mutation H175R compared with V98 and V94 isolates).

FIG. 5: Alignment of nucleotide sequences coding for F (1656 nucleotides) of the HPIV-2 Greer strain and HPIV-2 strains of the invention (isolates 18620, 20283, 20435, 26056 and 26632); from top to bottom:

sequence coding for F of Greer isolate NC_003443 (SEQ ID NO: 48);

sequence coding for F of isolate 18620 of the invention (SEQ ID NO: 23);

sequence coding for F of isolate 20283 of the invention (SEQ ID NO: 28);

sequence coding for F of isolate 20435 of the invention (SEQ ID NO: 33);

sequence coding for F of isolate 26056 of the invention (SEQ ID NO: 38);

sequence coding for F of isolate 26632 of the invention (SEQ ID NO: 43).

Each position which is not marked with an asterisk (*) is a position where at least one of the strains shown in alignment contains a nucleotide which is different from the others in that position.

Thus, it is easy to identify the positions and natures of the changes which each of the particular isolates of the invention contains, compared with one or more of the other strains shown in alignment, and more particularly compared with the Greer strain.

FIG. 6: Alignment of nucleotide sequences coding for HN (1716 nucleotides) of the HPIV-2 Greer strain and HPIV-2 strains of the invention (isolates 18620, 20283, 20435, 26056); from top to bottom:
- sequence coding for HN of Greer isolate NC_003443 (SEQ ID NO: 50);
- sequence coding for HN of isolate 18620 of the invention (SEQ ID NO: 25);
- sequence coding for HN of isolate 20283 of the invention (SEQ ID NO: 30);
- sequence coding for HN of isolate 20435 of the invention (SEQ ID NO: 35);
- sequence coding for HN of isolate 26056 of the invention (SEQ ID NO: 40).

Each position which is not marked with an asterisk (*) is a position where at least one of the strains shown in alignment contains a nucleotide which is different from the others in that position.

Thus, it is easy to identify the positions and natures of the changes which each of the isolates contains, compared with one or more of the other strains shown in alignment, and more particularly compared with the Greer strain.

Figure 7:
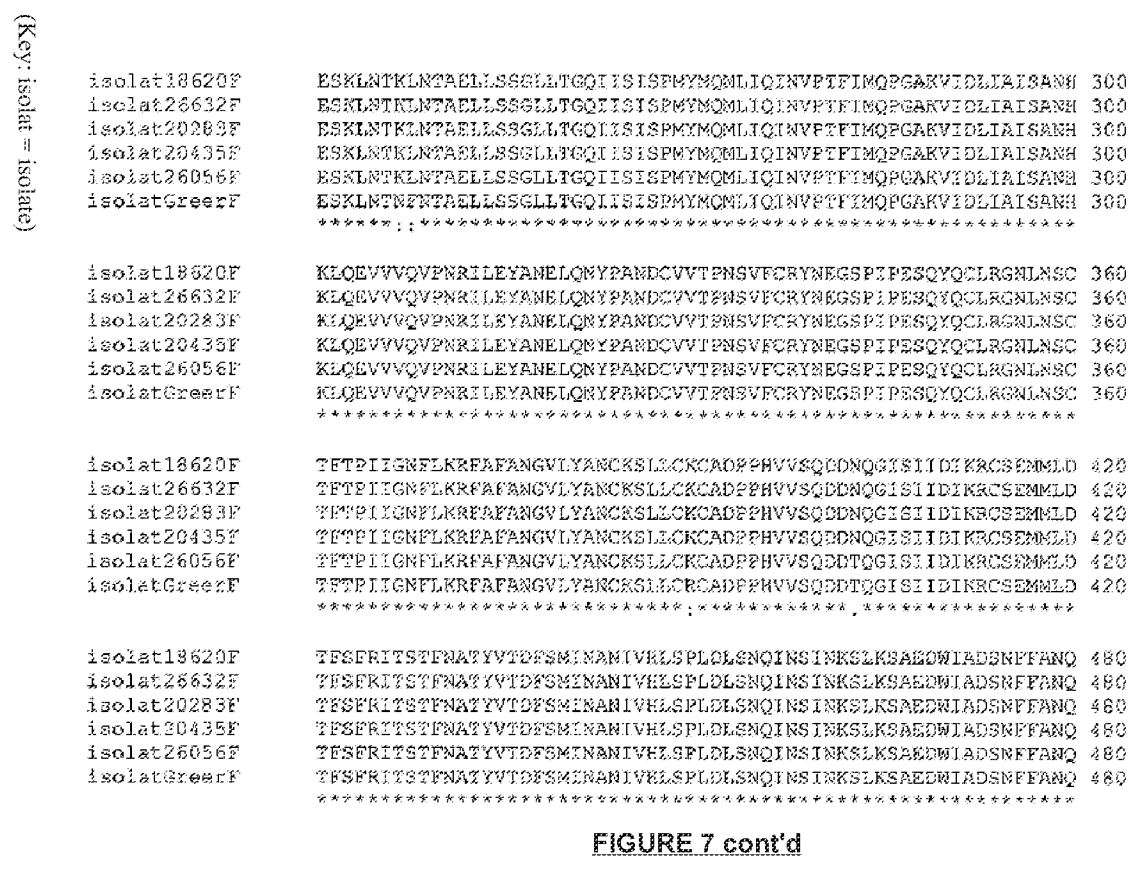

FIG. 7: Alignment of amino acid sequences for F (551 aa) of the HPIV-2 Greer strain and HPIV-2 strains of the invention (isolates 18620, 20283, 20435, 26056 and 26632); from top to bottom:
- sequence for F of isolate 18620 of the invention (SEQ ID NO: 24);
- sequence for F of isolate 26632 of the invention (SEQ ID NO: 44);
- sequence for F of isolate 20283 of the invention (SEQ ID NO: 29);
- sequence for F of isolate 20435 of the invention (SEQ ID NO: 34);
- sequence for F of isolate 26056 of the invention (SEQ ID NO: 39);
- sequence for F of Greer isolate NC_003443 (SEQ ID NO: 49).

Each position which is not marked with an asterisk (*) is a position where at least one of the strains shown in alignment contains an amino acid which is different from the others in that position.

Thus, it is easy to identify the positions and natures of the changes which each of the isolates contains, compared with one or more of the other strains shown in alignment, and more particularly compared with the Greer strain.

It may thus be noted that, compared with the Greer strain, the isolates of the invention have changes which are common to them in the sequence for F, especially in the following amino acid positions:
- position 32 (amino acid I for the Greer strain, amino acid V for the isolates of the invention, i.e. a I32V substitution);
- position 96 (amino acid T for the Greer strain, amino acid A for the isolates of the invention, i.e. a T96A substitution);
- position 102 (amino acid T for the Greer strain, amino acid P for the isolates of the invention, i.e. a T102P substitution);
- position 104 (amino acid Q for the Greer strain, amino acid P for the isolates of the invention, i.e. a Q104P substitution);
- position 112 (amino acid V for the Greer strain, amino acid I for the isolates of the invention, i.e. a V112I substitution);
- position 160 (amino acid D for the Greer strain, amino acid T for the isolates of the invention, i.e. a D160T substitution);
- position 247 (amino acid N for the Greer strain, amino acid K for the isolates of the invention, i.e. a N247K substitution);
- position 248 (amino acid F for the Greer strain, amino acid L for the isolates of the invention, i.e. a F248L substitution);
- position 390 (amino acid R for the Greer strain, amino acid K for the isolates of the invention, i.e. a R390K substitution);
- position 524 (amino acid S for the Greer strain, amino acid A for the isolates of the invention, i.e. a S524A substitution);
- position 538 (amino acid F for the Greer strain, amino acid V for the isolates of the invention, i.e. a F538V substitution).

Particular changes which are common compared with the Greer isolate which may be noted include the T102P and Q104R substitutions which the isolates of the invention have at the cleavage site (CS in FIG. 4), the V112I substitution which the isolates of the invention have at the fusion peptide (FP in FIG. 4), and the D160T substitution which the isolates of the invention have at the HR1 domain.

CDS=coding sequence.

Figure 8:
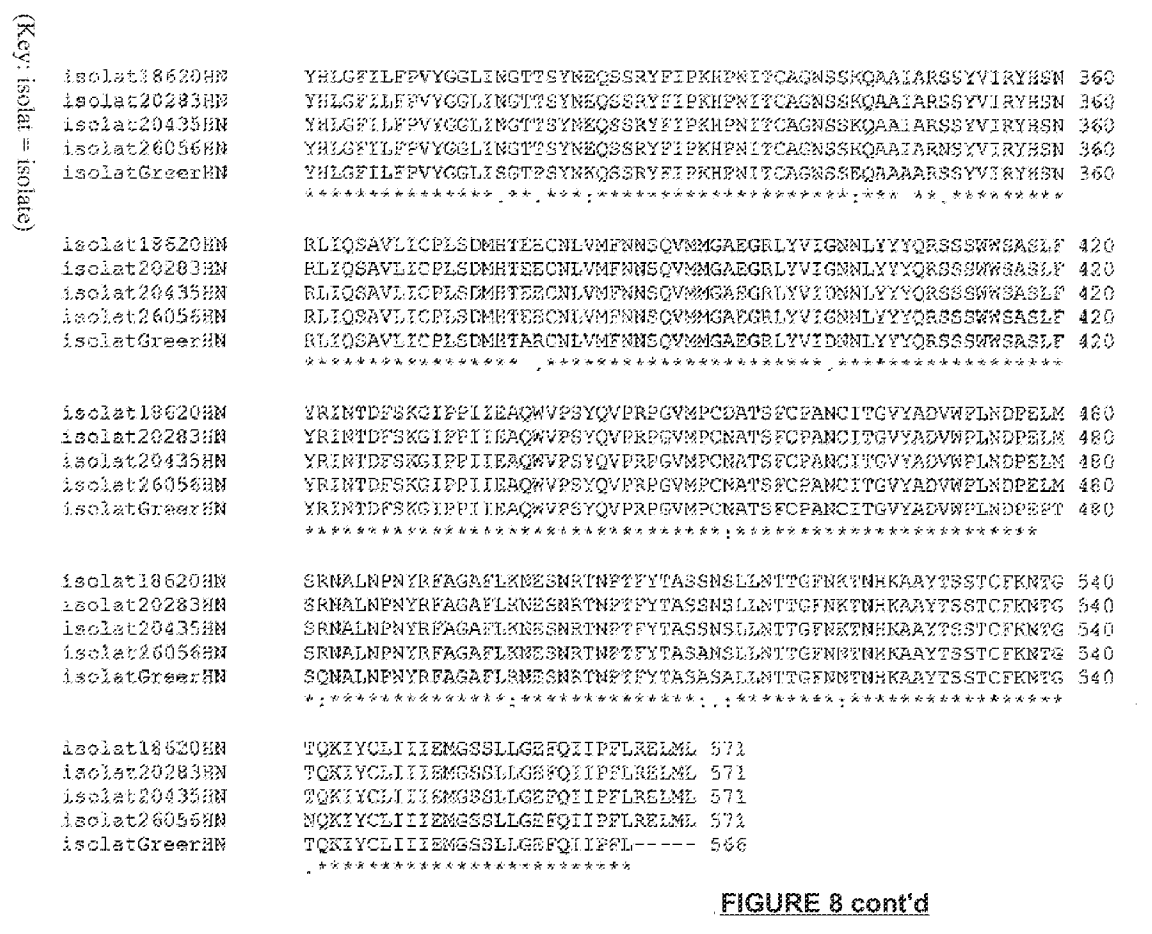

FIG. 8: Alignment of amino acids for HN (571 aa) of the HPIV-2 Greer strain and for the HPIV-2 strains of the invention (isolates 18620, 20283, 20435, 26056); from top to bottom:
- sequence for HN of isolate 18620 of the invention (SEQ ID NO: 26);
- sequence for HN of isolate 20283 of the invention (SEQ ID NO: 31);
- sequence for HN of isolate 20435 of the invention (SEQ ID NO: 36);
- sequence for HN of isolate 26056 of the invention (SEQ ID NO: 41);
- sequence for HN of isolate Greer NC_003443 (SEQ ID NO: 51).

Each position which is not marked with an asterisk (*) is a position where at least one of the strains shown in alignment contains an amino acid which is different from the others in that position.

Thus, it is easy to identify the positions and natures of the changes which each of the isolates contains, compared with one or more of the other strains shown in alignment, and more particularly compared with the Greer strain.

It may thus be noted that, compared with the Greer strain, the isolates of the invention have changes which are common to them in the sequence for HN, especially in the following amino acid positions:
- position 57 (amino acid D for the Greer strain, amino acid E for the isolates of the invention, i.e. a D57E substitution);
- position 100 (amino acid F for the Greer strain, amino acid L for the isolates of the invention, i.e. a F100L substitution);
- position 114 (amino acid T for the Greer strain, amino acid A for the isolates of the invention, i.e. a T114A substitution);
- position 139 (amino acid K for the Greer strain, amino acid E for the isolates of the invention, i.e. a K139E substitution);
- position 186 (amino acid M for the Greer strain, amino acid I for the isolates of the invention, i.e. a M186I substitution);
- position 195 (amino acid T for the Greer strain, amino acid A for the isolates of the invention, i.e. a T195A substitution);

position 201 (amino acid A for the Greer strain, amino acid S for the isolates of the invention, i.e. a A201S substitution);

position 316 (amino acid S for the Greer strain, amino acid N for the isolates of the invention, i.e. a S316N substitution);

position 319 (amino acid P for the Greer strain, amino acid T for the isolates of the invention, i.e. a P319T substitution);

position 323 (amino acid K for the Greer strain, amino acid E for the isolates of the invention, i.e. a K323E substitution);

position 344 (amino acid E for the Greer strain, amino acid K for the isolates of the invention, i.e. a E344K substitution);

position 348 (amino acid A for the Greer strain, amino acid I for the isolates of the invention, i.e. a A348I substitution);

position 378 (amino acid A for the Greer strain, amino acid E for the isolates of the invention, i.e. a A378E substitution);

position 379 (amino acid R for the Greer strain, amino acid E for the isolates of the invention, i.e. a R379E substitution);

position 479 (amino acid P for the Greer strain, amino acid L for the isolates of the invention, i.e. a P479L substitution);

position 480 (amino acid T for the Greer strain, amino acid M for the isolates of the invention, i.e. a T480M substitution);

position 482 (amino acid Q for the Greer strain, amino acid R for the isolates of the invention, i.e. a Q482R substitution);

position 497 (amino acid R for the Greer strain, amino acid K for the isolates of the invention, i.e. a R497K substitution);

position 513 (amino acid S for the Greer strain, amino acid N for the isolates of the invention, i.e. a S513N substitution);

position 514 (amino acid A for the Greer strain, amino acid S for the isolates of the invention, i.e. a A514S substitution).

CDS=coding sequence.

These common changes compared with the Greer isolate include the N316S substitution which introduces a new glycosylation site into the isolates of the invention compared with the Greer strain.

The amino acids in positions 512, 513, 514 and 515 of the HN protein, and more particularly the amino acids in position 513 and 514, should also be noted.

DETAILED DESCRIPTION

The present application relates to a novel phylogenetic group and to a novel phylogenetic sub-group of the HPIV-2 virus, and to medical applications which may arise from the teaching in the present document provided by the inventors, namely the existence of this novel phylogenetic group and sub-group.

More particularly, the present application pertains to means for detection, and more particularly diagnosis, of the HPIV-2 virus forming part of this group and/or this sub-group.

The inventors have isolated several strains of HPIV-2 which are variant strains compared with the HPIV-2 Greer isolate, and more particularly compared with the Greer, Toshiba and V98 isolates.

In the prior art, the Greer isolate is the reference isolate for developing detection tools, and more particularly diagnostic tools, for HPIV-2.

The inventors have now shown that there is an entire family of HPIV-2 viruses which are sufficiently different from the Greer isolate, and more particularly from the Greer, Toshiba and V98 isolates, not to be recognized by the anti-envelope protein antibodies which, in the prior art, are usually used for detecting HPIV-2.

More particularly, the HPIV-2 isolates forming part of the novel phylogenetic group or sub-group of the invention are not recognized by the anti-HN antibody marketed by ARGENE S.A. (Parc Technologique Delta Sud, 09120 Varilhes; France) with reference 12E12G9.

Now, however, these variant isolates of the invention have recently been observed in several patients suffering from respiratory diseases.

In contrast, the HPIV-2 strain which in the prior art acts as a reference for developing the HPIV-2 diagnostic means is a strain which dates from 1955 (Greer strain).

Thus, the inventors have shown that there is a mismatch between the means currently used for diagnosis of HPIV-2 and the nature of the HPIV-2 strains currently being observed in patients. As the strains evolve, it is highly probable that this mismatch will be accentuated.

The novel phylogenetic group of HPIV-2 isolates of the invention is characterized in that it does not include Greer, Toshiba and V98 isolates.

FIG. 3 shows a representation of the phylogenetic group of the invention, which is based on the F and HN envelope proteins (top tree: F protein; bottom tree: HN protein).

In particular, the novel phylogenetic group of the invention includes the isolates which, in FIG. 3, are denoted HPIV-2 Lyon/20283/2001, HPIV-2 Lyon/20435/2001, HPIV-2 Lyon/18620/2001 HPIV-2 Lyon/26632/1997 and HPIV-2 Lyon/26056/1997, i.e. five novel isolates which have been isolated by the inventors and which have been deposited with the CNCM under the auspices of the Treaty of Budapest. This novel phylogenetic group also includes the isolate HPIV-2 Vanderbilt/1994 (=V94 isolate).

In particular, the novel sub-group of the invention comprises the HPIV-2 isolates Lyon/20283/2001, HPIV-2 Lyon/20435/2001, HPIV-2 Lyon/18620/2001, HPIV-2 Lyon/26632/1997 and HPIV-2 Lyon/26056/1997, but does not comprise the HPIV-2 Vanderbilt/1994 isolate (=V94 isolate). Analyses of the F and HN sequences allows several differences between the V94 isolate and the sub-group which includes the five particular isolates of the invention to be distinguished.

As can be seen by the skilled person in the phylogenetic representation in FIG. 3, the HPIV-2 isolates which are closest to the novel phylogenetic group and the novel phylogenetic sub-group of HPIV-2 isolates of the invention but which are not included are the Greer, Toshiba and V98 isolates.

This also implies that the novel phylogenetic group and the novel phylogenetic sub-group of the invention does not comprise microorganisms which would not be Rubulavirus viruses, and more particularly that they do not include microorganisms which would not be HPIV-2 viruses.

The isolate which has the name Toshiba isolate in the prior art has 99.8% identity with the Greer isolate on the nucleotide level. The sequence for the Toshiba isolate has been recorded in the databases, in particular as Genbank number X57559, NC_003443. Allowances will be made for the fact that the prior art shows that the differences which the sequence for the Toshiba isolate appears to have with respect to the sequence for the Greer isolate are more likely to be due to errors in cDNA cloning, synthesis and/or sequence analysis than to the actual natural circumstance of the isolate in question (cf. Skiadopoulos et al. 2003, Journal of Virology, 77(1): 270-279).

In the present application, the Toshiba isolate is thus considered to be identical to the Greer isolate.

In any event, a difference compared with the Greer isolate is sufficient to constitute a difference compared with the Toshiba isolate.

The sequences for the Greer, Toshiba and V98 isolates are available on Genbank under accession numbers NC_003443 (Greer isolate), X57559 (Toshiba isolate), (V98 isolate).

In the present application, the novel phylogenetic group of the invention can, for simplification, be designated as a phylogenetic group of HPIV-2 variants or variant phylogenetic group, or group of the invention.

Similarly, the novel phylogenetic sub-group of the invention can be denoted as a phylogenetic sub-group of HPIV-2 variants, a variant phylogenetic sub-group or a sub-group of the invention.

The novel group of the invention is defined by the fact that the viruses of this group comprise:
 an F protein which differs from that of the Greer isolate; and/or
 an HN protein which differs from that of the Greer isolate.

Preferably, the viruses of the group of the invention comprise an F protein and an HN protein which are respectively different from the F and HN proteins of the Greer isolate.

More particularly, the viruses of the group of the invention may comprise:
 an F protein which differs from the F proteins of the Greer and V98 isolates; and/or
 an HN protein which differs from the HN proteins of the Greer and V98 isolates.

Preferably, the viruses of the group of the invention have an F protein which is different from the F proteins of the Greer and V98 isolates, and an HN protein which is different from the HN proteins of the Greer and V98 isolates.

This or these protein differences may in particular be one or more differences in the amino acid sequences.

Thus, a virus from the group of the invention has:
 an F protein which, when its amino acid sequence is aligned with that for the Greer isolate, comprises at least one amino acid which is different from that presented by the sequence for the F protein of the Greer isolate in the same position; and/or (preferably and)
 an HN protein which, when its amino acid sequence is aligned with that for the Greer isolate, comprises at least one amino acid which is different from that presented by the sequence for the HN protein of the Greer isolate in the same position.

More particularly, a virus from the group of the invention may thus have:
 an F protein which, when its amino acid sequence is aligned with those for the Greer and V98 isolates, comprises at least one amino acid which is different from that presented by the sequence for the F protein of the Greer isolate in the same position and at least one amino acid which is different from that presented by the sequence for the F protein of the V98 isolate in the same position; and/or (preferably and)
 an HN protein which, when its amino acid sequence is aligned with those for the Greer and V98 isolates, comprises at least one amino acid which is different from that presented by the sequence for the HN protein of the Greer isolate in the same position and at least one amino acid which is different from that presented by the sequence for the F protein of the V98 isolate in the same position.

Said at least one amino acid which is different from that of the Greer isolate and said at least one amino acid which is different from that of the V98 isolate may be found at different positions. In this case, the virus of the group of the invention has at least two types of differences (on its F protein and/or its HN protein), namely at least one difference at a given position with respect to the Greer isolate and at least one difference at another position with respect to the V98 isolate.

Alternatively, said at least one amino acid which is different with respect to the Greer isolate may be found at the same position as said at least one amino acid which is different with respect to the V98 isolate. In this case, the F protein of the virus of the group of the invention comprises, in its amino acid sequence, at least one position where the amino acid which is located there is different from that at the same position in the sequence for the Greer and V98 isolates, and/or (preferably and) the HN protein of the virus of the group of the invention comprises, in its amino acid sequence, at least one position where the amino acid which is located there is different from that shown in the same position in the sequence for the Greer and V98 isolates.

In the present application, the meaning of the expression "at least one" encompasses all whole number values greater than unity, up to the maximum value possible in the set under consideration. As an example, the meaning of the expression "at least one amino acid" encompasses "at least two amino acids", "at least three amino acids", etc, up to the maximum number of amino acid changes contained in the set under consideration. Similarly, the meaning of the expression "in at least one position" encompasses "in at least two positions", "in at least three positions" etc up to the maximum number of positions contained in the set under consideration.

Compared with the Greer isolate, and more particularly compared with the Greer, Toshiba and V98 isolates, the viruses of the variant phylogenetic group of the invention may be defined by the fact that they have an F protein and/or an HN protein (envelope proteins) with a particular sequence. More particularly:
 the amino acid sequence for their F protein has more than 99.3% identity, preferably at least 99.4%, more preferably at least 99.5% identity with the amino acid sequence for the F protein of at least one of the particular isolates of the invention, i.e. with at least one of the sequences with SEQ ID NO: 24, 29, 34, 39, 44 (F protein of isolates 18620, 20283, 20435, 26056, 26632 respectively); and/or by the fact that
 the amino acid sequence for their HN protein has more than 98.6% identity, preferably at least 98.7%, more preferably at least 98.8% identity with at least one of the amino acid sequences for the HN proteins of particular isolates of the invention, i.e. with at least one of the sequences with SEQ ID NO: 26, 31, 36, 41 (isolates 18620, 20283, 20435, 26056 respectively).

The percentage identities indicated above, and likewise for the remainder of the application unless otherwise indicated, are overall values for the identity, i.e. an identity calculated over the entire length of the sequence.

Preferably, the viruses of the variant phylogenetic group of the invention have the percentages indicated above with each of the indicated SEQ IDs.

An alternative or complementary means for defining the differences contained in the viruses of the variant phylogenetic group of the invention compared with the Greer isolate, and more particularly the Greer, Toshiba and V98 isolates, is the fact that the viruses of the variant phylogenetic group of the invention may have at least one change in the amino acid sequence for the F protein with respect to the Greer isolate, and more particularly with respect to the Greer, Toshiba and V98 isolates.

A virus of the group of the invention may have an F protein the amino acid sequence of which differs from that of the Greer isolate in at least one of the following positions (amino acid positions in the sequence for the F protein): positions 32, 102, 104, 112, 160, 247, 538, 96, 248, 390, 524.

More particularly, compared with the F protein of the Greer isolate, a virus of the group of the invention may have at least one of the following differences:
  a) in position 32, an amino acid other than I, preferably the amino acid C (amino acid I for the Greer strain, amino acid V for the five particular isolates of the invention, i.e. a I32V substitution); and/or
  b) in position 102, an amino acid other than T, preferably the amino acid P (amino acid T for the Greer strain, amino acid P for the five particular isolates of the invention, i.e. a T102P substitution); and/or
  c) in position 104, an amino acid other than Q, preferably the amino acid P (amino acid Q for the Greer strain, amino acid P for the five particular isolates of the invention, i.e. a Q104P substitution); and/or
  d) in position 112, an amino acid other than V, preferably the amino acid I (amino acid V for the Greer strain, amino acid I for the five particular isolates of the invention, i.e. a V112I substitution); and/or
  e) in position 160, an amino acid other than D, preferably the amino acid T (amino acid D for the Greer strain, amino acid T for the five particular isolates of the invention, i.e. a D160T substitution); and/or
  f) in position 247, an amino acid other than N, preferably the amino acid K (amino acid N for the Greer strain, amino acid K for the five particular isolates of the invention, i.e. a N247K substitution); and/or
  g) in position 538, an amino acid other than F, preferably the amino acid V (amino acid F for the Greer strain, amino acid V for the five particular isolates of the invention, i.e. a F538V substitution); and/or
  h) in position 96, an amino acid other than T, preferably the amino acid A (amino acid T for the Greer strain, amino acid A for the five particular isolates of the invention, i.e. a T96A substitution); and/or
  i) in position 248, an amino acid other than F, preferably the amino acid L (amino acid F for the Greer strain, amino acid L for the five particular isolates of the invention, i.e. a F248L substitution); and/or
  j) in position 390, an amino acid other than R, preferably the amino acid K (amino acid R for the Greer strain, amino acid K for the five particular isolates of the invention, i.e. a R390K substitution); and/or
  k) in position 524, an amino acid other than S, preferably the amino acid A (amino acid S for the Greer strain, amino acid A for the five particular isolates of the invention, i.e. a S524A substitution).

Some of the positions for the differences compared with the F protein of the Greer isolate discussed above may also be positions for the difference(s) compared with the V98 isolate. This is particularly the case with positions 32, 102, 104, 112, 160, 247, 538.

Thus, the present application pertains to any HPIV-2 virus the F protein of which comprises an amino acid which is different from that presented by the F protein of the Greer isolate and that presented by the F protein of the V98 isolate in at least one of the amino acid positions 32, 102, 104, 112, 160, 247, 538, preferably in at least two of these positions, preferably in at least three of these positions, more preferably in at least four of these positions, more preferably in at least five of these positions, and highly preferably in at least six of these positions, and more particularly in all of these seven positions.

More particularly, compared with the F protein of the Greer isolate and compared with the F protein of the V98 isolate, a virus of the group of the invention may have at least one of the F amino acid sequence differences a) to g) discussed above. The present application thus pertains to any HPIV-2 virus the F protein of which has at least one of the seven sequence differences a) to g) discussed above, preferably at least two of these differences, preferably at least three of these differences, more preferably at least four of these differences, still more preferably at least five of these differences, highly preferably at least six of these differences, and still more preferably all of these seven differences.

Of these differences which are jointly present compared with the Greer isolate and the V98 isolate, positions 102, 104, 112 and 160 of the sequence for the F protein are particularly notable, and more particularly the differences in the amino acid sequence F b), c), d) and e) discussed above.

In fact, these particular positions are located at characteristic sites in HPIV-2s:
  positions 102 and/or 104 are located at the cleavage site in the F protein (CS in FIG. 4);
  position 112 is located at the fusion peptide (FP in FIG. 4);
  position 160 is located at the HR1 domain of the protein F.

Advantageously, the present application thus pertains to any HPIV-2 virus the F protein of which comprises an amino acid which is different from that presented by the F protein of the Greer isolate and that presented by the F protein of the V98 isolate in at least one of amino acid positions 102, 104, 112, 160, preferably in at least two of these positions, preferably in at least three of these positions, more preferably in all of these four positions.

Such a virus may also have an F protein:
  the amino acid sequence for which comprises one amino acid which is different from that presented by the F protein of the Greer isolate and from that presented by the F protein of the V98 isolate in at least one of amino acid positions 32, 247, 538; and/or
  the amino acid sequence for which comprises one amino acid which is different from that presented by the F protein of the Greer isolate in at least one of amino acid positions 32, 96, 247, 248, 390, 524, 538.

More particularly, the present application pertains to any HPIV-2 virus the F protein of which has at least one of four particular differences in the F protein discussed above (F protein sequence differences b), c), d), e)), preferably at least two of these differences, preferably at least three of these differences, more preferably all of these four differences.

Such a HPIV-2 virus may clearly further have:
  compared with Greer and V98 isolates, at least one of the three other F protein sequence differences a) f) g) discussed above, preferably at least two of these differences a), f), g), preferably all of these three differences a), f), g); and/or
  compared with the Greer isolate, at least one of the F protein sequence differences a), f) to k) discussed above, preferably at least two of these differences a), f) to k), preferably all of these seven differences a), f) to k).

An alternative or complementary means for defining the differences which the viruses of the variant phylogenetic group of the invention present compared with the Greer isolate and more particularly compared with the Greer, Toshiba and V98 isolates, is the fact that the variant phylogenetic group of the invention may have changes in the amino acid sequence for the HN protein.

A virus of the group of the invention may comprise an HN protein the amino acid sequence for which differs from that of the Greer isolate in at least one of the following positions (positions of the amino acids in the sequence for the HN protein): positions 57, 114, 139, 195, 201, 319, 344, 348, 378, 379, 480, 482, 100, 186, 316, 323, 479, 497, 513, 514.

More particularly, compared with the HN protein of the Greer isolate, a virus of the group of the invention may have at least one of the following differences:

a) in position 57, an amino acid other than D, preferably the amino acid E (amino acid D for the Greer strain, amino acid E for the five particular isolates of the invention, i.e. a D57E substitution); and/or b) in position 114, an amino acid other than T, preferably the amino acid A (amino acid T for the Greer strain, amino acid A for the five particular isolates of the invention, i.e. a T114A substitution); and/or c) in position 139, an amino acid other than K, preferably the amino acid E (amino acid K for the Greer strain, amino acid E for the five particular isolates of the invention, i.e. a K139E substitution); and/or d) in position 195, an amino acid other than T, preferably the amino acid A (amino acid T for the Greer strain, amino acid A for the five particular isolates of the invention, i.e. a T195A substitution);

e) in position 201, an amino acid other than A, preferably the amino acid S (amino acid A for the Greer strain, amino acid S for the five particular isolates of the invention, i.e. a A201S substitution); and/or f) in position 319, an amino acid other than P, preferably the amino acid T (amino acid P for the Greer strain, amino acid T for the five particular isolates of the invention, i.e. a P319T substitution); and/or g) in position 344, an amino acid other than E, preferably the amino acid K (amino acid E for the Greer strain, amino acid K for the five particular isolates of the invention, i.e. a E344K substitution); and/or h) in position 348, an amino acid other than A, preferably the amino acid I (amino acid A for the Greer strain, amino acid I for the five particular isolates of the invention, i.e. a A348I substitution); and/or i) in position 378, an amino acid other than A, preferably the amino acid E (amino acid A for the Greer strain, amino acid E for the five particular isolates of the invention, i.e. a A378E substitution); and/or j) in position 379, an amino acid other than R, preferably the amino acid E (amino acid R for the Greer strain, amino acid E for the five particular isolates of the invention, i.e. a R379E substitution); and/or k) in position 480, an amino acid other than T, preferably the amino acid M (amino acid T for the Greer strain, amino acid M for the five particular isolates of the invention, i.e. a T480M substitution); and/or l) in position 482, an amino acid other than Q, preferably the amino acid R (amino acid Q for the Greer strain, amino acid R for the five particular isolates of the invention, i.e. a Q482R substitution); and/or m) in position 100, an amino acid other than F, preferably the amino acid L (amino acid F for the Greer strain, amino acid L for the five particular isolates of the invention, i.e. a F100L substitution); and/or n) in position 186, an amino acid other than M, preferably the amino acid I (amino acid M for the Greer strain, amino acid isoleucine for the five particular isolates of the invention, i.e. a M186I substitution); and/or o) in position 316, an amino acid other than S, preferably the amino acid N (amino acid S for the Greer strain, amino acid N for the five particular isolates of the invention, i.e. a S316N substitution); and/or p) in position 323, an amino acid other than K, preferably the amino acid E (amino acid K for the Greer strain, amino acid E for the five particular isolates of the invention, i.e. a K323E substitution); and/or q) in position 479, an amino acid other than P, preferably the amino acid L (amino acid P for the Greer strain, amino acid L for the five particular isolates of the invention, i.e. a P479L substitution); and/or r) in position 497, an amino acid other than R, preferably the amino acid K (amino acid R for the Greer strain, amino acid K for the five particular isolates of the invention, i.e. a R497K substitution); and/or s) in position 513, an amino acid other than S, preferably the amino acid N (amino acid S for the Greer strain, amino acid N for the five particular isolates of the invention, i.e. a S513N substitution); and/or t) in position 514, an amino acid other than A, preferably the amino acid S (amino acid A for the Greer strain, amino acid S for the five particular isolates of the invention, i.e. a A514S substitution).

Certain positions for difference compared with the HN protein of the Greer isolate discussed above may also be positions for difference(s) compared with the V98 isolate. This is particularly the case with the following positions: 57, 114, 139, 195, 201, 319, 344, 348, 378, 379, 480, 482.

The present application thus pertains to any HPIV-2 virus the HN protein of which comprises an amino acid which is different from that presented by the HN protein of the Greer isolate, and which is also different from that presented by the HN protein of the V98 isolate, in at least one of the amino acid positions 57, 114, 139, 195, 201, 319, 344, 348, 378, 379, 480, 482, preferably in at least two of these positions, preferably in at least three of these positions, more preferably in at least four of these positions, still more preferably in at least five of these positions, highly preferably in at least six of these positions, and more particularly in all of these twelve positions. In addition to this at least one difference, the HN protein of said virus may also include an amino acid which is different from that presented by the HN protein of the Greer isolate in at least one of the amino acid positions 100, 186, 316, 323, 479, 497, 513, 514.

More particularly, compared with the HN protein of the Greer isolate and compared with the HN protein of the V98 isolate, a virus of the group of the invention may have at least one of the HN amino acid sequence differences a) to l) discussed above. Thus, the present application pertains to any HPIV-2 virus the F protein of which has at least one of the twelve sequence differences a) to l) discussed above, preferably at least two of these differences, preferably at least three of these differences, more preferably at least four of these differences, still more preferably at least five of these differences, highly preferably at least six of these differences, and more particularly all of these twelve differences.

In addition to said at least one difference, the HN protein of said virus may also have at least one of the differences m) to t) discussed above.

Of the differences presented with respect to the Greer isolates, positions 316, 513 and 514 of the sequence for the HN protein are of particular note, and more particularly the HN amino acid sequence differences o), s) and t) discussed above.

The Greer isolate has the amino acid S in position 316 of their HN protein. The Greer isolate does not have a glycosylation site at this position.

In this position, the viruses of the variant phylogenetic group of the invention may have an amino acid other than S, and more particularly an amino acid other than S which creates a glycosylation site, preferably the amino acid N (asparagine). The viruses of the variant phylogenetic group of the invention may thus have a new glycosylation site compared with the Greer isolate.

Compared with the Greer isolate, the viruses from the phylogenetic group of the invention may, as an alternative or complement, be characterized in that the viruses of the variant phylogenetic group of the invention have, in positions 512-515, a different tertiary structure for the HN protein from that observed in the HPIV-2 Greer virus.

This structural difference is shown in particular in FIG. 1, which presents the predicted tertiary structure for the HN protein of the virus of the variant phylogenetic group of the invention. In FIG. 1, the arrow A indicates a loop which, in the Greer strain (left hand model), is orientated towards the interior of the HN protein, while in the isolates from the variant phylogenetic group of the invention (right hand model) this loop, indicated by an arrow A', is not orientated towards the interior of the protein but is orientated towards the exterior of the HN protein.

This loop corresponds to positions 512-515 of the HN protein, and more particularly to positions 513-514 of the HN protein of the isolates of the invention. In terms of the amino acid sequence, the amino acids which are in positions 513 and 514 of the HN protein sequence are S and A respectively for the Greer isolate, while they are N and S respectively for the five particular isolates of the invention.

The presence of an amino acid other than S, preferably the amino acid N, in position 513 of the HN protein, and of an amino acid other than A, preferably the amino acid S, in position 514 of the HN protein, is a means for defining the viruses forming part of the phylogenetic group of the variants of the invention.

Advantageously, the present application relates to any HPIV-2 virus the HN protein of which comprises:
  an amino acid which is different from that presented by the HN protein of the Greer isolate and which is also different from that presented by the HN protein of the V98 isolate in at least one of the amino acid positions 57, 114, 139, 195, 201, 319, 344, 348, 378, 379, 480, 482; and
  an amino acid which is different from that presented by the HN protein of the Greer isolate in at least one of the amino acid positions 316, 513, 514, preferably in position 316 or in positions 513 and 514, preferably in positions 36, 513 and 514.

More particularly, the present application relates to any HPIV-2 virus the HN protein of which presents:
  at least one of the HN protein sequence differences a) to l) discussed above (differences commonly present compared with the Greer isolate and the V98 isolate), preferably at least two of these differences, preferably at least three of these differences, more preferably at least four of these differences, still more preferably at least five of these differences, highly preferably all of these twelve differences; and
  at least one of the sequence differences of the HN protein o), s) and t) discussed above, preferably the difference o) and/or the differences s) and t), preferably at least two of these differences, more preferably at least the differences s) and t), still more preferably the differences o), s) and t).

In summary, a HPIV-2 virus forming part of the variant phylogenetic group of the invention may be defined by the fact that:
  i. the amino acid sequence for its F protein has more than 99.3% identity, preferably at least 99.4%, more preferably at least 99.5% identity with the amino acid sequence for the F protein of at least one of the five particular isolates of the invention, i.e. with at least one of the sequences with SEQ ID NO: 24, 29, 34, 39, 44 (F protein of isolates 18620, 20283, 20435, 26056, 26632, respectively), and preferably with each of these SEQ ID numbers; and/or by the fact that
  ii. the amino acid sequence for its HN protein has more than 98.6% identity, preferably at least 98.7%, more preferably at least 98.8% identity with at least one of the amino acid sequences for the HN proteins of particular isolates of the invention, i.e. with at least one of the sequences with SEQ ID NO: 26, 31, 36, 41 (isolates 18620, 20283, 20435, 26056, respectively), and preferably with each of these SEQ ID numbers; and/or by the fact that
  iii. the amino acid sequence for its F protein differs from that of the Greer isolate in at least one of the following amino acid positions: 32, 102, 104, 112, 160, 247, 538, 96, 248, 390, 524 (positions of the amino acids within the sequence for the F protein); and/or by the fact that
  iv. the amino acid sequence for its F protein has at least one of the eleven F sequence differences a) to k), as discussed above; and/or by the fact that
  v. the amino acid sequence for its F protein differs from that of the Greer isolate and that of the V98 isolate in at least one of the following amino acid positions: 32, 102, 104, 112, 160, 247, 538 (positions of the amino acids within the sequence for the F protein); and/or by the fact that
  vi. the amino acid sequence for its F protein has at least one of the seven F sequence differences a) to g), as discussed above; and/or by the fact that
  vii. the amino acid sequence for its F protein differs from that of the Greer isolate and that of the V98 isolate in at least one of the following amino acid positions: 102, 104, 112, 160 (positions of the amino acids within the sequence for the F protein), as discussed above; and/or by the fact that
  viii. the amino acid sequence for their F protein has at least one of the four F sequence differences b) to e), as discussed above; and/or by the fact that
  ix. the amino acid sequence for its F protein differs from that of the Greer isolate and that of the V98 isolate in at least one of the following amino acid positions: 102, 104, 112, 160 (positions of the amino acids within the F protein sequence), and also differs:
    from that of the Greer isolate and that of the V98 isolate in at least one of the amino acid positions 32, 247, 538; and/or
    from that of the Greer isolate in at least one of the amino acid positions 32, 96, 247, 248, 390, 524, 538; and/or by the fact that
  x. the amino acid sequence for their F protein has at least one of the four F sequence differences b) to e), as discussed above, and further has:
    at least one of the three F sequence differences a), f) g), as discussed above; and/or
    at least one of the F sequence differences a), f) to k) discussed above; and/or by the fact that
  xi. the amino acid sequence for its HN protein differs from that of the Greer isolate in at least one of the following amino acid positions: 57, 114, 139, 195, 201, 319, 344, 348, 378, 379, 480, 482, 100, 186, 316, 323, 479, 497, 513, 514 (positions of the amino acids within the HN protein); and/or by the fact that xii. the amino acid sequence for its HN protein has at least one of the twenty HN sequence differences a) to t), as discussed above; and/or by the fact that xiii. the amino acid sequence for its HN protein differs from that of the Greer isolate and that of the V98 isolate in at least one of the following amino acid positions: 57, 114, 139, 195, 201, 319, 344, 348, 378, 379, 480, 482; and/or by the fact that xiv. the amino acid sequence for its HN protein has at least one of the twelve HN sequence differences a) to l), as discussed above; and/or by the fact that xv. the amino acid sequence for its HN protein differs from that of the Greer isolate and that of the V98 isolate in at least one of the following amino acid positions: 57, 114, 139, 195, 201, 319, 344, 348, 378, 379, 480, 482, and also differs from that of the Greer isolate in at least one of the amino acid positions 100, 186, 316, 323, 479, 497, 513, 514; and/or by the fact that xvi. the amino acid sequence for its HN protein has at least one of the twelve HN sequence differences a) to l), as discussed above, and also has at least one of the HN sequence differences m) to t), as discussed above; and/or by the fact that xvii. the amino acid sequence for its HN protein differs from that of the Greer isolate and that of the V98 isolate in at least one of the following amino acid positions: 57, 114, 139, 195, 201, 319, 344, 348, 378, 379, 480, 482, and also differs from that of the Greer isolate in at least one of the amino acid positions 316, 513, 514; and/or by the fact that xviii. the amino acid sequence for its HN protein has at least one of the twelve HN sequence differences a) to l), as discussed above, and also has at least one of the HN sequence differences o), s), t), as discussed above.

Preferably, a virus of the group of the invention is defined by at least one of the characteristics listed above under i., ii., v. to x., xiii. to xviii, preferably by at least one of the characteristics listed above under i., ii., vii., xiii.

Preferably, a virus of the group of the invention is defined by:
at least one of the characteristics listed above under i., vii.; and/or by
at least one of the characteristics listed above under ii., xiii.;
for example by at least one of the characteristics i. and ii., and/or i. and xiii., and/or vii. and ii., and/or vii. and xiii.

Five isolates which form part of the variant phylogenetic group of the invention and which have been identified by the inventors have been deposited with the CNCM under the auspices of the Treaty of Budapest (Collection Nationale de Cultures de Microorganismes; C.N.C.M.; Institut Pasteur; 25, rue du Docteur Roux; F-75724 PARIS Cedex 15; France).

Their accession numbers are: I-3761 (isolate 26056), I-3762 (isolate 26632), I-3763 (isolate 18620), I-3764 (isolate 20283), I-3765 (isolate 20435).

They were deposited with the CNCM on 10 May 2007.

These isolates were isolated from nasal aspirates or broncheoalveolar lavages from patients suffering from respiratory infections.

The variant phylogenetic group of the invention also includes the V94 isolate.

The teaching of the prior art regarding V94 would clearly incite the skilled person to consider that the V94 isolate was an isolate which was very close to the Greer isolate and that there was no significant technical difference compared with the Greer isolate, or at least no significant technical difference for detection, and more particularly for diagnosis, of HPIV-2.

As an example, the article by Skiadopoulos et al. 2003 (Journal of Virology, vol. 77, No. 1, pp. 270-279) describes the complete sequencing of the V94 isolate, and reports comparative analyses of its sequence with those of the Greer and V98 isolates. All of the information reported in that article presents V94 as an isolate which is very close to the Greer isolate.

To the inventors' knowledge, none of the prior art discloses that the V94 isolate could present structural differences compared with the Greer isolate, which would be sufficiently significant to consider that a means which would detect the Greer isolate could not necessarily detect the V94 isolate.

To the inventors' knowledge, none of the prior art discloses that the V94 isolate could present envelope proteins, and more particularly F and/or HN proteins, which were sufficiently different from those of the Greer isolate to consider that a means which allowed the Greer isolate to be detected via detection of its envelope proteins could not necessarily detect the V94 isolate.

Further, to the knowledge of the inventors, none of the prior art discusses the fact nor induces the skilled person to consider that the V94 isolate is not an isolated case consigned to the past (the V94 isolate was isolated in 1994), but that it in fact forms part of a particular phylogenetic group which is distinct from the HPIV-2 group of which the Greer isolate forms a part, and which has members which can currently be isolated from patients.

To the inventors' knowledge, none of the prior art suggests that the V94 isolate, which was isolated in 1994, could be susceptible of being phylogenetically linked to other HPIV-2 viruses which could be isolated subsequently, in particular in the 2000s, from patients suffering from respiratory infections.

To the knowledge of the inventors, the general concept of the existence of a variant phylogenetic group of HPIV-2, which includes several viruses which in common present a variation in the envelope so that they could not be detected by the traditional means for diagnosing HPIV-2, has been neither disclosed nor suggested in the prior art.

The fact that the isolates forming part of this variant phylogenetic group are found in current patients while the reference Greer strain was isolated in 1955 further emphasizes the importance of the present invention.

A phylogenetic sub-group can be distinguished within the variant phylogenetic group of the invention. This sub-group includes all of the five particular isolates of the invention, and does not include the V94 isolate. This phylogenetic sub-group of the invention comprises HPIV-2 viruses which are extremely close to each other.

Compared with the Greer isolate, and more particularly compared with the Greer, Toshiba and V98 isolates, the viruses of the phylogenetic sub-group of the variants of the invention may be defined by the fact that they are not recognized by certain anti-HPIV-2 antibodies of the prior art, and more particularly by prior art antibodies which are directed against the HN envelope protein of the HPIV-2 virus. These prior art anti-HN antibodies have in fact been produced or constructed from epitope(s) of the HN protein of the HPIV-2 strain which acted as a reference in the prior art, namely the HPIV-2 Greer strain. The inventors have now shown that the HN protein of the phylogenetic sub-group of the variants of the invention does not include the same epitopes as the HN protein from the Greer isolate. More particularly, certain epitopes which are present in the HN protein of the Greer isolate are not present in the HN protein from the viruses of the variant phylogenetic group of the invention. For this reason, the viruses of the variant phylogenetic group of the invention are not recognized by certain prior art anti-HN antibodies.

One example of such prior art anti-HN antibodies is the antibody sold by ARGENE S.A. (Parc Technologique Delta Sud 09120 Varilhes; France) with reference 12E12G9. This prior art antibody recognizes an epitope on the HN protein of the Greer isolate, which is not present in the variant phylogenetic sub-group viruses of the invention.

Alternatively or as a complement, the viruses of the phylogenetic sub-group of the invention may be defined as having in common a substitution of the amino acid which is in position 175 in the sequence for the F protein, and/or a substitution of the amino acid which is in position 186 of the sequence for the HN protein.

Position 175 of the F protein is in the HR1 domain of the F1 polypeptide.

In position 175, the V94 isolate has the amino acid H (histidine).

Position 186 of the HN protein is very close to the catalytic site for the protein, and the nature of the amino acid present in this position is thus susceptible of having an influence on the activity of the protein.

In position 186 of the HN protein, the V94 isolate has the amino acid M (and incidentally, it may be noted that the Greer isolate also has the amino acid M in position 186).

A virus forming part of the phylogenetic sub-group of the variants of the invention may thus be defined by the fact that:
  it forms part of the phylogenetic group of the invention as defined hereinabove, for example using one of more of the characteristics of the group discussed above (such as the percentage identity of the F protein and/or HN protein, F and/or HN sequence differences, different tertiary structure for HN);
and also by the fact that:
  it is not recognized by prior art monoclonal anti-HN antibodies, such as the antibody sold by Argene with reference number 12E12G9, which were constructed and/or obtained from the HN protein for the Greer isolate; and/or
  it has an amino acid other than H in position 175 of the F protein and/or (preferably and) an amino acid other than M in position 186 of the HN protein.

Preferably, the amino acid in position 175 of the sequence for the F protein of a virus forming part of the phylogenetic sub-group of the variants of the invention is the amino acid R (asparagine).

Preferably, the amino acid in position 186 of the sequence for the HN protein of a virus forming part of the phylogenetic sub-group of the variants of the invention is the amino acid I (isoleucine).

Any combinations of characteristics of the group and characteristics of the sub-group are explicitly included in the present application.

As an example, a HPIV-2 virus which forms part of the phylogenetic sub-group of the variant HPIV-2s of the invention may be defined as follows:
  by the fact that it has at least one of the characteristics of group i., ii., v. to x., xiii. to xviii. listed above; and
  by the fact that it also has at least one of the following sub-group characteristics:
    in position 186 of the sequence for the HN protein, it has an amino acid other than M, preferably the amino acid I (isoleucine), and/or
    in position 175 of the sequence for its F protein, it has an amino acid other than H, preferably the amino acid R.

In order to define the viruses of the phylogenetic sub-group of the invention, one or more of the eighteen characteristics i. to xviii. may be used, as indicated above in the section defining the variant phylogenetic group of the invention.

All combinations of characteristics are explicitly envisaged in the present application.

As an example, a HPIV-2 virus which forms part of the phylogenetic sub-group of the variant HPIV-2s of the invention may be defined:
  by the fact that it has at least one of the characteristics of group i. to xviii. listed above, and
  by the fact that it also has at least one of the following sub-group characteristics:
    in position 186 of the sequence for the HN protein, it has an amino acid other than M, preferably the amino acid I (isoleucine); and/or
    in position 175 of the sequence for its F protein, it has an amino acid other than H, preferably the amino acid R; and/or
    it is not recognized by prior art anti-HN monoclonal antibodies which, like the antibody sold by Argene with reference 12E12G9, were constructed and/or obtained from the HN protein of the Greer isolate.

More particularly, the present application pertains to HPIV-2 viruses which form part of a phylogenetic sub-group of the variant HPIV-2s which does not comprise Greer, Toshiba, V98 and V94 HPIV-2 isolates, and which may be defined by the fact that:
  the amino acid sequence for their F protein has more than 99.85% identity, preferably at least 99.90%, more preferably at least 99.95% identity with the amino acid sequence for the F protein of at least one of the particular isolates of the invention, i.e. with at least one of the sequences with SEQ ID NO: 24, 29, 34, 39, 44 (F protein of isolates 18620, 20283, 20435, 26056, 26632, respectively), and preferably with each of these sequences; and/or
  the amino acid sequence for their HN protein has more than 99.15% identity, preferably at least 99.20%, more preferably at least 99.30% identity with at least one of the amino acid sequences for the HN proteins of particular isolates of the invention, i.e. with at least one of the sequences with SEQ ID NO: 26, 31, 36, 41 (isolates 18620, 20283, 20435, 26056, respectively), and preferably with each of these sequences;
and in addition by the fact that:
  in position 186 of the sequence for the HN protein, they have an amino acid other than M, preferably the amino acid I (isoleucine).

More particularly, the present application pertains to HPIV-2 viruses which form part of the phylogenetic sub-group of HPIV-2 variants which does not include the Greer, Toshiba, V98 and V94 HPIV-2 isolates, and which may be defined by the fact that:
  the amino acid sequence for their F protein has more than 99.85% identity, preferably at least 99.90%, more preferably at least 99.95% identity with the amino acid sequence for the F protein of at least one of the particular isolates of the invention, i.e. with at least one of the sequences with SEQ ID NO: 24, 29, 34, 39, 44 (F protein of isolates 18620, 20283, 20435, 26056, 26632, respectively), and preferably with each of these sequences; and/or
  the amino acid sequence for their HN protein has more than 99.15% identity, preferably at least 99.20%, more preferably at least 99.30% identity with at least one of the amino acid sequences for the HN proteins of particular isolates of the invention, i.e. with at least one of the sequences with SEQ ID NO: 26, 31, 36, 41 (isolates 18620, 20283, 20435, 26056, respectively), and preferably with each of these sequences;
and in addition by the fact that:
in position 175 of the sequence for its F protein, they have an amino acid other than H, preferably the amino acid R.

The following table is provided by way of summary or illustration:

The HPIV-2 viruses which satisfy these identity criteria form part of the phylogenetic sub-group of the invention without the necessity of having recourse to one of the characteristics of groups i. to xviii. discussed above.

Thus, the present application pertains to any HPIV-2 virus:
i. which satisfies at least one of the characteristics of group i. to xviii as discussed above, and at least one of the characteristics of the sub-group as discussed above (amino acid other than H in position 175 of its F protein,

TABLE 13

| Nature of differences common to isolates of the group or sub-group of the invention | Position within protein | Amino acid present in Greer/Toshiba isolate | Amino acid present in V98 isolate | Amino acid present in V94 isolate | Amino acid preferably present in isolates of phylogenetic group or sub-group of the invention |
|---|---|---|---|---|---|
| F protein | 32 | I | I | V | V |
|  | 96 | T | A | A | A |
|  | 102 | T | T | P | P |
|  | 104 | Q | Q | R | R |
|  | 112 | V | V | I | I |
|  | 160 | D | D | T | T |
|  | 175 | R | R | H | R |
|  | 247 | N | N | K | K |
|  | 248 | F | L | L | L |
|  | 390 | R | K | K | K |
|  | 524 | S | A | A | A |
|  | 538 | F | F | V | V |
| HN protein | 57 | D | D | E | E |
|  | 100 | F | L | L | L |
|  | 114 | T | T | A | A |
|  | 139 | K | K | E | E |
|  | 186 | M | I | M | I |
|  | 195 | T | T | A | A |
|  | 201 | A | A | S | S |
|  | 319 | S | P | T | T |
|  | 323 | P | E | E | E |
|  | 344 | K | E | K | K |
|  | 348 | E | A | I | I |
|  | 378 | A | A | E | E |
|  | 379 | A | R | E | E |
|  | 479 | R | L | L | L |
|  | 480 | P | T | M | M |
|  | 482 | Q | Q | R | R |
|  | 497 | R | K | K | K |
|  | 513 | S | N | N | N |
|  | 514 | A | S | S | S |

An alternative or complementary means of defining the viruses of the phylogenetic sub-group of the invention without necessarily calling on at least one of the characteristics of the groups discussed above, is the % identity which the amino acid sequence has with their F and/or HN proteins.

In fact, the viruses of the phylogenetic sub-group of the invention may be defined by the fact that:
the amino acid sequence for their F protein preferably has an identity of more than 99.85%, preferably at least 99.90%, more preferably at least 99.95% with the amino acid sequence for the F protein of at least one of the particular isolates of the invention, i.e. with at least one of the sequences with SEQ ID NO: 24, 29, 34, 39, 44 (F protein of isolates 18620, 20283, 20435, 26056, 26632, respectively), and preferably with each of these sequences; and/or
the amino acid sequence for their HN protein has more than 99.15% identity, preferably at least 99.20%, more preferably at least 99.30% identity with at least one of the amino acid sequences for the HN proteins of the particular isolates of the invention, i.e. with at least one of the sequences with SEQ ID NO: 26, 31, 36, 41 (isolates 18620, 20283, 20435, 26056 respectively), and preferably with each of these sequences.

preferably the amino acid R; amino acid other than M in position 186 of its HN protein, preferably the amino acid I; virus not recognized by prior art monoclonal anti-HN antibodies);

and/or ii. wherein the amino acid sequence for its F protein has more than 99.85% identity, preferably at least 99.90%, more preferably at least 99.95% identity with the amino acid sequence for the F protein of at least one of the particular isolates of the invention, i.e. with at least one of the sequences with SEQ ID NO: 24, 29, 34, 39, 44 (F protein of isolates 18620, 20283, 20435, 26056, 26632, respectively), and preferably with each of these sequences;

and/or iii. wherein the amino acid sequence for its HN protein has more than 99.15% identity, preferably at least 99.20%, more preferably at least 99.30% identity with at least one of the amino acid sequences for the HN proteins of particular isolates of the invention, i.e. with at least one of the sequences with SEQ ID NO: 26, 31, 36, 41 (isolates 18620, 20283, 20435, 26056, respectively), and preferably with each of these sequences.

A HPIV-2 virus forming part of the phylogenetic sub-group of the invention has at least one of these characteristics i. to iii. above, for example one, two or all of these characteristics.

More particularly, the application envisages five particular viruses. These five particular viruses are those which were deposited with the CNCM on 10 May 2007 with accession numbers I-3761 (isolate 26056), I-3762 (isolate 26632), I-3763 (isolate 18620), I-3764 (isolate 20283), I-3765 (isolate 20435). They form part of the phylogenetic group of the invention and also of the phylogenetic sub-group of the invention.

The physico-chemical parameters of the F and HN proteins of these particular viruses are shown in Tables 14 and 15 below (parameters calculated using CLC Free WorkBench version 3.2 software).

The present application pertains to any HPIV-2 viruses the F protein of which has a molecular mass and/or isoelectric point and/or aliphatic index which is identical to that (those) of the F protein of at least one of the particular viruses of the invention, and/or of which the HN protein has a molecular mass and/or isoelectric point and/or aliphatic index which is identical to that (those) of the HN protein of at least one of the particular viruses of the invention.

More particularly, the present application concerns any HPIV-2 viruses the F protein of which has an isoelectric point which is identical to that of the F protein of at least one of the particular viruses of the invention, and/or wherein the HN protein has an isoelectric point which is identical to that of the HN protein of one of the particular viruses of the invention.

Preferably, a HPIV-2 virus of the invention has an F protein which has at least two parameters selected from the parameters of molecular mass and/or isoelectric point and/or aliphatic index, wherein the values are identical to those respective parameters of at least one of the particular viruses of the invention, and/or wherein an HN protein which presents at least two parameters from the parameters of molecular mass and/or isoelectric point and/or aliphatic index wherein the values are identical to those respective parameters of at least one of the particular viruses of the invention.

Preferably, said at least two parameters include the isoelectric point parameter.

The application also concerns nucleic acids the sequence for which comprises or is constituted by the sequence for a nucleic acid of a HPIV-2 virus of the invention, and more particularly:
a) the genomic RNA sequence for a HPIV-2 virus from the group or sub-group of the invention; or
b) the sequence for a cDNA (single strand or double strand) which is susceptible of being obtained by reverse transcription (or reverse transcription plus polymerase) of said genomic RNA; or
c) the sequence which is the complement of one of the sequences envisaged in a) and b) above, over the entire length of said sequence a) or b).

Proteins:

The present application pertains to any protein which is that from a virus which forms part of a variant phylogenetic group or, if appropriate, sub-group, of the invention.

In the present application, the term "protein" encompasses within its scope non-glycosylated proteins as well as glycoproteins.

The viruses which form part of the variant phylogenetic group, or if appropriate, the sub-group of the invention has a different viral envelope from that normally observed in the prior art, more particularly different from that of the Greer isolate, preferably different from those of the Greer, Toshiba and V98 isolates.

The envelope of the viruses which form part of the phylogenetic sub-group of the invention is also different from that of the V94 isolate.

Thus, the present application pertains to any envelope protein of a virus which forms part of the variant phylogenetic group or, if appropriate, sub-group of the invention.

This envelope protein may be or may comprise the F protein of said virus and/or the HN protein of said virus.

More particularly, the present application pertains to envelope proteins which are specific to the viruses of the sub-group of the invention, preferably the five particular isolates of the invention which were deposited with the CNCM with accession numbers I-3761 to I-3765.

Said F protein has a certain number of difference(s) compared with an F protein from the Greer isolate, more particularly compared with F proteins from the Greer, Toshiba and

TABLE 14

| | HPIV-2 F | | | | | | | |
| --- | --- | --- | --- | --- | --- | --- | --- | --- |
| | | | | Particular isolates of the invention | | | | |
| | V94 | V98 | Greer | 18620 | 20283 | 20435 | 26056 | 26632 |
| Weight, kDA | 59.702 | 59.627 | 59.839 | 59.721 | 59.719 | 59.736 | 59.708 | 59.721 |
| Isoelectric point | 8.79 | 8.54 | 8.79 | 8.89 | 8.89 | 8.89 | 8.89 | 8.89 |
| Aliphatic index | 114.635 | 114.11 | 113.041 | 114.635 | 114.11 | 114.816 | 114.635 | 114.635 |

TABLE 15

| | HPIV-2 HN | | | | | | |
| --- | --- | --- | --- | --- | --- | --- | --- |
| | | | | Particular isolates of the invention | | | |
| | V94 | V98 | Greer | 18620 | 20283 | 20435 | 26056 |
| Weight, kDA | 63.362 | 63.191 | 63.262 | 63.461 | 63.422 | 63.447 | 63.36 |
| Isoelectric point | 8.3 | 8.3 | 8.54 | 8.13 | 8.43 | 8.13 | 8.13 |
| Aliphatic index | 93.292 | 92.046 | 91.944 | 93.8 | 93.292 | 93.975 | 93.468 |

V98 isolates, preferably with respect to the F proteins from the Greer, Toshiba, V98 and V94 isolates.

As an example, the sequence for this F protein may have a certain number of amino acid substitution(s) compared with the sequence for the F protein of the Greer isolate, more particularly compared with the F proteins of the Greer, Toshiba and V98 isolates, preferably with respect to the F proteins from the Greer, Toshiba, V98 and V94 isolates.

Each of the above definitions of the F and HN proteins presented in the section defining the viruses of the invention apply, of course, to the F and HN proteins per se.

Thus, as indicated above in the section on the viruses, the F and HN proteins may be defined by a combination of at least one characteristic from the group (at least one difference compared with the Greer, Toshiba and V98 isolates) and at least one characteristic from the sub-group (at least one difference compared with the V94 isolate).

As an example, of the differences which may be identified on the F protein of an isolate of the invention, compared with the Greer isolate, more particularly compared with the Greer, Toshiba and V98 isolates, the following differences may in particular be cited which are relevant to the cleavage site of the F protein (positions 102 to 106 of the complete sequence for the F protein; cf CS in FIG. 4):

in position 102, an amino acid other than T (threonine), preferably the amino acid P (proline); and/or
in position 104, an amino acid other than Q (glutamine), preferably the amino acid R (arginine).

Preferably, said F protein comprises both the amino acid P in position 102 and the amino acid R in position 104.

In position 102, the Greer, Toshiba and V98 isolates have the amino acid T (threonine), and not the amino acid P.

In position 104, the Greer, Toshiba and V98 isolates have the amino acid Q (glutamine), and not the amino acid R.

Preferably, said F protein has the amino acid E in position 105.

Advantageously, the sequence for this cleavage site is KPRRER (SEQ ID NO: 14).

Among the differences which may be identified on the F protein of an isolate of the invention compared with the Greer isolate, more particularly compared with the Greer, Toshiba and V98 isolates, the following differences may be cited alternatively or as a complement:

in position 112, an amino acid other than V (valine), preferably the amino acid I (isoleucine), and/or
in position 160, an amino acid other than D (aspartic acid), preferably the amino acid T (theonine).

Position 112 is located in the fusion peptide (FP); position 160 is located in the HR1 domain of the polypeptide F1.

In position 112, the Greer and V98 isolates have the amino acid V (valine).

In position 160, the Greer and V98 isolates have the amino acid D (aspartic acid).

Among the differences which may be identified on the F protein of an isolate of the invention compared with the Greer isolate, more particularly compared with the Greer, Toshiba and V98 isolates, the following differences may be cited alternatively or as a complement:

in position 32, an amino acid other than 1 (isoleucine), preferably the amino acid V;
in position 247, an amino acid other than N, preferably the amino acid K;
in position 538, an amino acid other than F, preferably the amino acid V.

Said viral F protein forming part of the variant phylogenetic group of the invention may have one, two, three or more or even all of the differences defined above. All combinations of these differences are envisaged in the application.

The viral F protein forming part of the phylogenetic sub-group of the variants of the invention may, in addition to the difference(s) defined above, have one or more difference(s) with respect to the F protein of the V94 isolate.

Advantageously, the F protein of a virus forming part of the phylogenetic sub-group of the invention has an amino acid other than H in position 175, preferably the amino acid R(H175R mutation).

Particular differences which may be identified on the F protein compared with the V94 isolate which may in particular be cited are as follows:

in position 4, an amino acid other than L, preferably the amino acid P; and/or
in position 403, an amino acid other than N, preferably the amino acid T; and/or
in position 516, an amino acid other than V, preferably the amino acid I (isoleucine).

For example:
the isolate 20283 of the invention has the substitution L4P and the substitution V516I, compared with the V94 isolate, and also compared with the Greer isolate;
the isolate 26056 of the invention presents 1a substitution N403T, compared with the V94 isolate;
the isolate 20435 presents the substitution V516I compared with the V94 isolate, and also compared with the Greer isolate.

Said viral F protein forming part of the phylogenetic sub-group of the variants of the invention may have one, two or three of the differences defined above, in addition to at least one F sequence difference compared with the Greer, Toshiba and V98 isolates. Any combination of these differences is explicitly envisaged by the application.

HPIV-2 viruses forming part of the variant phylogenetic group or, if appropriate, sub-group of the invention may thus be variants which present the mutation(s) V112I and/or D160T in the F protein compared with Greer, Toshiba and V98 isolates and the H175R mutation in the F protein compared with the V94 isolate.

As indicated above in the section on the viruses, the differences in the F proteins allow an F protein of a virus of a sub-group of the invention to be distinguished without having to combine this difference with a group difference. Thus, they are particular specific differences which distinguish the F proteins of viruses from the sub-group of the invention, such as the five particular isolates deposited at the CNCM with accession numbers I-3761 to I-3765 of the Greer Toshiba V98 and V94 isolates.

More particularly, the present application concerns any F protein the amino acid sequence for which has more than 99.85% identity, preferably at least 99.90%, more preferably at least 99.95% identity with the amino acid sequence for the F protein of at least one of the particular isolates of the invention, i.e. with at least one of the sequences with SEQ ID NO: 24, 29, 34, 39, 44 (F protein of isolates 18620, 20283, 20435, 26056, 26632, respectively), and preferably with each of these sequences.

The present application is more particularly pertinent to proteins and more particularly to envelope proteins which comprise at least one protein the sequence for which is selected from the sequences with SEQ ID NO: 24, 29, 34, 39, 44 (cf. Table 5).

An envelope protein of the invention may be, or may comprise, the HN protein of a virus forming part of the variant phylogenetic group or, if appropriate, sub-group of the invention.

This HN protein may have at least one of the following elements, preferably at least two of these elements, more preferably all of the following elements (differences compared with the HN proteins of the Greer, Toshiba and V98 isolates):

in position 57, an amino acid other than D, preferably the amino acid E;
in position 114, an amino acid other than T, preferably the amino acid A;
in position 139, an amino acid other than K, preferably the amino acid E;
in position 195, an amino acid other than T, preferably the amino acid A;
in position 201, an amino acid other than A, preferably the amino acid S;
in position 319, an amino acid other than P, preferably the amino acid T;
in position 344, an amino acid other than E, preferably the amino acid K;
in position 348, an amino acid other than A, preferably the amino acid I (isoleucine);
in position 378, an amino acid other than A, preferably the amino acid E;
in position 379, an amino acid other than R, preferably the amino acid E;
in position 480, an amino acid other than T, preferably the amino acid M;
in position 482, an amino acid other than Q, preferably the amino acid R.

An HN protein of a virus forming part of the phylogenetic sub-group of the invention also has at least one difference with respect to the HN protein of the V94 isolate.

Preferably, this HN protein has an amino acid other than M, preferably the amino acid I (isoleucine) in position 186.

The V94 isolate has the amino acid M in position 186. The Greer isolate also has the amino acid M in position 186.

The five particular isolates of the invention which have been deposited with the CNCM have the amino acid I (isoleucine) in position 186.

Thus, the present application pertains to any HN protein which has at least one of the differences listed above, compared with the Greer, Toshiba and V98 isolates, and which have an amino acid other than M in position 186.

More particularly, the present application pertains to any HN protein the amino acid sequence for which has more than 99.15% identity, preferably at least 99.20%, more preferably at least 99.30% identity with the amino acid sequence for the F protein of at least one of the particular isolates of the invention, i.e. with at least one of the sequences with SEQ ID NO: 26, 31, 36, 41 (HN protein from isolates 18620, 20283, 20435, 26056, 26632, respectively), and preferably with each of these sequences.

More particularly, the present application is pertinent to proteins, and more particularly to envelope proteins which comprise at least one protein the sequence for which is selected from the sequences with SEQ ID NO: 26, 31, 36, 41 (cf. Table 5).

Protein Fragments:

The present application also pertains to fragments of envelope proteins of the viruses of the variant phylogenetic group, or of the variant phylogenetic sub-group of the invention, and more particularly to fragments of the F and HN proteins of the viruses of the variant phylogenetic group, or of the variant phylogenetic sub-group of the invention.

More particularly, protein fragments are envisaged which are specific to the viruses of the phylogenetic sub-group of the invention, and more particularly the five particular isolates of the invention, which have been deposited at the CNCM with accession numbers I-3761 to I-3765.

More particularly, among the F protein fragments of the virus of the variant phylogenetic group or of the variant phylogenetic sub-group of the invention, the present application pertains to those fragments which comprise or are constituted by at least one fragment selected from:

the extracellular portion fragment;
the F2 polypeptide fragment;
the cleavage site (CS) fragment;
the fusion peptide (FP) fragment;
the HR1 domain fragment;
the HR2 domain fragment;
the F1 polypeptide fragment;
the transmembrane portion fragment;
the fragment intracytoplasmic portion of these F proteins.

FIG. 4 provides a diagrammatic presentation of such fragments.

These fragments extend from the following positions, calculated from the complete F protein sequence:

TABLE 12

Position of fragments in the complete F protein sequence

| Fragments of these F proteins | 1$^{st}$ amino acid | Last amino acid |
|---|---|---|
| Extracellular portion | 1 | 486 |
| F2 polypeptide | 1 | 100 |
| Cleavage site (CS) | 101 | 106 |
| Fusion peptide (FP) | 107 | 126 |
| HR1 domain | 133 | 177 |
| HR2 domain | 451 | 484 |
| F1 polypeptide | 101 | 486 |
| Transmembrane portion | 487 | 518 |
| Intracytoplasmic portion | 519 | 551 |

The complete F protein sequences for the five particular isolates of the invention are the sequences with SEQ ID NO: 24, 29, 34, 39, 44 (isolates 18620, 20283, 20435, 26056, 26632, respectively).

The present application is relative to any protein, polypeptide, peptide (glycosylated or otherwise) which comprises at least (or is constituted by) the sequence for the cleavage site of the F proteins of the viruses of the invention, i.e. the sequence KPRRER (SEQ ID NO: 14).

Such a protein or, if appropriate, such a polypeptide or peptide, may be of viral origin, more particularly derived from the envelope of a virus, preferably a HPIV-2 virus.

In particular, the present application envisages any F protein, preferably any F protein of HPIV-2, which includes the cleavage site sequence with SEQ ID NO: 14.

Among the F protein fragments of the virus of the variant phylogenetic group or of the variant phylogenetic sub-group of the invention, the present application also more particularly pertains to those fragments the sequence for which comprises at least 10 amino acids, and has conserved at least one amino acid (preferably at least two amino acids) which, in the F protein from which the fragment derives, was (were) in one of the following positions: positions 32, 102, 104, 112, 160, 247, 538.

Said fragment is at least 10 amino acids long. Preferably, it is at least a whole number selected to be between 11 and 550. More preferably, it is at least 14, still more preferably at least 19.

Highly preferably, said fragment conserves the capacity to be recognized by an antibody which binds specifically to the viruses of the variant phylogenetic group of the invention or of the variant phylogenetic sub-group of the invention.

Highly preferably, this fragment has conserved the capacity to induce the production of antibody when injected into a mammal, preferably a non-human mammal, preferably in the presence of alum.

Advantageously, a fragment of at least 10 amino acids of the F protein of the invention has also conserved the amino acid which, in the F protein from which the fragment derives, was in position 175 (amino acid other than H).

Advantageously, a fragment of at least 10 amino acids of the F protein of the invention has conserved the amino acid which, in the F protein from which the fragment derives, was in position 160 (amino acid other than D, such as T), and also has conserved the amino acid which, in the F protein from which the fragment derives, was in position 175 (amino acid other than H, such as R).

Among the fragments of HN proteins of the viruses of the variant phylogenetic group or of the variant phylogenetic sub-group of the invention, the present application is more particularly relevant to those fragments which comprise or are constituted by at least one fragment selected from fragments of at least 10 amino acids, and has conserved at least one amino acid (preferably at least two amino acids) which, in the HN protein from which the fragment derives, was (were) at one of the following positions:

57, 114, 139, 195, 201, 319, 344, 348, 378, 379, 480, 482.

Such fragments may also have conserved at least one, preferably at least two, more preferably the three amino acid(s) of those which, in the complete sequence for the HN protein from which the fragment derives, were:

in position 316 (amino acid other than S);
in position 513 (amino acid other than S);
in position 514 (amino acid other than A).

Preferably, such a fragment has conserved at least the amino acid which was in position 316.

Preferably, such a fragment has conserved at least the amino acid which was in position 513, and at least the amino acid which was in position 514.

Preferably, such a fragment has conserved at least the amino acid which was in position 316, at least the amino acid which was in position 513 and at least the amino acid which was in position 514.

The protein fragments of the invention are candidates of interest for the production of specific antibodies for the viruses of the phylogenetic group or sub-group of the invention and/or for the identification of epitopes for such antibodies.

The HN protein fragment is at least 10 amino acids in size. Preferably, this size is at least a whole number selected from between 11 and 570. More preferably, it is at least 14, and still more preferably at least 19.

Highly preferably, this fragment has conserved the capacity to be recognized by an antibody which specifically binds to the virus of the variant phylogenetic group of the invention or of the variant phylogenetic sub-group of the invention.

Highly preferably, this fragment has conserved the capacity to induce the production of antibodies when injected into a mammal, preferably a non-human mammal, preferably in the presence of alum.

Advantageously, a fragment of at least 10 amino acids of the HN protein of the invention has also conserved the amino acid which, in the HN protein from which the fragment derives, was in position 186 (amino acid other than M).

Nucleic Acids Coding for Proteins and Small Fragments

The present application also pertains to nucleic acids the sequence for which codes for at least one envelope protein of the invention, or at least one fragment of an envelope protein of the invention, allowing for the degeneracy of the universal genetic code.

These nucleic acids may be DNA or RNA.

Said envelope protein may be an F protein and/or HN protein of the invention.

These nucleic acids code for an envelope protein, or an envelope protein fragment, of at least one of the viruses of the variant phylogenetic group or sub-group of the invention.

The nucleic acids of the invention which are those of the virus forming part of the variant phylogenetic group of the invention have one or more differences compared with the Greer, Toshiba and V98 isolates, and more particularly compared with the Greer isolate.

Compared with Greer, Toshiba and V98 isolates, the nucleic acids of the invention which code for an F protein and/or an HN protein may have the nucleotide difference(s) which correspond to the amino acid difference(s) identified above for the proteins and protein fragments of the invention, in accordance with the universal genetic code, and allowing for degeneracy of that code.

Compared with Greer, Toshiba and V98 isolates, the nucleic acids of the invention which code for an F protein present at least one, preferably at least two, more preferably all of the following differences:

in positions 94-96, a codon coding for an amino acid other than I, preferably a codon coding for the amino acid V;
in positions 304-306, a codon coding for an amino acid other than T, preferably a codon coding for the amino acid P;
in positions 310-312, a codon coding for an amino acid other than Q, preferably a codon coding for the amino acid R;
in positions 334-336, a codon coding for an amino acid other than V, preferably a codon coding for the amino acid I;
in positions 478-480, a codon coding for an amino acid other than D, preferably a codon coding for the amino acid T;
in positions 739-741, a codon coding for an amino acid other than N, preferably a codon coding for the amino acid K;
in positions 1612-1614, a codon coding for an amino acid other than F, preferably a codon coding for the amino acid V.

The positions indicated are those calculated for the sequence coding for the protein F.

These nucleic acids are the nucleic acids of the virus forming part of the variant phylogenetic group of the invention.

Compared with the Greer, Toshiba and V98 isolates, the nucleic acids of the invention which code for an HN protein have at least one, preferably at least two, more preferably all of the following differences:

in positions 169-171, a codon coding for an amino acid other than D, preferably a codon coding for the amino acid E;
in positions 340-342, a codon coding for an amino acid other than T, preferably a codon coding for the amino acid A;
in positions 415-417, a codon coding for an amino acid other than K, preferably a codon coding for the amino acid E;
in positions 583-585, a codon coding for an amino acid other than T, preferably a codon coding for the amino acid A;

in positions 601-603, a codon coding for an amino acid other than A, preferably a codon coding for the amino acid S;

in positions 955-957, a codon coding for an amino acid other than P, preferably a codon coding for the amino acid T;

in positions 1030-1032, a codon coding for an amino acid other than E, preferably a codon coding for the amino acid K;

in positions 1042-1044, a codon coding for an amino acid other than A, preferably a codon coding for the amino acid I;

in positions 1132-1134, a codon coding for an amino acid other than A, preferably a codon coding for the amino acid E;

in positions 1135-1137, a codon coding for an amino acid other than R, preferably a codon coding for the amino acid E;

in positions 1438-1440, a codon coding for an amino acid other than T, preferably a codon coding for the amino acid M;

in positions 1444-1446, a codon coding for an amino acid other than Q, preferably a codon coding for the amino acid R.

The positions indicated are those calculated for the sequence coding for the HN protein.

These nucleic acids are the nucleic acids of the virus forming part of the variant phylogenetic group of the invention.

The nucleic acids of the invention which are those of the virus forming part of the phylogenetic sub-group of the variants of the invention present at least one of the above differences compared with Greer, Toshiba and V98 isolates, and more preferably compared with the Greer isolate, and also at least one difference compared with the V94 isolate.

Compared with the V94 isolate, the nucleic acids of the invention which code for an F protein of the virus of the phylogenetic sub-group of the invention present at least one, preferably at least two, more preferably all of the following differences:

in position 33, a nucleotide other than T, preferably the nucleotide C (for example, the codon 31-33 of the V94 isolate is ATT, while in the five particular isolates of the invention, this codon is ATC);

in position 525, a nucleotide other than A, preferably the nucleotide G (for example, the codon 524-526 of the V94 isolate is CAC, coding for the amino acid H in position 175 of the protein, while in the five particular isolates of the invention, this codon is CGC, coding for the amino acid R in position 175);

in position 1479, a nucleotide other than C, preferably the nucleotide A (for example, the codon 1479-1481 of V94 isolate is ATC, while in the five particular isolates of the invention, this codon is ATA).

The positions indicated are those calculated using the sequence coding for the F protein.

Preferably, the nucleic acids of the invention which code for an F protein have at least the difference discussed above for position 525.

These nucleic acids are nucleic acids of the virus forming part of the phylogenetic sub-group of the variants of the invention.

Compared with the V94 isolate, the nucleic acids of the invention which code for an HN protein of the virus of the phylogenetic sub-group of the invention have at least the following difference:

in position 558, a nucleotide other than G, preferably A (for example, the codon 556-558 is ATG in the V94 isolate, coding for the amino acid M in position 186 of the protein, while in the five particular isolates of the invention, this codon is ATA, coding for the amino acid I—isoleucine—in position 186).

The positions indicated are those calculated using the sequence coding for the HN protein.

These nucleic acids are nucleic acids of the virus forming part of the phylogenetic sub-group of the variants of the invention.

All combinations of nucleotide differences are explicitly envisaged by the present application.

The following table is presented by way of summary and illustration:

TABLE 16

| Positions of differences common to isolates of group or sub-group of the invention | Compared with the Greer/Toshiba isolate | | Compared with Greer/Toshiba and V98 isolates | | Compared with the V94 isolate | |
|---|---|---|---|---|---|---|
| | Amino acid | Codon for CDS | Amino acid | Codon for CDS | Amino acid | Codon for CDS |
| F protein | 32 | 94-96 | 32 | 94-96 | — | — |
| | 96 | 286-288 | — | — | — | — |
| | 102 | 304-306 | 102 | 304-306 | — | — |
| | 104 | 310-312 | 104 | 310-312 | — | — |
| | 112 | 334-336 | 112 | 334-336 | — | — |
| | 160 | 478-480 | 160 | 478-480 | — | — |
| | — | — | — | — | 175 | 523-525 |
| | 247 | 739-741 | 247 | 739-741 | — | — |
| | 248 | 742-744 | — | — | — | — |
| | 390 | 1168-1170 | — | — | — | — |
| | 524 | 1570-1572 | — | — | — | — |
| | 538 | 1612-1614 | 538 | 1612-1614 | — | — |
| HN protein | 57 | 169-171 | 57 | 169-171 | — | — |
| | 100 | 288-300 | — | — | — | — |
| | 114 | 340-342 | 114 | 340-342 | — | — |
| | 139 | 415-417 | 139 | 415-417 | — | — |
| | 186 | 556-558 | — | — | 186 | 556-558 |
| | 195 | 583-585 | 195 | 583-585 | — | — |
| | 201 | 601-603 | 201 | 601-603 | — | — |
| | 319 | 955-957 | 319 | 955-957 | — | — |
| | 323 | 957-969 | — | — | — | — |
| | 344 | 1030-1032 | 344 | 1030-1032 | — | — |

TABLE 16-continued

| Positions of differences common to isolates of group or sub-group of the invention | Compared with the Greer/Toshiba isolate | | Compared with Greer/Toshiba and V98 isolates | | Compared with the V94 isolate | |
|---|---|---|---|---|---|---|
| | Amino acid | Codon for CDS | Amino acid | Codon for CDS | Amino acid | Codon for CDS |
| | 348 | 1042-1044 | 348 | 1042-1044 | — | — |
| | 378 | 1132-1134 | 378 | 1132-1134 | — | — |
| | 379 | 1135-1137 | 379 | 1135-1137 | — | — |
| | 479 | 1435-1437 | — | — | — | — |
| | 480 | 1438-1440 | 480 | 1438-1440 | — | — |
| | 482 | 1444-1446 | 482 | 1444-1446 | — | — |
| | 497 | 1489-1491 | — | — | — | — |
| | 513 | 1537-1539 | — | — | — | — |
| | 514 | 1540-1542 | — | — | — | — |

More particularly, the present application envisages nucleic acids which code for F and/or HN proteins of the five particular isolates of the invention, i.e. the nucleic acids the sequence for which comprises or is constituted by a sequence from among the sequences with SEQ ID NO: 22, 27, 32, 37, 42, 23, 28, 33, 38, 43, 25, 30, 35, 40 (cf. Table 5).

Applications for the Detection of HPIV-2, and More Particularly for its Diagnosis (Immunological or Molecular Means):

Starting from the identification, description and characterization of the variant phylogenetic group and variant phylogenetic sub-group, the inventors propose novel means for detecting HPIV-2, and more particularly novel means for diagnosis of HPIV-2.

The novel detection means, and more particularly diagnosis means, for HPIV-2 in accordance with the invention allow all of the viruses of the variant phylogenetic group of the invention to be detected.

In particular, the invention proposes means which allow their detection and/or their diagnosis in a specific manner, i.e. without detection of Greer, Toshiba and V98 HPIV-2 isolates.

The invention also proposes means for allowing the detection and/or diagnosis of viruses which form part of the phylogenetic sub-group of the invention in a specific manner, i.e. without detection of the Greer, Toshiba and V98 isolates, and without detection of the V94 isolate.

Immunological Means

The present application also pertains to antibodies which bind to the HPIV-2 virus envelope.

The present application also pertains to fragments of said antibodies which have conserved the capacity to bind to a HPIV-2 envelope protein.

The term "antibody fragment" in particular comprises the Fab, F(ab)'2, Fv, CDR1, CDR2, CDR3 fragment as well as constructs deriving from said fragments, such as scFv or humanized antibodies.

The expression "bind" is used here in its habitual sense in the context of antibody-antigen binding.

More particularly, the present application pertains to said antibodies or antibody fragments which bind to the envelope of at least one virus of the variant phylogenetic group of the invention, preferably at least one of the five particular viruses deposited by the inventors with the CNCM, preferably at least two, three or four, more preferably these five viruses.

More particularly, the present application pertains to said antibodies or antibody fragments which do not bind to the envelope of the HPIV-2 Greer isolate (the sequence for the Greer isolate is available from Genbank with accession number NC_003443, and is reproduced in the present application after the "Examples" section, point B.2.), and more particularly without binding to an envelope protein of the Greer, Toshiba and V98 HPIV-2 isolates.

Preferably, said antibody does not bind to any microorganism which is not a HPIV-2 virus.

Preferably, an antibody or antibody fragment of the invention is a specific antibody for viruses forming part of the variant phylogenetic group of the invention.

Preferably, said envelope protein of at least one HPIV-2 virus of the invention comprises or is constituted by an F protein.

An antibody or antibody fragment of the invention may bind to an F protein of the invention and/or to an F protein fragment of the invention. The characteristics described above to define the F proteins and the fragments of F proteins of the invention are naturally applicable to the definition of the F proteins and F protein fragments which are the epitopic targets for antibodies and antibody fragments of the invention.

Advantageously, said antibody or antibody fragment binds to said F protein in at least one epitope which comprises at least one amino acid selected from amino acids which, in the sequence for said F protein, are located in positions 32, 96, 102, 104, 112, 160, 247, 248, 390, 524, 538, more particularly in positions 32, 102, 104, 112, 160, 247, 538.

Preferably, said envelope protein of at least one HPIV-2 virus of the invention comprises or is constituted by an HN protein.

An antibody or antibody fragment of the invention may bind to an HN protein of the invention and/or a fragment of HN protein of the invention. The characteristics described above to define the HN proteins of the invention naturally apply to the definition of the HN proteins and HN protein fragments of the invention which are epitopic targets for the antibodies and antibody fragments of the invention.

Advantageously, said antibody or antibody fragment binds to said HN protein in at least one epitope which comprises:
  at least one amino acid selected from amino acids which, in the sequence for said HN protein, are located in positions 316, 513, 514 (for example, an epitope of the HN protein comprises amino acids which, in the sequence for the HN protein, are located in positions 513-514, or 512-515); and/or
  at least one amino acid selected from amino acids which, in the sequence for said HN protein, are located in positions 57, 100, 114, 139, 186, 195, 201, 319, 323, 344, 348, 378, 379, 479, 480, 482, 497, more particularly in positions 57, 114, 139, 195, 201, 319, 344, 348, 378, 379, 480, 482.

Still more particularly, the application pertains to antibodies or antibody fragments which are specific to the viruses forming part of the phylogenetic sub-group of the variants of the invention. Such antibodies thus do not bind to the V94 HPIV-2 isolate.

Said antibody or antibody fragment may in particular bind to an F protein of at least one of the viruses of the variant phylogenetic sub-group in at least one epitope which comprises at least one amino acid selected from amino acids which, in the sequence for said F protein, is located in position 175.

An antibody or antibody fragment of the invention may naturally carry a marker to facilitate its detection, such as a fluorescent or enzymatic marker.

The present application also pertains to hybridomas producing said antibodies or antibody fragments.

The present application also pertains to transfected, infected or transformed cells which produce said antibodies or antibody fragments.

The present application also pertains to any composition which comprises at least one antibody, antibody fragment, hybridoma or transfected, infected or transformed cell of the invention, optionally with at least one pharmaceutically acceptable vehicle.

The present application also pertains to any kit, more particularly any diagnostic kit, which comprises at least one antibody, antibody fragment, hybridoma or transfected, infected or transformed cell of the invention.

Said diagnostic kit may also comprise means for detecting other microorganisms, and in particular:
- means for detecting HPIV-2s which do not form part of the variant phylogenetic group or, if appropriate, sub-group of the invention, such as Greer, Toshiba and V98 HPIV-2s; and/or
- means for detecting HPIV other than HPIV-2, such as HPIV-1, HPIV-3, HPIV-4; and/or
- means for detecting microorganisms which are not HPIV such as microorganisms, and more particularly viruses involved in respiratory infections or diseases (lower and/or upper respiratory systems), such as pneumonia, bronchiolitis, influenza.

The present application also pertains to a method for producing an antibody which is capable of binding to at least one virus of the variant phylogenetic group or, if appropriate, sub-group of the invention, and more particularly to at least one of the five particular isolates deposited by the inventors at the CNCM, and preferably to said particular five isolates. Preferably, the antibodies produced are specific antibodies for these viruses.

This method may include administration to a mammal (preferably a non-human mammal) of at least one of the five particular isolates of the invention, preferably the five particular isolates of the invention, and optionally also the V94 isolate, and/or at least one envelope protein or at least one fragment of the envelope protein of the invention, such as a fragment of HN protein which has conserved the amino acid which, in the sequence for the HN protein, was in position 316 and/or the two amino acids which, in the sequence for the HN protein, were in positions 513 and 514.

Administration is carried out such that the virus(es), protein(s), fragment(s) of F protein(s) administered induce the production of antibody by the mammal which receives it (them).

This administration may be carried out with an adjuvant which can increase immunogenicity, such as an alum.

The antibodies produced are then harvested and preferably isolated.

Monoclonal antibodies may be produced using techniques which are known to the skilled person.

Molecular Means
Reference Nucleic Acids (Large Nucleic Acid Fragments)

The inventors selected nucleic acids which are specially adapted to the specific detection of at least one of the isolates of the invention, preferably all of the isolates of the invention.

The nucleic acids which are specially adapted to the specific detection of all of the isolates of the invention allow all of the sub-groups which are susceptible of forming part of a variant phylogenetic group to be detected.

The present application pertains to nucleic acids which are specific to one or more viruses of the phylogenetic group or sub-group of the invention, which do not form part of the Greer, Toshiba and V98 HPIV-2 isolates, and which are specially adapted to the specific detection of one or more viruses of this phylogenetic group or sub-group and/or to the construction and production of probes and/or primers allowing said specific detection.

These nucleic acids are fragments of at least one virus of the phylogenetic group or, if appropriate, sub-group of the invention, of which the five particular isolates which have been deposited by the inventors form a part.

These nucleic acids hybridize with one or more viruses of the phylogenetic group or sub-group of the invention under high stringency conditions. High stringency conditions are conditions which are known to the skilled person, for example conditions for hybridization on DNA bound to a filter in SSC 5×, 2% sodium dodecyl sulphate (SDS), 100 micrograms/mL of single strand DNA, at 55-65° C. for 8 hours, and washing in SSC 02× and 0.2% SDS at 60-65° C. for 30 minutes.

Preferably, such nucleic acids hybridize to no other microorganism except for HPIV-2 under high stringency conditions.

Preferably, under high stringency conditions, such nucleic acids do not hybridize with HPIV-2 isolates which do not form part of the phylogenetic group or, if appropriate, sub-group of the invention such as Greer, Toshiba and V98 isolates.

Such nucleic acids are then nucleic acids which hybridize specifically to one, preferably to several, more preferably to all of the viruses of the phylogenetic group or sub-group of the invention.

Said nucleic acid can be characterized in that the sequence for said nucleic acid comprises or is constituted by:
- a fragment of at least 132 nucleotides of a sequence coding for the F protein and/or the HN protein of at least one of the HPIV-2 viruses according to claim 1; or
- the complementary sequence for said fragment over the entire length of said fragment.

Preferably, said fragment is a fragment of at least 133, 134, 135, 136, 137 nucleotides (for example fragments with 137, 180, 208, 210 nucleotides, or fragments with 137, 208, 210 nucleotides, or fragments with 180 nucleotides).

More preferably, said fragment is a fragment with at least 170, 175, 180 nucleotides (for example, 180, 208, 210 or 180, or 208, 210 nucleotides).

For example, said fragment is a fragment with at least 240 nucleotides.

Advantageously, in particular for the construction and production of primers and probe(s) adapted for use in real time amplification, said fragment is a fragment having at most 400 nucleotides.

Preferably, said sequence coding for the F protein is selected from the sequences with SEQ ID NO: 23, 28, 33, 38, 43, and/or in that said sequence coding for HN is selected from the sequences with SEQ ID NO: 25, 30, 35, 40, and/or said coding sequence coding for the F and HN proteins is selected from the sequences with SEQ ID NO: 22, 27, 32, 37, 42.

Preferably, the sequence for said nucleic acid comprises or is constituted by at least one of the sequences SEQ ID NO: 57 to 86.

More particularly, the application pertains to a nucleic acid which is specially adapted to the construction and to the production of probes or primers which are specific to the HPIV-2 variant phylogenetic group or sub-group of the invention, which includes no Greer, Toshiba and V98 HPIV-2 isolates, characterized in that said nucleic acid comprises or is constituted by:

a) at least one sequence selected from the sequences with SEQ ID NO: 57 to 86; or b) a conservative fragment from at least one of the sequences envisaged in a), said conservative fragment comprising or being constituted by at least one sequence selected from:

the sequences which extend from positions 241 to 420 of the sequences coding for F in the viruses of the group or sub-group of the invention;

the sequences which extend from positions 259 to 395 of the sequences coding for F in the viruses of the group or sub-group of the invention;

the sequences which extend from positions 234 to 443 of the sequences coding for HN in the viruses of the group or sub-group of the invention;

the sequences which extend from positions 241 to 420 of the sequences coding for HN in the viruses of the group or sub-group of the invention;

the sequences which extend from positions 961 to 1140 of the sequences coding for HN in the viruses of the group or sub-group of the invention;

the sequences which extend from positions 1381 to 1560 of the sequences coding for HN in the viruses of the group or sub-group of the invention;

the sequences which extend from positions 1466 to 1673 of the sequences coding for HN in the viruses of the group or sub-group of the invention; or c) the complementary sequence to one of the sequences envisaged in a) and b) over the entire length of said sequence a) or b).

More particularly, the present application pertains to a nucleic acid which is specially adapted to the construction and to the production of at least one pair of primers and at least one probe which are specially adapted to carrying out real time amplification for the specific detection of one or more viruses of said phylogenetic group or sub-group of HPIV-2 variants.

In the present application, said nucleic acids could be designated by the expression "real time nucleic acids" for the purposes of simplification.

Said nucleic acid may be defined by the fact that its sequence comprises or is constituted by:

a fragment of the sequence coding for F or the sequence coding for HN of a virus of the phylogenetic group or sub-group of the invention; or the sequence which is complementary to said fragment over the entire length of said fragment;

and in that said fragment extends:

from positions 259 to 395 of the sequence coding for F of said virus; or from positions 234 to 443 of the sequence coding for HN of said virus; or from positions 1466 to 1673 of the sequence coding for HN of said virus.

Preferably, said fragment extending from positions 259 to 395 of the sequence coding for F is constituted by one of the sequences with SEQ ID NO: 62 to 66, and/or said fragment extending from positions 234 to 443 of the sequence coding for HN is constituted by one of the sequences with SEQ ID NO: 67 to 70, and/or said fragment extending from positions 1466 to 1673 of the sequence coding for HN is constituted by one of the sequences with SEQ ID NO: 83 to 86.

The sequence for said nucleic acid sequence may thus comprise or be constituted by one of the following sequences:

The sequences with SEQ ID NO: 62 to 66, 67 to 70, 83 to 86, and the sequences which are complementary to said sequences with said defined SEQ ID number over the entire length of these sequences with said defined SEQ ID number.

The present application also pertains to nucleic acids which are specially adapted to the construction and to the production of probes which are specially adapted for use on a chip, for the specific detection of one or more viruses of the phylogenetic group or sub-group of the invention.

In the present application, said nucleic acids could be designated by the expression "chip nucleic acids" for the purposes of simplification.

The sequence for said nucleic acid advantageously comprises or is constituted by:

a fragment of the sequence coding for F and/or the sequence coding for HN of a virus of a phylogenetic group or sub-group of the invention; or the sequence which is complementary to said fragment over the entire length of said fragment;

and in that said fragment extends:

from positions 241 to 420 of the sequence coding for F of said virus; or from positions 241 to 420 of the sequence coding for HN of said virus; or from positions 961 to 1140 of the sequence coding for HN of said virus; or from positions 1381 to 1560 of the sequence coding for HN of said virus.

Thus, the present application pertains to nucleic acids which are specially adapted to the construction and to the production of at least one probe which is capable of hybridizing with a nucleic acid of one or more viruses of said variant phylogenetic group or sub-group without hybridizing with a nucleic acid of the Greer, Toshiba and V98 HPIV-2 isolates.

Advantageously, the sequence for said nucleic acid comprises or is constituted by one of the following sequences:

The sequences with SEQ ID NO: 57 to 61, 71 to 74, 75 to 78, 79 to 82, and the sequences which are complementary to said sequences with said defined SEQ ID number over the entire length of said sequences with said defined SEQ ID number.

Preferably, the sequence for said nucleic acid is constituted by one of the sequences SEQ ID NO: 57 to 61, 71 to 74, 75 to 78, 79 to 82.

Primers and Probes Specially Adapted to Real Time Amplification

The present application also pertains to pairs of primers and probes which may be associated therewith for carrying out real time amplification, preferably real time PCR.

The present application pertains to a pair of primers which is capable of amplifying a nucleic acid of at least one virus of the variant phylogenetic group or sub-group of the invention, without amplifying a nucleic acid from the Greer, Toshiba and V98 HPIV isolates.

A pair of primers of the invention may in particular be defined by the fact that the sequences for each of the primers of this pair are such that they allow amplification of a nucleic acid of at least one virus of a phylogenetic group or sub-group of the invention, without amplifying a nucleic acid of the Greer, Toshiba and V98 HPIV-2 viruses, when said pair of primers is placed in contact with RNA material from said at least one of the five viruses of claim 1, and also with the RNA material from each of said Greer, Toshiba and V98 viruses, for example in four distinct tubes, in the presence of suitable RT-PCR reagents such as:

TaqMan® EZ 5× buffer (250 mM Bicine—N,N-bis(2-hydroxyethyl glycine); 575 mM potassium acetate; 0.05 mM EDTA; 40% glycerol; pH 8.2): for a final concentration of 1×;

manganese acetate (25 mM): for a final concentration of 2 to 5 mM, for example a final concentration of 3 mM;

dATP, dCTP, dGTP: for a final concentration of 300 µM each;

dUTP: for a final concentration of 600 µM;

AmpErase UNG: for a final concentration of 0.01 U/µL;

500 nM of each primer of the test pair;

10 pg to 100 ng of viral RNA;

thermostable polymerase, with a reverse transcriptase activity and a DNA polymerase activity such as rTth polymerase (available, for example, from Applied Biosystems with product reference N808-0192): for a final concentration of 0.1 U/µL;

H$_2$O, demineralized and with no RNA;

and under appropriate RT-PCR conditions, such as the following experimental conditions, for example:

activation of AmpErase UNG (uracyl N-glycosylase enzyme; CE 3.2.2): 50° C. for 2 min;

reverse transcription (rTth polymerase) at 60° C. for 30 min;

deactivation of AmpErase UNG: 95° C. for 10 min;

PCR: 25 to 40 cycles of:

denaturing at a temperature of 95° C. to 97° C. for 15 seconds;

annealing and extension at a temperature which is preferably 15° C. to 5° C. less than the actual value of the melting point Tm of the pair of test primers and which is preferably more than 55° C., for example a temperature of 55° C. to 70° C., for example 60° C., for 1 min.

The reaction mixture sold by Applied Biosystems under the trade name "Taqman® EZ RT-PCR kit" is an example of a kit which provides a suitable reaction medium.

Thus, it is possible to determine whether the test pair of primers properly amplifies at least one of the five viruses of the invention, without amplifying the Greer, Toshiba and V98 isolates, i.e. whether the test primer pair has led to the production of an amplicon from RNA material from at least one of the five viruses of the invention, and has not led to the production of an amplicon from RNA material from each of the Greer, Toshiba and V98 isolates.

Any means that the skilled person can find which is suitable for detecting the presence or absence of an amplicon may be employed.

A simple means which does not necessitate the production of a detection probe may comprise electrophoresis of the nucleic acids (for example on a 1% agarose gel) in the presence of ethidium bromide and visual or densitometric analysis of the resulting bands after ultraviolet irradiation.

The appropriate primer pairs are those:

- wherein each of the two primers succeeds in hybridizing with a target on the nucleotide material from at least one of the five viruses of the invention, preferably each of the five viruses of the invention, in order to allow amplification of the region delimited by each of said two primers; and
- wherein at least one of the two primers does not find a target on the nucleotide material of each of the Greer, Toshiba and V98 isolates, which would allow amplification of a region of the nucleotide material of each of the Greer, Toshiba and V98 isolates.

Candidate primer pairs may thus be selected from those wherein at least one of the two primers presents a target on the nucleotide material of at least one of the five viruses of the invention, preferably on each of the five viruses of the invention, which are not identical in the nucleotide material from the Greer, Toshiba and V98 isolates (at least one nucleotide difference).

Preferably, primer pairs are selected:

- which contain 14 to 30 nucleotides;
- which have a G+C content of 20% to 80%;
- which have a melting point (Tm) of 58° C. to 60° C. for each primer; and
- wherein the last five nucleotides at the 3' end of each primer do not include more than two G and/or C bases.

The construction of primer pairs is a technique which is known to the skilled person. Automated means are available for this purpose, such as the "Primer Express" software version 3 or higher, sold by Applied Biosystems.

Sequences for the appropriate primer pairs may be that of a 5' fragment of the amplified sequence from at least one of the five viruses of the invention, and that of a 5' fragment of the complementary sequence for said amplified sequence (5' fragments comprising the entire first nucleotide at the 5' end).

In this case, the sequences for the appropriate primer pairs are that of a fragment of the sequence for at least one of the five viruses of the invention and that of a fragment of the complementary sequence for said viral sequence.

The sequences for the appropriate primer pairs may also be variant sequences for said fragments which may be obtained by substitution and/or addition and/or deletion of at least one nucleotide of the sequence for said fragments, and which have conserved the capacity to amplify at least one of the five viruses of the invention without amplifying Toshiba, Greer and V98. Preferably, said variant sequences have conserved at least one nucleotide difference with respect to all of their potential targets in each of the Greer, Toshiba and V98 isolates.

It is preferable to extract RNA from the viruses before bringing them into contact with the test primer pair in order to render said RNA readily accessible to said primer pair. Means which allow extraction of the RNA material from the virus are known to the skilled person. As an example, a sample of the virus may be treated with an extraction buffer containing 4M guanidium thiocyanate, 0.5% N-lauryl sarcosine, 1 mM dithiothreitol, 25 mM sodium citrate and 0.1 mg per mL of glycogen, then by precipitations with isopropanol and 70% ethanol.

Preferably, said primer pair amplifies a nucleic acid from each of the five particular viruses deposited by the inventors at the CNCM with accession numbers I-3761 to I-3765.

Advantageously, a primer pair of the invention is such that:

- the sequence for one of the primers of said pair is that of a 14 to 30 nucleotide 5' fragment of a real time nucleic acid of the invention; and in that
- the sequence for the other primer of said pair is that of a 14 to 30 nucleotide 5' fragment of the sequence which is complementary to the same real time nucleic acid over the entire length of said nucleic acid;

said 5' fragments being fragments which include the first nucleotide at the 5' end of the sequence whereof they are the fragment.

Preferably, a primer pair of the invention is capable of amplifying a nucleic acid of each of the five particular viruses deposited by the inventors, without amplifying a nucleic acid from the Greer, Toshiba and V98 HPIV isolates.

In a primer pair of the invention, each of said 5' fragments is (independently of the other) constituted by 14 to 30 nucleotides, preferably 18 to 23 nucleotides.

Preferably, a primer pair of the invention is constituted by (cf Tables 8 and 9 below):
  a primer with SEQ ID NO: 87, and a primer with SEQ ID NO: 88; or
  a primer with SEQ ID NO: 91, and a primer with SEQ ID NO: 92; or
  a primer with SEQ ID NO: 95, and a primer with SEQ ID NO: 96.

The present application also pertains to any set of primers which comprises at least one primer pair of the invention.

The present application also pertains to any primer which is selected from a primer pair of the invention.

The present application also pertains to a probe which may be used in real time amplification with a primer pair of the invention, for the specific detection of at least one virus from the phylogenetic group or sub-group of the invention.

Advantageously, said "real time" probe has a "hybridization" sequence which is:
  that of a 14 to 30 nucleotide fragment of a real time nucleic acid of the invention, said fragment preferably not comprising the first nucleotide at the 5' end of said nucleic acid, and preferably also not the last nucleotide at the 3' end of said nucleic acid; or
  that of the sequence which is complementary to said fragment over the entire length of said fragment.

Preferably, said nucleic acid fragment is constituted by 14 to 30 nucleotides, preferably by 23 to 28 nucleotides.

Advantageously, said "real time" probe is selected from the sequences with SEQ ID NO: 89, 90, 93, 94, 97, 98 (cf. Tables 8 and 9 below).

Said probe may carry a marker, for example to facilitate detection thereof, such as a radioactive, fluorescent or enzymatic marker.

Said probe may advantageously carry a fluorescent marker and a quencher in order to be suitable for use as a Taqman® type probe or beacon type or Scorpion® type probe. Such a probe may thus comprise arms which do not hybridize with HPIV-2 viruses and which are intended to form beacon arms.

The present application also pertains to a set of oligonucleotides, which comprises at least one "real time" primer pair of the invention and at least one "real time" probe of the invention.

Advantageously, said set comprises at least the primer pair with SEQ ID NO: 87-88, and the probe with SEQ ID NO: 89 or 90.

Advantageously, said set comprises at least the primer pair with SEQ ID NO: 91-92, and the probe with SEQ ID NO: 93 or 94.

Advantageously, said set comprises at least the primer pair with SEQ ID NO: 95-96, and the probe with SEQ ID NO: 97 or 98.

A set of the invention may, for example, comprise at least one primer pair of the invention and at least two "real time" probes of the invention.

Advantageously, said set comprises at least the primer pair with SEQ ID NO: 87-88, the probe with SEQ ID NO: 89 and the probe with SEQ ID NO: 90.

Advantageously, said set comprises at least the primer pair with SEQ ID NO: 91-92, the probe with SEQ ID NO: 93 and the probe with SEQ ID NO: 94.

Advantageously, said set comprises at least the primer pair with SEQ ID NO: 95-96, the probe with SEQ ID NO: 97 and the probe with SEQ ID NO: 98.

The present application also pertains to a kit for diagnosing a respiratory disease or infection which comprises at least one primer pair of the invention and/or at least one probe of the invention.

The present application also pertains to an amplification system which is specially adapted to real time amplification, which comprises at least one primer pair of the invention and at least one probe of the invention, and more particularly at least one primer pair of the invention and at least one probe of the invention which is capable of hybridizing to the amplicon produced by said primer pair from nucleic acid from a virus from the variant phylogenetic group or sub-group of the invention.

The present application also pertains to any composition, and more particularly to any pharmaceutical or biological composition which comprises at least one primer pair and/or at least one probe and/or at least one "real time" system of the invention.

The present application also pertains to a kit which is specially adapted to the detection of HPIV-2, more particularly to its diagnosis, which comprises at least one primer pair and/or at least one probe and/or at least one "real time" system of the invention.

Said diagnostic kit may also comprise means for detecting other microorganisms, and in particular:
  means for detecting HPIV-2s which do not form part of the variant phylogenetic group or, if appropriate, sub-group of the invention, such as Greer, Toshiba and V98 HPIV-2s; and/or
  means for detecting HPIV other than HPIV-2, such as HPIV-1, HPIV-3, HPIV-4; and/or
  means for detecting microorganisms which are not HPIV, such as microorganisms and more particularly viruses involved in respiratory infections or diseases (lower respiratory and/or upper respiratory systems) such as pneumonia, bronchiolitis, influenza.

The present application also pertains to a method for detecting, more particularly for diagnosing HPIV-2, which comprises bringing a sample which might contain at least one HPIV-2 virus into contact with at least one primer pair and at least one probe of the invention, under conditions which are suitable for real time amplification, for example real time PCR.

Detecting the presence of an amplicon produced by this primer pair and detected by said probe is indicative of the presence of a HPIV-2 virus forming part of the phylogenetic group or, as appropriate, sub-group of the invention.

The present application also pertains to any amplicon which might be obtained by amplification using a primer pair of the invention of a nucleic acid from a virus of the variant phylogenetic group or, as appropriate sub-group of the invention.

Probes, Specially Adapted for Use on a Chip

The present application describes the selection of nucleic acids which are specially adapted to the construction and to the production of probes which are specially adapted for use on a chip (nucleic acid chips above).

Thus, the present application pertains to a probe which is specially adapted for use on a chip and which is capable of hybridizing with a nucleic acid from one or more viruses of the phylogenetic group or sub-group of the invention without hybridizing to a nucleic acid from the Greer, Toshiba and V98 HPIV-2 isolates.

Preferably, said probe is a nucleic acid which hybridizes under high stringency conditions to a nucleic acid from one or more viruses of the phylogenetic group or sub-group of the invention, without hybridizing to a nucleic acid of the Greer, Toshiba and V98 HPIV-2 isolates under the same high stringency conditions. The high stringency conditions are known to the skilled person and an example of such conditions was described above.

Advantageously, said probe is such that its sequence is that of a fragment of a chip nucleic acid of the invention, or that of the sequence which is complementary to that fragment over the entire length of said fragment.

More particularly, the present application pertains to probes which are capable of hybridizing to at least one virus of the phylogenetic group or sub-group of the invention without hybridizing to the Greer strain HPIV-2 virus, characterized in that its sequence is that of a sub-fragment (with 14 to 30, preferably with 18 to 23 nucleotides) from the following fragments:

fragments 241-420 of sequences coding for F;

fragments 259-395 of sequences coding for F;

fragments 181-480 of sequences coding for HN;

fragments 234-443 of sequences coding for HN;

fragments 1381-1716 of sequences coding for HN;

fragments 1466-1673 of sequences coding for HN;

sequences which are complementary to said sequences over the entire length of said sequences.

Advantageously, said probe is selected from the sequences with SEQ ID NO: 99 to 117 (cf. Table 11 below).

The present application also pertains to any solid support adapted to circulating a microfluidic flux, such as a chip, which comprises at least one said probe.

Preferably, said probe is fixed to the support for said chip. Said chip may in the frozen or even freeze-dried form.

Examples of chips are known to the skilled person. For example, chips have been described by Korimbocus et al. 2005, Journal of Clinical Microbiology 43(8): 3779-3787, or sold by Affymetrix (California, USA).

TABLE 5

SEQ ID NO of sequences for proteins coded by the viruses of the invention and of sequences coding for said proteins

| SEQ ID NO: | CDS for HN and F | CDS for F (1656 nt) | F proteins (551 aa) | CDS for HN (1716 nt) | HN proteins (571 aa) | Cleavage site (CS) KPRRER | Fusion peptides (FP; 20 aa) cf. FIG. 2 |
|---|---|---|---|---|---|---|---|
| | cf. "sequence description" section following "Examples" section | | | | | | |
| Isolate 18620 | 22 | 23 | 24 | 25 | 26 | 14 | 16 |
| Isolate 20283 | 27 | 28 | 29 | 30 | 31 | 14 | 17 |
| Isolate 20435 | 32 | 33 | 34 | 35 | 36 | 14 | 18 |
| Isolate 26056 | 37 | 38 | 39 | 40 | 41 | 14 | 19 |
| Isolate 26632 | 42 | 43 | 44 | — | — | 14 | 20 |

TABLE 6

Sequences for regions of virus of the invention, specially adapted to the construction and to the production of specific primers and/or probes for at least one of the five isolates of the invention (specific detection compared with HPIV-2 isolates which do not form part of the variant phylogenetic group of the invention, such as the Greer, Toshiba and V98 HPIV-2 isolates)

| | Size | Isolate 18620 | Isolate 20283 | Isolate 20435 | Isolate 26056 | Isolate 26632 |
|---|---|---|---|---|---|---|
| Region 241-420 of sequence coding for F | 180 | SEQ ID NO: 57 | SEQ ID NO: 58 | SEQ ID NO: 59 | SEQ ID NO: 60 | SEQ ID NO: 61 |
| Region 259-395 of sequence coding for F | 137 | SEQ ID NO: 62 | SEQ ID NO: 63 | SEQ ID NO: 64 | SEQ ID NO: 65 | SEQ ID NO: 66 |
| Region 234-443 of sequence coding for HN | 210 | SEQ ID NO: 67 | SEQ ID NO: 68 | SEQ ID NO: 69 | SEQ ID NO: 70 | |
| Region 241-420 of sequence coding for HN | 180 | SEQ ID NO: 71 | SEQ ID NO: 72 | SEQ ID NO: 73 | SEQ ID NO: 74 | |
| Region 961-1140 of sequence coding for HN | 180 | SEQ ID NO: 75 | SEQ ID NO: 76 | SEQ ID NO: 77 | SEQ ID NO: 78 | |
| Region 1381-1560 of sequence coding for HN | 180 | SEQ ID NO: 79 | SEQ ID NO: 80 | SEQ ID NO: 81 | SEQ ID NO: 82 | |
| Region 1466-1673 of sequence coding for HN | 208 | SEQ ID NO: 83 | SEQ ID NO: 84 | SEQ ID NO: 85 | SEQ ID NO: 86 | |

The sequences coding for F and those coding for HN are shown in the "description of sequences" section below and in FIGS. 5 and 6.

TABLE 7

Sequences for regions of virus of the invention, specially adapted to the construction and to the production of specific primers and probes, said primers and probes being specially adapted for use in the context of real time amplification for the detection of at least one of the isolates of the invention (specific detection compared with HPIV-2 isolates which do not form part of the variant phylogenetic group of the invention, such as the Greer, Toshiba and V98 HPIV-2 isolates)

|  | Size | Isolate 18620 | Isolate 20283 | Isolate 20435 | Isolate 26056 | Isolate 26632 |
|---|---|---|---|---|---|---|
| Region 259-395 of sequence coding for F | 137 | SEQ ID NO: 62 | SEQ ID NO: 63 | SEQ ID NO: 64 | SEQ ID NO: 65 | SEQ ID NO: 66 |
| Region 234-443 of sequence coding for HN | 210 | SEQ ID NO: 67 | SEQ ID NO: 68 | SEQ ID NO: 69 | SEQ ID NO: 70 | |
| Region 1466-1673 of sequence coding for HN | 208 | SEQ ID NO: 83 | SEQ ID NO: 84 | SEQ ID NO: 85 | SEQ ID NO: 86 | |

TABLE 8

Examples of specific primers and probe sequences which are specially adapted for real time use for the detection of the set of the five isolates of the invention (specific detection compared with HPIV-2 isolates which do not form part of the variant phylogenetic group of the invention, such as the Greer, Toshiba and V98 HPIV-2 isolates)

|  | Sense primer | | Antisense primer | | Real time probes (SEQ ID numbers indicated, or their complementary sequences) | |
|---|---|---|---|---|---|---|
|  | SEQ ID NO: | position | SEQ ID NO: | position | SEQ ID NO: | position |
| Region 259-395 of sequence coding for F | 87 | 259-276 | 88 | 376-395 | 89 | 323-346 |
|  |  |  |  |  | 90 | 327-354 |
| Region 234-443 of sequence coding for HN | 91 | 234-254 | 92 | 423-443 | 93 | 317-344 |
|  |  |  |  |  | 94 | 334-360 |
| Region 1466-1673 of sequence coding for HN | 95 | 1466-1485 | 96 | 1650-1673 | 97 | 1521-1543 |
|  |  |  |  |  | 98 | 1524-1547 |

TABLE 9

Information regarding SEQ ID numbers in Table 8

| SEQ ID NO: | Sequence (5' to 3') | Size | % GC | Tm |
|---|---|---|---|---|
| 87 | CTG ATT GAG AAC CTG AGC | 18 | 50 | 48 |
| 88 | ACT ATT GCT ACA GCT GCG GT | 20 | 50 | 52 |
| 89 | CAG GAG TCG TTA TTG GGC TTG CTG | 24 | 54 | 60 |
| 90 | AGT CGT TAT TGG GCT TGC TGC ACT AGG | 27 | 52 | 61 |
| 91 | CCA GAT TCT GTA CAA TGT TGC | 21 | 43 | 50 |
| 92 | CCA TAT TTA GGC GTC CCA TTG | 21 | 48 | 52 |
| 93 | TGC ACA CCG GGA GTA TGT CCA ATG CCA A | 28 | 54 | 63 |
| 94 | TCC AAT GCC AAC TGC ACG CCA GGA AAT | 27 | 52 | 61 |
| 95 | ATC GAT TTG CTG GAG CCT TT | 20 | 47 | 50 |
| 96 | CCT AAA AGA GAT GAG CCC ATT TC | 23 | 43 | 50 |
| 97 | CTA CAC TGC ATC GTC TAA CTC CC | 23 | 52 | 57 |
| 98 | CAC TGC ATC GTC TAA CTC CCT CTT | 24 | 50 | 57 |

TABLE 10

Sequences for regions of the virus of the invention specially adapted to the construction and to the production of probes which are specific to at least one isolate of the invention and which are specially adapted for use on a chip (specific detection compared with HPIV-2 isolates which do not form part of the variant phylogenetic group of the invention, such as the Greer, Toshiba and V98 HPIV-2 isolates)

| | Size | Isolate 18620 | Isolate 20283 | Isolate 20435 | Isolate 26056 | Isolate 26632 |
|---|---|---|---|---|---|---|
| Region 241-420 of sequence coding for F | 180 | SEQ ID NO: 57 | SEQ ID NO: 58 | SEQ ID NO: 59 | SEQ ID NO: 60 | SEQ ID NO: 61 |
| Region 241-420 of sequence coding for HN | 180 | SEQ ID NO: 71 | SEQ ID NO: 72 | SEQ ID NO: 73 | SEQ ID NO: 74 | |
| Region 961-1140 of sequence coding for HN | 180 | SEQ ID NO: 75 | SEQ ID NO: 76 | SEQ ID NO: 77 | SEQ ID NO: 78 | |
| Region 1381-1560 of sequence coding for HN | 180 | SEQ ID NO: 79 | SEQ ID NO: 80 | SEQ ID NO: 81 | SEQ ID NO: 82 | |

TABLE 11

Examples of specific probes specially adapted for use on a chip for the specific detection of the set of the five isolates of the invention (specific detection compared with HPIV-2 isolates which do not form part of the variant phylogenetic group of the invention, such as the Greer, Toshiba and V98 HPIV-2 isolates)

| | Probes (SEQ ID NO indicated, or their complementary sequences) | | | | |
|---|---|---|---|---|---|
| | SEQ ID NO: | Sequences (5' to 3') | Position | Size | % GC |
| Region 241-420 of sequence coding for F | 99 | TAAGTTGCTAACGCCC | 243-258 | 16 | 50 |
| | 100 | GAGCAAAATTTCTGCTG | 273-289 | 17 | 41 |
| | 101 | GAGTCGTTATTGGGC | 326-340 | 15 | 53 |
| | 102 | GCTGCACAAATAACCG | 364-379 | 16 | 50 |
| | 103 | GTAAAAGCCAATGCAAATGC | 394-413 | 20 | 40 |
| | 104 | GGCTTGCTGCACTA | 337-350 | 14 | 57 |
| Region 241-420 of sequence coding for HN | 105 | AGATATGCACACCGG | 312-326 | 15 | 53 |
| | 106 | GCACACCGGGAGTAT | 318-332 | 15 | 60 |
| | 107 | ATGCCAACTGCACGC | 337-351 | 15 | 60 |
| | 108 | CCTTGTACTTGAATC | 405-419 | 15 | 40 |
| | 109 | AACTGCACGCCAG | 342-354 | 13 | 60 |
| Region 961-1140 of coding sequence HN | 110 | TACAATGAGCAGTCC | 961-975 | 15 | 47 |
| | 111 | GCAAACAGGCTGCAATAGC | 1028-1046 | 19 | 53 |
| | 112 | GTCATCCGTTATCACTC | 1059-1075 | 17 | 47 |
| | 113 | CACACAGAAGAGTG | 1126-1139 | 14 | 50 |
| Region 1381-1560 of sequence coding for HN | 114 | CATCGTCTAACTCCCTC | 1529-1545 | 17 | 53 |
| | 115 | CACGTAATGCTCTG | 1442-1455 | 14 | 50 |
| | 116 | TGATCCAGAACTCATG | 1425-1440 | 16 | 44 |
| | 117 | CCGAACTAATCCCACATTC | 1503-1521 | 19 | 47 |

In the present application, the term “comprising”, which is synonymous with “including” or “containing”, is an open term and does not exclude the presence of one or more additional element(s), ingredient(s) or step(s) in a method which have not been explicitly indicated, while the term “consisting” or “constituted” is a closed term which excludes the presence of any other additional element, step or ingredient which has not been explicitly defined. The term “essentially consisting” or “essentially constituted” is a partially open term which does not exclude the presence of one or more additional element(s), ingredient(s) or step(s) provided that said additional element(s), ingredient(s) or step(s) do not materially affect the base properties of the invention.

As a consequence, the term “comprising” (or “comprises (comprise)”) includes the terms “consisting”, “constituted” as well as the terms “essentially consisting” and “essentially constituted”.

The contents of the documents and bibliographic references which are cited in the present application are incorporated by reference.

The following examples are given purely by way of illustration and do not in any way limit the invention.

EXAMPLES

Materials and Methods

Variant HPIV-2 IKsolates

Five "atypical" HPIV-2 isolates were isolated on LLC-MK2 cells from respiratory samples, nasal aspirates or bronchoalveolar lavages collected from four hospitalized patients (see Table 1 below). These patients (one child and three adults) had been admitted to hospital with respiratory infections.

Five isolates were given the isolate references Lyon/18620/2001, Lyon/20283/2001, Lyon/20435/2001, Lyon/26056/1997 and Lyon/26632/1997.

In the present application, these isolates may also, for simplification, be termed 18620, 20283, 20435, 26056, 26632 respectively.

These five isolates were deposited with the CNCM under the auspices of the Treaty of Budapest (Collection Nationale de Cultures de Microorganismes; C.N.C.M.; Institut Pasteur; 25, rue du Docteur Roux; F-75724 PARIS Cedex 15; France).

TABLE 1

| Isolate | CNCM accession number | Date of CNCM deposition. |
|---|---|---|
| 18620 | I-3763 | 10 May 2007 |
| 20283 | I-3764 | 10 May 2007 |
| 20435 | I-3765 | 10 May 2007 |
| 26056 | I-3761 | 10 May 2007 |
| 26632 | I-3762 | 10 May 2007 |

Prototype Strains

The Greer HPIV-2 strain (ATCC number VR-1381) was isolated in 1955 (USA) from an 11 month old child. All of the tests were carried out using a stock frozen at −80° C. ($10^{7.5}$ TCID 50/50 µL).

Viral Culture

In order to isolate the virus, LLC-MK2 cells (monkey kidney cells, ATCC CCL-7) were cultured in 24-well shell vial plates. The cells were maintained in Minimum Essential Medium Eagle supplemented with strypsin (2 (g/mL). After inoculation, the plates were centrifuged (400 g for 30 min at 34° C.), the culture media were renewed, and the plates were then incubated at 34° C. in 5% $CO_2$. The cytopathic effect of the virus was monitored regularly for 10 days.

Immunofluorescence Test (IF Test)

IF tests were carried out with the specific monoclonal antibodies for each of the four types of HPIV (monoclonal anti-HPIV-1 antibody, monoclonal anti-HPIV-2 antibody, monoclonal anti-HPIV-3 antibody and monoclonal HPIV-4 antibody). Said antibodies can be produced by the skilled person or are commercially available. As an example, a specific monoclonal antibody of the HPIV-4 type is available from Chemicon (Temecula, Calif., USA) with reference "mAb 8780".

Other IF tests were carried out with specific monoclonal antibodies for HPIV-2. The monoclonal anti-HPIV-2 antibodies used recognize HN or a structure protein (internal proteins). Said antibodies may be produced by the skilled person or are commercially available. As an example, a monoclonal anti-HPIV-2 antibody which targets the HN protein of HPIV-2 is available from ARGENE S.A. (Parc Technologique Delta Sud, 09120 Varilhes; France) with reference 12E12G9.

Extraction and RT-PCR

Viral RNA was extracted from 100 µL of culture supernatant from LLC-MK2 cells using the "Absolutely RNA Microprep" kit (Stratagene, USA), following the manufacturer's instructions. Reverse transcription was carried out using pd(N)6 random hexamer (Amersham Biosciences, Great Britain). In brief, 5 µL of the extracted RNA suspensions was incubated with 1 µL of pd(N)$_6$ (1 (g/mL). A mixture of 4 µL of AMV-RT buffer (Promega Corporation, USA), 7.5 µL of sterile water, 1 µL of dNTP (20 mM) (Eurogentec, Belgium), 0.5 µL of Rnase inhibitor (40 U/µL) (Promega Corporation, USA), and 1 µL of AMV reverse transcriptase (10 U/µL) (Promega Corporation, USA) was then added. Reverse transcription was carried out by incubation at 37° C. for 1 hour and stopped by heating at 95° C. for 5 minutes.

In order to obtain the complete sequences for the F and HN genes, PCR amplifications were carried out with 6 pairs of primers (shown in Table 2 below) constructed using the nucleotide sequence for the available HPIV-2 isolate, namely the HPIV-2 Greer isolate (GenBank accession number NC_003443).

TABLE 2

| Primer | Hybridization site | Sequence for primer | SEQ ID NO: | Position (3'-5') | PCR products |
|---|---|---|---|---|---|
| Pd(N)6 | Non specific | Random hexamer | — | random | — |
| Para2S1 | M | TGGAAGCCATCAACTGAATGC | 1 | 4596 | 714 |
| Para2AS1 | F | TCCTGAATTGCTTGAACTGCG | 2 | 5309 | |
| Para2S2 | F | TCAAGAACAATTGCAACCGC | 3 | 5272 | 1038 |
| Para2AS2 | F | CAATCCCACGACAACCAAAGT | 4 | 6289 | |
| Para2S3 | F | AAGCCAGGACAGCCAAGACA | 5 | 6237 | 964 |
| Para2AS3 | HN | TCATGCAGAAGCAGATTTCCG | 6 | 7190 | |
| Para2S4 | HN | AACACCAACTGTACACCCGGA | 7 | 7153 | 1058 |
| Para2AS4 | HN | TGTGATGCAATTAGCAGGGC | 8 | 8201 | |
| Para2S5 | HN | TTGGTGGTCTGCATCGCTT | 9 | 8055 | 977 |
| Para2AS5 | L | GTTGCTCTAAATGCGGGCA | 10 | 9031 | |
| Para2.1* | HN | AACAATCTGCTGCAGCATTT | 11 | 7437 | 507 |
| Para2.2* | HN | ATGTCAGACAATGGGCAAAT | 12 | 7943 | |

*Echevarria et al. 1998, J. Clin. Microbiol. 36: 1388-1391

After optimization of the PCR conditions, amplification was carried out by adding 5 μL of the cDNA which had been synthesized above to a tube containing 45 μL of the following PCR mixture: 24.5 μL of sterile water, 5 μL of PCR buffer (15 mM $MgCl_2$) (Applied Biosystems, Roche, USA), 5 μL of dNTP (20 mM), 5 μL of each primer (sense and antisense) (20 μM) (Eurogentec, Belgium) and 0.5 μL of Taq DNA polymerase (5 U/μL) (Applied Biosystems, Roche, USA). The prototype HPIV-2 strain and sterile water were used as positive and negative controls respectively. Amplification was carried out using the following protocol: 95° C. for 5 minutes, followed by 40 cycles (95° C. for 30 seconds, 58° C. for 30 seconds, 72° C. for 1 minute and 30 seconds) and a final elongation step of 10 minutes at 72° C.

Sequencing

The PCR products were purified using a GFX purification kit (Amersham Biosciences, Great Britain), following the manufacturer's instructions. A quantity of 20 ng/100 bp of each product was sent for sequencing to MWG Biotech (Ebersberg, Germany).

Phylogenetic Analysis

The alignments were obtained using the ClustalX program (http://www-igbmc.u-strasbg.fr/Bioinfo/clustalX/Top.html). The distance matrix was calculated using DNADIST from the Phylip program package (version 3.64) (Felsenstein J., 1993, PHYLIP Phylogeny Interference Package version 3.64, Genetics Department, Washington University, Seattle, USA). The phylogenetic trees were constructed using the Neighbour-Joining (or NJ, or Saitou and Nei) algorithm) of the NEIGHBOR program from the Phylip program package. Bootstrap analysis was carried out on 1000 replications using SEQBOOT and CONSENSE from the Phylip program package. The rooted trees were edited using Njplot software (IBCP, Lyon).

18:213-214) and the Rasmol graphic interface (Rasmol molecular graphics, version 2.7.1). The domains which were likely to be involved in coiled coil domains (HR1 and 2) were predicted using Learncoil-VMF software (http://web.wi.mit-.edu/kim) (Singh M et al. 1999, J. Mol. Biol., 290:1031-1041).

RESULTS

Isolation and Identification of Viruses

Five strains were isolated from respiratory samples, nasal aspirates or bronchoalveolar lavages collected from four hospitalized patients. These five isolates have been deposited at the CNCM under the auspices of the Treaty of Budapest (see Table 1 above).

The 5 isolates grew well on LLC-MK2 cell lines and had a large syncytial cytopathogenic effect appearing 3 to 7 days after infection. Routine immunofluorescence tests were also carried out on 5 samples using specific monoclonal antibodies for 4 types of HPIV and other respiratory pathogens. All of these tests produced negative results. The isolates of the invention were not detected by these prior art anti-HPIV antibodies.

In contrast, the isolates all produced a positive HPIV-2 result when they were tested by specific HPIV RT-PCR. The five isolates thus appear to be "atypical" HPIV-2 isolates compared with the reference HPIV-2 Greer strain.

Reactivity with Monoclonal Antibodies

Immunofluorescence tests were carried out on the 5 isolates using 8 specific monoclonal antibodies for HPIV-2. Only the tests carried out with the monoclonal antibodies against the internal proteins produced positive results. The immunofluorescence tests carried out with the monoclonal antibodies directed against haemagglutinin-neuraminidase of the prior art produced negative results (the results of these immunofluorescence tests are shown in Table 3 below). Regarding the positive control, all of the monoclonal antibodies reacted with the prototype HPIV-2 Greer strain.

TABLE 3

| | Monoclonal antibodies directed against internal proteins | | | | | | Monoclonal antibodies directed against HN | |
|---|---|---|---|---|---|---|---|---|
| | 6C10E4 | 6E7F3 | 1B4G6 | 5E3D7 | 6D10F2 | 2B6F7 | 12E12B8F3 | 5C4E8 |
| HPIV-2 Lyon/26056/1997 | ++ | ++ | ++ | ++ | ++ | + | − | − |
| HPIV-2 Lyon/26632/1997 | + | + | ++ | ++ | ++ | ++ | − | − |
| HPIV-2 Lyon/18620/2001 | ++ | ++ | ++ | ++ | ++ | ++ | − | − |
| HPIV-2 Lyon/20283/2001 | ++ | ++ | + | + | ++ | + | − | − |
| HPIV-2 Lyon/20435/2001 | + | + | + | ++ | ++ | + | − | − |
| HPIV-2 Greer/1955 | ++ | ++ | ++ | ++ | ++ | ++ | ++ | ++ |
| SV5 simian virus | + | + | + | ++ | + | + | − | − |

− negative reaction
+ positive reaction
++ large positive reaction

Prediction of Secondary Structure and Analysis of Molecular Modelling

The secondary structures were predicted using the on-line SECCONS software (http://Seccons.pbil.ibcp.fr) (IBCP, Lyon, France) (Combet et al. 2000, Trends Biochem Sci, 25:147-150). This software gives the consensus secondary structure as determined by a unit of 8 different secondary structure prediction programs. Automatic molecular modelling was carried out using the GENO3D software (http://geno3D-pbil.ibcp.fr) (Combet et al. 2002, Bioinformatics, Molecular Characterisation After assembling the various fragments, the complete consensus nucleotide sequences for the F and HN genes were established for the Greer, 18620, 20283, 20435, 26056 and SV5 HPIV-2 isolates, and the complete consensus nucleotide sequence for the F gene was established for the HPIV-2 isolate 26632.

As the control, the complete consensus nucleotide sequence obtained for the prototype strain (nucleotide sequence SEQ ID NO: 45; amino acid sequence SEQ ID NO:

46) was compared with the equivalent sequence available on the GenBank/EMBL database. The two sequences had a percentage homology of 99.9%. The homology for the F and HN proteins was complete.

TABLE 4

| Type | Strain | Genbank accession number |
|---|---|---|
| HPIV-2 | Greer/1955/(USA) | NC_003443 |
| | Vanderbilt 9412-6 (V94)/1994 (USA) | AF533010 |
| | Vanderbilt 9811-18 (V98)/1998 (USA) | AF533011 |
| HPIV-2 of the invention | Lyon/18620/2001 | DQ072586 (F and HN genes; F CDS; F protein; HN CDS; HN protein) |
| | Lyon/20283/2001 | DQ072587 (F and HN genes; F CDS; F protein; HN CDS; HN protein) |
| | Lyon/20435/2001 | DQ072588 (F and HN genes; F CDS; F protein; HN CDS; HN protein) |
| | Lyon/26056/1997 | DQ072589 (F and HN genes; F CDS; F protein; HN CDS; HN protein) |
| | Lyon/26632/1997 | DQ072590 (F gene; F CDS; F protein) |

The content corresponding to Genbank accession numbers DQ072586, DQ072587, DQ072588, DQ072589, DQ072590 is reproduced hereinbelow in the "sequence description" section.

The nucleotide sequences for the F gene of the "atypical" HPIV-2 isolates were compared with their counterpart in the prototype strain. The alignment obtained showed 57 changes common to all of the "atypical" HPIV-2 isolates out of a total of 1656 nucleotides (3.4%). These common differences represent the vast majority (85%) of the observed differences. These changes result in 11 amino acid substitutions (cf description of FIGS. 4 and 7), i.e. 2% of substitutions.

The nucleotide sequences for the HN gene of the "atypical" HPIV-2 viruses were also compared with the reference strain. Thus, 79 changes common to the set of "atypical" viruses were shown out of a total of 1716 nucleotides (4.6%). These common differences also represent the majority of the observed differences (80%). These changes resulted in 20 common changes (cf. description of FIG. 8), i.e. 3.8% of substitutions.

HN Attachment Protein

Analysis of the potential glycosylation sites (N-X-S/T) in the HN gene shows that all of the 5 HPIV-2 variants have in common a S316N substitution responsible for the appearance of a new glycosylation site which is absent in the prototype strain. The principal differences between the variants and the prototype strain were observed in the carboxy-terminal portion of the protein.

The three-dimensional models of the HN proteins of the HPIV-2 Greer strain and the "atypical" isolates constructed from the structural homologies have a very strong similarity. Organization into 6 layers, characteristic of neuraminidase, was observed (cf FIG. 1). By analogy with the known structures of the HN proteins of NDV, SV5 and HPIV-3, the position and conformation of the catalytic site appear to be identical in the various HPIV-2 isolates. The models obtained confirm that the glycosylation site which is only present in the "atypical" HPIV-2 variants is located in a loop directed towards the exterior of the protein. The S316N substitution does not appear to change the structure of this loop. The amino acids which constitute the hydrophobic peak described above on the reference HPIV-2 Greer strain (positions 512-515) form a loop which is directed towards the interior of the protein (cf. loop indicated as A in the left hand model in FIG. 1), which is not the case for the "atypical" variant isolates of HPIV-2 (cf loop indicated by A' in the right hand model in FIG. 1).

Fusion Protein F

The alignment of 20 amino acids which constitute the fusion peptide of Paramyxovirus has a difference of one amino acid between the variant HPIV-2 isolates and the prototype strain (FIG. 2). The fusion peptide of the V94 and V98 strains is similar to the fusion peptide of the "atypical" HPIV-2 viruses and to the fusion peptide of the prototype HPIV-2 strain respectively (FIGS. 2 and 4).

The alignments of the other structurally significant domains (HR1 and 2, TM and CS, FIG. 4) of the HPIV-2 isolates do not indicate any large differences with the exception of the CS and HR1 domains. In the Greer and V98 isolates, the cleavage site is KTRQER (SEQ ID NO: 13) or KTRQKR (SEQ ID NO: 118), instead of KPRRER (SEQ ID NO: 14) for the other isolates.

Phylogenetic Analysis

The nucleotide sequences for the F and HN genes of the atypical isolates HPIV-2 of the HPIV-2 Greer prototype strain and SV5 were aligned with their counterparts available in the GenBank database. This analysis showed a similar evolution diagram for the F and HN proteins, indicating that the evolution of the F and HN proteins of atypical viruses diverges from those of the prototype strain thereby forming two distinct groups (or groupings). Looking at the internal branch topology, the two trees present the same evolution profile (FIG. 3). The envelope proteins of two HPIV-2 strains deriving from the USA also correspond well to this divergent evolution, each strain being present in one or two groupings (FIG. 3).

DISCUSSION

The aim of this study was to characterize clinical HPIV-2 isolates which have an atypical antigen reactivity towards the monoclonal antibodies used in diagnostics. Regarding HPIV-2 viruses, a few rare studies, which are already old, have demonstrated an antigenic variation between the isolates (Numazaki Y et al. 1968, Proc. Soc. Exp. Biol. Med. 127:992-996; Ray et al. 1992, Virus Res. 24:107-113). However, the link between antigenic variation and genetic variation had not been analyzed until now.

The F and HN proteins of the "atypical" HPIV-2 viruses have a marked percentage of substitutions compared with the prototype strain: 2% for the F gene and 3.8% for the HN gene.

By comparison, a HPIV-3 variant described in 1995 had only 4 amino acid substitutions in the HN protein, including 2 at known antigenic sites (0.7% substitution). The position of the antigenic sites has not yet been determined for HPIV-2, but it would be surprising if none of the 22 amino acid substitutions observed in the HN gene of "atypical" HPIV-2 viruses were located in the antigenic sites.

Haemagglutinin-Neuramidase

Among the observed substitutions, the S316N substitution is the origin of a new potential glycosylation site which is absent in the HN protein of the prototype HPIV-2 strain. The three-dimensional models of the HN protein show that this site is localized in a loop which is directed towards the exterior of the protein, i.e. an exposed zone which could correspond to an antigenic site. A glycosylation is capable of masking an epitope and could explain the absence of reaction with certain antibodies. The other potential glycosylation sites remain unchanged.

The differences observed in the primary structure of the HN protein of the atypical isolates potentially have consequences for the secondary structure in the carboxy-terminal portion of the protein. The results presented, which for the moment are only predictions, do not indicate any significant structural changes, in particular at the surface of the protein or at the catalytic site. However, these minor structural changes with no disturbance to function could be responsible for the disappearance of conformational epitopes.

Fusion Protein

The analysis of the fusion peptides from the "atypical" HPIV-2 isolates shows the existence of a difference of one amino acid compared with the F protein of the prototype strain. The hydrophobic domain constituted by the fusion peptide is presented as being the zone which is the most preserved in the F protein in the Paramyxoviridae family. This suggests that its structure and its function are subjected to more intense selection pressure than the other domains of the protein.

Analysis of the specific conservative and non-conservative changes which was carried out on SV5 and NDV showed that the peptide sequence is important for fusion activity (Horvath C M 1992, Sergel T A et al., 2001). The difference of one amino acid which we observe between the "atypical" viruses and the prototype strain of the same type thus does not appear to be negligible. It has been shown that changes which augment the hydrophobic nature of the fusion peptide, thereby encouraging interactions with the lipids of the cell membrane, had as a consequence an increase in the formation of syncytial structures. In the present case, the substitution of a valine by an isoleucine practically does not modify the hydrophobic nature. This substitution brings the peptides of the "atypical" viruses and SV5 virus closer together, SV5 being a virus with a similar cytopathogenic effect in the syncytial structure. However, the correlation between the observed substitution and a more significant fusion is not yet established.

The variant HPIV-2 isolates have a more basic cleavage site than the prototype strain. This could also explain the difference in terms of fusion activity. In the case of NDV (F gene) and influenza (HA gene), the importance of a cleavage site for viral virulence and pathogenicity was studied. Strains which had multibasic residues at the cleavage site are virulent and disseminate readily within the host. In certain non-pathogenic strains of influenza, it has been shown that arginine or lysine substitutions at the cleavage site for the HA gene in positions 5 or 6 result in acquisition of pathogenicity. Further analyses were carried out to determine the relationship between the basic nature of the cleavage site, the fusion activity and the virulence of "atypical" HPIV-2 variant isolates.

Phylogenetic Analysis

The phylogenetic analyses suggest two distinct groups (clusters) within HPIV-2, each group having different antigenic properties.

To the inventors' knowledge, this is the first time that phylogenetic analyses based on the F and HN genes of the HPIV-2 sequences have been carried out in parallel. The two phylogenetic trees (FIG. 3) have a very strong similarity in terms of topology, even though the HN protein appears to evolve substantially more rapidly than the F protein. The co-evolution of the two glycoproteins of HPIV-2 could be explained by an equivalent exposure to selection pressure, a pressure which is more marked than for the other structure proteins.

The laboratory diagnosis of HPIV was routinely carried out using conventional cell culture isolation, centrifuging the culture in shell vials and labelling by immunofluorescence (direct staining of rhinopharyngeal samples). The sequencing data clearly show the presence of novel HPIV-2 strains which have not yet been described. It is not yet known whether these variants which we have just isolated are predominant in the patient population. Sequencing studies are under way in order to analyse the variations in the F and HN genes in other clinical isolates of HPIV-2 available in our laboratory, in particular in order to determine whether HPIV-2 variants are emerging.

Continued viral surveillance is important in order to monitor antigenic changes which may occur in nature, more particularly compared with the selection of strains for vaccine development as well as for carrying out diagnostic tests which have been developed.

DESCRIPTION OF SEQUENCES

A. Sequences for Isolates of the Invention:
SEQ ID NO: 22-26 (Isolate 18620)

```
LOCUS      bankit721306    4333 pb   RNA linear
DEFINITION Complete CDS for F and HN genes of 18620/1997/Lyon isolate from
human parainfluenza type 2 virus, coding for the fusion protein (F) and
haemagglutinin-neuraminidase (HN)
ACCESSION Genbank accession number DQ072586
REFERENCE 1 (bases 1 to 4333)
FEATURES   Location/Qualifiers
source     1...4333 (SEQ ID NO: 22)
           /Organism = "Human parainfluenza type 2 virus; virus; negative polarity single
strand RNA virus; Mononegavirales; Paramyxoviridae; Paramyxovirinae; Rubulavirus."
           /isolate = "18620/1997/Lyon"
           /state = "France"
           /note = "type: 2"
gene       177...1832
           /gene = "F"
CDS        177...1832 (fragment 177-1832 of SEQ ID NO: 22 = SEQ ID NO: 23;
cf. FIG. 5)
           /gene = "F"
           /codon start = 1
           /product = "Fusion protein" (SEQ ID NO: 24)

/translation = "MHHLHPMIVCIFVMYTGIVGSDAIAGDQLLNVGVIQSKIRSLMYYTD
GGASFIVVKLLPNLPPSNGTCNITSLDAYNVTLFKLLTPLIENLSKISAVTDTKPRRE
```

-continued

RFAGVVIGLAALGVATAAQITAAVAIVKANANAAAINNLASSIQSTNKAVSDVIT
ASRTIATAVQAIQDRINGAIVNGITSASCRAHDALIGSILNLYLTELTTIFHNQITNP
ALTPLSIQALRILLGSTLPIVIESKLNTKLNTAELLSSGLLTGQIISISPMYMQMLIQ
INVPTFIMQPGAKVIDLIAISANHKLQEVVVQVPNRILEYANELQNYPANDCVVTPN
SVFCRYNEGSPIPESQYQCLRGNLNSCTFTPIIGNFLKRFAFANGVLYANCKSLLCK
CADPPHVVSQDDNQGISIIDIKRCSEMMLDTFSFRITSTFNATYVTDFSMINANIVHL
SPLDLSNQINSINKSLKSAEDWIADSNFFANQARTAKTLYSLSAIALILSVITLVVVG
LLIAYIIKLVSQIHQFRALAATTMFHRENPAVFSKNNHGNIYGIS"

```
gene       2205...3920
           /gene = "HN"
CDS        2205..3920 (fragment 2205-3920 of SEQ ID NO: 22  =  SEQ ID NO: 25;
cf. FIG. 6)
           /gene = "HN"
           /codon start = 1
           /product = "Haemagglutinin-neuraminidase" (SEQ ID NO: 26)
```

/translation = "MEDYSNLSLKSIPKRTCRIIFRTATILGICTLIVLCSSILHEII
HLDVSSDLMNSDESQQGIIQPIIESLKSLIALANQILYNVAIVIPLKIDSIETVILSALK
DMHTGSMSNANCTPGNLLLHDAAYINGINKFLVLESYNGTPKYGPLLNIPSFIPSAT
SPHGCTRIPSFSLIRTHWCYTHNVILGDCLDFTASNQYLSMGIIQQSAAGFPIFRTMK
TIYLSDGINRKSCSVTAIPGGCVLYCYVATRSEKEDYATTDLAELRLAFYYNDTFI
ERVISLPNTTGQWATINPAVGSGIYHLGFILFPVYGGLINGTTSYNEQSSRYFIPKHP
NITCAGNSSKQAAIARSSYVIRYHSNRLIQSAVLICPLSDMHTEECNLVMFNNSQV
MMGAEGRLYVIGNNLYYYQRSSSWWSASLFYRINTDFSKGIPPIIEAQWVPSYQVP
RPGVMPCDATSFCPANCITGVYADVWPLNDPELMSRNALNPNYRFAGAFLKNESNRTNP
TFYTASSNSLLNTTGFNKTNHKAAYTSSTCFKNTGTQKIYCLIIIEMGSSLLGEFQIIPFLRELML"

NUMBER OF BASES 1395 a  954 c  699 g  1285 t

ORIGIN (SEQ ID NO: 22)

```
   1 atgctccagc atctaggaat agaacaacaa ctaagtcata ccattattga ccatacaata
  61 atcaacaatt ttagccaact gattactaag atattatcat aggtccgaac tgatcaatct
 121 aacaaaaaaa ctaaacattc aataataaat caaagttcag gccaaattat ccagccatgc
 181 atcacctgca tccaatgata gtatgcatct ttgttatgta cactggaatt gtaggttcag
 241 atgccattgc tggagatcaa ctcctcaatg taggggtcat tcaatcaaag ataagatcac
 301 tcatgtacta cactgatggt ggcgctagct ttattgttgt aaaattacta ccaaatcttc
 361 ccccaagcaa tggaacatgc aacatcacca gtctagatgc atataatgtt accctattta
 421 agttgctaac gcccctgatt gagaacctga gcaaaatttc tgctgttaca gataccaaac
 481 ccgccgaga acgatttgca ggagtcgtta ttgggcttgc tgcactagga gtagctacag
 541 ctgcacaaat aaccgcagct gtagcaatag taaaagccaa tgcaaatgct gctgcgataa
 601 acaatcttgc atcttcaatt caatccacca acaaggcagt atccgatgtg ataactgcat
 661 caagaacaat tgcaaccgca gttcaagcaa ttcaggatcg catcaatgga gctattgtta
 721 atgggataac atctgcatca tgccgtgccc atgatgcact aattgggtca atattaaatt
 781 tgtatctcac tgagcttact acaatatttc ataatcaaat aacaaaccct gcgctgacac
 841 cactttccat ccaagcttta agaatcctcc tcggtagcac cttgccaatt gtcattgaat
 901 ccaaactcaa cacaaaactc aacacagcag agctgctcag ttccggactg ttaactggtc
 961 aaataatttc catttcccca atgtacatgc aaatgctaat tcaaatcaat gttccgacat
1021 ttataatgca acccggtgcg aaggtaattg atctaattgc tatctctgca accataaat
1081 tacaagaagt agttgtacaa gttcctaata gaattcagaa atacgcaaat gaactacaaa
1141 actacccagc caatgattgt gtcgtgacac caaactctgt atttgtaga tacaatgagg
1201 gttccccgat ccctgaatca caatatcaat gcttaagggg gaatcttaat tcttgcactt
1261 ttacccctat tatcgggaac tttctcaagc gattcgcatt tgccaatggt gtgctctatg
1321 ccaactgcaa atctttgcta tgtaagtgtg ccgaccctgc ccatgttgtg tctcaagatg
1381 acaaccaagg catccagcata attgatatta agaggtgctc tgagatgatg cttgcacctt
1441 tttcatttag gatcacatct acattcaatg ctacatacgt gacagacttc aatgatta
1501 atgcaaatat tgtacatcta agtcctctag acttgtcaaa tcaaattaat tcaataaaca
1561 aatctcttaa aagtgctgaa gattggattg cagatagcaa cttcttcgct aatcaagcca
1621 gaacagccaa gacactttat tcactaagtg caatagcatt aatactatca gtgattactt
1681 tggttgttgt gggattgctg attgcctaca tcatcaagct ggtttctcaa atccatcaat
1741 tcagagcact agctgctaca acaatgttcc acaggagaa tcctgctgtc ttttccaaga
1801 acaatcatgg aaacatatat gggatatctt aagaattcta tcataagtcc atatatgtcc
1861 atgattgacc tttaagagcc aacctccaat gattatccgt taattcaga tataacaatt
1921 caaaaatcaa tattaagcct ccagataccca atgaatatga atatatctct tagaaaactt
1981 gattattatg tgataacata gtacaattta agaaaaaacc taaataagc acgaacccctt
2041 aaggtgtcgt aacgtctcgt gacgccgggt tcagttcaaa catcgacccc tgacccaatt
2101 caatacccat ttccataaag gaacacagta taatttaatc ataaaagacc tcaaaatctg
2161 atacagctta atccactcaa catataatta taagactaat aataatggaa gattacagca
2221 atctatctct taaatcaatt cctaaaagga catgtagaat cattttccga actgccacaa
2281 ttcttggcat atgcacatta attgtgctat gttcaagtat tcttcatgag ataattcatc
2341 ttgatgtttc ctctgatctt atgaattctg atgagtcaga gcaaggcatt atccagccta
2401 tcatagaatc attaaaatca ttgattgctt tggccaacca gattctatat aatgttgcaa
2461 tagtaattcc tcttaaaatt gacagtatcg aaactgtaat actctctgct taaaaagata
2521 tgcacaccgg gagtatgtcc aatgccaact gcacgccagg aaatctactt ctgcatgatg
2581 cagcatacat caatggaata aacaaattcc ttgtacttga atcatccagt gggacgccta
2641 aatatggacc tctcctaaat atacccagct ttatccccctc agcaacatct cccatgggt
2701 gtactagaat accatcattt tcactcatca ggacccattg gtgttacact cacatgtaa
2761 tacttggaga ttgtcttgat ttcacggcat ctaaccagta tttatcaatg gggataatac
2821 aacaatctgc tgcagggttt ccaattttca ggactatgaa aaccatttac ctaagtgatg
2881 gaatcaatcg caaagctgt tcagtcactg ctataccagg aggttgtgtc ttgtattgct
```

-continued

```
2941 atgtagctac aaggtctgaa aaagaagatt atgccacgac tgatctagct gaactgagac
3001 ttgccttcta ttattataat gatacctta ttgaaagagt cat -continued RPGVMPCNATSFCPANCITGVYADVWPLNDPELMSRNALNPNYRFAGAFLKNESN
RTNPTFYTASSNSLLNTTGFNKTNHKAAYTSSTCFKNTGTQKIYCLIIIEMGSSLLGE
FQIIPFLRELML"

NUMBER OF BASES 1399 a 953 c 694 g 1287 t

ORIGIN
(SEQ ID NO: 27)

```
   1 gaatgctcca gcatctagga atagaacaac aactaagtca taccattatt gaccatacaa
  61 taatcaacaa ttttagccaa ctgattacta agatattatc ataggtccga actgatcaat
 121 ctaacaaaaa aactaaacat tcaataataa atcaaagttc aggccaaatt atccagccat
 181 gcatcacccg catccaatga tagtatgcat ctttgttatg tacactggaa ttgtaggttc
 241 agatgccatt gctggagatc aactcctcaa tgtaggggtc attcaatcaa agataagatc
 301 actcatgtac tacactgatg gtggcgctag ctttattgtt gtaaaattac taccaaatct
 361 tccccccaagc aatggaacat gcaacatcac cagtctagat gcatataatg ttaccctatt
 421 taagttgcta acgcccctga ttgagaacct gagcaaaatt tctgctgtta cagataccaa
 481 accccgccga gaacgatttg caggagtcgt tattgggctt gctgcactag gagtagctac
 541 agctgcacaa ataaccgcag ctgtagcaat agtaaaagcc aatgcaaatg ctgctgcgat
 601 aaacaatctt gcatcttcaa ttcaatccac caacaaggca gtatccgatg tgataactgc
 661 atcaagaaca attgcaaccg cagttcaagc aattcaggat cgcatcaatg gagctattgt
 721 taatgggata acatctgcat catgccgtgc ccatgatgca ctaattgggg caatattaaa
 781 tttgtatctc actgagctta ctacaatatt tcataatcaa ataacaaacc ctgcgctgac
 841 accactttcc atccaagctt taagaatcct cctcggtagc accttgccaa ttgtcattga
 901 atccaaactc aacacaaaac tcaacacagc agagctgctc agttccggac tgttaactgg
 961 tcaaataatt tccatttccc aatgtacat gcaaatgcta attcaaatca atgttccgac
1021 atttataatg caacccggtg cgaaggtaat tgatctaatt gctatctctg caaaccataa
1081 attacaagaa gtagttgtac aagttcctaa tagaattcta gaatacgcaa atgaactaca
1141 aaactaccca gccaatgatt gtgtcgtgac accaaactct gtattttgta gatacaatga
1201 gggttccccg atccctgaat cacaatatca atgcttaagg gggaatctta attcttgcac
1261 ttttaccccct attatcggga acttctcaa gcgattcgca tttgccaatg gtgtgctcta
1321 tgccaactgc aaatctttgc tatgtaagtg tgccgaccct cccatgttg tgtctcaaga
1381 tgacaaccaa ggcatcagca taattgatat taagagatgc tctgagatga tgcttgacac
1441 ttttttcattt aggatccat ctacattcaa tgctacatac gtgacagact tctcaatgat
1501 taatgcaaat attgtacatc taagtcctct agacttgtca aatcaaatca attcaataaa
1561 caaatctctt aaaagtgctg aggattggat tgcagatagc aacttcttcg ctaatcaagc
1621 cagaacagcc aagacacttt attcactaag tgcaatacca ttaatactat cagtgattac
1681 tttggttgtt gtgggattgc tgattgccta catcatcaag ctgatttctc aaatccatca
1741 attcagagca ctagctgcta caacaatgtt ccacagggag aatcctgccg tctttttccaa
1801 gaacaatcat ggaaacatat atgggatatc ttaagaattc tatcataagt ccatatatgt
1861 ccatgattga cctttaagag ccaacctcca atgattatcc gttaaattca gatataacaa
1921 ttcaaaaatc aatattaagc ctccagatac caatgaatat gaatatatct cttagaaaac
1981 ttgattatta tgtgataaca tagtacaatt taagaaaaaa cctaaaataa gcacgaaccc
2041 ttaaggtgtc gtaacgtctc gtgacgccgg gttcagttca aacatcgacc cctgacccaa
2101 ttcaataccc attttcataa aggaacacag tataatttaa tcataaaaga cctcaaaatc
2161 tgatacagct taatccactc aacatataat tataagacta ataataatgg aagattacag
2221 caatctatct cttaaatcaa ttcctaaaag gacatgtaga atcattttcc gaactgccac
2281 aattcttggc atatgcacat taattgtgct atgttcaagt attcttcatg agataattca
2341 tcttgatgtt tcctctggtc ttatgaattc tgatgagtca cagcaaggca ttatccagcc
2401 tatcatagaa tcattaaaat cattgattgc tttggccaac cagattctat ataatgttgc
2461 aatagtaatt cctcttaaaa ttgacagtat cgaaactgta atactctctg ctttaaaaga
2521 tatgcacacc gggagtatgt ccaatgccaa ctgcacgcca ggaaatctac ttctgcatga
2581 tgcagcatac atcaatggaa taaacaaatt cctgtactt gaatcataca atgggacgcc
2641 taaatatgga cctctcctaa atatacccag cttttatcccc tcagcaacat ctccccatgg
2701 gtgtactaga ataccatcat tttcactcat caagacccat tggtgttaca ctcacaatgt
2761 aatacttgga gattgtcttg atttcacagc atctaaccag tatttatcaa tggggataat
2821 acaacaatct gctgcagcat ttccattttt caggactatg aaaccatttt acctaagtga
2881 tggaatcaat cgcaaaagct gttcagtcac tgctatacca ggaggttgtg tcttgtattg
2941 ctatgtagct acaaggtctg aaaaagaaga ttatgccacg actgatctag ctgaattgag
3001 acttgccttc tattattata atgataccct tattgaaaga gtcatatctc ttccaaatac
3061 aacagggcag tgggccacaa tcaaccctgc agtcggaagc gggatctatc atctaggctt
3121 tatcttattt cctgtatatg gtggtctcat aaatgggact acttcttaca atgagcagtc
3181 ctcacgctat tttatcccaa aacatcccaa cataacttgt gccggtaact ccagcaaaca
3241 ggctgcaata gcacggagtt cctatgtcat ccgttatcac tcaaacaggt taattcagag
3301 tgctgttctt atttgtccat tgtctgacat gcacacagaa gagtgtaatc tagttatgtt
3361 taacaattct caagtcatga tgggtgcaga aggtaggctc tatgttattg gtaataattt
3421 gtattattat caacgcagtt cctcttggtg gtctgcatcg ctctttttaca ggatcaatac
3481 agattttttct aaaggaattc ctccgatcat tgaggctcaa tgggtaccgt cctatcaagt
3541 tcctcgtcct ggagtcatgc catgcaatgc aacaagtttt tgccctgcta ttgcatcac
3601 aggggtgtac gcagatgtgt ggccgcttaa tgatccagaa ctcatgtcac gtaatgctct
3661 gaaccccaac tatcgatttg ctggagcctt tctcaaaaat gagtccaacc gaactaatcc
3721 cacattctac actgcatcgt ctaactccct cttaaatact accggattca acaaaaccaa
3781 tcacaaagca gcatatacat cttcaacctg ctttaaaaat actggaaccc aaaaaattta
3841 tgttttaata ataattgaaa tgggctcatc tcttttaggg gagttccaaa taataccatt
3901 tttaagggaa ctaatgcttt aatcctattg aatgaagact ccagattcaa gaataattgg
3961 aaggctcttt attttatgcg atagttatac gttttggctg tattagaatg ctatagcatt
4021 ctgctgtttt tcccatatgg aaaaatcctt caacaccaac ttaggttcaa ttttctcatc
4081 atttactgtt gtaattcaat cttactaaag ttattctgat atttaagaaa aaataatctt
4141 tatataatgt aacaatacta ctaagattat aatataggcc agaatggcgg cctcttctga
```

```
4201 gatactcctt cctgaagtcc attgaactca ccaatagtca aacacaaact catatactac
4261 ttatatctag ggcacttccc acatgatctt gacatttctg aaataagccc ccttcacaat
4321 aatgattggg atc
//
```

SEQ ID NO: 32-36 (Isolate 20435)

```
LOCUS       bankit721328 4335 bp ARN linear
DEFINITION Complete CDS for F and HN genes of 20435/1997/Lyon isolate
from human parainfluenza type 2 virus, coding for the fusion protein
(F) and haemagglutinin-neuraminidase (HN)
ACCESSION Genbank accession number DQ072588
REFERENCE 1 (bases 1 to 4335) (SEQ ID NO: 32)
FEATURES   Location/Qualifiers
source     1...4335
           /Organism = "Human parainfluenza type 2 virus"
           isolate = "20435/1997/Lyon"
           /db_xref = "taxon:11212"
           /state = "France"
           /note = "type:2"
gene       179...1834
           /gene = "F"
CDS        179...1834 (fragment 179-1834 of SEQ ID NO: 32 =
           SEQ ID NO: 33; cf. FIG. 5)
           /gene = "F"
           /codon start = 1
           /product = "fusion protein" (SEQ ID NO: 34)

/translation = "MHHLHPMIVCIFVMYTGIVGSDAIAGDQLLNVGVIQSKIRSLMYYTDGGASFIVVKL
LPNLPPSNGTCNITSLDAYNVTLFKLLTPLIENLSKISAVTDTKPRRERFAGVVIGLAALGVATAAQITAA
VAIVKANANAAAINNLASSIQSTNKAVSDVITASRTIATAVQAIQDRINGAIVNGITSASCRAHDALIGSI
LNLYLTELTTIFHNQITNPALTPLSIQALRILLGSTLPIVIESKLNTKLNTAELLSSGLLTGQIISISPMY
MQMLIQINVPTFIMQPGAKVIDLIAISANHKLQEVVVQVPNRILEYANELQNYPANDCVVTPNSVFCRYNE
GSPIPESQYQCLRGNLNSCTFTPIIGNFLKRFAFANGVLYANCKSLLCKCADPPHVVSQDDNQGISIIDIK
RCSEMMLDTFSRITSTFNATYVTDFSMINANIVHLSPLDLSNQINSINKSLKSAEDWIADSNFFANQART
AKTLYSLSAIALILSVITLVVVGLLIAYIIKLISQIHQFRALAATTMFHRENPAVFSKNNHGNIYGIS"

gene       2207...3922
           /gene = "HN"
CDS        2207...3922 (fragment 2207-3922 of SEQ ID NO: 32 =
           SEQ ID NO: 35; cf. FIG. 6)
           /gene = "HN"
           /codon start = 1
           /product = "haemagglutinin-neuraminidase" (SEQ ID NO: 36)

/translation = "MEDYSNLSLKSIPKRTCRIIFRTATILGICTLIVLCSSILHEIIHLD
VSSGLMNSDESQQGIIQPIIESLKSLIALANQILYNVAIIPLKIDSIETVILSALKDMHTGSMSNANCTP
GNLLLHDAAYINGINKFLVLESYNGTPKYGPLLNIPSFIPSATSPHGCTRIPSFSLIKTHWCYTHNVILGD
CLDFTASDQYLSMGIIQQSAAGFPIFRTMKTIYLSDGINRKSCSVTAIPGGCVLYCYVATRSEKEDYATTD
LAELRLAFYYYNDTFIERVISLPNTTGQWATINPAVGSGIYHLGFILFPVYGGLINGTTSYNEQSSRYFIP
KHPNITCAGNSSKQAAIARSSYVIRYHSNRLIQSAVLICPLSDMHTEECNLVMFNNSQMVMGAEGRLYVID
NNLYYYQRSSSWWSASLFYRINTDFSKGIPPIIEAQWVPSYQVPRPGVMPCNATSFCPANCITGVYADVWP
LNDPELMSRNALNPNYRFAGAFLKNESNRTNPTFYTASSNSLLNTTGFNKTNHKAAYTSSTCFKNTGTQKI
YCLIIIEMGSSLLGEFQIIPFLRELML"

NUMBER OF BASES 1401 a 950 c 695 g 1289 t

ORIGIN
                                                       (SEQ ID NO: 32)
    1 gaatgctcca gcatctagga atagaacaac aactaagtca taccattatt gaccatacaa
   61 taatcaacaa ttttagccaa ctgattacta agatattatc ataggtccga actgatcaat
  121 ctaacaaaaa aactaaacat tcaataataa atcaaagttc aggccaaatt atccagccat
  181 gcatcacctg catccaatga tagtatgcat ctttgttatg tacactggaa ttgtaggttc
  241 agatgccatt gctggagatc aactcctcaa tgtaggggtc attcaatcaa agataagatc
  301 actcatgtac tacactgatg gtggcgctag ctttattgtt gtaaaattac taccaaatct
  361 tcccccaagc aatggaacat gcaacatcac cagtctagat gcatataatg ttacccttatt
  421 taagttgcta acgcccctga ttgagaacct gagcaaaatt tctgctgtta cagataccaa
  481 accccgccga gaacgatttg caggagtcgt tattgggctt gctgcactag gagtagctac
  541 agctgcacaa ataaccgcag ctgtagcaat agtaaaagcc aatgcaaatg ctgctgcgat
  601 aaacaatctt gcatcttcaa ttcaatccac caacaaggca gtatccgatg tgataactgc
  661 atcaagaaca attgcaaccg cagttcaagc cgcatcaagg agctattgt
  721 taatgggata acatctgcat catgccgtgc ccatgatgca ctaattgggt caatattaaa
  781 tttgtatctc actgagctta ctacaatatt tcataatcaa ataacaaacc ctgcgctgac
  841 accactttcc atccaagctt taagaatcct cctcggtagc accttgccaa ttgtcattga
  901 atccaaactc aacacagaac tcaacacage agagctgctc agttccggac tgttaactgg
  961 tcaaataatt tccatttccc caatgtacat gcaaatgcta attcaaatca atgttccgac
 1021 atttataatg caacccggtg cgaaggtaat tgatcctaatt gctatctctg caaaccataa
 1081 attacaagaa gtagttgtac aagttcctaa tagaattcta gaatacgcaa atgaactaca
 1141 aaactaccca gccaatgatt gtgtcgtgac accaaactct gtattttgta gatacaatga
```

```
-continued
1201 gggttccccg atccctgaat cacaatatca atgcttaagg gggaatctta attcttgcac
1261 ttttaccccct attatcggga actttctcaa gcgattcgca tttgccaatg gtgtgctcta
1321 tgccaactgc aaatctttgc tatgtaagtg tgccgaccct ccccatgttg tgtctcaaga
1381 tgacaaccaa ggcatcagca taattgatat taagagatgc tctgagatga tgcttgacac
1441 tttttcattt aggatcacat ctacattcaa tgctacatac gtgacagact tctcaatgat
1501 taatgcaaat attgtacatc taagtcctct agacttgtca aatcaaatca attcaataaa
1561 caaatctctt aaaagtgctg aggattggat tgcagatagc aacttcttcg ctaatcaagc
1621 cagaacagcc aagacacttt attcactaag tgcaatagca ttaatactat cagtgattac
1681 tttggttgtt gtgggattgc tgattgccta catcatcaag ctgatttctc aaatccatca
1741 attcagagca ctagctgcta caacaatgtt ccacagggag aatcctgccg tcttttccaa
1801 gaacaatcat ggaaacatat atgggatatc ttaagaattc tatcataagt ccatatatgt
1861 ccatgattga cctttaagag ccaacctcca atgattatcc gttaaattca gatataacaa
1921 ttcaaaaatc aatattaagc ctccagatac caatgaatat gaatatatct cttagaaaac
1981 ttgattatta tgtgataaca tagtacaatt taagaaaaaa cctaaaataa gcacgaaccc
2041 ttaaggtgtc gtaacgtctc gtgacgccgg gttcagttca aacatcgacc cctgacccaa
2101 ttcaataccc attttcataa aggaacacag tataatttaa tcataaaaga cctcaaaatc
2161 tgatacagct taatccactc aacatataat tataagacta ataataatgg aagattacag
2221 caatctatct cttaaatcaa ttcctaaaag gacatgtaga atcatttttcc gaactgccac
2281 aattcttggc atatgcacat taattgtgct atgttcaagt attcttcatg agataattca
2341 tcttgatgtt tcctctggtc ttatgaattc tgatgagtca cagcaaggca ttatccagcc
2401 tatcatagaa tcattaaaat cattgattgc tttggccaac cagattctat ataatgttgc
2461 aataataatt cctcttaaaa ttgacagtat cgaaactgta atactctctg ctttaaaaga
2521 tatgcacacc gggagtatgt ccaatgccaa ctgcacgcca ggaaatctac ttctgcatga
2581 tgcagcatac atcaatggaa taaacaaatt ccttgtactt gaatcataca atgggacgcc
2641 taaatatgga cctctcctaa atatacccag ctttatcccc tcagcaacat ctccccatgg
2701 gtgtactaga ataccatcat tttcactcat caagacccat tggtgttaca ctcacaatgt
2761 aatacttgga gattgtcttg atttcacagc atctgaccag tatttatcaa tggggataat
2821 acaacaatct gctgcagggt ttccaatttt caggactatg aaaaccattt acctaagtga
2881 tggaatcaat cgcaaaagct gttcagtcac tgctatacca ggaggttgtg tcttgtattg
2941 ctatgtagct acaaggtctg aaaaagaaga ttatgccacg actgatctag ctgaattgag
3001 acttgccttc tattattata atgataccct tattgaaaga gtcatatctc ttccaaatac
3061 aacagggcag tgggccacaa tcaaccctgc agtcggaagc gggatctatc atctaggctt
3121 tatcttattt cctgtatatg tggtctcat aaatgggact acttcttaca atgagcagtc
3181 ctcacgctat tttatcccaa aacatcccaa cataacttgt gccggtaact ccagcaaaca
3241 ggctgcaata gcacggagtt cctatgtcat ccgttatcac tcaaacaggt taattcagag
3301 tgctgttctt atttgtccat tgtctgacat gcacacagaa gagtgtaatc tagttatgtt
3361 taacaattcc caagtcatga tgggtgcaga aggtaggctc tatgttattg acaataattt
3421 gtattattat caacgtagtt cctcttggtg gtctgcatcg cttttttaca ggatcaatac
3481 agattttctc aaaggaattc ctccgatcat tgaggctcaa tgggtaccgt cctatcaagt
3541 tcctcgtcct ggagtcatgc catgcaatgc aacaagtttt tgccctgcta attgcatcac
3601 aggggtgtac gcagatgtgt ggccgcttaa tgatccagaa ctcatgtcac gtaatgctct
3661 gaaccccaac tatcgatttg ctggagcctt tctcaaaaat gagtccaacc gaactaatcc
3721 cacattctac actgcatcgt ctaactccct tcaaaatact accggattca acaaaaccaa
3781 tcacaaagca gcatatacat cttcaacctg ctttaaaaat actggaaccc aaaaaattta
3841 ttgtttaata ataattgaaa tgggctcatc tctttaggg gagttccaaa taataccatt
3901 tttaagggaa ctaatgcttt aatcctattg aatgaagact ccagattcaa gaataattgg
3961 aaggctcttt attttatgcg atagttatac gttttgggctg tattagaatg ctatagcatt
4021 ctgctgtttt tcccatatgg aaaaatcctt caacaccaac ttaggttcaa ttttctcatc
4081 atttactgtt gtaattcaat cttactaaag ttattctgat atttaagaaa aaataatctt
4141 tatataatgt aacaatacta ctaagattat aatataggcc agaatggcgg cctttttctga
4201 gatactcctt cctgaagtcc atttgaactc accaatagtc aaacacaaac tcatatacta
4261 cttattacta gggcacttcc cacatgatct tgacatttct gaaataagcc cccttcacaa
4321 taatgattgg gatca
//
```

SEQ ID NO: 37-41 (Isolate 26056)

```
LOCUS       bankit721330 4394 bp ARN linear VRL 24-MAY-2005
DEFINITION Complete CDS for F and HN genes of 26056/1997/Lyon isolate
from human parainfluenza type 2 virus, coding for the fusion protein (F)
and haemagglutinin-neuraminidase (HN)
ACCESSION Genbank accession number DQ072589
REFERENCE 1 (bases 1 to 4394) (SEQ ID NO: 37)
FEATURES   Location/Qualifiers
source     1...4394
           /Organism = "Human parainfluenza type 2 virus"
           /isolate = "26056/1997/Lyon"
           /db_xref = "taxon:11212"
           /state = "France"
           /note = "type: 2"
gene       179...1834
           /gene = "F"
CDS        179...1834 (fragment 179-1834 of SEQ ID NO: 37 =
           SEQ ID NO: 38; cf. FIG. 5)
           /gene = "F"
           /codon start = 1
           /product = "fusion protein" (SEQ ID NO: 39)

/translation="MHHLHPMIVCIFVMYTGIVGSDAIAGDQLLNVGVIQSKIRSLMYYTDGGASFIVVKLL
```

-continued

PNLPPSNGTCNITSLDAYNVTLFKLLTPLIENLSKISAVTDTKPRRERFAGVVIGLAALGVATAAQITAAVA
IVKANANAAAINNLASSIQSTNKAVSDVITASRTIATAVQAIQDRINGAIVNGITSASCRAHDALIGSILNL
YLTELTTIFHNQITNPALTPLSIQALRILLGSTLPIVIESKLNTKLNTAELLSSGLLTGQIISISPMYMQML
IQINVPTFIMQPGAKVIDLIAISANHKLQEVVVQVPNRILEYANELQNYPANDCVVTPNSVFCRYNEGSPIP
ESQYQCLRGNLNSCTFTPIIGNFLKRFAFANGVLYANCKSLLCKCADPPHVVSQDDTQGISIIDIKRCSEMM
LDTFSFRITSTFNATYVTDFSMINANIVHLSPLDLSNQINSINKSLKSAEDWIADSNFFANQARTAKTLYSL
SAIAILSVITLVVVGLLIAYIIKLVSQIHQFRALAATTMFHRENPAVFSKNNHGNIYGIS"

```
gene      2207...3922
          /gene = "HN"
CDS       2207...3922 (fragment 2207-3922 of SEQ ID NO: 37 =
          SEQ ID NO: 40; cf. FIG. 6)
          /gene = "HN"
          /codon start = 1
          /product = "haemagglutinin-neuraminidase" (SEQ ID NO: 41)
```

/translation = "MEDYSNLSLKSIPKRTCRIIFRTATILGICTLIVLCSSILHEIIHLDVSSGLMDSDES
QQGIIQPIIESLKSLIALANQILYNVAIIIPLKIDSIETVILSALKDMHTGSMSNANCTPGNLLLHDAAYIN
GINKFLVPESYNGTPKYGPLLNIPSFIPSATSPNGCTRIPSFSLIKTHWCYTHNVILGDCLDFTASNQYLSM
GIIQQSAAGFPIFRTMKTIYLSDGINRKSCSVTAIPGGCVLYCYVATRSEKEDYATTDLAELRLAFYYNDT
FIERVISLPNTTGQWATINPAVGSGIYHLGFILFPVYGGLINGTTSYNEQSSRYFIPKHPNITCAGNSSKQA
AIARNSYVIRYHSNRLIQSAVLICPLSDMHTEECNLVMFNNSQMVMGAEGRLYVIGNNLYYYQRSSSWWSAS
LFYRINTDFSKGIPPIIEAQWVPSYQVPRPGVMPCNATSFCPANCITGVYADVWPLNDPELMSRNALNPNYR
FAGAFLKNESNRTNPTFYTASANSLLNTTGFNNTNHKAAYTSSTCFKNTGNQKIYCLIIIEMGSSLLGEFQI
IPFLRELML"

NUMBER OF BASES 1416 a 961 c 714 g 1303 t

ORIGIN (SEQ ID NO: 37)
```
   1 gaatgctcca gcatctagga atagaacaac agctaagtca taccattatt gaccatacaa
  61 taatcaacaa ttttagccaa ctgattacta agatattatc ataggtccga actgatcaat
 121 ctaacaaaaa aactaaacat tcaataataa atcaaagttc aggccaaatt atccagccat
 181 gcatccacctg catccaatga tagtatgcat ctttgttatg tacactggaa ttgtaggttc
 241 agatgccatt gctgagatca aactcctcaa tagtagggtc attcaatcaa agtaagatct
 301 actcatgtac tacactgatg gtggcgctag ctttattgtt gtaaaattac tacccaatct
 361 tcccccaagc aatggaacat gcaacatcac cagtctagat gcatataatg ttaccctatt
 421 taagttgcta acaccctga ttgagaacct gagcaaaatt tccgctgtta cagataccaa
 481 accccgccga gaacgatttg caggggtcgt tattgggcgt gctgcactag gagtagctac
 541 agctgcacaa ataaccgcag ctgtagcaat agtgaaagcc aatgcaaatg ctgctgcgat
 601 aaacaatctt gcatcttcaa ttcaatccac caacaaggca gtatccgatg tgataactgc
 661 atcaagaaca attgcaaccg cagttcaagc aattcaggat cgcatcaatg gagccattgt
 721 caacgggata acatctgcat catgccgtgc ctaattgggt caatattaaa
 781 tttgtatctc actgagctta ctacaatatt tcataatcaa ataacaaacc ctgcgctgac
 841 accactttcc atccaagctt taagaatcct cctcggtagc accttgccaa ttgtcatcga
 901 atccaagctc aacacaaaac tcaacacagc agagttactc agttccggac tgttaactgg
 961 tcaaataatt tccatttccc caatgtacat gcaaatgcta attcaaatca atgttccgac
1021 atttataatg caacccggtg cgaaggtaat tgatctaatt gctatctctg caaaccataa
1081 attacaagaa gtagttgtac aagttcctaa tagaattcta gagtatgcaa atgaactaca
1141 aaactaccca gccaatgatt gtgtcgtgac accaaactct gtattttgta gatacaatga
1201 gggttccccg atccctgaat cacaatatca atgcttaagg gggaatctta attcttgcac
1261 ttttaccct attatcggaa actttctcaa gcgattcgca tttgccaatg gtgtgctcta
1321 tgccaactgc aaatctttgc tatgtaagtg tgccgaccct ccccatgttg tgtctcaaga
1381 tgacacccaa ggcatcagca taattgatat taagaggtgc tctgagatga tgcttgacac
1441 tttttcattt aggatcacat ctacattcaa tgctacatac gtgacagact tctcaatgat
1501 taatgcaaat attgtacatc taagtcctct agacttgtca aatcaaatca attcaataaa
1561 caaatctctt aaaagtgctg aggattggat tgcagatagc aacttcttg ctaatcaagc
1621 cagaacagcc aagcactttt attcactaag tgcaatagca ttaatactat cagtgattac
1681 tttggttgtc gtgggattgc tgattgccta catcatcaag ctggtttctc aaatccatca
1741 attcagagca ctagctgcta caacaatgtt ccacagggag aatcctgccg tcttttccaa
1801 gaacaatcat ggaaacatat atgggatatc ttaagaattc tatcataagt ccatatatgt
1861 ccatgattga cttttaagag ccaacctcca atgattatcc gttaaattca gatataacag
1921 ttcaaaaatc aatattaagc ctccagatac caatgaatat gaatatatct cttagaaaac
1981 ttgattatta tgtgataaca tagtacaatt taagaaaaaa cctaaaataa gcacgaaccc
2041 ttaaggtgtc gtaacgtctc gtgacgccgg gttcagttca aacatcgacc cctgacccaa
2101 ttcaataccc atttccataa aggaacacag tataatttaa tcataaaaga tctcaaaatc
2161 tgatacagct taatccactc aacatataat tataagacta ataataatgg aagattacag
2221 caatctatct cttaaatcaa ttcctaaaag gacatgtaga atcattttcc gaactgccac
2281 aattcttggc atatgcacat taattgtgct atgttcaagt attcttcatg agataattca
2341 tcttgatgtt tcctctggtc ttatggattc tgatgagtca cagcaaggca tcattcagcc
2401 tatcatagaa tcattaaaat cattgattgc tttggccaac cagattctat ataatgttgc
2461 aataataatt cctcttaaaa ttgacagtat cgaaactgta atactctctg cttttaaaaga
2521 tatgcacacc gggagtatgt ccaatgccaa ctgcacgcca ggaaatttgc ttctgcatga
2581 tgcagcatac atcaatggaa taaacaaatt ccttgtacct gaatcataca atgggacgcc
2641 taaatatgga cctctcctaa atatcccag ctttatcccc tcagcaacat ctcccaatgg
2701 gtgtactaga ataccatcat tttcactcat caagacccat tggtgttaca ctcacaatgt
2761 aatcttggga gattgtcttg atttcacagc atctaaccag tatttatcaa tggggataat
2821 acaacaatct gctgcagggt tccaattttt caggactatg aaaccatttt acctaagtga
2881 tggaatcaat cgcaaaagct gttcagtcac tgctatacca ggaggttgtg tcttgtattg
2941 ctatgtagct acaaggtctg aaaaagaaga ttatgccacg actgatctag ctgaactgag
3001 acttgctttc tattattata tgataccttt attgaaaga gtcatatctc ttccaaatac
```

```
3061 aacagggcag tgggccacaa tcaaccctgc agttggaagc gggatctatc atctaggctt
3121 tatcttattt cctgtatatg gtggtctcat aaatgggact acttcttaca atgagcagtc
3181 ctcacgctat tttatcccaa aacatcccaa cataacttgt gccggtaact ccagcaaaca
3241 ggctgcaata gcacggaatt cttatgtcat ccgttatcac tcaaacaggt taattcagag
3301 tgctgttctt atttgtccat tgtctgacat gcacacagaa gagtgtaatc tagttatgtt
3361 taacaattcc caagtcatga tgggtgcaga aggtaggctc tatgttattg gtaataattt
3421 gtattattat caacgcagtt cctcttggtg gtctgcatcg ctttttttaca ggatcaatac
3481 agatttttct aaaggaattc ctccgatcat tgaggctcaa tgggtaccgt cctatcaagt
3541 tcctcgtcct ggagtcatgc catgcaatgc aacaagtttt tgccctgcta attgcatcac
3601 aggggtgtac gcagatgtgt ggccgcttaa tgatccagaa ctcatgtcac gtaatgctct
3661 gaaccccaac tatcgatttg ctggagcctt tctcaaaaat gagtccaacc gaactaatcc
3721 cacatttac actgcatcgg ctaactccct cttaaatact accggattca acaacaccaa
3781 tcacaaagca gcatatacat cttcaacctg ctttaaaaac actggaaacc aaaaaattta
3841 ttgtttaata ataattgaaa tgggctcatc tcttttaggg gagttccaaa taataccatt
3901 tttaagggaa ctaatgcttt aatcctattg aatgaagact ccagattcaa gaataattgg
3961 aaggctcttt attttatgcg atagttatac gttttggctg tattagaatg ctatagcatt
4021 ctgctgtttt tcccatatgg aaaaatcctt caacaccaac ttaggttcaa ttttctcatc
4081 atttactgtt gtaattcaat tttactaaaa ttattctgat atttaagaaa aaataatctt
4141 tatataatgt aacaatacta ctaagattat gatataggcc agaatggcgg cctcttctga
4201 gatactcctt cctgaagtcc atttgaactc accaatagtc aaacacaaac tcatatacta
4261 cttattacta gggcacttcc cgcatgatct tgacatttct gaaataagcc cccttcacaa
4321 taatgattgg gatcagattg ccagagaaga atccaacaga agagtgtaat ctagttatgt
4381 ttaacaattc ccaa
//
```

SEQ ID NO: 42-44 (Isolate 26632)

```
LOCUS      bankit721338 2472 bp ARN linear VRL 24-MAY-2005
DEFINITION Complete CDS for F and HN genes of 26632/1997/Lyon isolate
from human parainfluenza type 2 virus, coding for the fusion protein
(F) and haemagglutinin-neuraminidase (HN)
ACCESSION Genbank accession number DQ 72590
REFERENCE 1 (bases 1 to 2472) (SEQ ID NO: 42)
FEATURES   Location/Qualifiers
source     1...2472
           /Organism = "Human parainfluenza type 2 virus"
           isolate = "26632/1997/Lyon"
           /db_xref = "taxon:11212"
           /state = "France"
           /note = "type: 2"
gene       179...1834
           /gene = "F"
CDS        179...1834 (fragment 179-1834 of SEQ ID NO: 42 =
           SEQ ID NO: 43; cf. FIG. 5)
           /gene =" F"
           /codon start = 1
           /product = "fusion protein" (SEQ ID NO: 44)

/translation = "MHHLHPMIVCIFVMYTGIVGSDAIAGDQLLNVGVIQSKIRSLMYYTDGGASFIVVKL
LPNLPPSNGTCNITSLDAYNVTLFKLLTPLIENLSKISAVTDTKPRRERFAGVVIGLAALGVATAAQITAA
VAIVKANANAAAINNLASSIQSTNKAVSDVITASRTIATAVQAIQDRINGAIVNGITSASCRAHDALIGSI
LNLYLTELTTIFHNQITNPALTPLSIQALRILLGSTLPIVIESKLNTKLNTAELLSSGLLTGQIISISPMY
MQMLIQINVPTFIMQPGAKVIDLIAISANHKLQEVVVQVPNRILEYANELQNYPANDCVVTPNSVFCRYNE
GSPIPESQYQCLRGNLNSCTFTPIIGNFLKRFAFANGVLYANCKSLLCKCADPPHVVSQDDNQGISIIDIK
RCSEMMLDTFSFRITSTFNATYVTDFSMINANIVHLSPLDLSNQINSINKSLKSAEDWIADSNFFANQART
AKTLYSLSAIALILSVITLVVVGLLIAYIIKLVSQIHQFRALAATTMFHRENPAVFSKNNHGNIYGIS"

NUMBER OF BASES 829 a  546 c  388 g  709 t

ORIGIN
                                                            (SEQ ID NO: 42)
    1 gaatgctcca gcatctagga atagaacaac aactaagtca taccattatt gaccatacaa
   61 taatcaacaa ttttagccaa ctgattacta agatattatc ataggtccga actgatcaat
  121 ctaacaaaaa aactaaacat tcaataataa atcaaagttc aggccaaatt atccagccat
  181 gcatcacctg catccaatga tagtatgcat ctttgttatg tacactggaa ttgtaggttc
  241 agatgccatt gctggagatc aactcctcaa tgtgggagtc attcaatcaa agataagatc
  301 actcatgtac tacactgatg gtggcgctag cttttattgt gtaaaattac taccaaatct
  361 tccccaagc aatggaacat gcaacatcac cagtctagat gcatataatg ttaccctatt
  421 taagttgcta acgcccctga ttgagaacct gagcaaaatt tctgctgtta cagataccaa
  481 accccgccga gaacgatttg caggagtcgt tattgggctt gctgcactag gagtagctac
  541 agctgcacaa ataaccgcag ctgtagcaat agtaaaagcc aatgcaaatg ctgctgcgat
  601 aaacaatctt gcatcttcaa ttcaatccac caacaaggca gtatccgatg tgataactgc
  661 atcaagaaca attgcaaccg cagttcaagc aattcaggat cgcatcaatg gagccattgt
  721 caacgggata acatctgcat catgccgtgc ccatgatgca ctaattgggt caatattaaa
  781 tttgtatctc actgagcta ctacaatatt tcataatcaa ataacaaacc ctgcgctgac
  841 accactttcc atccaagctt taagaatcct cctcggtagc accttgccaa ttgtcattga
  901 atccaaactc aacacaaaac tcaacacagc agagctgctc agttccggac tgttaactgg
  961 tcaaataatt tccatttccc caatgtacat gcaaatgcta attcaaatca atgttccgac
 1021 atttataatg caacccggtg cgaaggtaat tgatctaatt gctatctctg caaaccataa
```

-continued
```
1081 attacaagaa gtagttgtac aagttcctaa tagaattcta gaatacgcaa atgaactaca
1141 aaactaccca gccaatgatt gtgtcgtgac accaaactct gtattttgta gatacaatga
1201 gggttccccg atccctgaat cacaatatca atgcttaagg gggaatctta attcttgcac
1261 ttttacccct attatcggga actttctcaa gcgattcgca tttgccaatg gtgtgctcta
1321 tgccaactgc aaatctttgc tatgtaagtg tgccgaccct ccccatgttg tgtctcaaga
1381 tgacaaccaa ggcatcagca taattgatat taagaggtgc tctgagatga tgcttgacac
1441 ttttttcattt aggatcacat ctacattcaa tgctacatac gtgacagact tctcaatgat
1501 taatgcaaat attgtacatc taagtcctct agacttgtca aatcaaatca attcaataaa
1561 caaatctctt aaaagtgctg aggattggat tgcagatagc aacttcttcg ctaatcaagc
1621 cagaacagcc aagacacttt attcactaag tgcaatagca ttaatactat cagtgattac
1681 tttggttgtt gtgggattgc tgattgccta catcatcaag ctggtttctc aaatccatca
1741 attcagagca ctagctgcta caacaatgtt ccacagggag aatcctgccg tcttttccaa
1801 gaacaatcat ggaaacatat atgggatatc ttaagaattc tatcataagt ccatatatgt
1861 ccatgattga cctttaagag ccaacctcca atgattatcc gttaaattca gatataacaa
1921 ttcaaaaatc aatattaagc ctccagatac caatgaatat gaatatatct cttagaaaac
1981 ttgattatta tgtgataaca tagtacaatt taagaaaaaa cctaaaataa gcacgaaccc
2041 ttaaggtgtc gtaacgtctc gtgacgccgg gttcagttca aacatcgacc cctgacccaa
2101 ttcaataccc attttcataa aggaacacag tataatttaa tcataaaaga cctcaaaatc
2161 tgatacagct taatccactc aacatataat tataagacta ataataatgg aagattacag
2221 caatctatct cttaaatcaa ttcctaaaag gacatgtaga atcattttcc gaactgccac
2281 aattcttggc atatgcacat taattgtgct atgttcaagt attcttcatg agataattca
2341 tcttgatgtt tcctctggtc ttatgaattc tgatgagtca cagcaaggca ttatccagcc
2401 tatcatagaa tcattaaaat cattgattgc tttggccaac cagattctat ataatgttgc
2461 aatagtaatt cc
//
```

B. Greer Sequences:
B.1. Greer Strain Used in Laboratory
Nucleotide Sequence Coding for the F Protein of the Greer Isolate (Isolate no 27640), as Obtained in the Examples—Positive Sequencing Control—SEQ ID NO: 45 (1656 nt)

```
ATGCATCACCTGCATCCAATGATAGTATGCATCTTTGTTATGTACACTGG
AATTGTAGGTTCAGATGCCATTGCTGGAGATCAACTACTTAATATAGGGG
TCATTCAATCAAAGATAAGATCACTCATGTACTATACTGATGGTGGTGCT
AGCTTTATTGTTGTAAAATTGCTACCTAATCTTCCCCCAAGCAATGGAAC
ATGCAACATCACCAGTCTAGATGCATATAATGTTACCCTATTTAAGTTAC
TAACACCCCTGATTGAGAACCTGAGTAAAATTTCCACTGTTACAGATACC
AAAACCCGCCAAGAACGATTTGCAGGAGTAGTTGTTGGACTTGCTGCATT
AGGAGTAGCCACAGCCGCACAAATAACTGCAGCTGTAGCAATAGTGAAAG
CTAATGCAAATGCTGCTGCGATAAACAATCTTGCATCTTCAATTCAATCC
ACCAACAAGGCAGTATCCGATGTGATAGATGCATCAAGAACAATTGCAAC
CGCAGTTCAAGCAATTCAGGATCGCATCAATGGAGCTATTGTTAATGGGA
TAACATCTGCATCATGCCGTGCCCATGATGCACTCATTGGGTCAATATTA
AATCTTTATCTCACTGAGCTTACCACAATATTTCATAATCAAATAACAAA
CCCTGCGCTGACACCACTCTCCATCCAAGCTTTAAGAATCCTCCTCGGTA
GCACCTTGCCAATTGTCATTGAGTCCAAACTCAACACAAACTTCAACACA
GCAGAGCTGCTCAGTTCCGGACTGTTAACTGGTCAAATAATTTCCATTTC
CCCAATGTACATGCAAATGCTAATTCAAATCAATGTTCCGACATTTATAA
TGCAACCCGGTGCGAAGGTAATTGATCTAATTGCTATCTCCGCAAACCAT
AAATTGCAAGAAGTGGTTGTACAAGTTCCGAATAGGATTCTAGAGTATGC
AAATGAACTACAAAATTACCCAGCCAATGACTGTGTCGTGACACCGAACT
CTGTATTTTGTAGATACAATGAGGGTTCCCCTATCCCTGAATCACAATAT
CAATGCTTGAGGGGGAATCTTAATTCTTGCACTTTTACCCCTATTATCGG
GAACTTTCTTAAGCGATTCGCATTTGCTAATGGTGTGCTCTATGCCAACT
```

-continued

```
GCAAATCTTTGCTATGTAGGTGTGCCGACCCCCCCCATGTTGTATCCCAG
GATGATACCCAAGGCATCAGCATAATTGATATTAAGAGATGCTCTGAGAT
GATGCTTGACACTTTTTCATTTAGGATCACATCTACTTTCAATGCTACGT
ACGTGACAGACTTCTCAATGATTAATGCAAATATTGTACATCTAAGTCCT
CTAGATTTGTCAAATCAAATCAATTCAATAAACAAATCTCTTAAAAGTGC
TGAGGATTGGATTGCAGATAGCAACTTCTTTGCTAATCAAGCCAGGACAG
CCAAGACACTTTATTCACTAAGTGCAATAGCATTAATACTATCAGTGATT
ACTTTGGTTGTCGTGGGATTGCTGATTGCCTACATCATCAAGCTGGTTTC
TCAAATCCATCAATTCAGATCGCTAGCTGCTACAACAATGTTCCACAGGG
AAAATCCTGCCTTCTTTTCCAAGAATAACCATGGAAACATATATGGGATA
TCTTAA
```

Sequence for F Protein of Greer Labo Isolate (no 27640), as Obtained in the Examples—Positive Sequencing Control—SEQ ID NO: 46 (551 aa)

```
MHHLHPMIVCIFVMYTGIVGSDAIAGDQLLNIGVIQSKIRSLMYYTDGGA
SFIVVKLLPNLPPSNGTCNITSLDAYNVTLFKLLTPLIENLSKISTVTDT
KTRQERFAGVVVGLAALGVATAAQITAAVAIVKANANAAAINNLASSIQS
TNKAVSDVIDASRTIATAVQAIQDRINGAIVNGITSASCRAHDALIGSIL
NLYLTELTTIFHNQITNPALTPLSIQALRILLGSTLPIVIESKLNTNFNT
AELLSSGLLTGQIISISPMYMQMLIQINVPTFIMQPGAKVIDLIAISANH
KLQEVVVQVPNRILEYANELQNYPANDCVVTPNSVFCRYNEGSPIPESQY
QCLRGNLNSCTFTPIIGNFLKRFAFANGVLYANCKSLLCRCADPPHVVSQ
DDTQGISIIDIKRCSEMMLDTFSFRITSTFNATYVTDFSMINANIVHLSP
LDLSNQINSINKSLKSAEDWIADSNFFANQARTAKTLYSLSAIALILSVI
TLVVVGLLIAYIIKLVSQIHQFRSLAATTMFHRENPAFFSKNNHGNIYGI
S
```

B.2. Genbank Data for Greer:

```
LOCUS       NC_003443 15646 by ss-RNA linear VRL 30-MAR-2006
DEFINITION  Human parainfluenza virus 2, complete genome. (SEQ ID NO: 47)
ACCESSION   NC_003443
VERSION     NC_003443.1 GI: 19525721
KEYWORDS    F gene; fusion protein; haemagglutinin neuraminidase; HN gene; L
            gene; large protein; M-gene; matrix protein; NP gene; nucleocapsid
            protein; p gene; parainfluenza virus; phosphoprotein.
SOURCE      Human parainfluenza virus 2
ORGANISM    Human parainfluenza virus 2
            Viruses; ssRNA negative-strand viruses; Mononegavirales;
            Paramyxoviridae; Paramyxovirinae; Rubulavirus.
REFERENCE   1 (bases 8743 to 15646)
AUTHORS     Kawano, M., Okamoto, K., Bando, H., Kondo, K., Tsurudome, M.,
            Komada, H., Nishio, M. and Ito, Y.
TITLE       Characterizations of the human parainfluenza type 2 virus gene
            encoding the L protein and the intergenic sequences
JOURNAL     Nucleic Acids Res. 19 (10), 2739-2746 (1991)
PUBMED      1645865
REFERENCE   2 (sites)
AUTHORS     Ohgimoto, S., Bando, H., Kawano, M., Okamoto, K., Kondo, K.,
            Tsurudome, M., Nishio, M. and Ito, Y.
TITLE       Sequence analysis of P gene of human parainfluenza type 2 virus: P
            and cysteine-rich proteins are translated by two mRNAs that differ
            by two nontemplated G residues
JOURNAL     Virology 177 (1), 116-123 (1990)
PUBMED      2162103
REFERENCE   3 (bases 1 to 15646)
AUTHORS     Kawano, M., Bando, H., Yuasa, T., Kondo, K., Tsurudome, M.,
            Komada, H., Nishio, M. and Ito, Y.
TITLE       Sequence determination of the hemagglutinin-neuraminidase (HN) gene
            of human parainfluenza type 2 virus and the construction of a
            phylogenetic tree for HN proteins of all the paramyxoviruses that
            are infectious to humans
JOURNAL     Virology 174 (1), 308-313 (1990)
PUBMED      2152995
REFERENCE   4 (bases 1 to 15646)
CONSRTM     NCBI Genome Project
TITLE       Direct Submission
JOURNAL     Submitted (16-MAR-2002) National Center for Biotechnology
            Information, NIH, Bethesda, MD 20894, USA
REFERENCE   5 (bases 1 to 15646)
AUTHORS     Kawano, M.
TITLE       Direct Submission
JOURNAL     Submitted (04-MAR-1991) M. Kawano, Dept of Microbiology, Mie
            University School of Medicine, 2-174 Edobashi, Tsu-Shi Mie
            Prefecture 514, Japan
COMMENT     REVIEWED REFSEQ: This record has been curated by NCBI staff. The
            reference sequence was derived from X57559.
            Sequence overlaps with M38200 & M37751.
            COMPLETENESS: full length.
FEATURES    Location/Qualifiers
source      1...15646
            /organism = "Human parainfluenza virus 2"
            /mol_type = "genomic RNA"
            /db_xref = "taxon:11212"
gene        71...1919
            /gene = "NP"
            /locus_tag = "HPIV2gp1"
            /db_xref = "GeneID:935191"
mRNA        71...1919
            /gene = "NP"
            /locus_tag = "HPIV2gp1"
            /db_xref = "GeneID:935191"
CDS         157...1785
            /gene = "NP"
            /locus_tag = "HPIV2gp1"
            /codon_start = 1
            /product = "nucleocapsid protein"
            /protein_id = "NP 598401.1"
            /db_xref = "GI: 19525722"
            /db_xref = "UniProtKB/Swiss-Prot: P21737"
            /db_xref = "GeneID: 935191"

/translation = "MSSVLKTFERFTIQQELQEQSDDTPVPLETIKPTIRVFVINNNDPVVRSRL
            LFFNLRIIMSNTAREGHRAGALLSLLSLPSAAMSNHIKLAMHSPEASIDRVEITGFENNSFRVIP
            DARSTMSRGEVLAFEALALEDIPDTLNHQTPFVNNDVEDDIFDETEKFLDVCYSVLMQAWIVTCK
            CMTAPDQQPVSVAKMAKYQQQGRINARYVLQPEAQRLIQNAIRKSMVVRHFMTYELQLSQSRSLL
            ANRYYAMVGDIGKYIEHSGMGGFFLTLKYGLGTRWPTLALAAFSGELQKLKALMLHYQSLGPMAK
            YMALLESPKLMDFVPSEYPLDYSYAMGIGTVLDTNMRNYAYGRSYLNQQYFQLGVETARKQQGAV
```

-continued

DNRTAEDLGMTAADKADLTATISKLSLSQLPRGRQPISDPFAGANDREMGGQANDTPVYNFNPID
TRRYDNYDSDGEDRIDNDQDQAIRENRGEPGQPNNQTSDNQQRFNPPIPQRTSGMSSEEFQHSMN
QYIRAMHEQYRGSQDDDANDATDGNDISLELVGDFDS"

| | |
|---|---|
| gene | 1924...3365<br>/gene = "V"<br>/locus_tag = "HPIV2gp2"<br>/db_xref = "GeneID:935190" |
| mRNA | 1924...3365<br>/gene = "V"<br>/locus_tag = "HPIV2gp2"<br>/db_xref = "GeneID:935190" |
| CDS | join (1993...2481, 2480...3178)<br>/gene = "V"<br>/locus_tag = "HPIV2gp2"<br>/exception = "RNA editing"<br>/codon_start = 1<br>/product = "P protein"<br>/protein_id = "NP 599019.1"<br>/db_xref = "GI:19526784"<br>/db_xref = "GeneID:935190"<br><br>/translation = "MAEEPTYTTEQVDELIHAGLGTVDFFLSRPIDAQSSLGKGSIPPGVTAVLT<br>SAAETKSKPVAAGPVKPRRKKVISNTTPYTIADNIPPEKLPINTPIPNPLLPLARPHGKMTDIDI<br>VTGNITEGSYKGVELAKLGKQTLLTRFTSNEPVSSAGSAQDPNFKRGGELIEKEQEATIGENGVL<br>HGSEIRSKSSSGVIPGVPQSRPQLASSPAHADPAPASAENVKEIIELLKGLDLRLQTVEGKVDKI<br>LATSATIINLKNEMTSLKASVATMEGMITTIKIMDPSTPTMVPVEEIRKSLHNVPVVIAGPTSGG<br>FTAEQVILISMDELARPTLSSTKRITRKPESKKDLTGIKLTLMQLANDCISRPDTKTEFVTKIQA<br>ATTESQLNEIKRSIIRSAI" |
| CDS | 1993...2670<br>/gene = "V"<br>/locus_tag = "HPIV2gp2"<br>/codon_start = 1<br>/product = "phospho-protein"<br>/protein_id = "NP 5984021"<br>/db_xref = "GI: 19525723"<br>/db_xref = "UniProtKB/Swiss-Prot:P23057"<br>/db_xref = "GeneID:935190"<br><br>/translation="MAEEPTYTTEQVDLEIHAGLGTVDFFLSRPIDAQSSLGKGSIPPGVTAVLT<br>SAAETKSKPVAAGPVKPRRKKVISNTTPYTIADNIPPEKLPINTPIPNPLLPLARPHGKMTDIDI<br>VTGNITEGSYKGVELAKLGKQTLLTRFTSNEPVSSAGSAQDPNFKRGGANRERARGNHRREWSIA<br>WVGDQVKVFEWCNPRCAPVTASARKFTCTCGSCPSICGECEGDH" |
| gene | 3411...4742<br>/gene = "M"<br>/locus_tag = "HPIV2gp3"<br>/db_xref = "GeneID:935187" |
| mRNA | 3411...4742<br>/gene = "M"<br>/locus_tag = "HPIV2gp3"<br>/db_xref = "GeneID:935187" |
| CDS | 3479...4612<br>/gene = "M"<br>/locus_tag = "HPIV2gp3"<br>/codon_start = 1<br>/product = "matrix protein"<br>/protein_id = "NP 598403.1"<br>/db_xref = "GI:19525724"<br>/db_xref = "UniProtKB/Swiss-Prot:P24266"<br>/db_xref = "GeneID:935187"<br><br>/translation = "MPIISLPADPTSPSQSLTPFPIQLDTKDGKAGKLLKQIRIRYLNEPNSRHT<br>PITFINTYGFVYARDTSGGIHSEISSDLAAGSITACMMKLGPGPNIQNANLVLRSLNEFYVKVKK<br>TSSQREEAVFELVNIPTLLREHALCKRKMLVCSAEKFLKNPSKLQAGFEYVYIPTFVSITYSPRN<br>LNYQVARPILKFRSRFVYSIHLELILRLLCKSDSPLMKSYNADRTGRGCLASVWIHVCNILKNKS<br>IKQQGRESYFIAKCMSMQLQVSIADLWGPTIIIKSLGHIPKTALPFFSKDGIACHPLQDVSPNLA<br>KSLWSVGCEIESAKLILQESDLNELMGHQDLITDKIAIRSGQRTFERSKFSPFKKYASIPNLEAI<br>N" |
| gene | 4771...6630<br>/gene = "F"<br>/locus_tag = "HPIV2gp4"<br>/db_xref = "GeneID:935186" |
| mRNA | 4771...6630<br>/gene = "F"<br>/locus_tag = "HPIV2gp4"<br>/db_xref = "GeneID:935186" |
| CDS | 4789...6444 (SEQ ID NO: 48)<br>/gene = "F" |

-continued

```
                    /locus_tag = "HPIV2gp4"
                    /codon_start = 1
                    /product = "fusion protein"
                    /protein_id = "NP 598404.1"
                    /db_xref = "GI:19525725"
                    /db_xref = "UniProtKB/Swiss-Prot: P26
                    /db_xref = "GeneID:935186"

/translation = "MHHLHPMIVCIFVMYTGIVGSDAIAGDQLLNIGVIQSKIRSLMYYTDGGAS
                    FIVVKLLPNLPPSNGTCNITSLDAYNVTLFKLLTPLIENLSKISTVTDTKTRQKRFAGVVVGLAA
                    LGVATAAQITAAVIAVKANANAAAINNLASSIQSTNKAVSDVIDASRTIATAVQAIQDRINGAIV
                    NGITSASCRAHDALIGSILNLYLTELTTIFHNQITNPALTPLSIQALRILLGSTLPIVIESKLNT
                    NFNTAELLSSGLLTGQIISISPMYMQMLIQINVPTFIMQPGAKVIDLIAISANHKLQEVVVQVPN
                    RILEYANELQNYPANDCVVTPNSVFCRYNEGSPIPESQYQCLRGNLNSCTFTPIIGNFLKRFAFA
                    NGVLYANCKSLLCRCADPPHVVSQDDTQGISIIDIKRCSEMMLDTFSFRITSTFNATYVTDFSMI
                    NANIVHLSPLDLSNQINSINKSLKSAEDWIADSNFFANQARTAKTLYSLSAIALILSVITLVVVG
                    LLIAYIIKLVSQIHQFRSLAATTMFHRENPAFFSKNNHGNIYGIS" SEQ ID NO: 49 gene            6639...8742
                    /gene = "HN"
                    /locus_tag = "HPIV2gp5"
                    /db_xref = "GeneID:935188"
    mRNA            6639...8742
                    /gene = "HN"
                    /locus_tag = "HPIV2gp5"
                    /db_xref = "GeneID:935188"
    CDS             6817...8532 (SEQ ID NO: 50)
                    /gene = "HN"
                    /locus_tag = "HPIV2gp5"
                    /codon_start = 1
                    /product = "hemagglutinin-neuraminidase"
                    /protein_id = "NP 598405.1"
                    /db_xref = "GI:19525726"
                    /db_xref = "UniProtKB/Swiss-Prot: P25466"
                    /db_xref = "GeneID:935188"

/translation = "MEDYSNLSLKSIPKRTCRIIFRTATILGICTLIVLCSSILHEIIHLDVSSG
                    LMDSQQGIIQPIIESLKSLIALANQILYNVAIIIPLKIDSIETVIFSALKDMHTGSMSNTNCTPG
                    NLLLHDAAYINGINKFLVLKSYNGTPKYGPLLNIPSFIPSATSPNGCTRIPSFSLIKTHWCYTHN
                    VMLGDCLDFTTSNQYLAMGIIQQSAAAFPIFRTMKTIYLSDGINRKSCSVTAIPGGCVLYCYVAT
                    RSEKEDYATTDLAELRLAFYYYNDTFIERVISLPNTTGQWATINPAVGSGIYHLGFILFPVYGGL
                    ISGTPSYNKQSSRYFIPKHPNITCAGNSSEQAAAARSSYVIRYHSNRLIQSAVLICPLSDMHTAR
                    CNLVMFNNCQVMMGAEGRLYVIDNNLYYYQRSSSWWSASLFYRINTDFSKGIPPIIEAQWVPSYQ
                    VPRPGVMPCNATSFCPANCITGVYADVWPLNDPEPTSQNALNPNYRFAGAFLRNESNRTNPTFYT
                    ASASALLNTTGFNNTNKHAAYTSSTCFKNTGTQKIYCLIIIEMGSSLLGEFQIIPFLRELIP"
                    SEQ ID NO: 51 gene            8785...15625
                    /gene = "L"
                    /locus_tag = "HPIV2gp6"
                    /db_xref = "GeneID:935189"
    mRNA            8785...15625
                    /gene = "L"
                    /locus_tag = "HPIV2gp6"
                    /db_xref = "GeneID:935189"
    CDS             8793...15581
                    /gene = "L"
                    /locus_tag = "HPIV2gp6"
                    /codon_start = 1
                    /product = "Large protein"
                    /protein_id = "NP 598406.1"
                    /db_xref = "GI:19525727"
                    /db_xref = "UniProtKB/Swiss-Prot: P26676"
                    /db_xref = "GeneID:935189"

/translation = "MAASSEILLPEVHLNSPIVKHKLIYYLLLGHFPHDLDISEISPLHNNDWDQ
                    IAREESNLAERLGVAKSELIKRVPAFRATRWRSHAAVLIWPSCIPFLVKFLPHSKLQPVEQWYKL
                    INASCNTISDSIDRCMENISIKLTGKNNLFSRSRGTAGAGKNSKITLNDIQSIWESNKWQPNVSL
                    WLTIKYQMRQLIMHQSSRQPTDLVHIVDTRSGLIVITPELVICFDRLNSVLMYFTFEMTLMVSDM
                    FEGRMNVTALCTISHYLSPLGPRIDRLFSIVDELAQLLGDTVYKVIASLESLVYGCLQLKDPVVE
                    LAGSFHSFITQEIIDILIGSKALDKDESITVTTQLLDIFSNLSPDLIAEMLCLMRLWGHPTLTAA
                    QVGKVRESMCAGKLLDFPTIMKTLAFFHTILINGYRRKKNGMWPLILPKNASKSLIEPQHDNAE
                    ISYEYTLKHWKEISLIEFRKCFDFDPGEELSIFMKDKAISAPRSDWMSVFRRSLIKQRHQRHHIP
                    MPNPFNRRLLLNFLEDDSFDPVAELRYVTGGEYLQDDTFCASYSLKEKEIKPDGRIFAKLTNRMR
                    SCQVIAEAILANHAGTLMKENGVVLNQLSLTKSLLTMSQIGIISEKAKRYTRDNISSQGFHTIKT
                    DSKNKRKSKTASSYLTDPDDTFELSACFITTDLAKYCLQWRYQTIIHFARTLNRMYGVPHLFEWI
                    HLRLIRSTLYVGDPFNPPAATDAFDLDKVLNGDIFIVSKGGIEGLCQKMWTMISISVIILSSAES
                    KTRVMSMVQGDNQAIAVTTRVPRSLPSIQKKELAYAASKLFFERLRANNYGLGHQLKAQETIISS
                    TFFIYSKRVFYQGRILTQALKNASKLCLTADVLGECTQASCSNSATTIMRLTENGVEKDTCYKLN
                    IYQSIRQLTYDLIFPPQYSIPGETISEIFLQHPRLISRIVLLPSQLGGLNYLACSRLFNRNIGDPL
                    GTAVADLKRLIKCGALESWILYNLLARKPGKGSWATLAADPYSLNQEYLYPPTTILKRHTQNTLM
```

-continued

EICRNPMLKGVFTDNAKEEENLLAKFLLDRDIVLPRVAHIIDQSSIGRKKQIQGFFDTTRTIMR
RSFEIKPLSTKKTLSVIEYNTNYLSYNYPVILNPLPIPGYLNYITDQTCSIDISRSLRKLSWSSL
LNGRTLEGLETPDPIEVVNGFLIVGTGDCDFCMQGDDKFTWFFLPMGIIIDGNPETNPPIRVPYI
GSRTEERRVASMAYIKGATHSLKAALRGAGVYIWAFGDTVVNWNDALDIANTRVKISLEQLQTLT
PLPTSANITHRLDDGATTLKFTPASSYAFSSYTHISNDQQYLEIDQRVVDSNIIYQQLMITGLGI
IETYHNPPIRTSTQEITLHLHTSSSCCVRSVDGCLICESNGEVPQITVPYTNTFVYDPDPLADYE
IAHLDYLSYQAKIGSTDYYSLTDKIDLLAHLTAKQMINSIIGLDETVSIVNDAVILSDYTNNWIS
ECSYTKIDLVFKLMAWNFLLELAFQMYYLRISSWTNIFDYTYMTLRRIPGTALNNIAATISHPKL
LRRAMNLDIITPIHAPYLASDLYVKLSIDAIQWGVKQVLADLSNGIDLEILILSEDSMEISDRAM
NLIARKLTLLALVKGENYTFPKIKGMPPEEKCLVLTEYLAMCYQNTHHLDPDLQKYLYNLTNPKL
TAFPSNNFYLTRKILNQIRESDEGQYIITSYYESFEQLETDIILHSTLTAPYDNSENSNKVRFIP
FDIFPHPESLEKYPLPVDHDSQSAISTLIPGPPSHHVLRPLGVSSTAWYKGISYCRYLETQKIQT
GDHLYLAEGSGASMSLLELLFPGDTVYYNSLFSSGENPPQRNYAPLPTQFVQSVPYKLWQADLAD
DSNLIKDFVPLWNGNGAVTDLSTKDAVAFIIHKVGAEKASLVHIDLESTANINQQTLSRSQIHSL
IIATTVLKRGGILIYKTSWLPFSRFSQLAGLLWCFFDRIHLIRSSYSDPHSHEVYLVCRLAADFR
TIGFSAALVTATTLHNDGFTTIHPDVVCSYWQHHLENVGRVGKVIDEILDGLATNFFAGDNGLIL
RCGGTPSSRKWLEIDQLASFDLVQDALVTLITIHLKEIIEVQSSHTEDYTSLLFTPYNIGAAGKV
RTIIKLILERSLMYTVRNWLVLPSSIRDSVRQDLELGSFRLMSILSEQTFLKKTPTKKYLLDQLT
RTYISTFFNSHSVLPLHRPYQKQIWKALGSVIYCSETVDIPLIKDIQIEDINDFEDIERGIDEE
L"

ORIGIN

SEQ ID NO: 47
```
    1 accaagggga gaatcagatg gcatcgttat atgacgaatt gcaaaaagat tacgtaggtc
   61 cggaaccact agattcggtg ccggtaacga ttccagtttt atactatctg atcattctct
  121 atctctatta aggatatttc tagtctaaag ttcaaaatgt caagtgtttt aaagacattt
  181 gaaagattta ctatacaaca ggagcttcag gagcaatctg atgacactcc agtacctctt
  241 gagacaatca aacctacaat cagggtattt gtcatcaata ataatgatcc tgtcgtaaga
  301 tctagactttt tattctttaa tctacgaatt attatgagta acactgcaag agagggacat
  361 agagctggtg ctctcctcag tcttttatca ctaccttctg cagctatgag taatcacatc
  421 aaattagcca tgcattcacc agaagccagc atagatagag tagagataac agggtttgag
  481 aataattcat tccgagtcat tccagatgct cgatcaacta tgtccagagg agaggtgctg
  541 gcttttgaag cattagctga ggacattcct gatacccta atcaccaaac tccatttgta
  601 aataatgatg tagaagatga catatttgat gaaacagaga aattcttaga tgtttgctac
  661 agtgtgctta tgcaggcatg gatagtaaca tgcaagtgta tgactgctcc tgatcaacca
  721 ccagtatcga tagcaaagat ggctaaatat caacaacaag ggagaatcaa tgctaggtat
  781 gtactacaac ctgaagcaca aagactaatt cagaatgcca tccgcaagtc aatggtagta
  841 aggcattttca tgacttatga gcttcaactt tcacaatcaa gatctttgct agcaaaccgc
  901 tactatgcta tggtgggaga cattggcaag tacattgaac acagcggaat gggaggattt
  961 ttcttaacac ttaaatatgg acttggaaca agatggccta cattggctct tgcagcattt
 1021 tctggggaac tccagaaatt aaaagctctc atgctacatt atcagagtct aggacccatg
 1081 gccaagtaca tggctctatt agaatcacca aaactgatgg attttgtccc atctgaatat
 1141 ccattagatt atagctatgc aatggtatt ggaactgtcc ttgatacaaa tatgagaaat
 1201 tatgcatacg gtagatcata tttaaatcag caatattttc agctaggagt agaaacagca
 1261 aggaaacagc agggagctgt tgacaacagg acagcagagg acctcggcat gactgctgca
 1321 gacaaagcag acctcactgc aaccatatca aagctatcct tgtcccaatt acctaggggt
 1381 agacaaccaa tatctgaccc atttgctgga gcaaatgaca gagaaatggg aggacaagca
 1441 aatgatacac ctgtgtataa cttcaatcca atcgatactc ggaggtatga caactatgac
 1501 agtgatggtg aggacagaat tgacaacgat caagatcaag ctatcagaga aatagagga
 1561 gagcctggac aaccaaacaa ccagacaagt gacaaccagc agagattcaa ccccccata
 1621 ccgcaaagaa catcaggtat gagcagtgaa gagttccaac attcaatgaa tcagtacatc
 1681 cgtgctatgc atgagcaata cagaggctcc caggatgatg atgccaatga tgccacagat
 1741 gggaatgaca tttctcttga gctagttgga gattttgatt cctaactctc aatgtcatac
 1801 aaccagatat acacatccac atcactcaga gatacagctg ccactcacac actcatccag
 1861 acaaatcaaa ctagactcac atcattcgga aacaattctc tcataattta aagaaaaaat
 1921 cataggccgg acgggttaga atccggtgc ttgttcgtga tcagataacc tccacaccag
 1981 aatcatacaa tcatgccga ggaaccaaca tacaccactg agcaagttga tgaattaatc
 2041 catgctggac tgggaacagt agatttcttc ctatctagac ccatagatgc tcagtcttct
 2101 ttaggcaaag gcagcatccc accaggtgtc acagctgttc taactagtgc agcggagaca
 2161 aaatccaaac cagttgctgc tggtccagtt aaacccaggc ggaagaaagt gatcagcaat
 2221 actactccat acactattgc agacaatatt ccactgaga agctaccgat caacactcca
 2281 atacccaatc cattacttcc actggcacgc cctcacggaa agatgacaga cattgacatt
 2341 gtcactggga acattacaga aggatcgtac aaaggtgtgg agcttgctaa attagggaag
 2401 cagacactac tcacaaggtt cacctcgaat gagccagtct cctcagctgg atcgcccaa
 2461 gaccccaact ttaagagggg gggagctaat agagaaagag caagaggcaa ccataggaga
 2521 gaatggagta ttgcatgggt cggagatcag gtcaaagtct cgagtggtg taatcccagg
 2581 tgtgccccag tcacggcctc agctcgcaag ttcacctgca catgcggatc ctgcccagc
 2641 atctgcggag aatgtgaagg agatcattga gctcttaaag ggacttgatc ttcgcctca
 2701 gactgtagaa gggaaagtag ataaaattct tgcaacttct gcaactataa tcaatcttaa
 2761 aaatgaaatg actagtctca aggcgagtgt tgcaactatg gaaggtatga taacaacaat
 2821 taaaatcatg gatcccagta caccaactaa tgtccctgta gaggagatca gaaagagttt
 2881 acacaatgtt ccagtagtaa ttgccggtcc aactagtgga ggcttcacag ccgaacaggt
 2941 gatattgatt tcaatgatg aactagtag acctacactc tcatcaacaa aaaggatcac
 3001 acgaaagcct gaatccaaga aagatttaac aggcataaaa ctaactttga tgcagcttgc
 3061 aaatgactgc atctcgcgtc cagataccaa gactgagttc gtgactaaga ttcaggcagc
 3121 aaccacagaa tcacagctca agaaattaa acggtcactg atacgctctg caatataaaa
 3181 tgaggtgcag tcacacaaga gacactcaac atgcatccaa tcaagatcca gactccatcc
 3241 atccaaaaac acgccacaa ttgtcaacac caagaaacaa ccacagccga ccatgctca
 3301 accaaaagac ccaaacaaca cctcacatca atagaaggct ggacatgata aatttaataa
 3361 aaaaagaaaa gaagttaagt aaaatttaaa ggacacaata gagaaaatct aggtccgaaa
 3421 gcttgcctct cagacagatc ccaaaatcat agtccaaacc caaacacag cagcagacat
```

```
3481 gcctataata tcattaccag cagatccaac ttcacccagt caatcccttta ctccgtttcc
3541 aatacaactt gacaccaaag atggcaaggc agggaaactc cttaaacaga ttcgaattag
3601 gtatctaaat gagcctaatt ctcgccatac accaataact ttcatcaata cgtatggatt
3661 tgtttatgct cgagacactt caggggggcat tcacagtgag atcagcagtg acctagctgc
3721 agggtccata acagcatgca tgatgaagct aggacctggt ccaaatattc agaatgcaaa
3781 tctagtgcta agatctctga atgaattcta cgtaaaagtc aagaagacat caagccagag
3841 agaggaagca gtgtttgaat tagttaacat tccaacttta ttgagagaac atgctctttg
3901 caaacgcaaa atgttagtat gctctgcaga aaaattcctc aagaacccgt caaagctaca
3961 agctggattt gagtatgtat acataccaac ttttgtctcc attacatact caccacgaaa
4021 tctgaattac caagtggcca gacctatcct taagttcaga tcacgctttg tgtatagcat
4081 tcatttggaa ttaatcctga gattgctatg caaatctgac tcccccttga tgaaatccta
4141 caatgcagac agaacaggtc ggggatgcct cgcatcagtc tggatccatg tatgtaacat
4201 tctgaaaaac aaaagcatca agcaacaagg cagagaatca tatttcatag ctaagtgcat
4261 gagcatgcag ctgcaggtgt ccattgcaga tctttgggga ccaacaatca taatcaaatc
4321 attgggtcac atccccaaga ctgcacttcc tttttcagc aaagatggga ttgcctgtca
4381 tccattacaa gatgtttccc ctaatctagc aaaatcactg tggtcagttg gatgtgagat
4441 agaatctgcc aagttgatac ttcaagaatc tgatcttaat gagctaatgg gccaccagga
4501 ccttatcact gataagattg ccattagatc aggtcaacgg acatttgaga ggtccaaatt
4561 cagcccattc aaaaaatatg catcaattcc aaacttggaa gccatcaact gaatgctcca
4621 gcatctgaga atagaaccac aatcaagtca tactactagt cactatacaa taatcaacaa
4681 ttttagtcaa ctgattacca agatgttatc ataggtccga actgatcaat ctaacaaaaa
4741 aactaaacgt tccacaataa atcaacgttc aggccaaaat attcagccat gcatcacctg
4801 catccaatga tagtatgcat cttttgttatg tacactggaa ttgtaggttc agatgccatt
4861 gctggagatc aactacttaa tataggggtc attcaatcaa agataagatc actcatgtac
4921 tatactgatg gtggtgctag ctttattgtt gtaaaattgc tacctaatct tcccccaagc
4981 aatggaacat gcaacatcac cagtctagat gcatataatg ttaccctatt taagttacta
5041 acaccccctga ttgagaacct gagtaaaatt tccactgtta cagataccaa aacccgccaa
5101 aaacgatttg caggagtagt tgttggactt gctgcattag gagtagccac agccgcacaa
5161 ataactgcag ctgtagcaat agtgaaagct aatgcaaatg ctgctgcgat aaacaatctt
5221 gcatcttcaa ttcaatccac caacaaggca gtatccgatg tgatagatgc atcaagaaca
5281 attgcaaccg cagttcaagc aattcaggat cgcatcaatg gagctattgt taatgggata
5341 acatctgcat catgccgtgc ccatgatgca ctcattgggt caatattaaa tctttatctc
5401 actgagctta ccacaatatt tcataatcaa ataacaaacc ctgcgctgac accactctcc
5461 atccaagctt taagaatcct cctcggtagc accttgccaa ttgtcattga gtccaaactc
5521 aacacaaact tcaacacagc agagctgctc agttccggac tgttaactgg tcaaataatt
5581 tccatttccc caatgtacat gcaaatgcta attcaaatca atgttccgac atttataatg
5641 caacccggtg cgaaggtaat tgatctaatt gctatctccg caaaccataa attgcaagaa
5701 gtggttgtac aagttccgaa taggattcta gagtatgcaa atgaactaca aaattcccca
5761 gccaatgact gtgtcgtgac accgaactct gtatttttgta gatacaatga gggttcccct
5821 atccctgaat cacaaatatca atgcttgagg gggaatctta attcttgcac ttttaccccct
5881 attatcggga actttcttaa gcgattcgca tttgctaatg gtgtgctcta tgccaactgc
5941 aaaatcttttgc tatgtaggtg tgccgacccc ccccatgttg tatcccagga tgatacccaa
6001 ggcatcagca taattgatat taagagatgc tctgagatga tgcttgacac ttttttcattt
6061 aggatcacat ctactttcaa tgctacgtac gtgacagact tctcaatgat taatgcaaat
6121 attgtacatc taagtcctct agatttgtca aatcaaatca attcaataaa caaatctctt
6181 aaaagtgctg aggattggat tgcagatagc aacttctttg ctaatcaagc caggacagcc
6241 aagacacttt attcactaag tgcaaatagca ttaatactat cagtgattac tttggttgtc
6301 gtgggattgc tgattgccta catcatcaag ctggtttctc aaatccatca attccagatcg
6361 ctagctgcta caacaatgtt ccacaggaa aatcctgcct tcttttccaa gaataaccat
6421 ggaaacatat atgggatatc ttaagaaatc tatcacaagt ctatatatgt ccacaattga
6481 cccttaagaa ccaacttcca acgattatcc gttaaattta agtataatag tttaaaaatt
6541 aacattaagc ctccagatac caatgaatat gaatatatct cttagaaaac ctgattatta
6601 tgtgatagcg tagtacaatt taagaaaaaa cctaaaataa gcacgaaccc ttaaggtgtc
6661 gtaacgtctc gtgacaccgg gttcagttca aatatcgacc tctaacccaa tttaacaccc
6721 attcttatat aagaacacag tataaattaa tcacaaaaga cctcaaaaac tgacacagct
6781 tgatccactc aacatataat tgtaagatta ataataatgg aagattacag caatctatct
6841 cttaaatcaa ttcctaaaag gacatgtaga atcattttcc gaactgccac aattcttgga
6901 atatgcacat tgattgttct atgttcaagt attcttcatg agataattca tcttgatgtt
6961 tcctctggtc tcatggattc cgatgattca cagcaaggca ttattcagcc tattatagaa
7021 tcattaaaat cattaattgc tttggctaac cagattctgt acaatgttgc aataataatt
7081 cctcttaaaa ttgacagtat cgagactgta atattctctg ctttaaagga tatgcatact
7141 gggagcatgt ccaacaccaa ctgtacaccc ggaaatctgc ttctgcatga tgcagcgtac
7201 atcaatggaa taaacaaatt ccttgtactt aaatcataca atgggacgcc taaatatgga
7261 cctctcctaa atattcccag ctttatcccc tcagcaacat ctcccaacgg gtgcactaga
7321 ataccatcat tttcactcat taagacccat tggtgttaca ctcacaatgt aatgcttgga
7381 gattgcctcg atttcacgac atcaatcag tatttagcaa tggggataat acaacaatct
7441 gctgcagcat ttccaatctt caggactatg aaaaccattt acctaagtga tggaatcaat
7501 cgcaaaagct gttcagtcac tgctatacca ggaggttgtg tcttgtattg ctatgtagct
7561 acaagatctg agaaagaaga ttatgccaca actgatcgag ctgaactgag acttgctttc
7621 tattattata atgataccttt tattgaaaga gtcatatctc ttccaaatac aacagggcaa
7681 tgggccacaa tcaatcctgc agttggaagc gggatctatc atctaggctt tatcttattt
7741 cctgtatatg gtggtctcat aagtgggact ccttcctaca acaagcagtc ctcacgctat
7801 tttatcccaa aacatcccaa cataacctgt gccggtaact ccagcgaaca ggctgcagca
7861 gcacggagtt cctatgtaat ccgttatcac tcaaacaggt tgattcagag tgctgttctt
7921 atttgccccat tgtctgacat gcacacagca aggtgtaatc tagttatgtt taacaattct
7981 caagtcatga tgggtcagaa aggtaggctc tatgttattg acaataattt gtattattat
8041 caacgtagtt cctcttggtg gtctgcatcg ctttttttaca ggatcaatac agattttttct
8101 aaaggaattc ctcctatcat tgaggctcaa tgggtaccgt cctatcaagt tcccgtcct
8161 ggagtcatgc catgcaatgc aacaagtttt tgccctgcta attgcatcac aggggtgtac
8221 gcagatgtgt ggcgcttaa cgatccgaa cccacatcac aaaatgctct gaatcccaac
8281 tatcgatttg ctggagcctt tctcagaaat gagtccaacc gaaccaatcc cacattctac
```

-continued

```
8341 actgcatcag ccagcgccct actaaatact accgqattca acaacaccaa tcacaaagca
8401 gcatatacgt cttcaacctg ctttaagaat actggaactc aaaagattta ttgtttgata
8461 ataattgaaa tgggctcatc tcttttaggg gagttccaaa taataccatt tctaagggaa
8521 ctaatacctt aatactattg aatgaagact ccagattcaa taataattga aaggctctct
8581 atcttatgca atagttatac gttttggctg tattagaatg ttatagattc tgctgttttt
8641 cccatatgaa gcaatccttc aacaccgact taggttcaat tttctcatca tttactgttg
8701 taattcaatc ttactaaagt tattccgata tttaagaaaa aataaccttt atataatgta
8761 acaatactat taagattatg atataggcca gaatggcggc ctcttctgag atactccttc
8821 ctgaagtcca cttgaactca ccaatagtca aacacaaact catatactac ttattactag
8881 ggcacttccc gcatgatctt gacatttctg aaataagccc ccttcacaat aatgattggg
8941 atcaaattgc cagagaagaa tccaatcttg ctgaacgact tggagtagct aaatctgaat
9001 taattaaacg tgtgcccgca tttagagcaa ctagatggcg tagtcatgca gccgtcctta
9061 tatggccttc ttgtatacca tttcttgtta aattcctacc tcattctaag cttcaaccag
9121 tagaacaatg gtacaagttg atcaatgctt catgtaatac tatatctgac tcaattgata
9181 gatgtatgga gaatatttct attaagctta ctgggaaaaa caatctattc tctcgatcca
9241 gaggaactgc aggtgcaggt aaaaacagta aaatcaccct caatgatatc caatctattt
9301 gggaatcaaa caagtggcaa cctaatgtat ctttatggct tacaattaaa taccaaatgc
9361 gacaacttat aatgcatcaa agttctcgtc agccgactga tttagttcac attgttgaca
9421 cacgatctgg tctaatagtt atcaccccctg aacttgttat ttgttttgat cggttaaata
9481 gtgttttaat gtattttaca tttgagatga ctttaatggt aagtgacatg tttgagggaa
9541 ggatgaatgt caccgctctc tgcactatta gtcattactt atctccacta gggccaagga
9601 tagatagatt gttttccatt gtagatgaat tagcacaact attaggtgac actgtatata
9661 aagttattgc atctcttgaa tctttagtat atgggtgtct acaacttaaa gatccagtag
9721 tggaattagc agggtcattt cattccttta ttacacaaga gattatagat atcctaattg
9781 gttcaaaagc ccttgataag gatgaatcaa taactgttac tacacaattg ttagatatat
9841 tttccaacct ttctccagat ttaattgctg agatgttgtg tctcatgaga ctttgggqtc
9901 atcccactct tactgctgcg caagtgggta aagtgagaga atctatgtgt gcaggtaagt
9961 tacttgattt ccctacaata atgaaaactc ttgctttttt ccacacaatt ttaattaatg
10021 gttaccgtag aaagaaaaat ggaatgtggc ctccacttat acttcctaaa aatgcatcaa
10081 aaagcttaat agaatttcaa catgataatg ctgaaatatc ttacgaatat acactcaagc
10141 attggaaaga gatatctctc atagaattta gaaagtgctt tgactttgat cctggtgagg
10201 agctaagcat ttttatgaaa gacaaggcaa taagtgctcc aagaagtgat tggatgagtg
10261 tatttcgtag aagtctaata aaacaacgac atcagagaca tcatattcct atgcccaatc
10321 catttaatag acgtctatta ctcaatttct tagaagatga cagttttgat ccagttgccg
10381 agcttcgata tgttaccggt ggtgaatatc tccaagatga cacattttgt gcatcttact
10441 cattaaaaga gaaagaaata aaaccagatg gaaggatatt tgctaagctt actaatagaa
10501 tgcggtcctg tcaagtaatt gcggaagcaa ttctcgcaaa tcatgcaggt actctaatga
10561 aggaaaacgg agttgtcttg aatcaattat cactgactaa atcattgctt actatgagtc
10621 aaattggcat aatatcagaa aaggcgaaga gatatacgcg agataacatc tcatcccaag
10681 gtttccatac aatcaagact gattctaaaa ataagaggaa aagcaaaact gcatcatcat
10741 acctcacaga tcctgatgat acatttgaac ttagtgcatg ttttataact actgatcttg
10801 ctaaatactg tcttcaatgg agatatcaga ccataatcca ttttgctcga acattaaaca
10861 gaatgtatgg agttccacat ttatttgaat ggattcatct tcgtttaatt agatctacat
10921 tatatgttgg tgatccattc aatcctcctg ccgcaactga tgctttcgat ctagataaag
10981 tattaaatgg tgatatcttt atagtctcca agggaggtat tgaaggccta tgtcagaaaa
11041 tgtgtgacaat gatctctatt tctgtgatca tcctctcttc agccgaatcc aaaacaagag
11101 taatgagcat ggttcaagga gataatcagg cgattgcagt tacaacaaga gttcctagat
11161 cattacctag tattcagaaa aaggagttag cctatgcagc aagcaagtta tttttttgaaa
11221 gacttagggc aaataattat gggttgggtc atcagctaaa ggctcaagaa actataataa
11281 gttccacgtt cttcatatat agtaaacggg tattttatca aggacgtata ctaacacagg
11341 cactcaaaaa tgctagcaag ttatgtctta ctgcagatgt attaggtgaa tgtactcaag
11401 cttcctgttc aaaattctgct actaccatca tgagattaac agaaaatggg gttgagaaag
11461 atacatgtta taagcttaat atttatcagt ccattcgtca actcacatat gatctaatat
11521 ttcccccaata ctccatacca ggtgaaacta taagtgagat tttcctacag catccaagac
11581 taatctcacg tattgttctg ctcccttcac agctaggtgg tcttaattac ctcgcatgta
11641 gcagattatt taaccgcaac atcggagatc ctcttggtca agctgtggca gatctcaaga
11701 ggttaattaa atgtggtgct cttgaatcat ggatactgta taatttacta gcaagaaaac
11761 cagggaaagg ttcatgggca actttagcag ccgatccata ctcattgaat caagaatatc
11821 tttatcctcc tactactata cttaaaagac atactcaaaa tactttaatg gagatatgtc
11881 ggaatcctat gttaaaggga gtttttacag ataatgcaaa agaggaggaa aatctccttg
11941 caaaatttct tcttgatcgt gatatagtat tgccaagagt tgcacacatt ataatagatc
12001 aatctagcat cggaaggaag aaacagatac aaggattttt tgacaccaca aggaccataa
12061 tgagacgatc atttgaaatc aaaccactct caactaagaa gactctttca gtcatagaat
12121 ataatactaa ttacttatct tataactacc ctgtcatact taatccttca cctattcctg
12181 gatatttaaa ttatattact gaccaaactt gcagtattga tatatctaga agtttaagaa
12241 aattatcatg gtcttcttta ttgaatggaa gaacttagaa aggattagaa actccagatc
12301 caattgaagt tgtcaatggt ttcttgattg taggtacagg agattgtgat ttttgtatgc
12361 agggtgacga caaatttact tggttctttt tacctatggg gataattatt gatggaaatc
12421 ctgaaactaa tccacccatc agagttccat acattgggtc tagaacagag gaaagaagag
12481 ttgcatcaat ggcatatatt aaaggtgcca cacacagttt gaaggctgct cttagaggcg
12541 caggggtata tatttgggca ttcggggata ctgtagtgaa ctggaatgat gcacttgata
12601 tcgcaaatac tagggttaag atatccctag agcaacttca gaccccttca cctcttccta
12661 catctgcaaa cattacacac cgtttagatg atggagccac aacacttaaa ttcactccag
12721 ctagttccta tgcattttct agttatactc atatatcaaa tgatcaacaa tatttagaaa
12781 tagatcagag agtagtcgat tctaatatta tttatcaaca attaatgata acaggacttg
12841 ggattattga gacctaccat aacccaccta taaggacttc tacacaagaa atcactctcc
12901 atttgcacac tagctcatct tgttgtgtta gaagtgtaga tggttgcctt atatgtgaaa
12961 gcaatggaga ggttcctcag atcactgttc cctatactaa tacatttgta tatgatcctg
13021 atccactagc agattatgag attgcacacc tagattatct ctcctaccaa gctaaaattg
13081 gaagtacaga ttactactca ctcactgata aaattgacct attagcacat ttaactgcaa
13141 aacaaatgat aaactcaata attgggttag atgaaacagt atcaattgtc aatgatgcgg
```

-continued

```
13201 ttatcctatc tgactatact aataactgga ttagtgaatg ttcttatact aagatagatt
13261 tagtttttaa attaatggca tggaatttcc ttcttgagct tgcattccag atgtactact
13321 taaggatatc atcttggaca aatatatttg actatactta tatgactttg cgcaggatac
13381 ccggaactgc tctaaataat attgcagcta ctattagcca tccaaaatta ttaagacgtg
13441 caatgaatct tgatattatc actcctatac atgcaccgta tttagcttca ttagattatg
13501 tcaaattaag tattgatgca attcagtggg gagttaaaca agttcttgct gatttatcaa
13561 atggaattga tcttgaaatc ttgattcttt cagaggattc aatggaaatt agtgataggg
13621 caatgaatct cattgctaga aaactaactc tccttgcact tgttaaaggt gagaactata
13681 cttttccaaa aattaaaggg atgccaccag aagaaaagtg tttagtctta actgaatatc
13741 tagcaatgtg ttatcaaaat actcatcact tagatccaga tcttcaaaag tatttatata
13801 atctaactaa tccaaaattg actgcatttc ccagtaacaa cttctactta actagaaaaa
13861 tccttaatca aattagagaa tcagacgaag gacaatatat tatcacctca tattatgaat
13921 ccttcgaaca attagaaaca gatataattc ttcactctac tttaactgct ccttatgata
13981 attcagaaaa ctctaacaaa gttcgattta tccctttcga catctttcca catccagaat
14041 ctctcgagaa atatcctctt ccagttgatc atgactctca atctgcaatt tcaacactaa
14101 ttccaggccc tccttctcat catgtattac gaccactagg agtgtcatcc acagcttggt
14161 ataaagggat aagttattgt agatacctag aaacacaaaa gatacagact ggtgatcatc
14221 tttatttagc cgaaggaagc ggtgcttcaa tgtcacttct agaactctta tttccaggag
14281 atactgtcta ttataatagt cttttttagta gtggagagaa tcctccacag agaaactatg
14341 cccctcttcc aactcaattt gtacagagtg ttccatataa attgtggcaa gctgatcttg
14401 ctgatgatag caattttgata aaagattttg tcccattatg gaatggaaac ggtgcagtta
14461 cagacttatc aacaaaggat gcagttgcat tcataataca taaagtagga gcagagaaag
14521 catcccttgt ccatatagat ctcgaatcaa ctgctaatat aaatcagcaa actctgtcca
14581 gatcccagat tcattcatta attatagcaa ctactgttct taagaggggt gggatattaa
14641 tttataaaac atcatggctt ccgttttcta ggtttagtca actagcaggt ctactttggt
14701 gcttctttga ccggatccat ctaatacgta gtagctattc tgatcctcac agtcatgagg
14761 tttatcttgt atgtagactt gccgcagatt ttagaactat cggtttcagt gcagctctag
14821 taactgctac tactcttcac aatgacggat tcacaacaat acatcctgat gttgtttgta
14881 gttattggca acaccatctt gaaaatgttg ggagagtcgg aaaagtaatt gatgagatac
14941 ttgatggttt agccaccaac ttcttcgcag gagataatgg gcttattcta agatgtggag
15001 gaactccaag ctccagaaaa tggttagaga ttgaccagtt agcatcattt gatttggttc
15061 aagatgctct ggttacactt atcactatac acctaaagga aattatagaa gtgcagtcat
15121 cacatacaga ggattataca tctctcctct tcacaccttta taatattggt gcagcaggga
15181 aagtcagaac tatcatcaaa ttaattctag aacgatcttt aatgtataca gtccgaaatt
15241 ggttagtttt acccagttcc atccgggatt ctgtacgaca agatttagaa ttagggtcag
15301 ttagattaat gtctatttta agtgaacaga catttcttaa aaagacaccc acaaaaaat
15361 acttacttga tcagcttaca aggacatata tatcaaccctt ctttaactct cactcagtcc
15421 ttcccctcca ccgtccatat caaaaacaaa tatggaaagc cttaggtagt gtaatatatt
15481 gttcggagac agttgatata cctctaatta aagacattca gatagaagat attaatgatt
15541 ttgaagatat cgagaggggt atcgatggcg aagaattatg acaacaatga ttataagaac
15601 tcatgatagt tttatttaag aaaaacatat tgattttccc cttggt
```
//

B.3. Greer Sequences:

Nucleotide Sequence Coding for F Protein of Greer Isolate, as Obtained from Genbank Data NC_003443—SEQ ID NO: 48 (1656 nt)

Fragment 4789-6444 of SEQ ID NO: 47

Sequence for F Protein of Greer Isolate, as Obtained from Genbank data NC_003443—SEQ ID NO: 49 (551 aa)

MHHLHPMIVCIFVMYTGIVGSDAIAGDQLLNIGVIQSKIRSLMYYTDGGA

SFIVVKLLPNLPPSNGTCNITSLDAYNVTLFKLLTPLIENLSKISTVTDT

KTRQKRFAGVVVGLAALGVATAAQITAAVAIVKANANAAAINNLASSIQS

TNKAVSDVIDASRTIATAVQAIQDRINGAIVNGITSASCRAHDALIGSIL

NLYLTELTTIFHNQITNPALTPLSIQALRILLGSTLPIVIESKLNTNFNT

AELLSSGLLTGQIISISPMYMQMLIQINVPTFIMQPGAKVIDLIAISANH

KLQEVVVQVPNRILEYANELQNYPANDCVVTPNSVFCRYNEGSPIPESQY

QCLRGNLNSCTFTPIIGNFLKRFAFANGVLYANCKSLLCRCADPPHVVSQ

DDTQGISIIDIKRCSEMMLDTFSFRITSTFNATYVTDFSMINANIVHLSP

LDLSNQINSINKSLKSAEDWIADSNFFANQARTAKTLYSLSAIALILSVI

TLVVVGLLIAYIIKLVSQIHQFRSLAATTMFHRENPAFFSKNNHGNIYGI

S

Nucleotide Sequence Coding for HN Protein of Greer Isolate, as Obtained from Genbank Data NC_003443—SEQ ID NO: 50 (1716 nt)

Fragment 6817-8532 of SEQ ID NO: 47

Sequence for Hn Protein of Greer Isolate, as Obtained from Genbank Data NC_003443—SEQ ID NO: 51 (571 aa)

MEDYSNLSLKSIPKRTCRIIFRTATILGICTLIVLCSSILHEIIHLDVSS

GLMDSDDSQQGIIQPIIESLKSLIALANQILYNVAIIIPLKIDSIETVIF

SALKDMHTGSMSNTNCTPGNLLLHDAAYINGINKFLVLKSYNGTPKYGPL

LNIPSFIPSATSPNGCTRIPSFSLIKTHWCYTHNVMLGDCLDFTTSNQYL

AMGIIQQSAAAFPIFRTMKTIYLSDGINRKSCSVTAIPGGCVLYCYVATR

SEKEDYATTDLAELRLAFYYYNDTFIERVISLPNTTGQWATINPAVGSGI

YHLGFILFPVYGGLISGTPSYNKQSSRYFIPKHPNITCAGNSSEQAAAAR

SSYVIRYHSNRLIQSAVLICPLSDMHTARCNLVMFNNSQVMMGAEGRLYV

IDNNLYYYQRSSSWWSASLFYRINTDFSKGIPPIIEAQWVPSYQVPRPGV

MPCNATSFCPANCITGVYADVWPLNDPEPTSQNALNPNYRFAGAFLRNES

NRTNPTFYTASASALLNTTGFNNTNHKAAYTSSTCFKNTGTQKIYCLIII

EMGSSLLGEFQIIPFLRELIP

C. V94 Sequences:
C.1. Genbank Data for V94:

```
LOCUS       AF533010               15654 bp    RNA     Linear   VRL 16-DEC-2002
DEFINITION  Human parainfluenza virus 2 strain V94, complete genome (SEQ ID NO: 52)
ACCESSION   AF533010
VERSION     AF533010.1  GI:26655521
KEYWORDS    .
SOURCE      Human parainfluenza virus 2
ORGANISM    Human parainfluenza virus 2
            Viruses; ssRNA negative-strand viruses; Mononegavirales;
            Paramyxoviridae; Paramyxovirinae; Rubulavirus.
REFERENCE   1 (bases 1 to 15654)
AUTHORS     Skiadopoulos, M. H., Vogel, L., Riggs, J. M., Surman, S. R.,
            Collins, P. L. and Murphy, B. R.
TITLE       The Genome Length of Human Parainfluenza Virus Type 2 Follows the
            Rule of Six, and Recombinant Viruses Recovered from
            Non-Polyhexameric-Length Antigenomic cDNAs Contain a Biased
            Distribution of Correcting Mutations
JOURNAL     J. Virol. 77 (1), 270-279 (2003)
PUBMED      12477832
REFERENCE   2 (bases 1 to 15654)
AUTHORS     Skiadopoulos, M. H., Vogel, L., Riggs, J. M., Surman, S. R.,
            Collins, P. L. and Murphy, B. R.
TITLE       Direct Submission
JOURNAL     Submitted (29-JUL-2002) Laboratory of Infectious Diseases, NIAID,
            NIH, BLDG. 50/RM 6512 MSC 8007, Bethesda, MD 20892-8007, USA
FEATURES             Location/Qualifiers
source               1...15654
                     /organism = "Human parainfluenza virus 2"
                     /virion
                     /mol_type = "genomic RNA"
                     /strain = "V94"
                     /db_xref = "taxon:11212"

ORIGIN                                                         SEQ ID NO: 52
        1 accaagggga gaatcagatg gcatcgttat atgacgaatt gcaaaaagat tacgtaggtc
       61 cggaaccact agattccggt gccggtaacg atctcagttt tatactatct gatcattctt
      121 tatctctact aaggatattt ctaatctaag gttcaaaatg tcaagtgtct taaagacatt
      181 tgaaagattt actatacaac aggagcttca ggagcaatct gaagacactc caatacctct
      241 tgaaacaatc agacctacaa tcagagtatt tgtcatcaat aataatgatc ctattgtaag
      301 atctagactt ttattcttta atctacgaat tattatgagt aacactgcaa gagagggaca
      361 tagagctggt gctctcctca gtcttttatc actaccttct gcagctatga gtaatcacat
      421 caaactagcc atgcattcac cagaagccag catagataga gtagaaataa cagggtttga
      481 gaataattca ttccgagtta ttccagatgc tcgatcaact atgtccagag agaagtgct
      541 ggccttcgaa gcattagctg aggacattcc tgataccctt aatcaccaaa ctccatttgt
      601 aaataatgat gtggaagatg acatatttga tgaaacagag aaattcttgg atgtttgcta
      661 tagtgtactt atgcaggcat ggatagtaac atgcaagtgc atgactgctc ctgatcaacc
      721 accagtatca gtagcaaagc ggatggctaa atatcaacaa caagggagaa tcaatgctag
      781 atatgtacta caacctgaag cacaaagact aattcagaat gccatccgca agtcaatggt
      841 agtaaggcat ttcatgacct atgagcttca acttcaacaa tcaagatctt tgctagcgaa
      901 ccgttattat gccatggtgg gagacattgg caagtatatt gaacacagcg gaatgggaag
      961 gttttctta acacttaaat atggacttgg aacaagatgg cctacattgg ctcttgcagc
     1021 attctctggg gaactccaga aattaaaggc tctcatgcta cattatcaga gtctaggacc
     1081 catggccaag tacatggctc tattagaatc accaaagctg atggattttg tcccatctga
     1141 atatccatta gtttatagct atgcaatgga tattggaact gtccttgata caaacatgag
     1201 aaactatgca tatggtagat catatctaaa tccacaatat tttcagctag gggtagaaac
     1261 agcaaggaaa cagcaaggag ctgttgacaa caggacagca gaggacctcg gcatgactgc
     1321 tgcagataaa gcagacctca ctgcaaccat atcaaagcta tctttatccc aattacctag
     1381 gggtagacaa ccaatatccg acccatttgc tggagcaaat gacagagaaa caggaggaca
     1441 agcaactgat acacctgtgt ataacttcaa tccaatcaat aatcggaggt atgacaacta
     1501 tgacagtgat agtgaggaca gaattgacaa cgatcaagat caggctatca gagagaacag
     1561 aggagaacct ggacaaccaa caaccagac aagcgaaaac cagcagagac tcaatctccc
     1621 tgtaccgcaa agaacatcag gtatgagtag tgaagagttc caacattcaa tgaatcagta
     1681 catccgtgct atgcatgagc aatacagagg ctcccaggat gatgatgcca atgatgccac
     1741 agatgggaat gacatttcac ttgagctagt ggagattttt gattcctaac tctcacttttc
     1801 acataaccag acatacacat ccacaccacc cagagacata gctaccatcc acacactcac
     1861 ccagacaaat caaactagat tcaaatcatt ggaaacaat tctcctagaa tttaagaaaa
     1921 aaacataggc ccggacgggt tagagatccg gtgctcgtct gtgccagac aacctccaca
     1981 ccagagccac acaatcatgg ccgaggaacc aacatacacc actgagcaag ttgatgaatt
     2041 aatccatgct ggactaggaa cagtagattt cttcctatct agacccatag atgctcagtc
     2101 ttctttaggt aaaggcagca tcccaccagg tgtcacggct gttctaacca atgcagcaga
     2161 ggcaaaatcc aaaccagttg ctgctggtcc agtaaaaccc agacggaaga agtgatcag
     2221 caataccact ccatacacta ttgcagacaa catccccacct gagaagctac cgatcaacac
     2281 tccaataccc aatccattac ttccactggc acgccctcac ggaaagatga cagacattga
     2341 cattgtcact gggaacatta cagaaggtac ataaaaggt gtggagcttg ccaaattagg
     2401 gaagcaaaca ctactcacaa ggttccacctc gaatcagaca gtcctccatg ctggatccgc
     2461 ccaagacccc aactttaaga ggggggagc taatagagaa agagccaagag gcaacctag
     2521 gagagaatgg agtattgcat gggtcggaga tcaggtcaaa gtcttcgagt ggtgtaatcc
     2581 caggtgtgcc ccagtcacgg cttcagctcg caagttcacc tgcacatgtg gatcctgccc
     2641 cagcatctgc ggagaatgtg aaggagatca ttgagctctt aaagggcctt gatcttcgcc
```

-continued

```
2701  ttcagactgt agaagggaaa gtagataaaa ttcttgcaac ctctgcaact ataatcaatc
2761  ttaaaaatga aatgactagt cttaaggcga gcgttgcaac tgtggaaggt atgataacaa
2821  caattaaaat catggatccc agtacaccaa ccaatgtccc tgtagaggag atcagaaaga
2881  gtttacacaa tgttccagta gtaattgctg gtccgactag tggaggcttc acagccgaag
2941  gcagtgacat gatttcaatg gatgaactag ctaggcctac actctcatca acaaaaaaga
3001  tcacacgaaa gcctgaatcc aagaaagatt taacaggcat aaaactaacc ctgatgcagc
3061  ttgcaaatga ctgcatctcg cgtccagata ccaagactga gtttgtgact aagattcaag
3121  cagcaaccac agaatcacag ctcaacgaaa tcaaacggtc aataatacgc tctgcaatat
3181  aaaatgcggt gcaatcacac aagagacatt caacatgcat ccgatcaaga tccaaactcc
3241  ttccatccga aaacacactc accactgtca acaccaagaa acaactacag ccgaaccatg
3301  ctcaaccaaa agacccaaac aacatctcaa atcgacagaa ggctagacat gataaattta
3361  ataaaaaatt aaaagaagtt aagtaaaatt taagaacacc aatagagaaa acctaggtcc
3421  gaaagcttgc ctttcagaca gatcccaaaa tcatagttca aacttcaaac acagcagcag
3481  acatgcctat caatatcatta ccagcagatc caacttcacc cagtcaatcc cttactccgt
3541  ttccaataca acttgatacc aaagatggca aggcagggaa actccttaaa cagattagaa
3601  ttaggtatct aaatgaacct aactctcgtc ataccaat aactttcatc aatacgtatg
3661  gatttgttta tgctcgagac acttcaggag gcattcacag cgagatcagc agtgacctag
3721  ctgcagggtc cataacggca tgcatgatga cactaggtcc tggtccaaat attcagaatg
3781  caaatctagt gctaagatcc ctgaatgaat tctacgtaaa agtcaagaag acatcaagcc
3841  agagggagga agcagtgttt gaattagtta acattccaac cttattgaga gaacatgctc
3901  tttgcaaacg caaaacgtta gtatgctctg cagaaaaatt cctcaagaac ccatcaaagc
3961  tacaagctgg atttgaatat gtatacatcc caacttttgt ctccattaca tactcaccac
4021  gaaatctgaa ttaccaagtt gccagaccta tccttaagtt cagatcacgc tttgtgtata
4081  gcattcattt ggaattaatc ctgagattgc tatgcaaatc tgactcccct ttgatgaaat
4141  cttataatgc agatcgaaca ggtcgaggat gcctcgcatc agtctggatc cacgtatgta
4201  acattctgaa aaacaaaagc atcaagcaac aaggcagaga atcatatttc atagctaagt
4261  gcatgagtat gcagctgcag gtgtccattg cagatctttg gggaccaaca atcataatta
4321  aatcattggg tcacatcccc aagactgcac ttccttttt cagcaaagac gggattgcct
4381  gtcatccact acaagatgtt tcccctactc tgacaaaatc actgtggtca gtgggatgtg
4441  agatagaatc tgccaagttg atacttcaag aatctgatat taatgagcta atgggccacc
4501  aggacttgat tactgataag attgccatta gatcaggtca acggacattt gagaggtcca
4561  aattcagccc attcaaaaaa tacgcatcaa ttccaaactt agaagccatc aactgaatgc
4621  tccagcatct aggaatagaa caacaactaa gtcataccat tattgaccat acaataatca
4681  acaattttag ccaactgatt actaagatat tatcataggt ccgaactgat caatctaaca
4741  aaaaaactaa acattcaata ataatcaaa gttcaggcca aattatccag ccatgcatca
4801  cctgcatcca atgatagtat gcatttttgt tatgtacact ggaattgtag gttcagatgc
4861  cattgctgga gatcaactcc tcaatgtagg ggtcattcaa tcaaagataa gatcactcat
4921  gtactacact gatggtggcc ctagctttat tgttgtaaaa ttactacccca atcttccccc
4981  aagcaatgga acatgcaaca tcaccagtct agatgcatat aatgttaccc tatttaagtt
5041  gctaacaccc ctgattgaga acctgagcaa aatttctgct gttacagata ccaaaccccg
5101  ccgagaacga tttgcaggag tcgttattgg gcttgctgca ctaggagtag ctacagctgc
5161  acaaataacc gcagctgtag caatagtaaa agccaatgca aatgctgctg cgataaacaa
5221  tcttgcatct tcaattcaat ccaccaacaa ggcagtatcc gatgtgataa ctgcatcaag
5281  aacaattgca accgcagttc aagcgattca ggatcacatc aatggagcca ttgtcaacgg
5341  gataacatct gcatcatgcc gtgcccatga tgcactaatt gggtcaatat taaatttgta
5401  tctcactgag cttactacaa tatttcataa tcaaataaca aaccctgcgc tgacaccact
5461  ttccatccaa gctttaagaa tcctcctcgg tagcaccttg ccaattgtca ttgaatccaa
5521  actcaacaca aaactcaaca cagcagagct gctcagttcc ggactgttaa ctggtcaaat
5581  aatttccatt tccccaatgt acatgcaaat gctaattcaa atcaatgttc cgacatttat
5641  aatgcaaccc ggtgcgaagg taattgatct aattgctatc tctgcaaacc ataaattaca
5701  agaagtagtt gtacaagttc ctaatagaat tctagaatat gcaaatgaac tacaaaacta
5761  cccagccaat gattgtgtcg tgacaccaaa ctctgtattt tgtagataca atgagggttc
5821  cccgatccct gaatcacaat atcaatgctt aagggggaat cttaattctt gcacttttac
5881  ccctattatc gggaactttc tcaagcgatt cgcatttgcc aatggtgtgc tctatgccaa
5941  ctgcaaatct ttgctatgta agtgtgccga ccctccccat gttgtgtctc aagatgacaa
6001  ccaaggcatc agcataattg atattaagag gtgctctgag atgatgcttg acacttttc
6061  atttaggatc acatctacat tcaatgctac atacgtgaca gacttctcaa tgattaatgc
6121  aaatattgta catctaagtc ctctagactt gtcaaatcaa atcaattcaa taaacaaatc
6181  tcttaaaagt gctgaggatt ggattgcaga tagcaacttc ttcgctaatc aagccagaac
6241  agccaagaca cttttattcac taagtgcaat cgcattaata ctatcagtga ttactttggt
6301  tgttgtggga ttgctgattg cctacatcat caagctggtt tctcaaatcc atcaattcag
6361  agcactagct gctacaacaa tgttccacag ggagaatcct gccgtctttt ccaagaacaa
6421  tcatggaaac atatatggga tatcttaaga attctatcat aagtccatat atgtccatga
6481  ttgaccttta agagccaacc tccaatgatt atccgttaaa ttcagatata acaattcaaa
6541  aatcaatatt aagcctccag ataccaatga atatgaatat atctcttaga aaacttgatt
6601  attatgtgat aacatagtac aatttaagaa aaaacctaaa ataagcacga accctaaagg
6661  tgtcgtaacg tctcgtgacg ccgggttcag ttcaaacatc gaccctgac ccaattcaat
6721  acccatttc ataaggaac acagtataat ttaatcataa aagacctcaaa aatctgatac
6781  agcttaatcc actcaacata taattataag actaataata atggaagatt acagcaatct
6841  atctcttaaa tcaattccta aaaggacatg tagaatcatt ttccgaactg ccacaattct
6901  tggcatatgc acattaattg tgctatgttc aagtattctt catgagataa ttcatcttga
6961  tgtttcctct ggtcttatga attctgatga gtcacagcaa ggcattattc agcctatcat
7021  agaatcatta aaatcattga ttgctttggc caaccagatt ctatataatg ttgcaatagt
7081  aattcctctt aaaaattgaca gtatcgaaac tgtaatactc tctgctttaa aagatatgca
7141  caccgggagt atgtccaatg ccaactgcac gccaggaaat ctgcttctgc atgatgcagc
7201  atacatcaat ggaataaaca aattccttgt acttgaatca tacaatggga cctcctaaata
7261  tggacctctc ctaaatatac ccagctttat cccctcagca acatctcccc atgggtgtac
7321  tagaatacca tcatttcac tcatcaagac ccattggtgt tacactcaca atgtaatgct
7381  tggagattgt cttgatttca cggcatctaa ccagtattta tcaatgggga taatacaaca
7441  atctgctgca gggtttccaa ttttcaggac tatgaaaacc attaacctaa gtgatggaat
7501  caatcgcaaa agctgttcag tcactgctat accaggaggt tgtgtcttgt attgctatgt
```

```
7561  agctacaagg tctgaaaaag aagattatgc cacgactgat ctagctgaac tgagacttgc
7621  tttctattat tataatgata cctttattga aagagtcata tctcttccaa atacaacagg
7681  gcagtgggcc acaatcaacc ctgcagtcgg aagcgggatc tatcatctag gctttatctt
7741  atttcctgta tatggtggtc tcataaatgg gactacttct tacaatgagc agtcctcacg
7801  ctattttatc ccaaaacatc ccaacataac ttgtgccggt aactccagca aacaggctgc
7861  aatagcacgg agttcctatg tcatccgtta tcactcaaac aggttaattc agagtgctgt
7921  tcttatttgt ccattgtctg acatgcatac agaagagtgt aatctagtta tgtttaacaa
7981  ttcccaagtc atgatgggtg cagaaggtag gctctatgtt attggtaata atttgtatta
8041  ttatcaacgc agttcctctt ggtggtctgc atcgctcttt tacaggatca atacagattt
8101  ttctaaagga attcctccga tcattgaggc tcaatgggta ccgtcctatc aagttcctcg
8161  tcctggagtc atgccatgca atgcaacaag ttttttgccct gctaattgca tcacaggggt
8221  gtacgcagat gtgtggccgc ttaatgatcc agaactcatg tcacgtaatg ctctgaaccc
8281  caactatcga tttgctggag cctttctcaa aaatgagtcc aaccgaacta atcccacatt
8341  ctacactgca tcggctaact ccctccttaaa tactaccgga ttcaacaaca ccaatcacaa
8401  agcagcatat acatcttcaa cctgctttaa aaacactgga acccaaaaaa tttattgttt
8461  aataataatt gaaatgggct catctctttt aggggagttc caaataatac cattttttaag
8521  ggaactaatg ctttaatcct attgaatgaa gactccagat tcaagaataa ttggaaggct
8581  ctttatttta tgcgatagtt atacgttttg gctgtattag aatgctatag cattctgctg
8641  tttttcccat atggaaaaat ccttcaacac caacttaggt tcaatttttct catcatttac
8701  tgttgtaatt caatcttact aaagttattc tgatatttaa gaaaaataa tctttatata
8761  atgtaacaat actactaaga ttataatata ggccagaatg gcggcctctt ctgagatact
8821  ccttcctgaa gtccatttga actcaccaat agtcaaacac aaactcatat actacttatt
8881  actagggcac ttcccgcatg atcttgacat ttctgaaata agccccctc acaataatga
8941  ttgggatcag attgccagaa aagaatccaa tcttgctgaa cgactcggag tagctaaatc
9001  tgaattaatt aaacgtgtgc ccgcatttag agcaaccaga tggcgtagtc atgcagccgt
9061  ccttatatgg ccttcttgta taccattcct tgttaaattc ctaccccatt ctaagcttca
9121  accaatagaa caatggtaca agttgatcaa tgcttcatgc aatactatat ctgactcaat
9181  tgatagatgt atggagaata tttctattaa gcttactggg aaaaacaatc tattctctcg
9241  atccagagga actgcaggcg caggtaaaaa cagtaaaatc accctcaatg atatccaatc
9301  tatttgggaa tcaaacaaat ggcagcctaa tgtatcttta tggcttacaa ttaaatacca
9361  aatgcgacaa cttataatgc atcaaagttc tcgtcagcca actgatttag ttcacattgt
9421  tgacacacga tctggtctaa tagttatcac ccctgaactt gttatttgct ttgatcggtt
9481  gaataatgtt ttaatgtatt ttacatttga gatgacttta atggtaagtg acatgtttga
9541  gggacggatg aatgttgccg cgctctgcac tattagtcat tacttatcac cactagggcc
9601  aaggatagat agattgtttt ctattgtaga tgaattagca caactattgg gtgcacctgt
9661  atataaaatt attgcatctc ttgaatcttt agtatatggg tgtctacaac ttaaagatcc
9721  agtggttgaa ttaacaggat catttcattc ctttattacg caagagatta tagatatcct
9781  aattgggtca aaagcccttg ataaggatga atcaataact gtcactacac aattgctaga
9841  tatattttcc aacctttcc cagatttaat cgctgagatg ttgtgtctca tggacttttg
9901  gggtcatccc actcttactg ctgcgcaagc tgcaggtaaa gtgagagaat ctatgtgtgc
9961  aggtaagtta cttgatttcc ctacaataat gaaaactctt gctttttttcc acacaatttt
10021 aatcaatggt tatcgtagaa agaagaatgg aatgtggcct ccacttatac ttcctaaaaa
10081 tgcatcaaaa agcttaatag agtttcaaca tgataatgct gaaatatctt atgagtatac
10141 actcaagcat tggaaagaaa tctctctcat agaatttaga aagtgctttg actttgatcc
10201 tggtgaggag ctaagcattt ttatgaaaga caaggcaata agtgctccaa aaagtgattg
10261 gatgagtgta ttccgtagaa gtcaataaaa acaacgcact cagagacatc atattcctat
10321 gcccaatcca tttaacagac gtctattact caatttctta gaagatgaca gtttttgatcc
10381 agttgctgag cttcaatatg ttaccagtgg tgaatatctc cgagatgaca cattttgtgc
10441 atcttactca ttaaaagaga aagaaataaa accagatgga aggatatttg ctaagcttac
10501 taatagaatg cggtcttgtc aagtaattgc ggaagcaatt cttgcaaatc acgcaggtac
10561 tctaatgaag gaaaacggag ttgtcttgaa tcaattatct ctgactaaat cattgcttac
10621 tatgagtcaa attggcataa tatcagaaaa agcaaagaga tatcccgag ataacatctc
10681 atctcaaggt ttccatacaa tcaagactga ctcaaaaaat aagaagaaaa gcaaaattgc
10741 atcatcatac ctcacagatc ctgatgatac atttgaactt agtgcatgtt ttataactac
10801 tgatcttgct aaatactgtc ttcaatggag atatcagacc ataatccatt ttgctcgaac
10861 attaaacaga atgtatgtag ttccacattt atttgaatgg attcatcttc gtttgattag
10921 atctacatta tatgttggtg atccattcaa tcctcctgcc acaactgatg ccttcgatct
10981 agataaagta ttaaatggtg atatctttat agtctctccc aagggaggta ttgaaggcct
11041 atgtcagaaa atgtggacaa tgatctctat ttctgtgatc atcctttctt cagccgaatc
11101 caaaacaaga gtaatgacaa tggttcaagg agataatgac gcgattgcag ttacaacaag
11161 agttcctaga tcattgccta gtgttcagaa aaaggagtta gcctacgcag caagcaagtt
11221 attctttgaa agacttaggg caaataatta tggtttgggt catcaactaa aggctcaaga
11281 gactataata agttccacgt tcttcatata tagtaaacgg gtattctatc aaggacgtat
11341 actaacacag cgcacttaaaa atgctagcaa gttatgtctt actgcagatg tattaggtga
11401 atgtactcag gcttcctgct caaattctgc tactacaatc atgagattaa cagaaaatgg
11461 ggttgagaaa gatacatgtt ataagcttaa tatttatcaa tctattcgtc aactcacata
11521 tgatctaata ttttcccaat actccatacc aggtgaaaca ataagtgaaa ttttcttaca
11581 gcatccaaga ttaatctcac gtatcgttct gctcccttca cagctaggtg gtcttaatta
11641 cctcgcatgt agcagattat taaccgcaa tatcggagat cccccttggta cagccgtggc
11701 agacctcaag aggttaatta aatgtggtgc tcttgaatca tggatactgt acaatttact
11761 ggcaagaaaa ccagggaaag gttcatgggc cactttagca gccgatccat actcattgaa
11821 tcaagaatat ctttatcctc ctactactat acttaaaaga catctcaaaa atactttaat
11881 ggagatatgt cggaatccta tgttaaaggg agttttttaca gataatgcaa aagaggagga
11941 aaatctcctt gcaaaatttc ttcttgatcg tgatatagta ttgccaagag tcgcacacat
12001 tataatagat caatccagca ttggaaggaa gaaacagata caagggttt tgacaccac
12061 aaggaccata atgagacgat catttgagat caaaccactc tcaactagga gcaagactt
12121 agtcatgaaa tataatacta attatttatc ttataactac cctgtcatac ttaatccttt
12181 acctattcct ggatattttaa attatattac tgaccaaact tgcagtattg atatatctag
12241 aagtttaaga aaattatcat ggtcttcttt attgaatgga agaactttag aaggattaga
12301 aactccagat ccaattgaag ttgtcaatgg ttccttgatt gtaggtacag gagattgtga
12361 cttttgtatg caggggtgacg ataaattcac ttggttcttt ttacctatgg ggataattat
```

-continued

```
12421  tgatggaaat cctgaaacta atccacccat cagagttcca tacattgggt ctagaacaga
12481  ggaaagaaga gttgcatcaa tggcatatat taaaggtgcc acacacagtt tgaaggctgc
12541  tcttagaggc gcagggtat acatttgggc attcggagat acagtagtga actggaatga
12601  tgcacttgat atcgcaaata ctagggttaa gatatcccta gagcaacttc agactcttac
12661  acctcttcct acatctgcaa acattacaca tcgtttagat gatggagcca caacacttaa
12721  attcactcca gctagttcct atgcattttc tagttatact catatatcaa atgatcaaca
12781  atatttagaa atagatcaga gagtagtcga ttccaatatt atttatcaac aattaatgat
12841  aacagggctt gggatcattg agacctacca taacccacct atcaggacct ctacacagga
12901  aatcaccctc catttgcaca ctagctcatc ttgttgtgtt agaagtgtag atggttgcct
12961  tatatgtgag agcaatggag aggttcctca gatcactgtt ccctacacta attcatttgt
13021  atatgatcct gatccactag cagattatga gattgcacat ctagattatc tctcctacca
13081  agctaaaatt ggaagtacag attactactc acttactgat aaaattgatc tattggcaca
13141  tttaactgca aaacaaatga taaactcaat aattgggtta gatgaaacag tatcaattgt
13201  caatgatgcg gttattctat ctgattatac taataactgg attagtgaat gttcttatac
13261  taagatagat ttagttttta aattaatggc atggaatttc cttcttgagc ttgcattcca
13321  gatgtactac ctaagaatat catcttggac aaatatattt gactatactt acatgacttt
13381  acgcaggata cccgaactg ctctaaataa tattgcagct actattagcc acccaaaatt
13441  attaagacgt gcaatgaatc ttgatattat cactcctata catgcaccgt atttggcttc
13501  attagattat gtcaaattaa gtattgatgc aattcagtgg ggggttaaac aagttcttgc
13561  tgatttatca aatggaattg atcttgaaat cttgattctt tcagaggatt caatggaaat
13621  tagtgatagg gcaatgaatc tcattgctag aaaactaact ctccttgcac ttgttaaagg
13681  tgagaactat acatttccaa aaattaaagg gatgccacca gaggaaaagt gtttagtctt
13741  aactgaatac ctagcaatgt gttatcagaa tactcaccac ttagatccag atcttcaaaa
13801  gtatttatat aatctaacta atccaaaatt gactgcattt cccagtaaca acttctactt
13861  aacaaggaaa atccttaatc aaattagaga atcagacgaa ggacaatata ttatcaccctc
13921  atattatgaa tccttcgaac aattagaaac agatataatt cttcactcta ctttaactgc
13981  tccttatgat aattcagaaa ctctaacaaa gtttgattta tcccttgaca tctttccaca
14041  tccagaatct ctcgagaaat atcctcttcc agttgatcat gactctcaat ctgcaatttc
14101  aacactaatt ccaggccctc cctctcatca tgtattacga ccactaggag tgtcatctac
14161  agcttggtat aaagggataa gttattgcag atacctggaa acgcaaaaga tacagactgg
14221  tgatcatctt tatttagctg aaggaagcgg tgcttcaatg tcacttctag aactcctatt
14281  tccaggagat actgtctatt ataatagtct ttttagtagt ggagagaatc ctccacagag
14341  aaattatgct cctcttccaa ctcaatttgt acagagtgtt ccatataaat tgtggcaagc
14401  tgatcttgct gatgatagta acttaataaa agattttgtc ccattatgga atggaaacgg
14461  agcagttaca gacttatcga caaaggatgc agttgcattc ataatacata aagtaggagc
14521  ggagaaagca tcccttgttc atatagatct cgaatcgact gctaatataa atcagcaaac
14581  tctgtccaga tcccagattc attcgttaat tatagcaact actgttctta agaggggtgg
14641  gatattagtt tacaaaacat catggcttcc gttttctagg tttagtcaac tagcaagcct
14701  actttggtgc tttttttgacc ggatccatct aatacgtagt agttattctg atcctcacag
14761  tcatgaggtt tatcttgtat gtagacttgc tgcggatttt agaactatcg gtttcagtgc
14821  agctctagta actgctacta ctcttcacaa tgacggattc acaacaatac atcctgatgt
14881  tgtttgtagt tattggcaac accatcttga gaatgttggg agagtcgaaa aagtaattga
14941  tgagatactt gatggttttag ccaccaactt cttcgcagga gataatgggc ttattctaag
15001  atgtggagga actcccagct ctagaaaatg gttagagatt gatcagttag catcatttga
15061  ttcagttcaa gatgctctag tgacacttat caccatacac ctaaaggaaa ttatagaagt
15121  gcagtcatca catacagagg attatacatc tctccttttc acacccttata atattggtgc
15181  agcagggaaa gtaagaacta tcatcaaatt aattctagaa cgatctttaa tgtatacagt
15241  ccgaaattgg ttagttttac ccagttccat ccgggattcc gtacgacaag atctagagtt
15301  agggtcattt agattaatgt ctattttaag tgaacagaca tttcttaaaa agacacccac
15361  caaaaaatac ttacttgatc agcttacaag gacatatata tcaaccttct ttaattctca
15421  ctcagtcctc cccctccacc gtccatatca aaaacaaata tggaaagcct taggtagctgt
15481  aatatattgt tcggagacgt tgatataccc tctaattaga gacattcaga tagaagatat
15541  taatgatttt gaagatatcg agaggggtat cgatggcgaa gaattatgac aacagtgatt
15601  ataagaactc atgatagttt tatttaagaa aaacatattg attttcccct tggt
//
```

C.2. V94 Sequences:

Nucleotide Sequence Coding for F Protein of V94 Isolate, as Obtained from Genbank Data AF_533010—SEQ ID NO: 53 (1656 nt)

```
atgcatca cctgcatcca atgatagtat gcattttttgt tatgtacact ggaattgtag gttcagatgc cattgctgga gatcaactcc tcaatgtagg ggtcattcaa tcaaagataa gatcactcat gtactacact gatggtgcg ctagcttat tgttgtaaaa ttactaccca atcttccccc aagcaatgga acatgcaaca tcaccagtct agatgcatat aatgttaccc tatttaagtt gctaacaccc ctgattgaga acctgagcaa aatttctgct gttacagata ccaaaccccg ccgagaacga tttgcaggag tcgttattgg gcttgctgca ctaggagtag ctacagctgc acaaataacc gcagctgtat caatagtaaa agccaatgca aatgctgctg cgataaacaa tcttgcatct tcaattcaat ccaccaacaa ggcagtatcc gatgtgataa ctgcatcaag aacaattgca accgcagttc aagcgattca ggatcacatc aatggagcca ttgtcaacgg gataacatct gcatcatgcc gtgcccatga tgcactaatt gggtcaatat taaatttgta tctcactgag cttactacaa tatttcataa tcaaataaca aaccctgcgc tgacaccact ttccatccaa gctttaagaa tcctcctcgg tagcaccttg ccaattgtca ttgaatccaa
```

```
actcaacaca aaactcaaca cagcagagct gctcagttcc ggactgttaa ctggtcaaat aatttccatt tccccaatgt acatgcaaat gctaattcaa atcaatgttc cgacatttat aatgcaaccc ggtgcgaagg taattgatct aattgctatc tctgcaaacc ataaattaca agaagtagtt gtacaagttc ctaatagaat tctagaatat gcaaatgaac tacaaaacta cccagccaat gattgtgtcg tgacaccaaa ctctgtattt tgtagataca atgagggttc cccgatccct gaatcacaat atcaatgctt aaggggggaat cttaattctt gcactttttac ccctattatc gggaactttc tcaagcgatt cgcatttgcc aatggtgtgc tctatgccaa ctgcaaatct ttgctatgta agtgtgccga ccctccccat gttgtgtctc aagatgacaa ccaaggcatc agcataattg atattaagag gtgctctgag atgatgcttg acactttttc atttaggatc acatctacat tcaatgctac atacgtgaca gacttctcaa tgattaatgc aaatattgta catctaagtc ctctagactt gtcaaatcaa atcaattcaa taaacaaatc tcttaaaagt gctgaggatt ggattgcaga tagcaacttc ttcgctaatc aagccagaac agccaagaca ctttattcac taagtgcaat cgcattaata ctatcagtga ttactttggt tgttgtggga ttgctgattg cctacatcat caagctggtt tctcaaatcc atcaattcag agcactagct gctacaacaa tgttccacag ggagaatcct gccgtctttt ccaagaacaa tcatggaaac atatatggga tatctta
```

Sequence for F Protein of V94 Isolate, as Obtained from Genbank Data AF__533010—SEQ ID NO: 54 (551 aa)

```
MHHLHPMIVCIFVMYTGIVGSDAIAGDQLLNVGVIQSKIRSLMYYTDGGA

SFIVVKLLPNLPPSNGTCNITSLDAYNVTLFKLLTPLIENLSKISAVTDT

KPRRERFAGVVIGLAALGVATAAQITAAVAIVKANANAAAINNLASSIQS

TNKAVSDVITASRTIATAVQAIQDHINGAIVNGITSASCRAHDALIGSIL

NLYLTELTTIFHNQITNPALTPLSIQALRILLGSTLPIVIESKLNTKLNT

AELLSSGLLTGQIISISPMYMQMLIQINVPTFIMQPGAKVIDLIAISANH

KLQEVVVQVPNRILEYANELQNYPANDCVVTPNSVFCRYNEGSPIPESQY

QCLRGNLNSCTFTPIIGNFLKRFAFANGVLYANCKSLLCKCADPPHVVSQ

DDNQGISIIDIKRCSEMMLDTFSFRITSTFNATYVTDFSMINANIVHLSP

LDLSNQINSINKSLKSAEDWIADSNFFANQARTAKTLYSLSAIALILSVI

TLVVVGLLIAYIIKLVSQIHQFRALAATTMFHRENPAVFSKNNHGNIYGI

SX
```

Nucleotide Sequence Coding for HN Protein of V94 Isolate, as Obtained from Genbank Data AF__533010—SEQ ID NO: 55 (1716 nt)

```
atggaagatt acagcaatct atctcttaaa tcaattccta aaaggacatg tagaatcatt ttccgaactg ccacaattct tggcatatgc acattaattg tgctatgttc aagtattctt catgagataa ttcatcttga tgtttcctct ggtcttatga attctgatga gtcacagcaa ggcattattc agcctatcat agaatcatta aaatcattga ttgctttggc caaccagatt ctatataatg ttgcaatagt aattcctctt aaaattgaca gtatcgaaac tgtaatactc tctgctttaa aagatatgca caccgggagt atgtccaatg ccaactgcac gccaggaaat ctgcttctgc atgatgcagc atacatcaat ggaataaaca aattccttgt acttgaatca tacaatggga cgcctaaata tggacctctc ctaaatatac ccagctttat cccctcagca acatctcccc atgggtgtac tagaatacca tcattttcac tcatcaagac ccattggtgt tacactcaca atgtaatgct tggagattgt cttgatttca cggcatctaa ccagtattta tcaatgggga taatacaaca atctgctgca gggtttccaa ttttcaggac tatgaaaacc atttacctaa gtgatggaat caatcgcaaa agctgttcag tcactgctat accaggaggt tgtgtcttgt attgctatgt agctacaagg tctgaaaaag aagattatgc cacgactgat ctagctgaac tgagacttgc tttctattat tataatgata cctttattga aagagtcata tctcttccaa atacaacagg gcagtgggcc acaatcaacc ctgcagtcgg aagcgggatc tatcatctag gctttatctt atttcctgta tatggtggtc tcataaatgg gactacttca tacaatgagc agtcctcacg ctattttatc ccaaaacatc ccaacataac ttgtgccggt aactccagca aacaggctgc aatagcacgg agttcctatg tcatccgtta tcactcaaac aggttaattc agagtgctgt tcttatttgt ccattgtctg acatgcatac agaagagtgt aatctagtta tgtttaacaa ttcccaagtc atgatggggtg cagaaggtag gctctatgtt attggtaata atttgtatta ttatcaacgc agttcctctt ggtggtctgc atcgctcttt tacaggatca atacagattt ttctaaagga attcctccga tcattgaggc tcaatgggta ccgtcctatc aagttcctcg tcctggagtc atgccatgca atgcaacaag tttttgccct gctaattgca tcacagggt gtacgcagat gtgtggccgc ttaatgatcc agaactcatg tcacgtaatg ctctgaaccc caactatcga tttgctggag ccttttctcaa aaatgagtcc aaccgaacta atcccacatt ctacactgca tcggctaact ccctcttaaa tactaccgga ttcaacaaca ccaatcacaa agcagcatat acatcttcaa cctgctttaa aaacactgga
```

-continued acccaaaaaa tttattgttt aataataatt gaaatgggct catctctttt aggggagttc caaataatac catttttaag ggaactaatg ctttaa

Sequence for HN Protein of V94 Isolate, as Obtained from Genbank data AF_533010—SEQ ID NO: 56 (571 aa)

MEDYSNLSLKSIPKRTCRIIFRTATILGICTLIVLCSSILHEIIHLDVSS

GLMNSDESQQGIIQPIIESLKSLIALANQILYNVAIVIPLKIDSIETVIL

SALKDMHTGSMSNANCTPGNLLLHDAAYINGINKFLVLESYNGTPKYGPL

-continued

LNIPSFIPSATSPHGCTRIPSFSLIKTHWCYTHNVMLGDCLDFTASNQYL

SMGIIQQSAAGFPIFRTMKTIYLSDGINRKSCSVTAIPGGCVLYCYVATR

SEKEDYATTDLAELRLAFYYYNDTFIERVISLPNTTGQWATINPAVGSGI

YHLGFILFPVYGGLINGTTSYNEQSSRYFIPKHPNITCAGNSSKQAAIAR

SSYVIRYHSNRLIQSAVLICPLSDMHTEECNLVMFNNSQVMMGAEGRLYV

IGNNLYYYQRSSSWWSASLFYRINTDFSKGIPPIIEAQWVPSYQVPRPGV

MPCNATSFCPANCITGVYADVWPLNDPELMSRNALNPNYRFAGAFLKNES

NRTNPTFYTASANSLLNTTGFNNTNHKAAYTSSTCFKNTGTQKIYCLIII

EMGSSLLGEFQIIPFLRELML

---

SEQUENCE LISTING

<160> NUMBER OF SEQ ID NOS: 118

<210> SEQ ID NO 1
<211> LENGTH: 21
<212> TYPE: DNA
<213> ORGANISM: Human parainfluenza virus 2

<400> SEQUENCE: 1
tggaagccat caactgaatg c                                        21

<210> SEQ ID NO 2
<211> LENGTH: 21
<212> TYPE: DNA
<213> ORGANISM: Human parainfluenza virus 2

<400> SEQUENCE: 2
tcctgaattg cttgaactgc g                                        21

<210> SEQ ID NO 3
<211> LENGTH: 20
<212> TYPE: DNA
<213> ORGANISM: Human parainfluenza virus 2

<400> SEQUENCE: 3
tcaagaacaa ttgcaaccgc                                          20

<210> SEQ ID NO 4
<211> LENGTH: 21
<212> TYPE: DNA
<213> ORGANISM: Human parainfluenza virus 2

<400> SEQUENCE: 4
caatcccacg acaaccaaag t                                        21

<210> SEQ ID NO 5
<211> LENGTH: 20
<212> TYPE: DNA
<213> ORGANISM: Human parainfluenza virus 2

<400> SEQUENCE: 5
aagccaggac agccaagaca                                          20

<210> SEQ ID NO 6
<211> LENGTH: 21
<212> TYPE: DNA
<213> ORGANISM: Human parainfluenza virus 2

<400> SEQUENCE: 6
tcatgcagaa gcagatttcc g                                            21

<210> SEQ ID NO 7
<211> LENGTH: 21
<212> TYPE: DNA
<213> ORGANISM: Human parainfluenza virus 2

<400> SEQUENCE: 7
aacaccaact gtacacccgg a                                            21

<210> SEQ ID NO 8
<211> LENGTH: 20
<212> TYPE: DNA
<213> ORGANISM: Human parainfluenza virus 2

<400> SEQUENCE: 8
tgtgatgcaa ttagcagggc                                              20

<210> SEQ ID NO 9
<211> LENGTH: 19
<212> TYPE: DNA
<213> ORGANISM: Human parainfluenza virus 2

<400> SEQUENCE: 9
ttggtggtct gcatcgctt                                               19

<210> SEQ ID NO 10
<211> LENGTH: 19
<212> TYPE: DNA
<213> ORGANISM: Human parainfluenza virus 2

<400> SEQUENCE: 10
gttgctctaa atgcgggca                                               19

<210> SEQ ID NO 11
<211> LENGTH: 20
<212> TYPE: DNA
<213> ORGANISM: Human parainfluenza virus 2

<400> SEQUENCE: 11
aacaatctgc tgcagcattt                                              20

<210> SEQ ID NO 12
<211> LENGTH: 20
<212> TYPE: DNA
<213> ORGANISM: Human parainfluenza virus 2

<400> SEQUENCE: 12
atgtcagaca atgggcaaat                                              20

<210> SEQ ID NO 13
<211> LENGTH: 6
<212> TYPE: PRT
<213> ORGANISM: Human parainfluenza virus 2

<400> SEQUENCE: 13

Lys Thr Arg Gln Glu Arg
1               5

<210> SEQ ID NO 14
<211> LENGTH: 6
<212> TYPE: PRT

```
<213> ORGANISM: Human parainfluenza virus 2

<400> SEQUENCE: 14

Lys Pro Arg Arg Glu Arg
1               5

<210> SEQ ID NO 15
<211> LENGTH: 20
<212> TYPE: PRT
<213> ORGANISM: Simian parainfluenza virus 5

<400> SEQUENCE: 15

Phe Ala Gly Val Val Ile Gly Leu Ala Ala Leu Gly Val Ala Thr Ala
1               5                   10                  15

Ala Gln Val Thr
            20

<210> SEQ ID NO 16
<211> LENGTH: 20
<212> TYPE: PRT
<213> ORGANISM: Human parainfluenza virus 2

<400> SEQUENCE: 16

Phe Ala Gly Val Val Ile Gly Leu Ala Ala Leu Gly Val Ala Thr Ala
1               5                   10                  15

Ala Gln Ile Thr
            20

<210> SEQ ID NO 17
<211> LENGTH: 20
<212> TYPE: PRT
<213> ORGANISM: Human parainfluenza virus 2

<400> SEQUENCE: 17

Phe Ala Gly Val Val Ile Gly Leu Ala Ala Leu Gly Val Ala Thr Ala
1               5                   10                  15

Ala Gln Ile Thr
            20

<210> SEQ ID NO 18
<211> LENGTH: 20
<212> TYPE: PRT
<213> ORGANISM: Human parainfluenza virus 2

<400> SEQUENCE: 18

Phe Ala Gly Val Val Ile Gly Leu Ala Ala Leu Gly Val Ala Thr Ala
1               5                   10                  15

Ala Gln Ile Thr
            20

<210> SEQ ID NO 19
<211> LENGTH: 20
<212> TYPE: PRT
<213> ORGANISM: Human parainfluenza virus 2

<400> SEQUENCE: 19

Phe Ala Gly Val Val Ile Gly Leu Ala Ala Leu Gly Val Ala Thr Ala
1               5                   10                  15

Ala Gln Ile Thr
            20

<210> SEQ ID NO 20
```

```
<211> LENGTH: 20
<212> TYPE: PRT
<213> ORGANISM: Human parainfluenza virus 2

<400> SEQUENCE: 20

Phe Ala Gly Val Val Ile Gly Leu Ala Ala Leu Gly Val Ala Thr Ala
1               5                   10                  15

Ala Gln Ile Thr
            20

<210> SEQ ID NO 21
<211> LENGTH: 20
<212> TYPE: PRT
<213> ORGANISM: Human parainfluenza virus 2

<400> SEQUENCE: 21

Phe Ala Gly Val Val Val Gly Leu Ala Ala Leu Gly Val Ala Thr Ala
1               5                   10                  15

Ala Gln Ile Thr
            20

<210> SEQ ID NO 22
<211> LENGTH: 4333
<212> TYPE: DNA
<213> ORGANISM: Human parainfluenza virus 2

<400> SEQUENCE: 22
atgctccagc atctaggaat agaacaacaa ctaagtcata ccattattga ccatacaata      60
atcaacaatt ttagccaact gattactaag atattatcat aggtccgaac tgatcaatct     120
aacaaaaaaa ctaaacattc aataataaat caaagttcag gccaaattat ccagccatgc     180
atcacctgca tccaatgata gtatgcatct ttgttatgta cactggaatt gtaggttcag     240
atgccattgc tggagatcaa ctcctcaatg tagggggtcat tcaatcaaag ataagatcac     300
tcatgtacta cactgatggt ggcgctagct ttattgttgt aaaattacta ccaaatcttc     360
ccccaagcaa tggaacatgc aacatcacca gtctagatgc atataatgtt accctatttta    420
agttgctaac gccctgatt gagaacctga gcaaaatttc tgctgttaca gataccaaac      480
cccgccgaga acgatttgca ggagtcgtta ttgggcttgc tgcactagga gtagctacag     540
ctgcacaaat aaccgcagct gtagcaatag taaaagccaa tgcaaatgct gctgcgataa     600
acaatcttgc atcttcaatt caatccacca caaggcagt atccgatgtg ataactgcat     660
caagaacaat tgcaaccgca gttcaagcaa ttcaggatcg catcaatgga gctattgtta     720
atgggataac atctgcatca tgccgtgccc atgatgcact aattgggtca atattaaatt     780
tgtatctcac tgagcttact acaatatttc ataatcaaat aacaaaccct gcgctgacac     840
cactttccat ccaagcttta agaatcctcc tcggtagcac cttgccaatt gtcattgaat     900
ccaaactcaa cacaaaactc aacacagcag agctgctcag ttccggactg ttaactggtc     960
aaataatttc catttcccca atgtacatgc aaatgctaat tcaaatcaat gttccgacat    1020
ttataatgca acccggtgcg aaggtaattg atctaattgc tatctctgca aaccataaat    1080
tacaagaagt agttgtacaa gttcctaata gaattctaga atcgcaaat gaactacaaa    1140
actacccagc caatgattgt gtcgtgacac caaactctgt attttgtaga tacaatgagg    1200
gttccccgat ccctgaatca caatatcaat gcttaagggg gaatcttaat tcttgcactt    1260
ttaccccctat tatcgggaac tttctcaagc gattcgcatt tgccaatggt gtgctctatg    1320
ccaactgcaa atctttgcta tgtaagtgtg ccgaccctcc ccatgttgtg tctcaagatg    1380
```

-continued

```
acaaccaagg catcagcata attgatatta agaggtgctc tgagatgatg cttgacactt    1440
tttcatttag gatcacatct acattcaatg ctacatacgt gacagacttc tcaatgatta    1500
atgcaaatat tgtacatcta agtcctctag acttgtcaaa tcaaattaat tcaataaaca    1560
aatctcttaa aagtgctgaa gattggattg cagatagcaa cttcttcgct aatcaagcca    1620
gaacagccaa gacactttat tcactaagtg caatagcatt aatactatca gtgattactt    1680
tggttgttgt gggattgctg attgcctaca tcatcaagct ggtttctcaa atccatcaat    1740
tcagagcact agctgctaca caatgttcc acagggagaa tcctgctgtc ttttccaaga     1800
acaatcatgg aaacatatat gggatatctt aagaattcta tcataagtcc atatatgtcc    1860
atgattgacc tttaagagcc aacctccaat gattatccgt taaattcaga tataacaatt    1920
caaaaatcaa tattaagcct ccagataccca atgaatatga atatatctct tagaaaactt    1980
gattattatg tgataacata gtacaattta agaaaaaacc taaaataagc acgaaccctt    2040
aaggtgtcgt aacgtctcgt gacgccgggt tcagttcaaa catcgacccc tgacccaatt    2100
caataccat ttccataaag gaacacagta taatttaatc ataaaagacc tcaaaatctg     2160
atacagctta atccactcaa catataatta taagactaat aataatggaa gattacagca    2220
atctatctct taaatcaatt cctaaaagga catgtagaat cattttccga actgccacaa    2280
ttcttggcat atgcacatta attgtgctat gttcaagtat tcttcatgag ataattcatc    2340
ttgatgtttc ctctgatctt atgaattctg atgagtcaca gcaaggcatt atccagccta    2400
tcatagaatc attaaaatca ttgattgctt tggccaacca gattctatat aatgttgcaa    2460
tagtaattcc tcttaaaatt gacagtatcg aaactgtaat actctctgct ttaaaagata    2520
tgcacaccgg gagtatgtcc aatgccaact gcacgccagg aaatctactt ctgcatgatg    2580
cagcatacat caatggaata aacaaattcc ttgtacttga atcatacaat gggacgccta    2640
aatatggacc tctcctaaat atacccagct ttatcccctc agcaacatct ccccatgggt    2700
gtactagaat accatcattt tcactcatca ggacccattg gtgttacact cacaatgtaa    2760
tacttggaga ttgtcttgat ttcacggcat ctaaccagta tttatcaatg gggataatac    2820
aacaatctgc tgcagggttt ccaattttca ggactatgaa aaccatttac ctaagtgatg    2880
gaatcaatcg caaaagctgt tcagtcactg ctataccagg aggttgtgtc ttgtattgct    2940
atgtagctac aaggtctgaa aaagaagatt atgccacgac tgatctagct gaactgagac    3000
ttgccttcta ttattataat gatacccttta ttgaaagagt catatctctt ccaaatacaa    3060
cagggcagtg ggccacaatc aaccctgcag tcggaagcgg gatctatcat ctaggcttta    3120
tcttatttcc tgtatatggt ggtctcataa atgggactac ttcttacaat gagcagtcct    3180
cacgctattt tatcccaaaa catcccaaca taacttgtgc cggtaactcc agcaaacagg    3240
ctgcaatagc acggagttcc tatgtcatcc gttatcactc aaacaggtta attcagagtg    3300
ctgttcttat ttgtccattg tctgacatgc acacagaaga gtgtaatcta gttatgttta    3360
acaattccca agtcatgatg ggtgcagaag gtaggctcta tgttattggt aataatttgt    3420
attattatca acgcagttcc tcttggtggt ctgcatcgct cttttacagg atcaatacag    3480
attttttctaa aggaattcct ccgatcattg aggctcaatg ggtaccgtcc tatcaagttc    3540
cccgtcctgg agtcatgcca tgcgatgcaa caagtttttg ccctgctaat tgcatcacag    3600
gggtgtacgc agatgtgtgg ccgcttaatg atccagaact catgtcacgt aatgctctga    3660
accccaacta tcgatttgct ggagcctttc tcaaaaatga gtccaaccga actaatccca    3720
```

| | |
|---|---|
| cattctacac tgcatcgtct aactccctct taaatactac cggattcaac aaaaccaatc | 3780 |
| acaaagcagc atatacatct tcaacctgct ttaaaaacac tggaacccaa aaaatttatt | 3840 |
| gtttaataat aattgaaatg ggctcatctc ttttagggga gttccaaata ataccatttt | 3900 |
| taagggaact aatgctttaa tcctattgaa tgaagactcc agattcaaga ataattggaa | 3960 |
| ggctctttat tttatgcgat agttatacgt tttggctgta ttagaatgct atagcattct | 4020 |
| gctgttttc ccatatggaa aaatccttca acaccaactt aggttcaatt ttctcatcat | 4080 |
| ttactgttgt aattcaatct tactaaagtt attctgatat ttaagaaaaa ataatcttta | 4140 |
| tataatgtaa caatactact aagattataa tataggccag aatggcggcc tcttctgaga | 4200 |
| tactccttcc tgaagtccat ttgaactcac caatagtcaa acacaaactc atatactact | 4260 |
| tattactagg gcacttcccg catgatcttg acatttctga ataagcccc cttcacaata | 4320 |
| atgattggga tca | 4333 |

<210> SEQ ID NO 23
<211> LENGTH: 1656
<212> TYPE: DNA
<213> ORGANISM: Human parainfluenza virus 2

<400> SEQUENCE: 23

| | |
|---|---|
| atgcatcacc tgcatccaat gatagtatgc atctttgtta tgtacactgg aattgtaggt | 60 |
| tcagatgcca ttgctggaga tcaactcctc aatgtagggg tcattcaatc aaagataaga | 120 |
| tcactcatgt actacactga tggtggcgct agctttattg ttgtaaaatt actaccaaat | 180 |
| cttcccccaa gcaatggaac atgcaacatc accagtctag atgcatataa tgttacccta | 240 |
| tttaagttgc taacgcccct gattgagaac ctgagcaaaa tttctgctgt tacagatacc | 300 |
| aaaccccgcc gagaacgatt tgcaggagtc gttattgggc ttgctgcact aggagtagct | 360 |
| acagctgcac aaataaccgc agctgtagca atagtaaaag ccaatgcaaa tgctgctgcg | 420 |
| ataaacaatc ttgcatcttc aattcaatcc accaacaagg cagtatccga tgtgataact | 480 |
| gcatcaagaa caattgcaac cgcagttcaa gcaattcagg atcgcatcaa tggagctatt | 540 |
| gttaatggga taacatctgc atcatgccgt gcccatgatg cactaattgg gtcaatatta | 600 |
| aatttgtatc tcactgagct tactacaata tttcataatc aaataacaaa ccctgcgctg | 660 |
| acaccacttt ccatccaagc tttaagaatc ctcctcggta gcaccttgcc aattgtcatt | 720 |
| gaatccaaac tcaacacaaa actcaacaca gcagagctgc tcagttccgg actgttaact | 780 |
| ggtcaaataa tttccatttc cccaatgtac atgcaaatgc taattcaaat caatgttccg | 840 |
| acatttataa tgcaacccgg tgcgaaggta attgatctaa ttgctatctc tgcaaaccat | 900 |
| aaattacaag aagtagttgt acaagttcct aatagaattc tagaatacgc aaatgaacta | 960 |
| caaaactacc cagccaatga ttgtgtcgtg acaccaaact ctgtattttg tagatacaat | 1020 |
| gagggttccc cgatccctga atcacaatat caatgcttaa gggggaatct taattcttgc | 1080 |
| acttttaccc ctattatcgg gaactttctc aagcgattcg catttgccaa tggtgtgctc | 1140 |
| tatgccaact gcaaatcttt gctatgtaag tgtgccgacc ctcccatgt tgtgtctcaa | 1200 |
| gatgacaacc aaggcatcag cataattgat attaagaggt gctctgagat gatgcttgac | 1260 |
| acttttttcat ttaggatcac atctacattc aatgctacat acgtgacaga cttctcaatg | 1320 |
| attaatgcaa atattgtaca tctaagtcct ctagacttgt caaatcaaat taattcaata | 1380 |
| aacaaatctc ttaaaagtgc tgaagattgg attgcagata gcaacttctt cgctaatcaa | 1440 |
| gccagaacag ccaagacact ttattcacta agtgcaatag cattaatact atcagtgatt | 1500 |

```
actttggttg ttgtgggatt gctgattgcc tacatcatca agctggtttc tcaaatccat    1560
caattcagag cactagctgc tacaacaatg ttccacaggg agaatcctgc tgtcttttcc    1620
aagaacaatc atggaaacat atatgggata tcttaa                              1656
```

<210> SEQ ID NO 24
<211> LENGTH: 551
<212> TYPE: PRT
<213> ORGANISM: Human parainfluenza virus 2

<400> SEQUENCE: 24

```
Met His His Leu His Pro Met Ile Val Cys Ile Phe Val Met Tyr Thr
1               5                   10                  15

Gly Ile Val Gly Ser Asp Ala Ile Ala Gly Asp Gln Leu Leu Asn Val
            20                  25                  30

Gly Val Ile Gln Ser Lys Ile Arg Ser Leu Met Tyr Tyr Thr Asp Gly
        35                  40                  45

Gly Ala Ser Phe Ile Val Val Lys Leu Leu Pro Asn Leu Pro Pro Ser
    50                  55                  60

Asn Gly Thr Cys Asn Ile Thr Ser Leu Asp Ala Tyr Asn Val Thr Leu
65                  70                  75                  80

Phe Lys Leu Leu Thr Pro Leu Ile Glu Asn Leu Ser Lys Ile Ser Ala
                85                  90                  95

Val Thr Asp Thr Lys Pro Arg Arg Glu Arg Phe Ala Gly Val Val Ile
            100                 105                 110

Gly Leu Ala Ala Leu Gly Val Ala Thr Ala Ala Gln Ile Thr Ala Ala
        115                 120                 125

Val Ala Ile Val Lys Ala Asn Ala Asn Ala Ala Ala Ile Asn Asn Leu
    130                 135                 140

Ala Ser Ser Ile Gln Ser Thr Asn Lys Ala Val Ser Asp Val Ile Thr
145                 150                 155                 160

Ala Ser Arg Thr Ile Ala Thr Ala Val Gln Ala Ile Gln Asp Arg Ile
                165                 170                 175

Asn Gly Ala Ile Val Asn Gly Ile Thr Ser Ala Ser Cys Arg Ala His
            180                 185                 190

Asp Ala Leu Ile Gly Ser Ile Leu Asn Leu Tyr Leu Thr Glu Leu Thr
        195                 200                 205

Thr Ile Phe His Asn Gln Ile Thr Asn Pro Ala Leu Thr Pro Leu Ser
    210                 215                 220

Ile Gln Ala Leu Arg Ile Leu Leu Gly Ser Thr Leu Pro Ile Val Ile
225                 230                 235                 240

Glu Ser Lys Leu Asn Thr Lys Leu Asn Thr Ala Glu Leu Leu Ser Ser
                245                 250                 255

Gly Leu Leu Thr Gly Gln Ile Ile Ser Ile Ser Pro Met Tyr Met Gln
            260                 265                 270

Met Leu Ile Gln Ile Asn Val Pro Thr Phe Ile Met Gln Pro Gly Ala
        275                 280                 285

Lys Val Ile Asp Leu Ile Ala Ile Ser Ala Asn His Lys Leu Gln Glu
    290                 295                 300

Val Val Val Gln Val Pro Asn Arg Ile Leu Glu Tyr Ala Asn Glu Leu
305                 310                 315                 320

Gln Asn Tyr Pro Ala Asn Asp Cys Val Val Thr Pro Asn Ser Val Phe
                325                 330                 335

Cys Arg Tyr Asn Glu Gly Ser Pro Ile Pro Glu Ser Gln Tyr Gln Cys
```

```
            340               345                350
Leu Arg Gly Asn Leu Asn Ser Cys Thr Phe Thr Pro Ile Ile Gly Asn
            355               360                365

Phe Leu Lys Arg Phe Ala Phe Ala Asn Gly Val Leu Tyr Ala Asn Cys
            370               375                380

Lys Ser Leu Leu Cys Lys Cys Ala Asp Pro Pro His Val Val Ser Gln
385               390               395                400

Asp Asp Asn Gln Gly Ile Ser Ile Ile Asp Ile Lys Arg Cys Ser Glu
                405               410               415

Met Met Leu Asp Thr Phe Ser Phe Arg Ile Thr Ser Thr Phe Asn Ala
                420               425               430

Thr Tyr Val Thr Asp Phe Ser Met Ile Asn Ala Asn Ile Val His Leu
            435               440               445

Ser Pro Leu Asp Leu Ser Asn Gln Ile Asn Ser Ile Asn Lys Ser Leu
            450               455               460

Lys Ser Ala Glu Asp Trp Ile Ala Asp Ser Asn Phe Phe Ala Asn Gln
465               470               475               480

Ala Arg Thr Ala Lys Thr Leu Tyr Ser Leu Ser Ala Ile Ala Leu Ile
                485               490               495

Leu Ser Val Ile Thr Leu Val Val Val Gly Leu Leu Ile Ala Tyr Ile
                500               505               510

Ile Lys Leu Val Ser Gln Ile His Gln Phe Arg Ala Leu Ala Ala Thr
            515               520               525

Thr Met Phe His Arg Glu Asn Pro Ala Val Phe Ser Lys Asn Asn His
            530               535               540

Gly Asn Ile Tyr Gly Ile Ser
545               550
```

<210> SEQ ID NO 25
<211> LENGTH: 1716
<212> TYPE: DNA
<213> ORGANISM: Human parainfluenza virus 2

<400> SEQUENCE: 25

| | | | | | |
|---|---|---|---|---|---|
| atggaagatt | acagcaatct | atctcttaaa | tcaattccta | aaaggacatg | tagaatcatt | 60 |
| ttccgaactg | ccacaattct | tggcatatgc | acattaattg | tgctatgttc | aagtattctt | 120 |
| catgagataa | ttcatcttga | tgtttcctct | gatcttatga | attctgatga | gtcacagcaa | 180 |
| ggcattatcc | agcctatcat | agaatcatta | aaatcattga | ttgctttggc | caaccagatt | 240 |
| ctatataatg | ttgcaatagt | aattcctctt | aaaattgaca | gtatcgaaac | tgtaatactc | 300 |
| tctgctttaa | agatatgca | caccgggagt | atgtccaatg | ccaactgcac | gccaggaaat | 360 |
| ctacttctgc | atgatgcagc | atacatcaat | ggaataaaca | aattccttgt | acttgaatca | 420 |
| tacaatggga | cgcctaaata | tggacctctc | ctaaatatac | cagctttat | ccctcagca | 480 |
| acatctcccc | atgggtgtac | tagaatacca | tcattttcac | tcatcaggac | ccattggtgt | 540 |
| tacactcaca | atgtaatact | tggagattgt | cttgatttca | cggcatctaa | ccagtattta | 600 |
| tcaatgggga | taatacaaca | atctgctgca | gggtttccaa | ttttcaggac | tatgaaaacc | 660 |
| atttacctaa | gtgatggaat | caatcgcaaa | agctgttcag | tcactgctat | accaggaggt | 720 |
| tgtgtcttgt | attgctatgt | agctacaagg | tctgaaaaag | aagattatgc | cacgactgat | 780 |
| ctagctgaac | tgagacttgc | cttctattat | tataatgata | cctttattga | aagagtcata | 840 |
| tctcttccaa | atacaacagg | gcagtgggcc | acaatcaacc | ctgcagtcgg | aagcgggatc | 900 |

| | | |
|---|---|---|
| tatcatctag gctttatctt atttcctgta tatggtggtc tcataaatgg gactacttct | 960 | |
| tacaatgagc agtcctcacg ctattttatc ccaaaacatc ccaacataac ttgtgccggt | 1020 | |
| aactccagca acaggctgc aatagcacgg agttcctatg tcatccgtta tcactcaaac | 1080 | |
| aggttaattc agagtgctgt tcttatttgt ccattgtctg acatgcacac agaagagtgt | 1140 | |
| aatctagtta tgtttaacaa ttcccaagtc atgatgggtg cagaaggtag gctctatgtt | 1200 | |
| attggtaata atttgtatta ttatcaacgc agttcctctt ggtggtctgc atcgctcttt | 1260 | |
| tacaggatca atacagattt ttctaaagga attcctccga tcattgaggc tcaatgggta | 1320 | |
| ccgtcctatc aagttccccg tcctggagtc atgccatgcg atgcaacaag ttttttgccct | 1380 | |
| gctaattgca tcacaggggt gtacgcagat gtgtggccgc ttaatgatcc agaactcatg | 1440 | |
| tcacgtaatg ctctgaaccc caactatcga tttgctggag cctttctcaa aaatgagtcc | 1500 | |
| aaccgaacta atcccacatt ctacactgca tcgtctaact ccctcttaaa tactaccgga | 1560 | |
| ttcaacaaaa ccaatcacaa agcagcatat acatcttcaa cctgctttaa aaacactgga | 1620 | |
| acccaaaaaa tttattgttt aataataatt gaaatgggct catctctttt aggggagttc | 1680 | |
| caaataatac cattttttaag ggaactaatg ctttaa | 1716 | |

<210> SEQ ID NO 26
<211> LENGTH: 571
<212> TYPE: PRT
<213> ORGANISM: Human parainfluenza virus 2

<400> SEQUENCE: 26

Met Glu Asp Tyr Ser Asn Leu Ser Leu Lys Ser Ile Pro Lys Arg Thr
1               5                   10                  15

Cys Arg Ile Ile Phe Arg Thr Ala Thr Ile Leu Gly Ile Cys Thr Leu
            20                  25                  30

Ile Val Leu Cys Ser Ser Ile Leu His Glu Ile Ile His Leu Asp Val
        35                  40                  45

Ser Ser Asp Leu Met Asn Ser Asp Glu Ser Gln Gln Gly Ile Ile Gln
    50                  55                  60

Pro Ile Ile Glu Ser Leu Lys Ser Leu Ile Ala Leu Ala Asn Gln Ile
65                  70                  75                  80

Leu Tyr Asn Val Ala Ile Val Ile Pro Leu Lys Ile Asp Ser Ile Glu
                85                  90                  95

Thr Val Ile Leu Ser Ala Leu Lys Asp Met His Thr Gly Ser Met Ser
            100                 105                 110

Asn Ala Asn Cys Thr Pro Gly Asn Leu Leu His Asp Ala Ala Tyr
            115                 120                 125

Ile Asn Gly Ile Asn Lys Phe Leu Val Leu Glu Ser Tyr Asn Gly Thr
    130                 135                 140

Pro Lys Tyr Gly Pro Leu Leu Asn Ile Pro Ser Phe Ile Pro Ser Ala
145                 150                 155                 160

Thr Ser Pro His Gly Cys Thr Arg Ile Pro Ser Phe Ser Leu Ile Arg
                165                 170                 175

Thr His Trp Cys Tyr Thr His Asn Val Ile Leu Gly Asp Cys Leu Asp
            180                 185                 190

Phe Thr Ala Ser Asn Gln Tyr Leu Ser Met Gly Ile Gln Gln Ser
            195                 200                 205

Ala Ala Gly Phe Pro Ile Phe Arg Thr Met Lys Thr Ile Tyr Leu Ser
    210                 215                 220

Asp Gly Ile Asn Arg Lys Ser Cys Ser Val Thr Ala Ile Pro Gly Gly

```
                225                 230                 235                 240
            Cys Val Leu Tyr Cys Tyr Val Ala Thr Arg Ser Glu Lys Glu Asp Tyr
                            245                 250                 255

Ala Thr Thr Asp Leu Ala Glu Leu Arg Leu Ala Phe Tyr Tyr Tyr Asn
                        260                 265                 270

Asp Thr Phe Ile Glu Arg Val Ile Ser Leu Pro Asn Thr Thr Gly Gln
                    275                 280                 285

Trp Ala Thr Ile Asn Pro Ala Val Gly Ser Gly Ile Tyr His Leu Gly
                290                 295                 300

Phe Ile Leu Phe Pro Val Tyr Gly Gly Leu Ile Asn Gly Thr Thr Ser
            305                 310                 315                 320

Tyr Asn Glu Gln Ser Ser Arg Tyr Phe Ile Pro Lys His Pro Asn Ile
                            325                 330                 335

Thr Cys Ala Gly Asn Ser Ser Lys Gln Ala Ala Ile Ala Arg Ser Ser
                        340                 345                 350

Tyr Val Ile Arg Tyr His Ser Asn Arg Leu Ile Gln Ser Ala Val Leu
                    355                 360                 365

Ile Cys Pro Leu Ser Asp Met His Thr Glu Glu Cys Asn Leu Val Met
                370                 375                 380

Phe Asn Asn Ser Gln Val Met Met Gly Ala Glu Gly Arg Leu Tyr Val
            385                 390                 395                 400

Ile Gly Asn Asn Leu Tyr Tyr Tyr Gln Arg Ser Ser Ser Trp Trp Ser
                            405                 410                 415

Ala Ser Leu Phe Tyr Arg Ile Asn Thr Asp Phe Ser Lys Gly Ile Pro
                        420                 425                 430

Pro Ile Ile Glu Ala Gln Trp Val Pro Ser Tyr Gln Val Pro Arg Pro
                    435                 440                 445

Gly Val Met Pro Cys Asp Ala Thr Ser Phe Cys Pro Ala Asn Cys Ile
                450                 455                 460

Thr Gly Val Tyr Ala Asp Val Trp Pro Leu Asn Asp Pro Glu Leu Met
            465                 470                 475                 480

Ser Arg Asn Ala Leu Asn Pro Asn Tyr Arg Phe Ala Gly Ala Phe Leu
                            485                 490                 495

Lys Asn Glu Ser Asn Arg Thr Asn Pro Thr Phe Tyr Thr Ala Ser Ser
                        500                 505                 510

Asn Ser Leu Leu Asn Thr Thr Gly Phe Asn Lys Thr Asn His Lys Ala
                    515                 520                 525

Ala Tyr Thr Ser Ser Thr Cys Phe Lys Asn Thr Gly Thr Gln Lys Ile
                530                 535                 540

Tyr Cys Leu Ile Ile Ile Glu Met Gly Ser Ser Leu Leu Gly Glu Phe
            545                 550                 555                 560

Gln Ile Ile Pro Phe Leu Arg Glu Leu Met Leu
                            565                 570

<210> SEQ ID NO 27
<211> LENGTH: 4333
<212> TYPE: DNA
<213> ORGANISM: Human parainfluenza virus 2

<400> SEQUENCE: 27
gaatgctcca gcatctagga atagaacaac aactaagtca taccattatt gaccatacaa     60
taatcaacaa ttttagccaa ctgattacta agatattatc ataggtccga actgatcaat    120
ctaacaaaaa aactaaacat tcaataataa atcaagttc aggccaaatt atccagccat     180
```

```
gcatcacccg catccaatga tagtatgcat ctttgttatg tacactggaa ttgtaggttc    240
agatgccatt gctggagatc aactcctcaa tgtaggggtc attcaatcaa agataagatc    300
actcatgtac tacactgatg gtggcgctag ctttattgtt gtaaaattac taccaaatct    360
tcccccaagc aatggaacat gcaacatcac cagtctagat gcatataatg ttaccctatt    420
taagttgcta acgcccctga ttgagaacct gagcaaaatt tctgctgtta cagataccaa    480
accccgccga aacgatttg caggagtcgt tattgggctt gctgcactag gagtagctac    540
agctgcacaa ataaccgcag ctgtagcaat agtaaaagcc aatgcaaatg ctgctgcgat    600
aaacaatctt gcatcttcaa ttcaatccac caacaaggca gtatccgatg tgataactgc    660
atcaagaaca attgcaaccg cagttcaagc aattcaggat cgcatcaatg gagctattgt    720
taatgggata acatctgcat catgccgtgc ccatgatgca ctaattgggt caatattaaa    780
tttgtatctc actgagctta ctacaatatt tcataatcaa ataacaaacc ctgcgctgac    840
accactttcc atccaagctt taagaatcct cctcggtagc accttgccaa ttgtcattga    900
atccaaactc aacacaaaac tcaacacagc agagctgctc agttccggac tgttaactgg    960
tcaaataatt tccatttccc caatgtacat gcaaatgcta attcaaatca atgttccgac   1020
atttataatg caacccggtg cgaaggtaat tgatctaatt gctatctctg caaaccataa   1080
attacaagaa gtagttgtac aagttcctaa tagaattcta gaatacgcaa atgaactaca   1140
aaactaccca gccaatgatt gtgtcgtgac accaaactct gtattttgta gatacaatga   1200
gggttccccg atccctgaat cacaatatca atgcttaagg gggaatctta attcttgcac   1260
ttttacccct attatcggga actttctcaa gcgattcgca tttgccaatg gtgtgctcta   1320
tgccaactgc aaatctttgc tatgtaagtg tgccgaccct ccccatgttg tgtctcaaga   1380
tgacaaccaa ggcatcagca taattgatat taagagatgc tctgagatga tgcttgacac   1440
tttttcattt aggatcacat ctacattcaa tgctacatac gtgacagact tctcaatgat   1500
taatgcaaat attgtacatc taagtcctct agacttgtca aatcaaatca attcaataaa   1560
caaatctctt aaaagtgctg aggattggat tgcagatagc aacttcttcg ctaatcaagc   1620
cagaacagcc aagacacttt attcactaag tgcaatagca ttaatactat cagtgattac   1680
tttggttgtt gtgggattgc tgattgccta catcatcaag ctgatttctc aaatccatca   1740
attcagagca ctagctgcta caacaatgtt ccacagggag aatcctgccg tcttttccaa   1800
gaacaatcat ggaaacatat atgggatatc ttaagaattc tatcataagt ccatatatgt   1860
ccatgattga cctttaagag ccaacctcca atgattatcc gttaaattca gatataacaa   1920
ttcaaaaatc aatattaagc ctccagatac caatgaatat gaatatatct cttagaaaac   1980
ttgattatta tgtgataaca tagtacaatt taagaaaaaa cctaaaataa gcacgaaccc   2040
ttaaggtgtc gtaacgtctc gtgacgccgg gttcagttca aacatcgacc cctgacccaa   2100
ttcaataccc atttttcataa aggaacacag tataatttaa tcataaaaga cctcaaaatc   2160
tgatacagct taatccactc aacatataat tataagacta ataataatgg aagattacag   2220
caatctatct cttaaatcaa ttcctaaaag gacatgtaga atcattttcc gaactgccac   2280
aattcttggc atatgcacat taattgtgct atgttcaagt attcttcatg agataattca   2340
tcttgatgtt tcctctggtc ttatgaattc tgatgagtca cagcaaggca ttatccagcc   2400
tatcatagaa tcattaaaat cattgattgc tttggccaac cagattctat ataatgttgc   2460
aatagtaatt cctcttaaaa ttgacagtat cgaaactgta atactctctg ctttaaaaga   2520
tatgcacacc gggagtatgt ccaatgccaa ctgcacgcca ggaaatctac ttctgcatga   2580
```

```
tgcagcatac atcaatggaa taaacaaatt ccttgtactt gaatcataca atgggacgcc    2640
taaatatgga cctctcctaa atatacccag ctttatcccc tcagcaacat ctccccatgg    2700
gtgtactaga ataccatcat tttcactcat caagacccat tggtgttaca ctcacaatgt    2760
aatacttgga gattgtcttg atttcacagc atctaaccag tatttatcaa tggggataat    2820
acaacaatct gctgcagcat ttccattttt caggactatg aaaaccattt acctaagtga    2880
tggaatcaat cgcaaaagct gttcagtcac tgctatacca ggaggttgtg tcttgtattg    2940
ctatgtagct acaaggtctg aaaaagaaga ttatgccacg actgatctag ctgaattgag    3000
acttgccttc tattattata tgataccttt tattgaaaga gtcatatctc ttccaaatac    3060
aacagggcag tgggccacaa tcaaccctgc agtcggaagc gggatctatc atctaggctt    3120
tatcttattt cctgtatatg gtggtctcat aaatgggact acttcttaca atgagcagtc    3180
ctcacgctat tttatcccaa acatcccaa cataacttgt gccggtaact ccagcaaaca    3240
ggctgcaata gcacggagtt cctatgtcat ccgttatcac tcaaacaggt taattcagag    3300
tgctgttctt atttgtccat tgtctgacat gcacacagaa gagtgtaatc tagttatgtt    3360
taacaattct caagtcatga tgggtgcaga aggtaggctc tatgttattg gtaataattt    3420
gtattattat caacgcagtt cctcttggtg gtctgcatcg ctcttttaca ggatcaatac    3480
agatttttct aaaggaattc ctccgatcat tgaggctcaa tgggtaccgt cctatcaagt    3540
tcctcgtcct ggagtcatgc catgcaatgc aacaagtttt tgccctgcta attgcatcac    3600
agggtgtac gcagatgtgt ggccgcttaa tgatccagaa ctcatgtcac gtaatgctct    3660
gaacccccaac tatcgatttg ctggagcctt tctcaaaaat gagtccaacc gaactaatcc    3720
cacattctac actgcatcgt ctaactccct cttaaatact accggattca acaaaaccaa    3780
tcacaaagca gcatatacat cttcaacctg cttttaaaaat actggaaccc aaaaaattta    3840
ttgtttaata ataattgaaa tgggctcatc tcttttaggg gagttccaaa taataccatt    3900
tttaagggaa ctaatgcttt aatcctattg aatgaagact ccagattcaa gaataattgg    3960
aaggctcttt attttatgcg atagttatac gttttggctg tattagaatg ctatagcatt    4020
ctgctgtttt tcccatatgg aaaaatcctt caacaccaac ttaggttcaa ttttctcatc    4080
atttactgtt gtaattcaat cttactaaag ttattctgat atttaagaaa aaataatctt    4140
tatataatgt aacaatacta ctaagattat aatataggcc agaatggcgg cctcttctga    4200
gatactcctt cctgaagtcc attgaactca ccaatagtca aacacaaact catatactac    4260
ttatatctag ggcacttccc acatgatctt gacatttctg aaataagccc ccttcacaat    4320
aatgattggg atc                                                       4333
```

```
<210> SEQ ID NO 28
<211> LENGTH: 1812
<212> TYPE: DNA
<213> ORGANISM: Human parainfluenza virus 2

<400> SEQUENCE: 28
atgcatcacc cgcatccaat gatagtatgc atctttgtta tgtacactgg aattgtaggt     60
tcagatgcca ttgctggaga tcaactcctc aatgtagggg tcattcaatc aaagataaga    120
tcactcatgt actacactga tggtggcgct agctttattg ttgtaaaatt actaccaaat    180
cttcccccaa gcaatggaac atgcaacatc ccagtctag atgcatataa tgttacccta    240
tttaagttgc taacgcccct gattgagaac ctgagcaaaa tttctgctgt tacagatacc    300
```

```
aaacccccgcc gagaacgatt tgcaggagtc gttattgggc ttgctgcact aggagtagct    360
acagctgcac aaataaccgc agctgtagca atagtaaaag ccaatgcaaa tgctgctgcg    420
ataaacaatc ttgcatcttc aattcaatcc accaacaagg cagtatccga tgtgataact    480
gcatcaagaa caattgcaac cgcagttcaa gcaattcagg atcgcatcaa tggagctatt    540
gcatcaagaa caattgcaac cgcagttcaa gcaattcagg atcgcatcaa tggagctatt    600
gttaatggga taacatctgc atcatgccgt gcccatgatg cactaattgg gtcaatatta    660
aatttgtatc tcactgagct tactacaata tttcataatc aaataacaaa ccctgcgctg    720
aatttgtatc tcactgagct tactacaata tttcataatc aaataacaaa ccctgcgctg    780
acaccacttt ccatccaagc tttaagaatc ctcctcggta gcaccttgcc aattgtcatt    840
gaatccaaac tcaacacaaa actcaacaca gcagagctgc tcagttccgg actgttaact    900
ggtcaaataa tttccatttc cccaatgtac atgcaaatgc taattcaaat caatgttccg    960
acatttataa tgcaacccgg tgcgaaggta attgatctaa ttgctatctc tgcaaaccat   1020
aaattacaag aagtagttgt acaagttcct aatagaattc tagaatacgc aaatgaacta   1080
caaaactacc cagccaatga ttgtgtcgtg acaccaaact ctgtattttg tagatacaat   1140
gagggttccc cgatccctga atcacaatat caatgcttaa gggggaatct taattcttgc   1200
acttttaccc ctattatcgg gaactttctc aagcgattcg catttgccaa tggtgtgctc   1260
tatgccaact gcaaatcttt gctatgtaag tgtgccgacc ctccccatgt tgtgtctcaa   1320
gatgacaacc aaggcatcag cataattgat attaagagat gctctgagat gatgcttgac   1380
acttttccat ttaggatcac atctacattc aatgctacat acgtgacaga cttctcaatg   1440
attaatgcaa atattgtaca tctaagtcct ctagacttgt caaatcaaat caattcaata   1500
aacaaatctc ttaaaagtgc tgaggattgg attgcagata gcaacttctt cgctaatcaa   1560
gccagaacag ccaagacact ttattcacta agtgcaatag cattaatact atcagtgatt   1620
actttggttg ttgtgggatt gctgattgcc tacatcatca agctgatttc tcaaatccat   1680
caattcagag cactagctgc tacaacaatg ttccacaggg agaatcctgc cgtcttttcc   1740
aagaataacc atggaaacat atatgggata tcttaaaaga caatcatgg aaacatatat   1800 gggatatctt aa                                                        1812
```

<210> SEQ ID NO 29
<211> LENGTH: 551
<212> TYPE: PRT
<213> ORGANISM: Human parainfluenza virus 2

<400> SEQUENCE: 29

```
Met His His Pro His Pro Met Ile Val Cys Ile Phe Val Met Tyr Thr
1               5                   10                  15

Gly Ile Val Gly Ser Asp Ala Ile Ala Gly Asp Gln Leu Leu Asn Val
            20                  25                  30

Gly Val Ile Gln Ser Lys Ile Arg Ser Leu Met Tyr Tyr Thr Asp Gly
        35                  40                  45

Gly Ala Ser Phe Ile Val Val Lys Leu Leu Pro Asn Leu Pro Pro Ser
    50                  55                  60

Asn Gly Thr Cys Asn Ile Thr Ser Leu Asp Ala Tyr Asn Val Thr Leu
65                  70                  75                  80

Phe Lys Leu Leu Thr Pro Leu Ile Glu Asn Leu Ser Lys Ile Ser Ala
                85                  90                  95

Val Thr Asp Thr Lys Pro Arg Arg Glu Arg Phe Ala Gly Val Val Ile
```

```
              100                 105                 110
Gly Leu Ala Ala Leu Gly Val Ala Thr Ala Gln Ile Thr Ala Ala
            115                 120                 125

Val Ala Ile Val Lys Ala Asn Ala Asn Ala Ala Ile Asn Asn Leu
    130                 135                 140

Ala Ser Ser Ile Gln Ser Thr Asn Lys Ala Val Ser Asp Val Ile Thr
145                 150                 155                 160

Ala Ser Arg Thr Ile Ala Thr Ala Val Gln Ala Ile Gln Asp Arg Ile
                165                 170                 175

Asn Gly Ala Ile Val Asn Gly Ile Thr Ser Ala Ser Cys Arg Ala His
            180                 185                 190

Asp Ala Leu Ile Gly Ser Ile Leu Asn Leu Tyr Leu Thr Glu Leu Thr
            195                 200                 205

Thr Ile Phe His Asn Gln Ile Thr Asn Pro Ala Leu Thr Pro Leu Ser
    210                 215                 220

Ile Gln Ala Leu Arg Ile Leu Leu Gly Ser Thr Leu Pro Ile Val Ile
225                 230                 235                 240

Glu Ser Lys Leu Asn Thr Lys Leu Asn Thr Ala Glu Leu Leu Ser Ser
                245                 250                 255

Gly Leu Leu Thr Gly Gln Ile Ile Ser Ile Ser Pro Met Tyr Met Gln
            260                 265                 270

Met Leu Ile Gln Ile Asn Val Pro Thr Phe Ile Met Gln Pro Gly Ala
    275                 280                 285

Lys Val Ile Asp Leu Ile Ala Ile Ser Ala Asn His Lys Leu Gln Glu
            290                 295                 300

Val Val Val Gln Val Pro Asn Arg Ile Leu Glu Tyr Ala Asn Glu Leu
305                 310                 315                 320

Gln Asn Tyr Pro Ala Asn Asp Cys Val Val Thr Pro Asn Ser Val Phe
                325                 330                 335

Cys Arg Tyr Asn Glu Gly Ser Pro Ile Pro Glu Ser Gln Tyr Gln Cys
                340                 345                 350

Leu Arg Gly Asn Leu Asn Ser Cys Thr Phe Thr Pro Ile Ile Gly Asn
            355                 360                 365

Phe Leu Lys Arg Phe Ala Phe Ala Asn Gly Val Leu Tyr Ala Asn Cys
    370                 375                 380

Lys Ser Leu Leu Cys Lys Cys Ala Asp Pro Pro His Val Val Ser Gln
385                 390                 395                 400

Asp Asp Asn Gln Gly Ile Ser Ile Ile Asp Ile Lys Arg Cys Ser Glu
                405                 410                 415

Met Met Leu Asp Thr Phe Ser Phe Arg Ile Thr Ser Thr Phe Asn Ala
            420                 425                 430

Thr Tyr Val Thr Asp Phe Ser Met Ile Asn Ala Asn Ile Val His Leu
    435                 440                 445

Ser Pro Leu Asp Leu Ser Asn Gln Ile Asn Ser Ile Asn Lys Ser Leu
    450                 455                 460

Lys Ser Ala Glu Asp Trp Ile Ala Asp Ser Asn Phe Phe Ala Asn Gln
465                 470                 475                 480

Ala Arg Thr Ala Lys Thr Leu Tyr Ser Leu Ser Ala Ile Ala Leu Ile
                485                 490                 495

Leu Ser Val Ile Thr Leu Val Val Val Gly Leu Leu Ile Ala Tyr Ile
            500                 505                 510

Ile Lys Leu Ile Ser Gln Ile His Gln Phe Arg Ala Leu Ala Ala Thr
    515                 520                 525
```

```
Thr Met Phe His Arg Glu Asn Pro Ala Val Phe Ser Lys Asn Asn His
    530                 535                 540
Gly Asn Ile Tyr Gly Ile Ser
545                 550

<210> SEQ ID NO 30
<211> LENGTH: 1776
<212> TYPE: DNA
<213> ORGANISM: Human parainfluenza virus 2

<400> SEQUENCE: 30
atggaagatt acagcaatct atctcttaaa tcaattccta aaaggacatg tagaatcatt      60
ttccgaactg ccacaattct tggcatatgc acattaattg tgctatgttc aagtattctt     120
catgagataa ttcatcttga tgtttcctct ggtcttatga attctgatga gtcacagcaa     180
ggcattatcc agcctatcat agaatcatta aaatcattga ttgctttggc caaccagatt     240
ctatataatg ttgcaatagt aattcctctt aaaattgaca gtatcgaaac tgtaatactc     300
tctgctttaa aagatatgca caccgggagt atgtccaatg ccaactgcac gccaggaaat     360
ctacttctgc atgatgcagc atacatcaat ggaataaaca aattccttgt acttgaatca     420
tacaatggga cgcctaaata tggacctctc ctaaatatac ccagctttat cccctcagca     480
acatctcccc atgggtgtac tagaatacca tcattttcac tcatcaagac ccattggtgt     540
tacactcaca atgtaatact tggagattgt cttgatttca cagcatctaa ccagtattta     600
tcaatgggga taatacaaca atctgctgca gcatttccat ttttcaggac tatgaaaacc     660
atttacctaa gtgatggaat caatcgcaaa agctgttcag tcactgctat accaggaggt     720
tgtgtcttgt attgctatgt agctacaagg tctgaaaaag aagattatgc cacgactgat     780
tgtgtcttgt attgctatgt agctacaagg tctgaaaaag aagattatgc cacgactgat     840
ctagctgaat tgagacttgc cttctattat tataatgata ccttattga aagagtcata      900 tctcttccaa atacaacagg gcagtgggcc acaatcaacc ctgcagtcgg aagcgggatc     960
tatcatctag ctttatcctt atttcctgta tatggtggtc tcataaatgg gactacttct    1020
tacaatgagc agtcctcacg ctattttatc ccaaaacatc ccaacataac ttgtgccggt    1080
aactccagca acaggctgc aatagcacgg agttcctatg tcatccgtta tcactcaaac    1140
aggttaattc agagtgctgt tcttatttgt ccattgtctg acatgcacac agaagagtgt    1200
aatctagtta tgtttaacaa ttctcaagtc atgatgggtg cagaaggtag gctctatgtt    1260
attggtaata atttgtatta ttatcaacgc agttcctctt ggtggtctgc atcgctcttt    1320
tacaggatca atacagattt ttctaaagga attcctccga tcattgaggc tcaatgggta    1380
ccgtcctatc aagttcctcg tcctggagtc atgccatgca atgcaacaag ttttgccct    1440 gctaattgca tcacaggggt gtacgcagat gtgtggccgc ttaatgatcc agaactcatg    1500
tcacgtaatg ctctgaaccc caactatcga tttgctggag ccttctcaa aaatgagtcc    1560 aaccgaacta atcccacatt ctacactgca tcgtctaact ccctcttaaa tactaccgga    1620
ttcaacaaaa ccaatcacaa agcagcatat acatcttcaa cctgctttaa aaatactgga    1680
acccaaaaaa tttattgttt aataataatt gaaatgggct catctctttt agggagttc    1740 caaataatac cattttaag ggaactaatg ctttaa                              1776

<210> SEQ ID NO 31
<211> LENGTH: 571
<212> TYPE: PRT
```

<213> ORGANISM: Human parainfluenza virus 2

<400> SEQUENCE: 31

```
Met Glu Asp Tyr Ser Asn Leu Ser Leu Lys Ser Ile Pro Lys Arg Thr
  1               5                  10                  15
Cys Arg Ile Ile Phe Arg Thr Ala Thr Ile Leu Gly Ile Cys Thr Leu
             20                  25                  30
Ile Val Leu Cys Ser Ser Ile Leu His Glu Ile Ile His Leu Asp Val
         35                  40                  45
Ser Ser Gly Leu Met Asn Ser Asp Glu Ser Gln Gln Gly Ile Ile Gln
     50                  55                  60
Pro Ile Ile Glu Ser Leu Lys Ser Leu Ile Ala Leu Ala Asn Gln Ile
 65                  70                  75                  80
Leu Tyr Asn Val Ala Ile Val Ile Pro Leu Lys Ile Asp Ser Ile Glu
                 85                  90                  95
Thr Val Ile Leu Ser Ala Leu Lys Asp Met His Thr Gly Ser Met Ser
            100                 105                 110
Asn Ala Asn Cys Thr Pro Gly Asn Leu Leu Leu His Asp Ala Ala Tyr
        115                 120                 125
Ile Asn Gly Ile Asn Lys Phe Leu Val Leu Glu Ser Tyr Asn Gly Thr
    130                 135                 140
Pro Lys Tyr Gly Pro Leu Leu Asn Ile Pro Ser Phe Ile Pro Ser Ala
145                 150                 155                 160
Thr Ser Pro His Gly Cys Thr Arg Ile Pro Ser Phe Ser Leu Ile Lys
                165                 170                 175
Thr His Trp Cys Tyr Thr His Asn Val Ile Leu Gly Asp Cys Leu Asp
            180                 185                 190
Phe Thr Ala Ser Asn Gln Tyr Leu Ser Met Gly Ile Ile Gln Gln Ser
        195                 200                 205
Ala Ala Ala Phe Pro Phe Phe Arg Thr Met Lys Thr Ile Tyr Leu Ser
    210                 215                 220
Asp Gly Ile Asn Arg Lys Ser Cys Ser Val Thr Ala Ile Pro Gly Gly
225                 230                 235                 240
Cys Val Leu Tyr Cys Tyr Val Ala Thr Arg Ser Glu Lys Glu Asp Tyr
                245                 250                 255
Ala Thr Thr Asp Leu Ala Glu Leu Arg Leu Ala Phe Tyr Tyr Tyr Asn
            260                 265                 270
Asp Thr Phe Ile Glu Arg Val Ile Ser Leu Pro Asn Thr Thr Gly Gln
        275                 280                 285
Trp Ala Thr Ile Asn Pro Ala Val Gly Ser Gly Ile Tyr His Leu Gly
    290                 295                 300
Phe Ile Leu Phe Pro Val Tyr Gly Gly Leu Ile Asn Gly Thr Thr Ser
305                 310                 315                 320
Tyr Asn Glu Gln Ser Ser Arg Tyr Phe Ile Pro Lys His Pro Asn Ile
                325                 330                 335
Thr Cys Ala Gly Asn Ser Ser Lys Gln Ala Ala Ile Ala Arg Ser Ser
            340                 345                 350
Tyr Val Ile Arg Tyr His Ser Asn Arg Leu Ile Gln Ser Ala Val Leu
        355                 360                 365
Ile Cys Pro Leu Ser Asp Met His Thr Glu Glu Cys Asn Leu Val Met
    370                 375                 380
Phe Asn Asn Ser Gln Val Met Met Gly Ala Glu Gly Arg Leu Tyr Val
385                 390                 395                 400
```

-continued

```
Ile Gly Asn Asn Leu Tyr Tyr Tyr Gln Arg Ser Ser Ser Trp Trp Ser
                405                 410                 415

Ala Ser Leu Phe Tyr Arg Ile Asn Thr Asp Phe Ser Lys Gly Ile Pro
            420                 425                 430

Pro Ile Ile Glu Ala Gln Trp Val Pro Ser Tyr Gln Val Pro Arg Pro
        435                 440                 445

Gly Val Met Pro Cys Asn Ala Thr Ser Phe Cys Pro Ala Asn Cys Ile
    450                 455                 460

Thr Gly Val Tyr Ala Asp Val Trp Pro Leu Asn Asp Pro Glu Leu Met
465                 470                 475                 480

Ser Arg Asn Ala Leu Asn Pro Asn Tyr Arg Phe Ala Gly Ala Phe Leu
                485                 490                 495

Lys Asn Glu Ser Asn Arg Thr Asn Pro Thr Phe Tyr Thr Ala Ser Ser
            500                 505                 510

Asn Ser Leu Leu Asn Thr Thr Gly Phe Asn Lys Thr Asn His Lys Ala
        515                 520                 525

Ala Tyr Thr Ser Ser Thr Cys Phe Lys Asn Thr Gly Thr Gln Lys Ile
    530                 535                 540

Tyr Cys Leu Ile Ile Ile Glu Met Gly Ser Ser Leu Leu Gly Glu Phe
545                 550                 555                 560

Gln Ile Ile Pro Phe Leu Arg Glu Leu Met Leu
                565                 570
```

<210> SEQ ID NO 32
<211> LENGTH: 4335
<212> TYPE: DNA
<213> ORGANISM: Human parainfluenza virus 2

<400> SEQUENCE: 32

```
gaatgctcca gcatctagga atagaacaac aactaagtca taccattatt gaccatacaa     60
taatcaacaa ttttagccaa ctgattacta agatattatc ataggtccga actgatcaat    120
ctaacaaaaa aactaaacat tcaataataa atcaaagttc aggccaaatt atccagccat    180
gcatcacctg catccaatga tagtatgcat ctttgttatg tacactggaa ttgtaggttc    240
agatgccatt gctggagatc aactcctcaa tgtaggggtc attcaatcaa agataagatc    300
actcatgtac tacactgatg gtggcgctag ctttattgtt gtaaaattac taccaaatct    360
tcccccaagc aatggaacat gcaacatcac cagtctagat gcatataatg ttaccctatt    420
taagttgcta acgcccctga ttgagaacct gagcaaaatt tctgctgtta cagataccaa    480
accccgccga gaacgatttg caggagtcgt tattgggctt gctgcactag gagtagctac    540
agctgcacaa ataaccgcag ctgtagcaat agtaaaagcc aatgcaaatg ctgctgcgat    600
aaacaatctt gcatcttcaa ttcaatccac caacaaggca gtatccgatg tgataactgc    660
atcaagaaca attgcaaccg cagttcaagc aattcaggat cgcatcaatg gagctattgt    720
taatgggata acatctgcat catgccgtgc ccatgatgca ctaattgggt caatattaaa    780
tttgtatctc actgagctta ctacaatatt tcataatcaa ataacaaacc ctgcgctgac    840
accactttcc atccaagctt taagaatcct cctcggtagc accttgccaa ttgtcattga    900
atccaaactc aacacaaaac tcaacacagc agagctgctc agttccggac tgttaactgg    960
tcaaataatt tccatttccc caatgtacat gcaaatgcta attcaaatca atgttccgac   1020
atttataatg caacccggtg cgaaggtaat tgatctaatt gctatctctg caaaccataa   1080
attacaagaa gtagttgtac aagttcctaa tagaattcta gaatacgcaa atgaactaca   1140
```

```
aaactaccca gccaatgatt gtgtcgtgac accaaactct gtattttgta gatacaatga    1200
gggttccccg atccctgaat cacaatatca atgcttaagg gggaatctta attcttgcac    1260
ttttacccct attatcggga actttctcaa gcgattcgca tttgccaatg gtgtgctcta    1320
tgccaactgc aaatctttgc tatgtaagtg tgccgaccct ccccatgttg tgtctcaaga    1380
tgacaaccaa ggcatcagca taattgatat aagagatgc tctgagatga tgcttgacac    1440
tttttcattt aggatcacat ctacattcaa tgctacatac gtgacagact tctcaatgat    1500
taatgcaaat attgtacatc taagtcctct agacttgtca aatcaaatca attcaataaa    1560
caaatctctt aaaagtgctg aggattggat tgcagatagc aacttcttcg ctaatcaagc    1620
cagaacagcc aagacacttt attcactaag tgcaatagca ttaatactat cagtgattac    1680
tttggttgtt gtgggattgc tgattgccta catcatcaag ctgatttctc aaatccatca    1740
attcagagca ctagctgcta caacaatgtt ccacagggag aatcctgccg tcttttccaa    1800
gaacaatcat ggaaacatat atgggatatc ttaagaattc tatcataagt ccatatatgt    1860
ccatgattga cctttaagag ccaacctcca atgattatcc gttaaattca gatataacaa    1920
ttcaaaaatc aatattaagc ctccagatac caatgaatat gaatatatct cttagaaaac    1980
ttgattatta tgtgataaca tagtacaatt taagaaaaaa cctaaaataa gcacgaaccc    2040
ttaaggtgtc gtaacgtctc gtgacgccgg gttcagttca aacatcgacc cctgacccaa    2100
ttcaataccc attttcataa aggaacacag tataatttaa tcataaaaga cctcaaaatc    2160
tgatacagct taatccactc aacatataat tataagacta ataataatgg aagattacag    2220
caatctatct cttaaatcaa ttcctaaaag gacatgtaga atcattttcc gaactgccac    2280
aattcttggc atatgcacat taattgtgct atgttcaagt attcttcatg agataattca    2340
tcttgatgtt tcctctggtc ttatgaattc tgatgagtca cagcaaggca ttatccagcc    2400
tatcatagaa tcattaaaat cattgattgc tttggccaac cagattctat ataatgttgc    2460
aataataatt cctcttaaaa ttgacagtat cgaaactgta atactctctg ctttaaaaga    2520
tatgcacacc gggagtatgt ccaatgccaa ctgcacgcca ggaaatctac ttctgcatga    2580
tgcagcatac atcaatggaa taaacaaatt ccttgtactt gaatcataca atgggacgcc    2640
taaatatgga cctctcctaa atatacccag ctttatcccc tcagcaacat ctccccatgg    2700
gtgtactaga ataccatcat tttcactcat caagacccat tggtgttaca ctcacaatgt    2760
aatacttgga gattgtcttg atttcacagc atctgaccag tatttatcaa tggggataat    2820
acaacaatct gctgcagggt tccaatttt caggactatg aaaaccattt acctaagtga    2880
tggaatcaat cgcaaaagct gttcagtcac tgctatacca ggaggttgtg tcttgtattg    2940
ctatgtagct acaaggtctg aaaaagaaga ttatgccacg actgatctag ctgaattgag    3000
acttgccttc tattattata tgataccctt tattgaaaga gtcatatctc ttccaaatac    3060
aacagggcag tgggccacaa tcaaccctgc agtcggaagc gggatctatc atctaggctt    3120
tatcttattt cctgtatatg gtggtctcat aaatgggact acttcttaca atgagcagtc    3180
ctcacgctat tttatcccaa acatcccaa cataacttgt gccggtaact ccagcaaaca    3240
ggctgcaata gcacggagtt cctatgtcat ccgttatcac tcaaacaggt taattcagag    3300
tgctgttctt atttgtccat tgtctgacat gcacacagaa gagtgtaatc tagttatgtt    3360
taacaattcc caagtcatga tgggtgcaga aggtaggctc tatgttattg acaataattt    3420
gtattattat caacgtagtt cctcttggtg gtctgcatcg cttttttaca ggatcaatac    3480
agatttttct aaaggaattc ctccgatcat tgaggctcaa tgggtaccgt cctatcaagt    3540
```

```
tcctcgtcct ggagtcatgc catgcaatgc aacaagtttt tgccctgcta attgcatcac    3600 agggggtgtac gcagatgtgt ggccgcttaa tgatccagaa ctcatgtcac gtaatgctct    3660 gaacccccaac tatcgatttg ctggagcctt tctcaaaaat gagtccaacc gaactaatcc    3720
cacattctac actgcatcgt ctaactccct cttaaatact accggattca acaaaaccaa    3780
tcacaaagca gcatatacat cttcaacctg ctttaaaaat actggaaccc aaaaaattta    3840
ttgtttaata ataattgaaa tgggctcatc tcttttaggg gagttccaaa taataccatt    3900
tttaagggaa ctaatgcttt aatcctattg aatgaagact ccagattcaa gaataattgg    3960
aaggctcttt attttatgcg atagttatac gttttggctg tattagaatg ctatagcatt    4020
ctgctgtttt tcccatatgg aaaaatcctt caacaccaac ttaggttcaa ttttctcatc    4080
atttactgtt gtaattcaat cttactaaag ttattctgat atttaagaaa aaataatctt    4140
tatataatgt aacaatacta ctaagattat aatataggcc agaatggcgg cctttttctga   4200 gatactcctt cctgaagtcc atttgaactc accaatagtc aaacacaaac tcatatacta    4260
cttattacta gggcacttcc cacatgatct tgacatttct gaaataagcc cccttcacaa    4320
taatgattgg gatca                                                     4335

<210> SEQ ID NO 33
<211> LENGTH: 1716
<212> TYPE: DNA
<213> ORGANISM: Human parainfluenza virus 2

<400> SEQUENCE: 33
atgcatcacc t

```
gatgacaacc aaggcatcag cataattgat attaagagat gctctgagat gatgcttgac      1320 acttttcat ttaggatcac atctacattc aatgctacat acgtgacaga cttctcaatg       1380
attaatgcaa atattgtaca tctaagtcct ctagacttgt caaatcaaat caattcaata      1440
aacaaatctc ttaaaagtgc tgaggattgg attgcagata gcaacttctt cgctaatcaa     1500
gccagaacag ccaagacact ttattcacta agtgcaatag cattaatact atcagtgatt     1560
actttggttg ttgtgggatt gctgattgcc tacatcatca agctgatttc tcaaatccat     1620
caattcagag cactagctgc tacaacaatg ttccacaggg agaatcctgc cgtcttttcc     1680
aagaacaatc atggaaacat atatgggata tcttaa                                1716
```

<210> SEQ ID NO 34
<211> LENGTH: 551
<212> TYPE: PRT
<213> ORGANISM: Human parainfluenza virus 2

<400> SEQUENCE: 34

```
Met His His Leu His Pro Met Ile Val Cys Ile Phe Val Met Tyr Thr
1               5                   10                  15

Gly Ile Val Gly Ser Asp Ala Ile Ala Gly Asp Gln Leu Leu Asn Val
            20                  25                  30

Gly Val Ile Gln Ser Lys Ile Arg Ser Leu Met Tyr Tyr Thr Asp Gly
        35                  40                  45

Gly Ala Ser Phe Ile Val Val Lys Leu Leu Pro Asn Leu Pro Pro Ser
    50                  55                  60

Asn Gly Thr Cys Asn Ile Thr Ser Leu Asp Ala Tyr Asn Val Thr Leu
65                  70                  75                  80

Phe Lys Leu Leu Thr Pro Leu Ile Glu Asn Leu Ser Lys Ile Ser Ala
                85                  90                  95

Val Thr Asp Thr Lys Pro Arg Arg Glu Arg Phe Ala Gly Val Val Ile
            100                 105                 110

Gly Leu Ala Ala Leu Gly Val Ala Thr Ala Ala Gln Ile Thr Ala Ala
        115                 120                 125

Val Ala Ile Val Lys Ala Asn Ala Asn Ala Ala Ala Ile Asn Asn Leu
    130                 135                 140

Ala Ser Ser Ile Gln Ser Thr Asn Lys Ala Val Ser Asp Val Ile Thr
145                 150                 155                 160

Ala Ser Arg Thr Ile Ala Thr Ala Val Gln Ala Ile Gln Asp Arg Ile
                165                 170                 175

Asn Gly Ala Ile Val Asn Gly Ile Thr Ser Ala Ser Cys Arg Ala His
            180                 185                 190

Asp Ala Leu Ile Gly Ser Ile Leu Asn Leu Tyr Leu Thr Glu Leu Thr
        195                 200                 205

Thr Ile Phe His Asn Gln Ile Thr Asn Pro Ala Leu Thr Pro Leu Ser
    210                 215                 220

Ile Gln Ala Leu Arg Ile Leu Leu Gly Ser Thr Leu Pro Ile Val Ile
225                 230                 235                 240

Glu Ser Lys Leu Asn Thr Lys Leu Asn Thr Ala Glu Leu Leu Ser Ser
                245                 250                 255

Gly Leu Leu Thr Gly Gln Ile Ile Ser Ile Ser Pro Met Tyr Met Gln
            260                 265                 270

Met Leu Ile Gln Ile Asn Val Pro Thr Phe Ile Met Gln Pro Gly Ala
        275                 280                 285

Lys Val Ile Asp Leu Ile Ala Ile Ser Ala Asn His Lys Leu Gln Glu
```

```
          290                 295                 300
Val Val Val Gln Val Pro Asn Arg Ile Leu Glu Tyr Ala Asn Glu Leu
305                 310                 315                 320

Gln Asn Tyr Pro Ala Asn Asp Cys Val Val Thr Pro Asn Ser Val Phe
                325                 330                 335

Cys Arg Tyr Asn Glu Gly Ser Pro Ile Pro Glu Ser Gln Tyr Gln Cys
                340                 345                 350

Leu Arg Gly Asn Leu Asn Ser Cys Thr Phe Thr Pro Ile Ile Gly Asn
            355                 360                 365

Phe Leu Lys Arg Phe Ala Phe Ala Asn Gly Val Leu Tyr Ala Asn Cys
        370                 375                 380

Lys Ser Leu Leu Cys Lys Cys Ala Asp Pro Pro His Val Val Ser Gln
385                 390                 395                 400

Asp Asp Asn Gln Gly Ile Ser Ile Ile Asp Ile Lys Arg Cys Ser Glu
                405                 410                 415

Met Met Leu Asp Thr Phe Ser Phe Arg Ile Thr Ser Thr Phe Asn Ala
                420                 425                 430

Thr Tyr Val Thr Asp Phe Ser Met Ile Asn Ala Asn Ile Val His Leu
            435                 440                 445

Ser Pro Leu Asp Leu Ser Asn Gln Ile Asn Ser Ile Asn Lys Ser Leu
        450                 455                 460

Lys Ser Ala Glu Asp Trp Ile Ala Asp Ser Asn Phe Phe Ala Asn Gln
465                 470                 475                 480

Ala Arg Thr Ala Lys Thr Leu Tyr Ser Leu Ser Ala Ile Ala Leu Ile
                485                 490                 495

Leu Ser Val Ile Thr Leu Val Val Gly Leu Leu Ile Ala Tyr Ile
            500                 505                 510

Ile Lys Leu Ile Ser Gln Ile His Gln Phe Arg Ala Leu Ala Ala Thr
        515                 520                 525

Thr Met Phe His Arg Glu Asn Pro Ala Val Phe Ser Lys Asn Asn His
530                 535                 540

Gly Asn Ile Tyr Gly Ile Ser
545                 550

<210> SEQ ID NO 35
<211> LENGTH: 1716
<212> TYPE: DNA
<213> ORGANISM: Human parainfluenza virus 2

<400> SEQUENCE: 35
atggaagatt acagcaatct atctcttaaa tcaattccta aaaggacatg tagaatcatt      60
ttccgaactg ccacaattct tggcatatgc acattaattg tgctatgttc aagtattctt     120
catgagataa ttcatcttga tgtttcctct ggtcttatga attctgatga gtcacagcaa     180
ggcattatcc agcctatcat agaatcatta aaatcattga ttgctttggc caaccagatt     240
ctatataatg ttgcaataat aattcctctt aaaattgaca gtatcgaaac tgtaatactc     300
tctgctttaa aagatatgca accgggagtg atgtccaatg ccaactgcac gccaggaaat     360
ctacttctgc atgatgcagc atacatcaat ggaataaaca aattccttgt acttgaatca     420
tacaatggga cgcctaaata tggacctctc ctaaatatac ccagctttat cccctcagca     480
acatctcccc atgggtgtac tagaatacca tcattttcac tcatcaagac ccattggtgt     540
tacactcaca atgtaatact tggagattgt cttgatttca cagcatctga ccagtattta     600
tcaatgggga taatacaaca atctgctgca gggtttccaa ttttcaggac tatgaaaacc     660
```

-continued

```
atttacctaa gtgatggaat caatcgcaaa agctgttcag tcactgctat accaggaggt    720
tgtgtcttgt attgctatgt agctacaagg tctgaaaaag aagattatgc cacgactgat    780
ctagctgaat tgagacttgc cttctattat tataatgata cctttattga agagtcata    840
tctcttccaa atacaacagg gcagtgggcc acaatcaacc ctgcagtcgg aagcgggatc    900
tatcatctag gctttatctt atttcctgta tatggtggtc tcataaatgg gactacttct    960
tacaatgagc agtcctcacg ctattttatc ccaaaacatc ccaacataac ttgtgccggt   1020
aactccagca acaggctgc aatagcacgg agttcctatg tcatccgtta tcactcaaac   1080
aggttaattc agagtgctgt tcttatttgt ccattgtctg acatgcacac agaagagtgt   1140
aatctagtta tgtttaacaa ttcccaagtc atgatgggtg cagaaggtag gctctatgtt   1200
attgacaata atttgtatta ttatcaacgt agttcctctt ggtggtctgc atcgcttttt   1260
tacaggatca atacagattt ttctaaagga attcctccga tcattgaggc tcaatgggta   1320
ccgtcctatc aagttcctcg tcctggagtc atgccatgca atgcaacaag ttttttgccct   1380
gctaattgca tcacagggt gtacgcagat gtgtggccgc ttaatgatcc agaactcatg   1440
tcacgtaatg ctctgaaccc caactatcga tttgctggag cctttctcaa aaatgagtcc   1500
aaccgaacta atcccacatt ctacactgca tcgtctaact ccctcttaaa tactaccgga   1560
ttcaacaaaa ccaatcacaa agcagcatat acatcttcaa cctgctttaa aaatactgga   1620
acccaaaaaa tttattgttt aataataatt gaaatgggct catctctttt aggggagttc   1680
caaataatac cattttttaag ggaactaatg cttttaa                           1716
```

<210> SEQ ID NO 36
<211> LENGTH: 571
<212> TYPE: PRT
<213> ORGANISM: Human parainfluenza virus 2

<400> SEQUENCE: 36

```
Met Glu Asp Tyr Ser Asn Leu Ser Leu Lys Ser Ile Pro Lys Arg Thr
1               5                   10                  15

Cys Arg Ile Ile Phe Arg Thr Ala Thr Ile Leu Gly Ile Cys Thr Leu
            20                  25                  30

Ile Val Leu Cys Ser Ser Ile Leu His Glu Ile Ile His Leu Asp Val
        35                  40                  45

Ser Ser Gly Leu Met Asn Ser Asp Glu Ser Gln Gln Gly Ile Ile Gln
    50                  55                  60

Pro Ile Ile Glu Ser Leu Lys Ser Leu Ile Ala Leu Ala Asn Gln Ile
65                  70                  75                  80

Leu Tyr Asn Val Ala Ile Ile Pro Leu Lys Ile Asp Ser Ile Glu
                85                  90                  95

Thr Val Ile Leu Ser Ala Leu Lys Asp Met His Thr Gly Ser Met Ser
            100                 105                 110

Asn Ala Asn Cys Thr Pro Gly Asn Leu Leu His Asp Ala Ala Tyr
        115                 120                 125

Ile Asn Gly Ile Asn Lys Phe Leu Val Leu Glu Ser Tyr Asn Gly Thr
    130                 135                 140

Pro Lys Tyr Gly Pro Leu Leu Asn Ile Pro Ser Phe Ile Pro Ser Ala
145                 150                 155                 160

Thr Ser Pro His Gly Cys Thr Arg Ile Pro Ser Phe Ser Leu Ile Lys
                165                 170                 175

Thr His Trp Cys Tyr Thr His Asn Val Ile Leu Gly Asp Cys Leu Asp
```

```
                180             185             190
Phe Thr Ala Ser Asp Gln Tyr Leu Ser Met Gly Ile Ile Gln Gln Ser
            195                 200                 205

Ala Ala Gly Phe Pro Ile Phe Arg Thr Met Lys Thr Ile Tyr Leu Ser
            210                 215                 220

Asp Gly Ile Asn Arg Lys Ser Cys Ser Val Thr Ala Ile Pro Gly Gly
225                 230                 235                 240

Cys Val Leu Tyr Cys Tyr Val Ala Thr Arg Ser Glu Lys Glu Asp Tyr
                245                 250                 255

Ala Thr Thr Asp Leu Ala Glu Leu Arg Leu Ala Phe Tyr Tyr Tyr Asn
            260                 265                 270

Asp Thr Phe Ile Glu Arg Val Ile Ser Leu Pro Asn Thr Thr Gly Gln
            275                 280                 285

Trp Ala Thr Ile Asn Pro Ala Val Gly Ser Gly Ile Tyr His Leu Gly
            290                 295                 300

Phe Ile Leu Phe Pro Val Tyr Gly Gly Leu Ile Asn Gly Thr Thr Ser
305                 310                 315                 320

Tyr Asn Glu Gln Ser Ser Arg Tyr Phe Ile Pro Lys His Pro Asn Ile
                325                 330                 335

Thr Cys Ala Gly Asn Ser Ser Lys Gln Ala Ala Ile Ala Arg Ser Ser
            340                 345                 350

Tyr Val Ile Arg Tyr His Ser Asn Arg Leu Ile Gln Ser Ala Val Leu
            355                 360                 365

Ile Cys Pro Leu Ser Asp Met His Thr Glu Glu Cys Asn Leu Val Met
370                 375                 380

Phe Asn Asn Ser Gln Met Val Met Gly Ala Glu Gly Arg Leu Tyr Val
385                 390                 395                 400

Ile Asp Asn Asn Leu Tyr Tyr Tyr Gln Arg Ser Ser Ser Trp Trp Ser
                405                 410                 415

Ala Ser Leu Phe Tyr Arg Ile Asn Thr Asp Phe Ser Lys Gly Ile Pro
            420                 425                 430

Pro Ile Ile Glu Ala Gln Trp Val Pro Ser Tyr Gln Val Pro Arg Pro
            435                 440                 445

Gly Val Met Pro Cys Asn Ala Thr Ser Phe Cys Pro Ala Asn Cys Ile
            450                 455                 460

Thr Gly Val Tyr Ala Asp Val Trp Pro Leu Asn Asp Pro Glu Leu Met
465                 470                 475                 480

Ser Arg Asn Ala Leu Asn Pro Asn Tyr Arg Phe Ala Gly Ala Phe Leu
                485                 490                 495

Lys Asn Glu Ser Asn Arg Thr Asn Pro Thr Phe Tyr Thr Ala Ser Ser
            500                 505                 510

Asn Ser Leu Leu Asn Thr Thr Gly Phe Asn Lys Thr Asn His Lys Ala
            515                 520                 525

Ala Tyr Thr Ser Thr Thr Cys Phe Lys Asn Thr Gly Thr Gln Lys Ile
            530                 535                 540

Tyr Cys Leu Ile Ile Ile Glu Met Gly Ser Ser Leu Leu Gly Glu Phe
545                 550                 555                 560

Gln Ile Ile Pro Phe Leu Arg Glu Leu Met Leu
                565                 570

<210> SEQ ID NO 37
<211> LENGTH: 4394
<212> TYPE: DNA
<213> ORGANISM: Human parainfluenza virus 2
```

<400> SEQUENCE: 37

```
gaatgctcca gcatctagga atagaacaac agctaagtca taccattatt gaccatacaa      60
taatcaacaa ttttagccaa ctgattacta agatattatc ataggtccga actgatcaat     120
ctaacaaaaa aactaaacat tcaataataa atcaaagttc aggccaaatt atccagccat     180
gcatcacctg catccaatga tagtatgcat ctttgttatg tacactggaa ttgtaggttc     240
agatgccatt gctggagatc aactcctcaa tgtaggggtc attcaatcaa agataagatc     300
actcatgtac tacactgatg gtggcgctag ctttattgtt gtaaaattac tacccaatct     360
tcccccaagc aatggaacat gcaacatcac cagtctagat gcatataatg ttaccctatt     420
taagttgcta acacccctga ttgagaacct gagcaaaatt tccgctgtta cagataccaa     480
accccgccga gaacgatttg caggggtcgt tattgggctt gctgcactag gagtagctac     540
agctgcacaa ataaccgcag ctgtagcaat agtgaaagcc aatgcaaatg ctgctgcgat     600
aaacaatctt gcatcttcaa ttcaatccac caacaaggca gtatccgatg tgataactgc     660
atcaagaaca attgcaaccg cagttcaagc aattcaggat cgcatcaatg gagccattgt     720
caacgggata acatctgcat catgccgtgc ccatgatgca ctaattgggt caatattaaa     780
tttgtatctc actgagctta ctacaatatt tcataatcaa ataacaaacc ctgcgctgac     840
accactttcc atccaagctt taagaatcct cctcggtagc accttgccaa ttgtcatcga     900
atccaagctc aacacaaaac tcaacacagc agagttactc agttccggac tgttaactgg     960
tcaaataatt tccatttccc caatgtacat gcaaatgcta attcaaatca atgttccgac    1020
atttataatg caacccggtg cgaaggtaat tgatctaatt gctatctctg caaaccataa    1080
attacaagaa gtagttgtac aagttcctaa tagaattcta gagtatgcaa atgaactaca    1140
aaactaccca gccaatgatt gtgtcgtgac accaaactct gtattttgta gatacaatga    1200
gggttccccg atccctgaat cacaatatca atgcttaagg gggaatctta attcttgcac    1260
ttttacccct attatcggaa actttctcaa gcgattcgca tttgccaatg gtgtgctcta    1320
tgccaactgc aaatctttgc tatgtaagtg tgccgaccct cccatgttg tgtctcaaga    1380
tgacacccaa ggcatcagca taattgatat taagaggtgc tctgagatga tgcttgacac    1440
tttttcattt aggatcacat ctacattcaa tgctacatac gtgacagact tctcaatgat    1500
taatgcaaat attgtacatc taagtcctct agacttgtca aatcaaatca attcaataaa    1560
caaatctctt aaaagtgctg aggattggat tgcagatagc aacttctttg ctaatcaagc    1620
cagaacagcc aagacacttt attcactaag tgcaatagca ttaatactat cagtgattac    1680
tttggttgtc gtgggattgc tgattgccta catcatcaag ctggtttctc aaatccatca    1740
attcagagca ctagctgcta caacaatgtt ccacagggag aatcctgccg tcttttccaa    1800
gaacaatcat ggaaacatat atgggatatc ttaagaattc tatcataagt ccatatatgt    1860
ccatgattga cttttaagag ccaacctcca atgattatcc gttaaattca gatataacag    1920
ttcaaaaatc aatattaagc ctccagatac caatgaatat gaatatatct cttagaaaac    1980
ttgattatta tgtgataaca tagtacaatt taagaaaaaa cctaaaataa gcacgaaccc    2040
ttaaggtgtc gtaacgtctc gtgacgccgg gttcagttca aacatcgacc cctgacccaa    2100
ttcaataccc atttccataa aggaacacag tataatttaa tcataaaaga tctcaaaatc    2160
tgatacagct taatccactc aacatataat tataagacta ataataatgg aagattacag    2220
caatctatct cttaaatcaa ttcctaaaag gacatgtaga atcattttcc gaactgccac    2280
```

```
aattcttggc atatgcacat taattgtgct atgttcaagt attcttcatg agataattca    2340
tcttgatgtt tcctctggtc ttatggattc tgatgagtca cagcaaggca tcattcagcc    2400
tatcatagaa tcattaaaat cattgattgc tttggccaac cagattctat ataatgttgc    2460
aataataatt cctcttaaaa ttgacagtat cgaaactgta atactctctg ctttaaaaga    2520
tatgcacacc gggagtatgt ccaatgccaa ctgcacgcca ggaaatttgc ttctgcatga    2580
tgcagcatac atcaatggaa taaacaaatt ccttgtacct gaatcataca atgggacgcc    2640
taaatatgga cctctcctaa atatacccag ctttatcccc tcagcaacat ctcccaatgg    2700
gtgtactaga ataccatcat tttcactcat caagacccat tggtgttaca ctcacaatgt    2760
aatacttgga gattgtcttg atttcacagc atctaaccag tatttatcaa tggggataat    2820
acaacaatct gctgcagggt ttccaatttt caggactatg aaaaccattt acctaagtga    2880
tggaatcaat cgcaaaagct gttcagtcac tgctatacca ggaggttgtg tcttgtattg    2940
ctatgtagct acaaggtctg aaaaagaaga ttatgccacg actgatctag ctgaactgag    3000
acttgctttc tattattata tgataccctt tattgaaaga gtcatatctc ttccaaatac    3060
aacagggcag tgggccacaa tcaaccctgc agttggaagc gggatctatc atctaggctt    3120
tatcttattt cctgtatatg gtggtctcat aaatgggact acttcttaca atgagcagtc    3180
ctcacgctat tttatcccaa acatcccaa cataacttgt gccggtaact ccagcaaaca    3240
ggctgcaata gcacggaatt cttatgtcat ccgttatcac tcaaacaggt taattcagag    3300
tgctgttctt atttgtccat tgtctgacat gcacacagaa gagtgtaatc tagttatgtt    3360
taacaattcc caagtcatga tgggtgcaga aggtaggctc tatgttattg gtaataattt    3420
gtattattat caacgcagtt cctcttggtg gtctgcatcg cttttttaca ggatcaatac    3480
agattttct aaaggaattc ctccgatcat tgaggctcaa tgggtaccgt cctatcaagt    3540
tcctcgtcct ggagtcatgc catgcaatgc aacaagtttt tgccctgcta attgcatcac    3600
aggggtgtac gcagatgtgt ggccgcttaa tgatccagaa ctcatgtcac gtaatgctct    3660
gaaccccaac tatcgatttg ctggagcctt tctcaaaaat gagtccaacc gaactaatcc    3720
cacattttac actgcatcgg ctaactccct cttaaatact accggattca acaacaccaa    3780
tcacaaagca gcatatacat cttcaacctg ctttaaaaac actggaaacc aaaaaattta    3840
ttgtttaata ataattgaaa tgggctcatc tcttttaggg gagttccaaa taataccatt    3900
tttaagggaa ctaatgcttt aatcctattg aatgaagact ccagattcaa gaataattgg    3960
aaggctcttt attttatgcg atagttatac gttttggctg tattagaatg ctatagcatt    4020
ctgctgtttt tcccatatgg aaaaatcctt caacaccaac ttaggttcaa ttttctcatc    4080
atttactgtt gtaattcaat tttactaaaa ttattctgat attaagaaa aaataatctt    4140
tatataatgt aacaatacta ctaagattat gatataggcc agaatggcgg cctcttctga    4200
gatactcctt cctgaagtcc atttgaactc accaatagtc aaacacaaac tcatatacta    4260
cttattacta gggcacttcc cgcatgatct tgacatttct gaaataagcc cccttcacaa    4320
taatgattgg gatcagattg ccagagaaga atccaacaga agagtgtaat ctagttatgt    4380
ttaacaattc ccaa                                                      4394
```

<210> SEQ ID NO 38
<211> LENGTH: 1716
<212> TYPE: DNA
<213> ORGANISM: Human parainfluenza virus 2

<400> SEQUENCE: 38

```
atgcatcacc tgcatccaat gatagtatgc atctttgtta tgtacactgg aattgtaggt      60
tcagatgcca ttgctggaga tcaactcctc aatgtagggg tcattcaatc aaagataaga     120
tcactcatgt actacactga tggtggcgct agctttattg ttgtaaaatt actacccaat     180
cttcccccaa gcaatggaac atgcaacatc accagtctag atgcatataa tgttaccta      240
tttaagttgc taacacccct gattgagaac ctgagcaaaa tttccgctgt tacagatacc     300
aaaccccgcc gagaacgatt tgcagggtc gttattgggc ttgctgcact aggagtagct      360
acagctgcac aaataaccgc agctgtagca atagtgaaag ccaatgcaaa tgctgctgcg     420
ataaacaatc ttgcatcttc aattcaatcc accaacaagg cagtatccga tgtgataact     480
gcatcaagaa caattgcaac cgcagttcaa gcaattcagg atcgcatcaa tggagccatt     540
gtcaacggga taacatctgc atcatgccgt gcccatgatg cactaattgg gtcaatatta     600
aatttgtatc tcactgagct tactacaata tttcataatc aaataacaaa ccctgcgctg     660
acaccacttt ccatccaagc tttaagaatc ctcctcggta gcaccttgcc aattgtcatc     720
gaatccaagc tcaacacaaa actcaacaca gcagagttac tcagttccgg actgttaact     780
ggtcaaataa tttccatttc cccaatgtac atgcaaatgc taattcaaat caatgttccg     840
acatttataa tgcaacccgg tgcgaaggta attgatctaa ttgctatctc tgcaaaccat     900
aaattacaag aagtagttgt acaagttcct aatagaattc tagaatacgc aaatgaacta     960
aaattacaag aagtagttgt acaagttcct aatagaattc tagagtatgc aaatgaacta    1020
caaaactacc cagccaatga ttgtgtcgtg acaccaaact ctgtattttg tagatacaat    1080
gagggttccc cgatccctga atcacaatat caatgcttaa gggggaatct taattcttgc    1140
acttttaccc ctattatcgg aaactttctc aagcgattcg catttgccaa tggtgtgctc    1200
tatgccaact gcaaatcttt gctatgtaag tgtgccgacc ctccccatgt tgtgtctcaa    1260
gatgacaccc aaggcatcag cataattgat attaagaggt gctctgagat gatgcttgac    1320
acttttcat ttaggatcac atctacattc aatgctacat acgtgacaga cttctcaatg     1380
attaatgcaa atattgtaca tctaagtcct ctagacttgt caaatcaaat caattcaata    1440
aacaaatctc ttaaaagtgc tgaggattgg attgcagata gcaacttctt tgctaatcaa    1500
gccagaacag ccaagacact ttattcacta agtgcaatag cattaatact atcagtgatt    1560
actttggttg tcgtgggatt gctgattgcc tacatcatca gctggtttc tcaaatccat    1620
caattcagag cactagctgc tacaacaatg ttccacaggg agaatcctgc cgtctttttcc    1680
aagaacaatc atgaaacat atatgggata tcttaa                                1716
```

<210> SEQ ID NO 39
<211> LENGTH: 551
<212> TYPE: PRT
<213> ORGANISM: Human parainfluenza virus 2

<400> SEQUENCE: 39

```
Met His His Leu His Pro Met Ile Val Cys Ile Phe Val Met Tyr Thr
1               5                   10                  15

Gly Ile Val Gly Ser Asp Ala Ile Ala Gly Asp Gln Leu Leu Asn Val
            20                  25                  30

Gly Val Ile Gln Ser Lys Ile Arg Ser Leu Met Tyr Tyr Thr Asp Gly
        35                  40                  45

Gly Ala Ser Phe Ile Val Val Lys Leu Leu Pro Asn Leu Pro Pro Ser
    50                  55                  60
```

```
Asn Gly Thr Cys Asn Ile Thr Ser Leu Asp Ala Tyr Asn Val Thr Leu
 65                  70                  75                  80

Phe Lys Leu Leu Thr Pro Leu Ile Glu Asn Leu Ser Lys Ile Ser Ala
                 85                  90                  95

Val Thr Asp Thr Lys Pro Arg Arg Glu Arg Phe Ala Gly Val Val Ile
            100                 105                 110

Gly Leu Ala Ala Leu Gly Val Ala Thr Ala Ala Gln Ile Thr Ala Ala
        115                 120                 125

Val Ala Ile Val Lys Ala Asn Ala Ala Ala Ile Asn Asn Leu
130                 135                 140

Ala Ser Ser Ile Gln Ser Thr Asn Lys Ala Val Ser Asp Val Ile Thr
145                 150                 155                 160

Ala Ser Arg Thr Ile Ala Thr Ala Val Gln Ala Ile Gln Asp Arg Ile
                165                 170                 175

Asn Gly Ala Ile Val Asn Gly Ile Thr Ser Ala Ser Cys Arg Ala His
            180                 185                 190

Asp Ala Leu Ile Gly Ser Ile Leu Asn Leu Tyr Leu Thr Glu Leu Thr
        195                 200                 205

Thr Ile Phe His Asn Gln Ile Thr Asn Pro Ala Leu Thr Pro Leu Ser
210                 215                 220

Ile Gln Ala Leu Arg Ile Leu Leu Gly Ser Thr Leu Pro Ile Val Ile
225                 230                 235                 240

Glu Ser Lys Leu Asn Thr Lys Leu Asn Thr Ala Glu Leu Leu Ser Ser
                245                 250                 255

Gly Leu Leu Thr Gly Gln Ile Ile Ser Ile Ser Pro Met Tyr Met Gln
            260                 265                 270

Met Leu Ile Gln Ile Asn Val Pro Thr Phe Ile Met Gln Pro Gly Ala
        275                 280                 285

Lys Val Ile Asp Leu Ile Ala Ile Ser Ala Asn His Lys Leu Gln Glu
290                 295                 300

Val Val Val Gln Val Pro Asn Arg Ile Leu Glu Tyr Ala Asn Glu Leu
305                 310                 315                 320

Gln Asn Tyr Pro Ala Asn Asp Cys Val Val Thr Pro Asn Ser Val Phe
                325                 330                 335

Cys Arg Tyr Asn Glu Gly Ser Pro Ile Pro Glu Ser Gln Tyr Gln Cys
            340                 345                 350

Leu Arg Gly Asn Leu Asn Ser Cys Thr Phe Thr Pro Ile Ile Gly Asn
        355                 360                 365

Phe Leu Lys Arg Phe Ala Phe Ala Asn Gly Val Leu Tyr Ala Asn Cys
370                 375                 380

Lys Ser Leu Leu Cys Lys Cys Ala Asp Pro Pro His Val Val Ser Gln
385                 390                 395                 400

Asp Asp Thr Gln Gly Ile Ser Ile Ile Asp Ile Lys Arg Cys Ser Glu
                405                 410                 415

Met Met Leu Asp Thr Phe Ser Phe Arg Ile Thr Ser Thr Phe Asn Ala
            420                 425                 430

Thr Tyr Val Thr Asp Phe Ser Met Ile Asn Ala Asn Ile Val His Leu
        435                 440                 445

Ser Pro Leu Asp Leu Ser Asn Gln Ile Asn Ser Ile Asn Lys Ser Leu
450                 455                 460

Lys Ser Ala Glu Asp Trp Ile Ala Asp Ser Asn Phe Phe Ala Asn Gln
465                 470                 475                 480

Ala Arg Thr Ala Lys Thr Leu Tyr Ser Leu Ser Ala Ile Ala Leu Ile
```

```
                485                 490                 495
Leu Ser Val Ile Thr Leu Val Val Gly Leu Leu Ile Ala Tyr Ile
            500                 505                 510

Ile Lys Leu Val Ser Gln Ile His Gln Phe Arg Ala Leu Ala Ala Thr
        515                 520                 525

Thr Met Phe His Arg Glu Asn Pro Ala Val Phe Ser Lys Asn Asn His
    530                 535                 540

Gly Asn Ile Tyr Gly Ile Ser
545                 550

<210> SEQ ID NO 40
<211> LENGTH: 1716
<212> TYPE: DNA
<213> ORGANISM: Human parainfluenza virus 2

<400> SEQUENCE: 40
```

| | | | | |
|---|---|---|---|---|
| atggaagatt | acagcaatct | atctcttaaa | tcaattccta | aaaggacatg tagaatcatt | 60 |
| ttccgaactg | ccacaattct | tggcatatgc | acattaattg | tgctatgttc aagtattctt | 120 |
| catgagataa | ttcatcttga | tgtttcctct | ggtcttatgg | attctgatga gtcacagcaa | 180 |
| ggcatcattc | agcctatcat | agaatcatta | aatcattgca | ttgctttggc caaccagatt | 240 |
| ctatataatg | ttgcaataat | aattcctctt | aaaattgaca | gtatcgaaac tgtaatactc | 300 |
| tctgctttaa | aagatatgca | caccgggagt | atgtccaatg | ccaactgcac gccaggaaat | 360 |
| tgcttctgc | atgatgcagc | atacatcaat | ggaataaaca | aattccttgt acctgaatca | 420 |
| tacaatggga | cgcctaaata | tggacctctc | ctaaatatac | ccagctttat ccctcagca | 480 |
| acatctccca | tgggtgtac | tagaatacca | tcattttcac | tcatcaagac ccattggtgt | 540 |
| tacactcaca | atgtaatact | tggagattgt | cttgatttca | cagcatccaa ccagtattta | 600 |
| tcaatgggga | taatacaaca | atctgctgca | gggtttccaa | ttttcaggac tatgaaaacc | 660 |
| atttacctaa | gtgatggaat | caatcgcaaa | agctgttcag | tcactgctat accaggaggt | 720 |
| tgtgtcttgt | attgctatgt | agctacaagg | tctgaaaaag | aagattatgc cacgactgat | 780 |
| ctagctgaac | tgagacttgc | tttctattat | tataatgata | cctttattga agagtcata | 840 |
| tctcttccaa | atacaacagg | gcagtgggcc | acaatcaacc | ctgcagttgg aagcgggatc | 900 |
| tatcatctag | ctttatcttc | atttcctgta | tatggtggtc | tcataaatgg gactacttct | 960 |
| tacaatgagc | agtcctcacg | ctattttatc | ccaaaacatc | ccaacataac ttgtgccggt | 1020 |
| aactccagca | acaggctgc | aatagcacgg | aattcttatg | tcatccgtta tcactcaaac | 1080 |
| aggttaattc | agagtgctgt | tcttatttgt | ccattgtctg | acatgcacac agaagagtgt | 1140 |
| aatctagtta | tgtttaacaa | ttcccaagtc | atgatgggtg | cagaaggtag gctctatgtt | 1200 |
| attggtaata | atttgtatta | ttatcaacgc | agttcctctt | ggtggtctgc atcgcttttt | 1260 |
| tacaggatca | atacagattt | ttctaaagga | attcctccga | tcattgaggc tcaatgggta | 1320 |
| ccgtcctatc | aagttcctcg | tcctggagtc | atgccatgca | atgcaacaag ttttttgccct | 1380 |
| gctaattgca | tcacaggggt | gtacgcagat | gtgtggccgc | ttaatgatcc agaactcatg | 1440 |
| tcacgtaatg | ctctgaaccc | caactatcga | tttgctggag | cctttctcaa aaatgagtcc | 1500 |
| aaccgaacta | atcccacatt | ttacactgca | tcggctaact | ccctcttaaa tactaccgga | 1560 |
| ttcaacaaca | ccaatcacaa | agcagcatat | acatcttcaa | cctgctttaa aaacactgga | 1620 |
| aaccaaaaaa | tttattgttt | aataataatt | gaaatgggct | catctctttt aggggagttc | 1680 |
| caaataatac | cattttttaag | ggaactaatg | ctttaa | | 1716 |

```
<210> SEQ ID NO 41
<211> LENGTH: 571
<212> TYPE: PRT
<213> ORGANISM: Human parainfluenza virus 2

<400> SEQUENCE: 41

Met Glu Asp Tyr Ser Asn Leu Ser Leu Lys Ser Ile Pro Lys Arg Thr
1               5                   10                  15

Cys Arg Ile Ile Phe Arg Thr Ala Thr Ile Leu Gly Ile Cys Thr Leu
            20                  25                  30

Ile Val Leu Cys Ser Ser Ile Leu His Glu Ile Ile His Leu Asp Val
        35                  40                  45

Ser Ser Gly Leu Met Asp Ser Asp Glu Ser Gln Gln Gly Ile Ile Gln
    50                  55                  60

Pro Ile Ile Glu Ser Leu Lys Ser Leu Ile Ala Leu Ala Asn Gln Ile
65                  70                  75                  80

Leu Tyr Asn Val Ala Ile Ile Ile Pro Leu Lys Ile Asp Ser Ile Glu
                85                  90                  95

Thr Val Ile Leu Ser Ala Leu Lys Asp Met His Thr Gly Ser Met Ser
            100                 105                 110

Asn Ala Asn Cys Thr Pro Gly Asn Leu Leu Leu His Asp Ala Ala Tyr
        115                 120                 125

Ile Asn Gly Ile Asn Lys Phe Leu Val Pro Glu Ser Tyr Asn Gly Thr
    130                 135                 140

Pro Lys Tyr Gly Pro Leu Leu Asn Ile Pro Ser Phe Ile Pro Ser Ala
145                 150                 155                 160

Thr Ser Pro Asn Gly Cys Thr Arg Ile Pro Ser Phe Ser Leu Ile Lys
                165                 170                 175

Thr His Trp Cys Tyr Thr His Asn Val Ile Leu Gly Asp Cys Leu Asp
            180                 185                 190

Phe Thr Ala Ser Asn Gln Tyr Leu Ser Met Gly Ile Ile Gln Gln Ser
        195                 200                 205

Ala Ala Gly Phe Pro Ile Phe Arg Thr Met Lys Thr Ile Tyr Leu Ser
    210                 215                 220

Asp Gly Ile Asn Arg Lys Ser Cys Ser Val Thr Ala Ile Pro Gly Gly
225                 230                 235                 240

Cys Val Leu Tyr Cys Tyr Val Ala Thr Arg Ser Glu Lys Glu Asp Tyr
                245                 250                 255

Ala Thr Thr Asp Leu Ala Glu Leu Arg Leu Ala Phe Tyr Tyr Tyr Asn
            260                 265                 270

Asp Thr Phe Ile Glu Arg Val Ile Ser Leu Pro Asn Thr Thr Gly Gln
        275                 280                 285

Trp Ala Thr Ile Asn Pro Ala Val Gly Ser Gly Ile Tyr His Leu Gly
    290                 295                 300

Phe Ile Leu Phe Pro Val Tyr Gly Gly Leu Ile Asn Gly Thr Thr Ser
305                 310                 315                 320

Tyr Asn Glu Gln Ser Ser Arg Tyr Phe Ile Pro Lys His Pro Asn Ile
                325                 330                 335

Thr Cys Ala Gly Asn Ser Ser Lys Gln Ala Ala Ile Ala Arg Asn Ser
            340                 345                 350

Tyr Val Ile Arg Tyr His Ser Asn Arg Leu Ile Gln Ser Ala Val Leu
        355                 360                 365

Ile Cys Pro Leu Ser Asp Met His Thr Glu Glu Cys Asn Leu Val Met
```

```
                370             375             380
Phe Asn Ser Gln Met Val Met Gly Ala Glu Gly Arg Leu Tyr Val
385                 390             395             400

Ile Gly Asn Asn Leu Tyr Tyr Gln Arg Ser Ser Trp Trp Ser
                405             410             415

Ala Ser Leu Phe Tyr Arg Ile Asn Thr Asp Phe Ser Lys Gly Ile Pro
                420             425             430

Pro Ile Ile Glu Ala Gln Trp Val Pro Ser Tyr Gln Val Pro Arg Pro
                435             440             445

Gly Val Met Pro Cys Asn Ala Thr Ser Phe Cys Pro Ala Asn Cys Ile
                450             455             460

Thr Gly Val Tyr Ala Asp Val Trp Pro Leu Asn Asp Pro Glu Leu Met
465             470             475             480

Ser Arg Asn Ala Leu Asn Pro Asn Tyr Arg Phe Ala Gly Ala Phe Leu
                485             490             495

Lys Asn Glu Ser Asn Arg Thr Asn Pro Thr Phe Tyr Thr Ala Ser Ala
                500             505             510

Asn Ser Leu Leu Asn Thr Thr Gly Phe Asn Asn Thr Asn His Lys Ala
                515             520             525

Ala Tyr Thr Ser Ser Thr Cys Phe Lys Asn Thr Gly Asn Gln Lys Ile
                530             535             540

Tyr Cys Leu Ile Ile Ile Glu Met Gly Ser Ser Leu Leu Gly Glu Phe
545             550             555             560

Gln Ile Ile Pro Phe Leu Arg Glu Leu Met Leu
                565             570

<210> SEQ ID NO 42
<211> LENGTH: 2472
<212> TYPE: DNA
<213> ORGANISM: Human parainfluenza virus 2

<400> SEQUENCE: 42
gaatgctcca gcatctagga atagaacaac aactaagtca taccattatt gaccatacaa      60
taatcaacaa ttttagccaa ctgattacta agatattatc ataggtccga actgatcaat     120
ctaacaaaaa aactaaacat tcaataataa atcaaagttc aggccaaatt atccagccat     180
gcatcacctg catccaatga tagtatgcat ctttgttatg tacactgaaa ttgtaggttc     240
agatgccatt gctggagatc aactcctcaa tgtaggggtc attcaatcaa agataagatc     300
actcatgtac tacactgatg gtggcgctag ctttattgtt gtaaaattac taccaaatct     360
tcccccaagc aatggaacat gcaacatcac cagtctagat gcatataatg ttaccctatt     420
taagttgcta acgcccctga ttgagaacct gagcaaaatt tctgctgtta cagataccaa     480
accccgccga gaacgatttg caggagtcgt tattgggctt gctgcactag gagtagctac     540
agctgcacaa ataaccgcag ctgtagcaat agtaaaagcc aatgcaaatg ctgctgcgat     600
aaacaatctt gcatcttcaa ttcaatccac caacaaggca gtatccgatg tgataactgc     660
atcaagaaca attgcaaccg cagttcaagc aattcaggat cgcatcaatg gagccattgt     720
caacgggata acatctgcat catgccgtgc ccatgatgca ctaattgggt caatattaaa     780
tttgtatctc actgagctta caacaatatt tcataatcaa ataacaaacc ctgcgctgac     840
accactttcc atccaagctt taagaatcct cctcggtagc accttgccaa ttgtcattga     900
atccaaactc aacacaaaac tcaacacagc agagctgctc agttccggac tgttaactgg     960
tcaaataatt tccatttccc caatgtacat gcaaatgcta attcaaatca atgttccgac    1020
```

```
atttataatg caacccggtg cgaaggtaat tgatctaatt gctatctctg caaaccataa    1080
attacaagaa gtagttgtac aagttcctaa tagaattcta gaatacgcaa atgaactaca    1140
aaactaccca gccaatgatt gtgtcgtgac accaaactct gtattttgta gatacaatga    1200
gggttccccg atccctgaat cacaatatca atgcttaagg gggaatctta attcttgcac    1260
ttttacccct attatcggga actttctcaa gcgattcgca tttgccaatg tgtgctcta     1320 tgccaactgc aaatctttgc tatgtaagtg tgccgaccct ccccatgttg tgtctcaaga    1380
tgacaaccaa ggcatcagca taattgatat taagaggtgc tctgagatga tgcttgacac    1440
tttttcattt aggatcacat ctacattcaa tgctacatac gtgacagact tctcaatgat    1500
taatgcaaat attgtacatc taagtcctct agacttgtca aatcaaatca attcaataaa    1560
caaatctctt aaaagtgctg aggattggat tgcagatagc aacttcttcg ctaatcaagc    1620
cagaacagcc aagacacttt attcactaag tgcaatagca ttaatactat cagtgattac    1680
tttggttgtt gtgggattgc tgattgccta catcatcaag ctggtttctc aaatccatca    1740
attcagagca ctagctgcta acaatgttt ccacagggag aatcctgccg tcttttccaa     1800
gaacaatcat ggaaacatat atgggatatc ttaagaattc tatcataagt ccatatatgt    1860
ccatgattga cctttaagag ccaacctcca atgattatcc gttaaattca gatataacaa    1920
ttcaaaaatc aatattaagc ctccagatac caatgaatat gaatatatct cttagaaaac    1980
ttgattatta tgtgataaca tagtacaatt taagaaaaaa cctaaaataa gcacgaaccc    2040
ttaaggtgtc gtaacgtctc gtgacgccgg gttcagttca acatcgacc cctgaccccaa    2100 ttcaataccc attttcataa aggaacacag tataatttaa tcataaaaga cctcaaaatc    2160
tgatacagct taatccactc aacatataat tataagacta ataataatgg aagattacag    2220
caatctatct cttaaatcaa ttcctaaaag gacatgtaga atcattttcc gaactgccac    2280
aattcttggc atatgcacat taattgtgct atgttcaagt attcttcatg agataattca    2340
tcttgatgtt tcctctggtc ttatgaattc tgatgagtca cagcaaggca ttatccagcc    2400
tatcatagaa tcattaaaat cattgattgc tttggccaac cagattctat ataatgttgc    2460
aatagtaatt cc                                                         2472

<210> SEQ ID NO 43
<211> LENGTH: 1656
<212> TYPE: DNA
<213> ORGANISM: Human parainfluenza virus 2

<400> SEQUENCE: 43
atgcatcacc tgcatccaat gatagtatgc atctttgtta tgtacactgg aattgtaggt      60
tcagatgcca ttgctggaga tcaactcctc aatgtagggg tcattcaatc aaagataaga    120
tcactcatgt actacactga tggtggcgct agctttattg ttgtaaaatt actaccaaat    180 cttccccccaa gcaatggaac atgcaacatc accagtctag atgcatataa tgttaccta     240 tttaagttgc taacgccccct gattgagaac ctgagcaaaa tttctgctgt tacagatacc    300
aaaccccgcc gagaacgatt tgcaggagtc gttattgggc ttgctgcact aggagtagct    360
acagctgcac aaataaccgc agctgtagca atagtaaaag ccaatgcaaa tgctgctgcg    420
ataaacaatc ttgcatcttc aattcaatcc accaacaagg cagtatccga tgtgataact    480
gcatcaagaa caattgcaac cgcagttcaa gcaattcagg atcgcatcaa tggagccatt    540
gtcaacggga taacatctgc atcatgccgt gcccatgatg cactaattgg gtcaatatta    600
```

```
aatttgtatc tcactgagct tactacaata tttcataatc aaataacaaa ccctgcgctg    660
acaccacttt ccatccaagc tttaagaatc ctcctcggta gcaccttgcc aattgtcatt    720
gaatccaaac tcaacacaaa actcaacaca gcagagctgc tcagttccgg actgttaact    780
ggtcaaataa tttccatttc cccaatgtac atgcaaatgc taattcaaat caatgttccg    840
acatttataa tgcaacccgg tgcgaaggta attgatctaa ttgctatctc tgcaaaccat    900
aaattacaag aagtagttgt acaagttcct aatagaattc tagaatacgc aaatgaacta    960
caaaactacc cagccaatga ttgtgtcgtg acaccaaact ctgtattttg tagatacaat   1020
gagggttccc cgatccctga atcacaatat caatgcttaa gggggaatct taattcttgc   1080
acttttaccc ctattatcgg gaactttctc aagcgattcg catttgccaa tggtgtgctc   1140
tatgccaact gcaaatcttt gctatgtaag tgtgccgacc ctccccatgt tgtgtctcaa   1200
gatgacaacc aaggcatcag cataattgat attaagaggt gctctgagat gatgcttgac   1260 acttttcat ttaggatcac atctacattc aatgctacat acgtgacaga cttctcaatg   1320
attaatgcaa atattgtaca tctaagtcct ctagacttgt caaatcaaat caattcaata   1380
aacaaatctc ttaaaagtgc tgaggattgg attgcagata gcaacttctt cgctaatcaa   1440
gccagaacag ccaagacact ttattcacta agtgcaatag cattaatact atcagtgatt   1500
actttggttg ttgtgggatt gctgattgcc tacatcatca agctggtttc tcaaatccat   1560
caattcagag cactagctgc tacaacaatg ttccacaggg agaatcctgc cgtcttttcc   1620
aagaacaatc atggaaacat atatgggata tcttaa                             1656
```

<210> SEQ ID NO 44
<211> LENGTH: 551
<212> TYPE: PRT
<213> ORGANISM: Human parainfluenza virus 2

<400> SEQUENCE: 44

```
Met His His Leu His Pro Met Ile Val Cys Ile Phe Val Met Tyr Thr
1               5                   10                  15

Gly Ile Val Gly Ser Asp Ala Ile Ala Gly Asp Gln Leu Leu Asn Val
            20                  25                  30

Gly Val Ile Gln Ser Lys Ile Arg Ser Leu Met Tyr Tyr Thr Asp Gly
        35                  40                  45

Gly Ala Ser Phe Ile Val Val Lys Leu Leu Pro Asn Leu Pro Pro Ser
    50                  55                  60

Asn Gly Thr Cys Asn Ile Thr Ser Leu Asp Ala Tyr Asn Val Thr Leu
65                  70                  75                  80

Phe Lys Leu Leu Thr Pro Leu Ile Glu Asn Leu Ser Lys Ile Ser Ala
                85                  90                  95

Val Thr Asp Thr Lys Pro Arg Arg Glu Arg Phe Ala Gly Val Val Ile
            100                 105                 110

Gly Leu Ala Ala Leu Gly Val Ala Thr Ala Ala Gln Ile Thr Ala Ala
        115                 120                 125

Val Ala Ile Val Lys Ala Asn Ala Asn Ala Ala Ala Ile Asn Asn Leu
    130                 135                 140

Ala Ser Ser Ile Gln Ser Thr Asn Lys Ala Val Ser Asp Val Ile Thr
145                 150                 155                 160

Ala Ser Arg Thr Ile Ala Thr Ala Val Gln Ala Ile Gln Asp Arg Ile
                165                 170                 175

Asn Gly Ala Ile Val Asn Gly Ile Thr Ser Ala Ser Cys Arg Ala His
            180                 185                 190
```

Asp Ala Leu Ile Gly Ser Ile Leu Asn Leu Tyr Leu Thr Glu Leu Thr
       195                 200                 205

Thr Ile Phe His Asn Gln Ile Thr Asn Pro Ala Leu Thr Pro Leu Ser
    210                 215                 220

Ile Gln Ala Leu Arg Ile Leu Leu Gly Ser Thr Leu Pro Ile Val Ile
225                 230                 235                 240

Glu Ser Lys Leu Asn Thr Lys Leu Asn Thr Ala Glu Leu Leu Ser Ser
                245                 250                 255

Gly Leu Leu Thr Gly Gln Ile Ile Ser Ile Ser Pro Met Tyr Met Gln
                260                 265                 270

Met Leu Ile Gln Ile Asn Val Pro Thr Phe Ile Met Gln Pro Gly Ala
            275                 280                 285

Lys Val Ile Asp Leu Ile Ala Ile Ser Ala Asn His Lys Leu Gln Glu
            290                 295                 300

Val Val Val Gln Val Pro Asn Arg Ile Leu Glu Tyr Ala Asn Glu Leu
305                 310                 315                 320

Gln Asn Tyr Pro Ala Asn Asp Cys Val Val Thr Pro Asn Ser Val Phe
                325                 330                 335

Cys Arg Tyr Asn Glu Gly Ser Pro Ile Pro Glu Ser Gln Tyr Gln Cys
                340                 345                 350

Leu Arg Gly Asn Leu Asn Ser Cys Thr Phe Thr Pro Ile Ile Gly Asn
            355                 360                 365

Phe Leu Lys Arg Phe Ala Phe Ala Asn Gly Val Leu Tyr Ala Asn Cys
            370                 375                 380

Lys Ser Leu Leu Cys Lys Cys Ala Asp Pro Pro His Val Val Ser Gln
385                 390                 395                 400

Asp Asp Asn Gln Gly Ile Ser Ile Ile Asp Ile Lys Arg Cys Ser Glu
                405                 410                 415

Met Met Leu Asp Thr Phe Ser Phe Arg Ile Thr Ser Thr Phe Asn Ala
                420                 425                 430

Thr Tyr Val Thr Asp Phe Ser Met Ile Asn Ala Asn Ile Val His Leu
            435                 440                 445

Ser Pro Leu Asp Leu Ser Asn Gln Ile Asn Ser Ile Asn Lys Ser Leu
            450                 455                 460

Lys Ser Ala Glu Asp Trp Ile Ala Asp Ser Asn Phe Phe Ala Asn Gln
465                 470                 475                 480

Ala Arg Thr Ala Lys Thr Leu Tyr Ser Leu Ser Ala Ile Ala Leu Ile
                485                 490                 495

Leu Ser Val Ile Thr Leu Val Val Val Gly Leu Leu Ile Ala Tyr Ile
                500                 505                 510

Ile Lys Leu Val Ser Gln Ile His Gln Phe Arg Ala Leu Ala Ala Thr
            515                 520                 525

Thr Met Phe His Arg Glu Asn Pro Ala Val Phe Ser Lys Asn Asn His
            530                 535                 540

Gly Asn Ile Tyr Gly Ile Ser
545                 550

<210> SEQ ID NO 45
<211> LENGTH: 1656
<212> TYPE: DNA
<213> ORGANISM: Human parainfluenza virus 2

<400> SEQUENCE: 45
atgcatcacc tgcatccaat gatagtatgc atctttgtta tgtacactgg aattgtaggt       60

```
tcagatgcca ttgctggaga tcaactactt aatataggg tcattcaatc aaagataaga    120
tcactcatgt actatactga tggtggtgct agctttattg ttgtaaaatt gctacctaat    180
cttcccccaa gcaatggaac atgcaacatc accagtctag atgcatataa tgttaccta     240 tttaagttac taacacccct gattgagaac ctgagtaaaa tttccactgt tacagatacc    300
aaaacccgcc aagaacgatt tgcaggagta gttgttggac ttgctgcatt aggagtagcc    360
acagccgcac aaataactgc agctgtagca atagtgaaag ctaatgcaaa tgctgctgcg    420
ataaacaatc ttgcatcttc aattcaatcc accaacaagg cagtatccga tgtgatagat    480
gcatcaagaa caattgcaac cgcagttcaa gcaattcagg atcgcatcaa tggagctatt    540
gttaatggga taacatctgc atcatgccgt gcccatgatg cactcattgg gtcaatatta    600
aatctttatc tcactgagct taccacaata tttcataatc aaataacaaa ccctgcgctg    660
acaccactct ccatccaagc tttaagaatc ctcctcggta gcaccttgcc aattgtcatt    720
gagtccaaac tcaacacaaa cttcaacaca gcagagctgc tcagttccgg actgttaact    780
ggtcaaataa tttccatttc cccaatgtac atgcaaatgc taattcaaat caatgttccg    840
acatttataa tgcaacccgg tgcgaaggta attgatctaa ttgctatctc cgcaaaccat    900
aaattgcaag aagtggttgt acaagttccg aataggattc tagagtatgc aaatgaacta    960
caaaattacc cagccaatga ctgtgtcgtg acaccgaact ctgtatttg tagatacaat    1020 gagggttccc ctatccctga atcacaatat caatgcttga gggggaatct taattcttgc    1080
acttttaccc ctattatcgg gaactttctt aagcgattcg catttgctaa tggtgtgctc    1140
tatgccaact gcaaatcttt gctatgtagg tgtgccgacc cccccatgt tgtatcccag     1200 gatgataccc aaggcatcag cataattgat attaagagat gctctgagat gatgcttgac    1260 acttttcat ttaggatcac atctactttc aatgctacgt acgtgacaga cttctcaatg     1320
attaatgcaa atattgtaca tctaagtcct ctagatttgt caaatcaaat caattcaata    1380
aacaaatctc ttaaaagtgc tgaggattgg attgcagata gcaacttctt tgctaatcaa    1440
gccaggacag ccaagacact ttattcacta agtgcaatag cattaatact atcagtgatt    1500
actttggttg tcgtgggatt gctgattgcc tacatcatca agctggtttc tcaaatccaa    1560
caattcagat cgctagctgc tacaacaatg ttccacaggg aaaatcctgc cttctttcc     1620 aagaataacc atgaaacat atatgggata tcttaa                              1656
```

<210> SEQ ID NO 46  
<211> LENGTH: 551  
<212> TYPE: PRT  
<213> ORGANISM: Human parainfluenza virus 2

<400> SEQUENCE: 46

Met His His Leu His Pro Met Ile Val Cys Ile Phe Val Met Tyr Thr
1               5                   10                  15

Gly Ile Val Gly Ser Asp Ala Ile Ala Gly Asp Gln Leu Leu Asn Ile
            20                  25                  30

Gly Val Ile Gln Ser Lys Ile Arg Ser Leu Met Tyr Tyr Thr Asp Gly
        35                  40                  45

Gly Ala Ser Phe Ile Val Val Lys Leu Leu Pro Asn Leu Pro Ser
    50                  55                  60

Asn Gly Thr Cys Asn Ile Thr Ser Leu Asp Ala Tyr Asn Val Thr Leu
65                  70                  75                  80

Phe Lys Leu Leu Thr Pro Leu Ile Glu Asn Leu Ser Lys Ile Ser Thr

-continued

```
                85                  90                  95
Val Thr Asp Thr Lys Thr Arg Gln Glu Arg Phe Ala Gly Val Val
            100                 105                 110
Gly Leu Ala Ala Leu Gly Val Ala Thr Ala Ala Gln Ile Thr Ala Ala
            115                 120                 125
Val Ala Ile Val Lys Ala Asn Ala Asn Ala Ala Ile Asn Asn Leu
130                 135                 140
Ala Ser Ser Ile Gln Ser Thr Asn Lys Ala Val Ser Asp Val Ile Asp
145                 150                 155                 160
Ala Ser Arg Thr Ile Ala Thr Ala Val Gln Ala Ile Gln Asp Arg Ile
                165                 170                 175
Asn Gly Ala Ile Val Asn Gly Ile Thr Ser Ala Ser Cys Arg Ala His
            180                 185                 190
Asp Ala Leu Ile Gly Ser Ile Leu Asn Leu Tyr Leu Thr Glu Leu Thr
            195                 200                 205
Thr Ile Phe His Asn Gln Ile Thr Asn Pro Ala Leu Thr Pro Leu Ser
        210                 215                 220
Ile Gln Ala Leu Arg Ile Leu Leu Gly Ser Thr Leu Pro Ile Val Ile
225                 230                 235                 240
Glu Ser Lys Leu Asn Thr Asn Phe Asn Thr Ala Glu Leu Leu Ser Ser
                245                 250                 255
Gly Leu Leu Thr Gly Gln Ile Ile Ser Ile Ser Pro Met Tyr Met Gln
            260                 265                 270
Met Leu Ile Gln Ile Asn Val Pro Thr Phe Ile Met Gln Pro Gly Ala
            275                 280                 285
Lys Val Ile Asp Leu Ile Ala Ile Ser Ala Asn His Lys Leu Gln Glu
        290                 295                 300
Val Val Val Gln Val Pro Asn Arg Ile Leu Glu Tyr Ala Asn Glu Leu
305                 310                 315                 320
Gln Asn Tyr Pro Ala Asn Asp Cys Val Val Thr Pro Asn Ser Val Phe
                325                 330                 335
Cys Arg Tyr Asn Glu Gly Ser Pro Ile Pro Glu Ser Gln Tyr Gln Cys
            340                 345                 350
Leu Arg Gly Asn Leu Asn Ser Cys Thr Phe Thr Pro Ile Ile Gly Asn
            355                 360                 365
Phe Leu Lys Arg Phe Ala Phe Ala Asn Gly Val Leu Tyr Ala Asn Cys
        370                 375                 380
Lys Ser Leu Leu Cys Arg Cys Ala Asp Pro Pro His Val Val Ser Gln
385                 390                 395                 400
Asp Asp Thr Gln Gly Ile Ser Ile Ile Asp Ile Lys Arg Cys Ser Glu
                405                 410                 415
Met Met Leu Asp Thr Phe Ser Phe Arg Ile Thr Ser Thr Phe Asn Ala
            420                 425                 430
Thr Tyr Val Thr Asp Phe Ser Met Ile Asn Ala Asn Ile Val His Leu
            435                 440                 445
Ser Pro Leu Asp Leu Ser Asn Gln Ile Asn Ser Ile Asn Lys Ser Leu
        450                 455                 460
Lys Ser Ala Glu Asp Trp Ile Ala Asp Ser Asn Phe Phe Ala Asn Gln
465                 470                 475                 480
Ala Arg Thr Ala Lys Thr Leu Tyr Ser Leu Ser Ala Ile Ala Leu Ile
                485                 490                 495
Leu Ser Val Ile Thr Leu Val Val Val Gly Leu Leu Ile Ala Tyr Ile
            500                 505                 510
```

```
Ile Lys Leu Val Ser Gln Ile His Gln Phe Arg Ser Leu Ala Ala Thr
        515                 520                 525

Thr Met Phe His Arg Glu Asn Pro Ala Phe Phe Ser Lys Asn Asn His
        530                 535                 540

Gly Asn Ile Tyr Gly Ile Ser
545                 550

<210> SEQ ID NO 47
<211> LENGTH: 15646
<212> TYPE: DNA
<213> ORGANISM: Human parainfluenza virus 2

<400> SEQUENCE: 47
accaggggga gaatcagatg gcatcgttat atgacgaatt gcaaaaagat tacgtaggtc      60
cggaaccact agattcggtg ccggtaacga ttccagtttt atactatctg atcattctct    120
atctctatta aggatatttc tagtctaaag ttcaaaatgt caagtgtttt aaagacattt    180
gaaagattta ctatacaaca ggagcttcag gagcaatctg atgacactcc agtacctctt    240
gagacaatca aacctacaat cagggtattt gtcatcaata ataatgatcc tgtcgtaaga    300
tctagacttt tattctttaa tctacgaatc attatgagta cactgcaag agagggacat     360 agagctggtg ctctcctcag tcttttatca ctaccttctg cagctatgag taatcacatc    420
aaattagcca tgcattcacc agaagccagc atagatagag tagagataac aggggtttgag   480 ataattcat tccgagtcat tccagatgct cgatcaacta tgtccagagg agaggtgctg    540 gctttttgaag cattagctga ggacattcct gataccctta tcaccaaaac tccatttgta    600
aataatgatg tagaagatga catatttgat gaaacagaga aattcttaga tgtttgctac   660
agtgtgctta tgcaggcatg gatagtaaca tgcaagtgta tgactgctcc tgatcaacca    720
ccagtatcag tagcaaagat ggctaaatat caacaacaag ggagaatcaa tgctaggtat    780
gtactacaac tgaagcaca aagactaatt cagaatgcca tccgcaagtc aatggtagta    840
aggcatttca tgacttatga gcttcaactt tcacaatcaa gatctttgct agcaaaccgc   900
tactatgcta tggtgggaga cattggcaag tacattgaac acagcggaat gggaggattt    960
ttcttaacac ttaaatatgg acttggaaca agatggccta cattggctct tgcagcattt   1020
tctggggaac tccagaaatt aaaagctctc atgctacatt atcagagtct aggacccatg   1080
gccaagtaca tggctctatt agaatcacca aaactgatgg attttgtccc atctgaatat   1140
ccattagatt atagctatgc aatgggtatt ggaactgtcc ttgatacaaa tatgagaaat   1200
tatgcatacg gtagatcata tttaaatcag caatattttc agctaggagt agaaacagca   1260
aggaaacagc agggagctgt tgacaacagg acagcagagg acctcggcat gactgctgca   1320
gacaaagcag acctcactgc aaccatatca aagctatcct tgtcccaatt acctagggt   1380 agacaaccaa tatctgaccc atttgctgga gcaaatgaca gagaaatggg aggacaagca   1440
aatgatacac ctgtgtataa cttcaatcca atcgatactc ggaggtatga caactatgac   1500
agtgatggtg aggacagaat tgacaacgat caagatcaag ctatcagaga aatagagga   1560 gagcctggac aacccaacaa ccagacaagt gacaaccagc agagattcaa ccccccata    1620 ccgcaaagaa catcaggtat gagcagtgaa gagttccaac attcaatgaa tcagtacatc   1680
cgtgctatgc atgagcaata cagaggctcc caggatgatg atgccaatga tgccacagat   1740
gggaatgaca tttctcttga gctagttgga gattttgatt cctaactctc aatgtcatac   1800
aaccagatat acacatccac atcactcaga gatacagctg ccactcacac actcatccag   1860
```

```
acaaatcaaa ctagactcac atcattcgga aacaattctc tcataattta aagaaaaaat    1920
cataggccgg acgggttaga aatccggtgc ttgttcgtga tcagataacc tccacaccag    1980
aatcatacaa tcatggccga ggaaccaaca taccactg agcaagttga tgaattaatc      2040
catgctggac tgggaacagt agatttcttc ctatctagac ccatagatgc tcagtcttct    2100
ttaggcaaag gcagcatccc accaggtgtc acagctgttc taactagtgc agcggagaca    2160
aaatccaaac cagttgctgc tggtccagtt aaacccaggc ggaagaaagt gatcagcaat    2220
actactccat acactattgc agacaatatt ccacctgaga agctaccgat caacactcca    2280
atacccaatc cattacttcc actggcacgc cctcacggaa agatgacaga cattgacatt    2340
gtcactggga acattacaga aggatcgtac aaaggtgtgg agcttgctaa attagggaag    2400
cagacactac tcacaaggtt cacctcgaat gagccagtct cctcagctgg atccgcccaa    2460
gaccccaact ttaagagggg gggagctaat agagaaagag caagaggcaa ccataggaga    2520
gaatggagta ttgcatgggt cggagatcag gtcaaagtct tcgagtggtg taatcccagg    2580
tgtgccccag tcacggcctc agctcgcaag ttcacctgca catgcggatc ctgccccagc    2640
atctgcggag aatgtgaagg agatcattga gctcttaaag ggacttgatc ttcgccttca    2700
gactgtagaa gggaaagtag ataaaattct tgcaacttct gcaactataa tcaatcttaa    2760
aaatgaaatg actagtctca aggcgagtgt tgcaactatg gaaggtatga taacaacaat    2820
taaaatcatg gatcccagta caccaactaa tgtccctgta gaggagatca gaaagagttt    2880
acacaatgtt ccagtagtaa ttgccggtcc aactagtgga ggcttcacag ccgaacaggt    2940
gatattgatt tcaatggatg aactagctag acctacactc tcatcaacaa aaaggatcac    3000
acgaaagcct gaatccaaga agatttaac aggcataaaa ctaactttga tgcagcttgc     3060
aaatgactgc atctcgcgtc cagataccaa gactgagttc gtgactaaga ttcaggcagc    3120
aaccacagaa tcacagctta acgaaattaa acggtcaata atacgctctg caatataaaa    3180
tgaggtgcag tcacacaaga gacactcaac atgcatccaa tcaagatcca gactccatcc    3240
atccaaaaac acgcccacaa ttgtcaacac caagaaacaa ccacagccga accatgctca    3300
accaaaagac ccaaacaaca cctcacatca atagaaggct ggacatgata aatttaataa    3360
aaaaagaaaa gaagttaagt aaaatttaaa ggacacaata gagaaaatct aggtccgaaa    3420
gcttgcctct cagacagatc ccaaaatcat agtccaaacc ccaaacacag cagcagacat    3480
gcctataata tcattaccag cagatccaac ttcacccagt caatccctta ctccgttcc     3540
aatacaactt gacaccaaag atggcaaggc agggaaactc cttaaacaga ttcgaattag    3600
gtatctaaat gagcctaatt ctcgccatac accataaact ttcatcaata cgtatggatt    3660
tgtttatgct cgagacactt caggggcat tcacagtgag atcagcagtg acctagctgc     3720
agggtccata acagcatgca tgatgaagct aggacctggt ccaaatattc agaatgcaaa    3780
tctagtgcta agatctctga tgaattcta cgtaaaagtc aagaagacat caagccagag     3840
agaggaagca gtgtttgaat tagttaacat tccaactta ttgagagaac atgctctttg      3900
caaacgcaaa atgttagtat gctctgcaga aaaattcctc aagaacccgt caaagctaca    3960
agctggattt gagtatgtat acatccaac ttttgtctcc attacatact caccacgaaa      4020
tctgaattac caagtggcca gacctatcct taagttcaga tcacgctttg tgtatagcat    4080
tcatttggaa ttaatcctga gattgctatg caaatctgac tccccttga tgaaatccta      4140
caatgcagac agaacaggtc ggggatgcct cgcatcagtc tggatccatg tatgtaacat    4200
```

```
tctgaaaaac aaaagcatca agcaacaagg cagagaatca tatttcatag ctaagtgcat    4260
gagcatgcag ctgcaggtgt ccattgcaga tctttgggga ccaacaatca taatcaaatc    4320
attgggtcac atccccaaga ctgcacttcc tttttcagc aaagatggga ttgcctgtca     4380
tccattacaa gatgtttccc ctaatctagc aaaatcactg tggtcagttg gatgtgagat    4440
agaatctgcc aagttgatac ttcaagaatc tgatcttaat gagctaatgg ccaccagga    4500
ccttatcact gataagattg ccattagatc aggtcaacgg acatttgaga ggtccaaatt    4560
cagcccattc aaaaaatatg catcaattcc aaacttggaa gccatcaact gaatgctcca    4620
gcatctgaga atagaaccac aatcaagtca tactactagt cactatacaa taatcaacaa    4680
ttttagtcaa ctgattacca agatgttatc ataggtccga actgatcaat ctaacaaaaa    4740
aactaaacgt tccacaataa atcaacgttc aggccaaaat attcagccat gcatcacctg    4800
catccaatga tagtatgcat cttttgttatg tacactggaa ttgtaggttc agatgccatt   4860
gctggagatc aactacttaa tataggggtc attcaatcaa agataagatc actcatgtac    4920
tatactgatg gtggtgctag ctttattgtt gtaaaattgc tacctaatct tcccccaagc    4980
aatggaacat gcaacatcac cagtctagat gcatataatg ttaccctatt taagttacta   5040
acaccctga ttgagaacct gagtaaaatt tccactgtta cagataccaa aacccgccaa    5100
aaacgatttg caggagtagt tgttggactt gctgcattag gagtagccac agccgcacaa    5160
ataactgcag ctgtagcaat agtgaaagct aatgcaaatg ctgctgcgat aaacaatctt   5220
gcatcttcaa ttcaatccac caacaaggca gtatccgatg tgatagatgc atcaagaaca   5280
attgcaaccg cagttcaagc aattcaggat cgcatcaatg gagctattgt taatgggata   5340
acatctgcat catgccgtgc ccatgatgca ctcattgggt caatattaaa tctttatctc   5400
actgagctta ccacaatatt tcataatcaa ataacaaacc ctgcgctgac accactctcc   5460
atccaagctt taagaatcct cctcggtagc accttgccaa ttgtcattga gtccaaactc   5520
aacacaaact tcaacacagc agagctgctc agttccggac tgttaactgg tcaaataatt   5580
tccatttccc caatgtacat gcaaatgcta attcaaatca atgttccgac atttataatg   5640
caacccggtg cgaaggtaat tgatctaatt gctatctccg caaaccataa attgcaagaa   5700
gtggttgtac aagttccgaa taggattcta gagtatgcaa atgaactaca aaattaccca   5760
gccaatgact gtgtcgtgac accgaactct gtattttgta gatacaatga gggttcccct   5820
atccctgaat cacaatatca atgcttgagg gggaatctta attcttgcac ttttacccct   5880
attatcggga acttctcttaa gcgattcgca tttgctaatg gtgtgctcta tgccaactgc   5940
aaaatctttg tatgtaggtg tgccgacccc cccatgttg tatcccagga tgatacccaa   6000
ggcatcagca taattgatat taagagatgc tctgagatga tgcttgacac ttttcatt    6060
aggatcacat ctactttcaa tgctacgtac gtgacagact tctcaatgat taatgcaaat   6120
attgtacatc taagtcctct agatttgtca aatcaaatca attcataaa caatctctt    6180
aaaagtgctg aggattggat tgcagatagc aacttctttg ctaatcaagc caggacagcc   6240
aagacacttt attcactaag tgcaatagca ttaatactat cagtgattac tttggttgtc   6300
gtgggattgc tgattgccta catcatcaag ctggtttctc aaatccatca attcagatcg   6360
ctagctgcta caacaatgtt ccacagggaa atcctgcct tcttttccaa gaataaccat   6420
ggaaacatat atgggatatc ttaagaaatc tatcacaagt ctatatatgt ccacaattga   6480
cccttaagaa ccaacttcca acgattatcc gttaaattta agtataatag tttaaaaatt   6540
aacattaagc ctccagatac caatgaatat gaatatatct cttagaaaac ctgattatta   6600
```

```
tgtgatagcg tagtacaatt taagaaaaaa cctaaaataa gcacgaaccc ttaaggtgtc    6660
gtaacgtctc gtgacaccgg gttcagttca aatatcgacc tctaacccaa tttaacaccc    6720
attcttatat aagaacacag tataatttaa tcacaaaaga cctcaaaaac tgacacagct    6780
tgatccactc aacatataat tgtaagatta ataataatgg aagattacag caatctatct    6840
cttaaatcaa ttcctaaaag gacatgtaga atcattttcc gaactgccac aattcttgga    6900
atatgcacat tgattgttct atgttcaagt attcttcatg agataattca tcttgatgtt    6960
tcctctggtc tcatggattc cgatgattca cagcaaggca ttattcagcc tattatagaa    7020
tcattaaaat cattaattgc tttggctaac cagattctgt acaatgttgc aataataatt    7080
cctcttaaaa ttgacagtat cgagactgta atattctctg ctttaaagga tatgcatact    7140
gggagcatgt ccaacaccaa ctgtacaccc ggaaatctgc ttctgcatga tgcagcgtac    7200
atcaatggaa taaacaaatt ccttgtactt aaatcataca atgggacgcc taaatatgga    7260
cctctcctaa atattcccag ctttatcccc tcagcaacat ctcccaacgg gtgcactaga    7320
ataccatcat tttcactcat taagacccat tggtgttaca ctcacaatgt aatgcttgga    7380
gattgcctcg atttcacgac atctaatcag tatttagcaa tggggataat acaacaatct    7440
gctgcagcat ttccaatctt caggactatg aaaaccattt acctaagtga tggaatcaat    7500
cgcaaaagct gttcagtcac tgctatacca ggaggttgtg tcttgtattg ctatgtagct    7560
acaagatctg agaaagaaga ttatgccaca actgatctag ctgaactgag acttgctttc    7620
tattattata atgataccct tattgaaaga gtcatatctc ttccaaatac aacagggcaa    7680
tgggccacaa tcaatcctgc agttggaagc gggatctatc atctaggctt tatcttattt    7740
cctgtatatg gtggtctcat aagtgggact ccttcctaca acaagcagtc ctcacgctat    7800
tttatcccaa aacatcccaa cataacctgt gccggtaact ccagcgaaca ggctgcagca    7860
gcacggagtt cctatgtaat ccgttatcac tcaaacaggt tgattcagag tgctgttctt    7920
atttgcccat tgtctgacat gcacacagca aggtgtaatc tagttatgtt taacaattct    7980
caagtcatga tgggtgcaga aggtaggctc tatgttattg acaataattt gtattattat    8040
caacgtagtt cctcttggtg gtctgcatcg ctttttttaca ggatcaatac agattttctt    8100
aaaggaattc ctcctatcat tgaggctcaa tgggtaccgt cctatcaagt tccccgtcct    8160
ggagtcatgc catgcaatgc aacaagtttt tgccctgcta attgcatcac aggggtgtac    8220
gcagatgtgt ggccgcttaa cgatccagaa cccacatcac aaaatgctct gaatcccaac    8280
tatcgatttg ctggagcctt tctcagaaat gagtccaacc gaaccaatcc cacattctac    8340
actgcatcag ccagcgccct actaaatact accggattca acaacaccaa tcacaaagca    8400
gcatatacgt cttcaacctg ctttaagaat actggaactc aaaagattta ttgtttgata    8460
ataattgaaa tgggctcatc tctttttaggg gagttccaaa taataccatt tctaagggaa    8520
ctaatacctt aatactattg aatgaagact ccagattcaa taataattga aaggctctct    8580
atcttatgca atagttatac gttttggctg tattagaatg ttatagattc tgctgttttt    8640
cccatatgaa gcaatccttc aacaccgact taggttcaat tttctcatca tttactgttg    8700
taattcaatc ttactaaagt tattccgata tttaagaaaa aataaccttt atataatgta    8760
acaatactat taagattatg atataggcca gaatggcggc ctcttctgag atactccttc    8820
ctgaagtcca cttgaactca ccaatagtca aacacaaact catatactac ttattactag    8880
ggcacttccc gcatgatctt gacatttctg aaataagccc ccttcacaat aatgattggg    8940
```

```
atcaaattgc cagagaagaa tccaatcttg ctgaacgact tggagtagct aaatctgaat    9000
taattaaacg tgtgcccgca tttagagcaa ctagatggcg tagtcatgca gccgtcctta    9060
tatggccttc ttgtatacca tttcttgtta aattcctacc tcattctaag cttcaaccag    9120
tagaacaatg gtacaagttg atcaatgctt catgtaatac tatatctgac tcaattgata    9180
gatgtatgga gaatatttct attaagctta ctgggaaaaa caatctattc tctcgatcca    9240
gaggaactgc aggtgcaggt aaaaacagta aaatcaccct caatgatatc caatctattt    9300
gggaatcaaa caagtggcaa cctaatgtat ctttatggct tacaattaaa taccaaatgc    9360
gacaacttat aatgcatcaa agttctcgtc agccgactga tttagttcac attgttgaca    9420
cacgatctgg tctaatagtt atcacccctg aacttgttat ttgttttgat cggttaaata    9480
gtgttttaat gtattttaca tttgagatga ctttaatggt aagtgacatg tttgagggaa    9540
ggatgaatgt caccgctctc tgcactatta gtcattactt atctccacta gggccaagga    9600
tagatagatt gttttccatt gtagatgaat tagcacaact attaggtgac actgtatata    9660
aagttattgc atctcttgaa tctttagtat atgggtgtct acaacttaaa gatccagtag    9720
tggaattagc agggtcattt cattccttta ttacacaaga gattatagat atcctaattg    9780
gttcaaaagc ccttgataag gatgaatcaa taactgttac tacacaattg ttagatatat    9840
tttccaacct ttctccagat ttaattgctg agatgttgtg tctcatgaga ctttggggtc    9900
atcccactct tactgctgcg caagtgggta agtgagaga atctatgtgt gcaggtaagt    9960
tacttgattt ccctacaata atgaaaactc ttgcttttt ccacacaatt ttaattaatg    10020
gttaccgtag aaagaaaaat ggaatgtggc ctccacttat acttcctaaa aatgcatcaa    10080
aaagcttaat agaatttcaa catgataatg ctgaaatatc ttacgaatat acactcaagc    10140
attggaaaga gatatctctc atagaattta gaaagtgctt tgactttgat cctggtgagg    10200
agctaagcat ttttatgaaa gacaaggcaa taagtgctcc aagaagtgat tggatgagtg    10260
tatttcgtag aagtctaata aaacaacgac atcagagaca tcatattcct atgcccaatc    10320
catttaatag acgtctatta ctcaatttct tagaagatga cagttttgat ccagttgccg    10380
agcttcgata tgttaccggt ggtgaatatc tccaagatga cacattttgt gcatcttact    10440
cattaaaaga gaaagaaata aaaccagatg gaaggatatt tgctaagctt actaatagaa    10500
tgcggtcctg tcaagtaatt gcggaagcaa ttctcgcaaa tcatgcaggt actctaatga    10560
aggaaaacgg agttgtcttg aatcaattat cactgactaa atcattgctt actatgagtc    10620
aaattggcat aatatcagaa aaggcgaaga gatatacgcg agataacatc tcatcccaag    10680
gtttccatac aatcaagact gattctaaaa ataagaggaa aagcaaaact gcatcatcat    10740
acctcacaga tcctgatgat acatttgaac ttagtgcatg ttttataact actgatcttg    10800
ctaaatactg tcttcaatgg agatatcaga ccataatcca ttttgctcga acattaaaca    10860
gaatgtatgg agttccacat ttatttgaat ggattcatct tcgtttaatt agatctacat    10920
tatatgttgg tgatccattc aatcctcctg ccgcaactga tgctttcgat ctagataaag    10980
tattaaatgg tgatatcttt atagtctcca agggaggtat tgaaggccta tgtcagaaaa    11040
tgtggacaat gatctctatt tctgtgatca tcctctcttc agccgaatcc aaaacaagag    11100
taatgagcat ggttcaagga gataatcagg cgattgcagt tacaacaaga gttcctagat    11160
cattacctag tattcagaaa aaggagttag cctatcagc aagcaagtta ttttttgaaa    11220
gacttagggc aaataattat gggttgggtc atcagctaaa ggctcaagaa actataataa    11280
gttccacgtt cttcatatat agtaaacggg tattttatca aggacgtata ctaacacagg    11340
```

```
cactcaaaaa tgctagcaag ttatgtctta ctgcagatgt attaggtgaa tgtactcaag    11400
cttcctgttc aaattctgct actaccatca tgagattaac agaaaatggg gttgagaaag    11460
atacatgtta taagcttaat atttatcagt ccattcgtca actcacatat gatctaatat    11520
ttccccaata ctccatacca ggtgaaacta taagtgagat tttcctacag catccaagac    11580
taatctcacg tattgttctg ctcccttcac agctaggtgg tcttaattac ctcgcatgta    11640
gcagattatt taaccgcaat atcggagatc ctcttggtac agctgtggca gatctcaaga    11700
ggttaattaa atgtggtgct cttgaatcat ggatactgta taatttacta gcaagaaaac    11760
cagggaaagg ttcatgggca actttagcag ccgatccata ctcattgaat caagaatatc    11820
tttatcctcc tactactata cttaaaagac atactcaaaa tactttaatg gagatatgtc    11880
ggaatcctat gttaaaggga gttttttacag ataatgcaaa agaggaggaa aatctccttg    11940
caaaatttct tcttgatcgt gatatagtat tgccaagagt tgcacacatt ataatagatc    12000
aatctagcat cggaaggaag aaacagatac aaggattttt tgacaccaca aggaccataa    12060
tgagacgatc atttgaaatc aaaccactct caactaagaa gactctttca gtcatagaat    12120
ataatactaa ttacttatct tataactacc ctgtcatact taatcctttta cctattcctg    12180 gatatttaaa ttatattact gaccaaactt gcagtattga tatatctaga agtttaagaa    12240
aattatcatg gtcttcttta ttgaatggaa gaactttaga aggattagaa actccagatc    12300
caattgaagt tgtcaatggt ttcttgattg taggtacagg agattgtgat ttttgtatgc    12360
agggtgacga caaatttact tggttctttt tacctatggg gataattatt gatggaaatc    12420
ctgaaactaa tccacccatc agagttccat acattgggtc tagaacagag gaaagaagag    12480
ttgcatcaat ggcatatatt aaaggtgcca cacacagttt gaaggctgct cttagaggcg    12540
caggggtata tatttgggca ttcggggata ctgtagtgaa ctggaatgat gcacttgata    12600
tcgcaaatac tagggttaag atatccctag agcaacttca gacccttaca cctcttccta    12660
catctgcaaa cattacacac cgtttagatg atggagccac aacacttaaa ttcactccag    12720
ctagttccta tgcatttttct agttatactc atatatcaaa tgatcaacaa tatttagaaa    12780
tagatcagag agtagtcgat ctaatatta tttatcaaca attaatgata acaggacttg    12840
ggattattga gacctaccat aacccaccta taaggacttc tacacaagaa atcactctcc    12900
atttgcacac tagctcatct tgttgtgtta gaagtgtaga tggttgcctt atatgtgaga    12960
gcaatggaga ggttcctcag atcactgttc cctatactaa tacatttgta tatgatcctg    13020
atccactagc agattatgag attgcacacc tagattatct ctcctaccaa gctaaaattg    13080
gaagtacaga ttactactca ctcactgata aaattgacct attagcacat ttaactgcaa    13140
aacaaatgat aaactcaata attgggttag atgaaacagt atcaattgtc aatgatgcgg    13200
ttatcctatc tgactatact aataactgga ttagtgaatg ttcttatact aagatagatt    13260 tagttttttaa attaatggca tggaatttcc ttctgagct tgcattccag atgtactact    13320
taaggatatc atcttggaca aatatatttg actatactta tatgactttg cgcaggatac    13380
ccggaactgc tctaaataat attgcagcta ctattagcca tccaaaatta ttaagacgtg    13440
caatgaatct tgatattatc actcctatac atgcaccgta tttagcttca ttagattatg    13500
tcaaattaag tattgatgca attcagtggg gagttaaaca agttcttgct gatttatcaa    13560
atggaattga tcttgaaatc ttgattcttt cagaggattc aatggaaatt agtgataggg    13620
caatgaatct cattgctaga aaactaactc tccttgcact tgttaaaggt gagaactata    13680
```

```
cttttccaaa aattaaaggg atgccaccag aagaaaagtg tttagtctta actgaatatc    13740
tagcaatgtg ttatcaaaat actcatcact tagatccaga tcttcaaaag tatttatata    13800
atctaactaa tccaaaattg actgcatttc ccagtaacaa cttctactta actagaaaaa    13860
tccttaatca aattagagaa tcagacgaag gacaatatat tatcacctca tattatgaat    13920
ccttcgaaca attagaaaca gatataattc ttcactctac tttaactgct ccttatgata    13980
attcagaaaa ctctaacaaa gttcgattta tcccttcga catctttcca catccagaat    14040
ctctcgagaa atatcctctt ccagttgatc atgactctca atctgcaatt tcaacactaa    14100
ttccaggccc tccttctcat catgtattac gaccactagg agtgtcatcc acagcttggt    14160
ataaagggat aagttattgt agatacctag aaacacaaaa gatacagact ggtgatcatc    14220
tttatttagc cgaaggaagc ggtgcttcaa tgtcacttct agaactctta tttccaggag    14280
atactgtcta ttataatagt cttttagta gtggagagaa tcctccacag agaaactatg    14340
cccctcttcc aactcaattt gtacagagtg ttccatataa attgtggcaa gctgatcttg    14400
ctgatgatag caatttgata aaagattttg tcccattatg gaatgaaaac ggtgcagtta    14460
cagacttatc aacaaaggat gcagttgcat tcataataca taaagtagga gcagagaaag    14520
catcccttgt ccatatagat ctcgaatcaa ctgctaatat aaatcagcaa actctgtcca    14580
gatcccagat tcattcatta attatagcaa ctactgttct taagaggggt gggatattaa    14640
tttataaaac atcatggctt ccgttttcta ggtttagtca actagcaggt ctactttggt    14700
gcttctttga ccggatccat ctaatacgta gtagctattc tgatcctcac agtcatgagg    14760
tttatcttgt atgtagactt gccgcagatt ttagaactat cggtttcagt gcagctctag    14820
taactgctac tactcttcac aatgacggat tcacaacaat acatcctgat gttgtttgta    14880
gttattggca acaccatctt gaaaatgttg ggagagtcgg aaaagtaatt gatgagatac    14940
ttgatggttt agccaccaac ttcttcgcag gagataatgg gcttattcta agatgtggag    15000
gaactccaag ctccagaaaa tggttagaga ttgaccagtt agcatcattt gatttggttc    15060
aagatgctct ggttacactt atcactatac acctaaagga aattatagaa gtgcagtcat    15120
cacatacaga ggattataca tctctcctct tcacacctta taatattggt gcagcaggga    15180
aagtcagaac tatcatcaaa ttaattctag aacgatcttt aatgtataca gtccgaaatt    15240
ggttagtttt acccagttcc atccgggatt ctgtacgaca agatttagaa ttagggtcat    15300
ttagattaat gtctattta agtgaacaga catttcttaa aaagacaccc acaaaaaaat    15360
acttacttga tcagcttaca aggacatata tcaacccctt ctttaactct cactcagtcc    15420
ttcccctcca ccgtccatat caaaaacaaa tatggaaagc cttaggtagt gtaatatatt    15480
gttcggagac agttgatata cctctaatta aagacattca gatagaagat attaatgatt    15540
ttgaagatat cgagaggggt atcgatggcg aagaattatg acaacaatga ttataagaac    15600
tcatgatagt tttatttaag aaaaacatat tgatttccc cttggt            15646
```

<210> SEQ ID NO 48
<211> LENGTH: 1656
<212> TYPE: DNA
<213> ORGANISM: Human parainfluenza virus 2

<400> SEQUENCE: 48

```
atgcatcacc tgcatccaat gatagtatgc atctttgtta tgtacactgg aattgtaggt      60
tcagatgcca ttgctggaga tcaactactt aatataggg tcattcaatc aaagataaga     120
tcactcatgt actatactga tggtggtgct agctttattg ttgtaaaatt gctacctaat     180
```

```
cttcccccaa gcaatggaac atgcaacatc accagtctag atgcatataa tgttaccta      240 tttaagttac taacacccct gattgagaac ctgagtaaaa tttccactgt tacagatacc      300
aaaacccgcc aaaaacgatt tgcaggagta gttgttggac ttgctgcatt aggagtagcc      360
acagccgcac aaataactgc agctgtagca atagtgaaag ctaatgcaaa tgctgctgcg      420
ataaacaatc ttgcatcttc aattcaatcc accaacaagg cagtatccga tgtgatagat      480
gcatcaagaa caattgcaac cgcagttcaa gcaattcagg atcgcatcaa tggagctatt      540
gttaatggga taacatctgc atcatgccgt gcccatgatg cactcattgg gtcaatatta      600
aatctttatc tcactgagct taccacaata tttcataatc aaataacaaa ccctgcgctg      660
acaccactct ccatccaagc tttaagaatc ctcctcggta gcaccttgcc aattgtcatt      720
gagtccaaac tcaacacaaa cttcaacaca gcagagctgc tcagttccgg actgttaact      780
ggtcaaataa tttccatttc cccaatgtac atgcaaatgc taattcaaat caatgttccg      840
acatttataa tgcaacccgg tgcgaaggta attgatctaa ttgctatctc cgcaaaccat      900
aaattgcaag aagtggttgt acaagttccg aataggattc tagagtatgc aaatgaacta      960
caaaattacc cagccaatga ctgtgtcgtg acaccgaact ctgtatttg tagatacaat     1020 gagggttccc ctatccctga atcacaatat caatgcttga gggggaatct taattcttgc     1080
acttttaccc ctattatcgg gaactttctt aagcgattcg catttgctaa tggtgtgctc     1140
tatgccaact gcaaatcttt gctatgtagg tgtgccgacc cccccatgt tgtatcccag     1200 gatgatacccc aaggcatcag cataattgat attaagagat gctctgagat gatgcttgac     1260 acttttttcat ttaggatcac atctactttc aatgctacgt acgtgacaga cttctcaatg     1320
attaatgcaa atattgtaca tctaagtcct ctagatttgt caaatcaaat caattcaata     1380
aacaaatctc ttaaagtgc tgaggattgg attgcagata gcaacttctt tgctaatcaa     1440
gccaggacag ccaagacact ttattcacta agtgcaatag cattaatact atcagtgatt     1500
actttggttg tcgtgggatt gctgattgcc tacatcatca agctggtttc tcaaatccat     1560
caattcagat cgctagctgc tacaacaatg ttccacaggg aaaatcctgc cttcttttcc     1620
aagaataacc atggaaacat atatgggata tcttaa                              1656
```

<210> SEQ ID NO 49
<211> LENGTH: 551
<212> TYPE: PRT
<213> ORGANISM: Human parainfluenza virus 2

<400> SEQUENCE: 49

```
Met His His Leu His Pro Met Ile Val Cys Ile Phe Val Met Tyr Thr
1               5                   10                  15

Gly Ile Val Gly Ser Asp Ala Ile Ala Gly Asp Gln Leu Leu Asn Ile
            20                  25                  30

Gly Val Ile Gln Ser Lys Ile Arg Ser Leu Met Tyr Tyr Thr Asp Gly
        35                  40                  45

Gly Ala Ser Phe Ile Val Val Lys Leu Leu Pro Asn Leu Pro Pro Ser
    50                  55                  60

Asn Gly Thr Cys Asn Ile Thr Ser Leu Asp Ala Tyr Asn Val Thr Leu
65                  70                  75                  80

Phe Lys Leu Leu Thr Pro Leu Ile Glu Asn Leu Ser Lys Ile Ser Thr
                85                  90                  95

Val Thr Asp Thr Lys Thr Arg Gln Lys Arg Phe Ala Gly Val Val Val
            100                 105                 110
```

```
Gly Leu Ala Ala Leu Gly Val Ala Thr Ala Ala Gln Ile Thr Ala Ala
        115                 120                 125

Val Ala Ile Val Lys Ala Asn Ala Asn Ala Ala Ile Asn Asn Leu
130                 135                 140

Ala Ser Ser Ile Gln Ser Thr Asn Lys Ala Val Ser Asp Val Ile Asp
145                 150                 155                 160

Ala Ser Arg Thr Ile Ala Thr Ala Val Gln Ala Ile Gln Asp Arg Ile
                165                 170                 175

Asn Gly Ala Ile Val Asn Gly Ile Thr Ser Ala Ser Cys Arg Ala His
                180                 185                 190

Asp Ala Leu Ile Gly Ser Ile Leu Asn Leu Tyr Leu Thr Glu Leu Thr
        195                 200                 205

Thr Ile Phe His Asn Gln Ile Thr Asn Pro Ala Leu Thr Pro Leu Ser
        210                 215                 220

Ile Gln Ala Leu Arg Ile Leu Leu Gly Ser Thr Leu Pro Ile Val Ile
225                 230                 235                 240

Glu Ser Lys Leu Asn Thr Asn Phe Asn Thr Ala Glu Leu Leu Ser Ser
                245                 250                 255

Gly Leu Leu Thr Gly Gln Ile Ile Ser Ile Ser Pro Met Tyr Met Gln
                260                 265                 270

Met Leu Ile Gln Ile Asn Val Pro Thr Phe Ile Met Gln Pro Gly Ala
        275                 280                 285

Lys Val Ile Asp Leu Ile Ala Ile Ser Ala Asn His Lys Leu Gln Glu
        290                 295                 300

Val Val Val Gln Val Pro Asn Arg Ile Leu Glu Tyr Ala Asn Glu Leu
305                 310                 315                 320

Gln Asn Tyr Pro Ala Asn Asp Cys Val Val Thr Pro Asn Ser Val Phe
                325                 330                 335

Cys Arg Tyr Asn Glu Gly Ser Pro Ile Pro Glu Ser Gln Tyr Gln Cys
                340                 345                 350

Leu Arg Gly Asn Leu Asn Ser Cys Thr Phe Thr Pro Ile Ile Gly Asn
        355                 360                 365

Phe Leu Lys Arg Phe Ala Phe Ala Asn Gly Val Leu Tyr Ala Asn Cys
        370                 375                 380

Lys Ser Leu Leu Cys Arg Cys Ala Asp Pro Pro His Val Val Ser Gln
385                 390                 395                 400

Asp Asp Thr Gln Gly Ile Ser Ile Ile Asp Ile Lys Arg Cys Ser Glu
                405                 410                 415

Met Met Leu Asp Thr Phe Ser Phe Arg Ile Thr Ser Thr Phe Asn Ala
                420                 425                 430

Thr Tyr Val Thr Asp Phe Ser Met Ile Asn Ala Asn Ile Val His Leu
        435                 440                 445

Ser Pro Leu Asp Leu Ser Asn Gln Ile Asn Ser Ile Asn Lys Ser Leu
        450                 455                 460

Lys Ser Ala Glu Asp Trp Ile Ala Asp Ser Asn Phe Phe Ala Asn Gln
465                 470                 475                 480

Ala Arg Thr Ala Lys Thr Leu Tyr Ser Leu Ser Ala Ile Ala Leu Ile
                485                 490                 495

Leu Ser Val Ile Thr Leu Val Val Gly Leu Leu Ile Ala Tyr Ile
                500                 505                 510

Ile Lys Leu Val Ser Gln Ile His Gln Phe Arg Ser Leu Ala Ala Thr
        515                 520                 525
```

```
Thr Met Phe His Arg Glu Asn Pro Ala Phe Phe Ser Lys Asn Asn His
        530                 535                 540

Gly Asn Ile Tyr Gly Ile Ser
545                 550

<210> SEQ ID NO 50
<211> LENGTH: 1716
<212> TYPE: DNA
<213> ORGANISM: Human parainfluenza virus 2

<400> SEQUENCE: 50
atggaagatt acagcaatct atctcttaaa tcaattccta aaaggacatg tagaatcatt      60
ttccgaactg ccacaattct tggaatatgc acattgattg ttctatgttc aagtattctt     120
catgagataa ttcatcttga tgtttcctct ggtctcatgg attccgatga ttcacagcaa     180
ggcattattc agcctattat agaatcatta aaatcattaa ttgctttggc taaccagatt     240
ctgtacaatg ttgcaataat aattcctctt aaaattgaca gtatcgagac tgtaatattc     300
tctgctttaa aggatatgca tactgggagc atgtccaaca ccaactgtac acccggaaat     360
ctgcttctgc atgatgcagc gtacatcaat ggaataaaca aattccttgt acttaaatca     420
tacaatggga cgcctaaata tggacctctc ctaaatattc ccagctttat ccctcagca     480 acatctccca cgggtgcac tagaatacca tcattttcac tcattaagac ccattggtgt     540
tacactcaca atgtaatgct tggagattgc ctcgatttca cgacatctaa tcagtattta     600
gcaatgggga taatacaaca atctgctgca gcatttccaa tcttcaggac tatgaaaacc     660
atttacctaa gtgatggaat caatcgcaaa agctgttcag tcactgctat accaggaggt     720
tgtgtcttgt attgctatgt agctacaaga tctgagaaag aagattatgc cacaactgat     780
ctagctgaac tgagacttgc tttctattat tataatgata cctttattga aagagtcata     840
tctcttccaa atacaacagg gcaatgggcc acaatcaatc ctgcagttgg aagcgggatc     900
tatcatctag gctttatctt atttcctgta tatggtggtc tcataagtgg gactccttcc     960
tacaacaagc agtcctcacg ctattttatc ccaaaacatc ccaacataac ctgtgccggt    1020
aactccagcg aacaggctgc agcagcacgg agttcctatg taatccgtta tcactcaaac    1080
aggttgattc agagtgctgt tcttatttgc ccattgtctg acatgcacac agcaaggtgt    1140
aatctagtta tgtttaacaa ttctcaagtc atgatgggtg cagaaggtag gctctatgtt    1200
attgacaata atttgtatta ttatcaacgt agttcctctt ggtggtctgc atcgcttttt    1260
tacaggatca atacagattt ttctaaagga attcctccta tcattgaggc tcaatgggta    1320
ccgtcctatc aagttccccg tcctggagtc atgccatgca atgcaacaag ttttttgccct    1380 gctaattgca tcacagggt gtacgcagat gtgtggccgc ttaacgatcc agaacccaca    1440
tcacaaaatg ctctgaatcc caactatcga tttgctggag cctttctcag aaatgagtcc    1500
aaccgaacca atcccacatt ctacactgca tcagccagcg ccctactaaa tactaccgga    1560
ttcaacaaca ccaatcacaa agcagcatat acgtcttcaa cctgctttaa gaatactgga    1620
actcaaaaga tttattgttt gataataatt gaaatgggct catctctttt agggagttc    1680 caaataatac catttctaag ggaactaata ccttaa                              1716

<210> SEQ ID NO 51
<211> LENGTH: 571
<212> TYPE: PRT
<213> ORGANISM: Human parainfluenza virus 2

<400> SEQUENCE: 51
```

```
Met Glu Asp Tyr Ser Asn Leu Ser Leu Lys Ser Ile Pro Lys Arg Thr
1               5                   10                  15

Cys Arg Ile Ile Phe Arg Thr Ala Thr Ile Leu Gly Ile Cys Thr Leu
                20                  25                  30

Ile Val Leu Cys Ser Ser Ile Leu His Glu Ile His Leu Asp Val
                35                  40                  45

Ser Ser Gly Leu Met Asp Ser Asp Asp Ser Gln Gln Gly Ile Ile Gln
        50                  55                  60

Pro Ile Ile Glu Ser Leu Lys Ser Leu Ile Ala Leu Ala Asn Gln Ile
65                  70                  75                  80

Leu Tyr Asn Val Ala Ile Ile Pro Leu Lys Ile Asp Ser Ile Glu
                    85                  90                  95

Thr Val Ile Phe Ser Ala Leu Lys Asp Met His Thr Gly Ser Met Ser
                    100                 105                 110

Asn Thr Asn Cys Thr Pro Gly Asn Leu Leu Leu His Asp Ala Ala Tyr
        115                 120                 125

Ile Asn Gly Ile Asn Lys Phe Leu Val Leu Lys Ser Tyr Asn Gly Thr
        130                 135                 140

Pro Lys Tyr Gly Pro Leu Leu Asn Ile Pro Ser Phe Ile Pro Ser Ala
145                 150                 155                 160

Thr Ser Pro Asn Gly Cys Thr Arg Ile Pro Ser Phe Ser Leu Ile Lys
                165                 170                 175

Thr His Trp Cys Tyr Thr His Asn Val Met Leu Gly Asp Cys Leu Asp
                180                 185                 190

Phe Thr Thr Ser Asn Gln Tyr Leu Ala Met Gly Ile Ile Gln Gln Ser
                195                 200                 205

Ala Ala Ala Phe Pro Ile Phe Arg Thr Met Lys Thr Ile Tyr Leu Ser
        210                 215                 220

Asp Gly Ile Asn Arg Lys Ser Cys Ser Val Thr Ala Ile Pro Gly Gly
225                 230                 235                 240

Cys Val Leu Tyr Cys Tyr Val Ala Thr Arg Ser Glu Lys Glu Asp Tyr
                245                 250                 255

Ala Thr Thr Asp Leu Ala Glu Leu Arg Leu Ala Phe Tyr Tyr Tyr Asn
                260                 265                 270

Asp Thr Phe Ile Glu Arg Val Ile Ser Leu Pro Asn Thr Thr Gly Gln
        275                 280                 285

Trp Ala Thr Ile Asn Pro Ala Val Gly Ser Gly Ile Tyr His Leu Gly
        290                 295                 300

Phe Ile Leu Phe Pro Val Tyr Gly Gly Leu Ile Ser Gly Thr Pro Ser
305                 310                 315                 320

Tyr Asn Lys Gln Ser Ser Arg Tyr Phe Ile Pro Lys His Pro Asn Ile
                325                 330                 335

Thr Cys Ala Gly Asn Ser Ser Glu Gln Ala Ala Ala Arg Ser Ser
        340                 345                 350

Tyr Val Ile Arg Tyr His Ser Asn Arg Leu Ile Gln Ser Ala Val Leu
            355                 360                 365

Ile Cys Pro Leu Ser Asp Met His Thr Ala Arg Cys Asn Leu Val Met
        370                 375                 380

Phe Asn Asn Ser Gln Val Met Met Gly Ala Glu Gly Arg Leu Tyr Val
385                 390                 395                 400

Ile Asp Asn Asn Leu Tyr Tyr Tyr Gln Arg Ser Ser Trp Trp Ser
                    405                 410                 415
```

-continued

```
Ala Ser Leu Phe Tyr Arg Ile Asn Thr Asp Phe Ser Lys Gly Ile Pro
            420                 425                 430

Pro Ile Ile Glu Ala Gln Trp Val Pro Ser Tyr Gln Val Pro Arg Pro
        435                 440                 445

Gly Val Met Pro Cys Asn Ala Thr Ser Phe Cys Pro Ala Asn Cys Ile
    450                 455                 460

Thr Gly Val Tyr Ala Asp Val Trp Pro Leu Asn Asp Pro Glu Pro Thr
465                 470                 475                 480

Ser Gln Asn Ala Leu Asn Pro Asn Tyr Arg Phe Ala Gly Ala Phe Leu
                485                 490                 495

Arg Asn Glu Ser Asn Arg Thr Asn Pro Thr Phe Tyr Thr Ala Ser Ala
            500                 505                 510

Ser Ala Leu Leu Asn Thr Thr Gly Phe Asn Asn Thr Asn His Lys Ala
        515                 520                 525

Ala Tyr Thr Ser Ser Thr Cys Phe Lys Asn Thr Gly Thr Gln Lys Ile
    530                 535                 540

Tyr Cys Leu Ile Ile Ile Glu Met Gly Ser Ser Leu Leu Gly Glu Phe
545                 550                 555                 560

Gln Ile Ile Pro Phe Leu Arg Glu Leu Ile Pro
                565                 570

<210> SEQ ID NO 52
<211> LENGTH: 15654
<212> TYPE: DNA
<213> ORGANISM: Human parainfluenza virus 2

<400> SEQUENCE: 52
accaagggga gaatcagatg gcatcgttat atgacgaatt gcaaaaagat tacgtaggtc      60
cggaaccact agattccggt gccggtaacg atctcagttt tatactatct gatcattctt     120
tatctctact aaggatattt ctaatctaag gttcaaaatg tcaagtgtct taaagacatt     180
tgaaagattt actatacaac aggagcttca ggagcaatct gaagcactc caatacctct     240 tgaaacaatc agacctacaa tcagagtatt tgtcatcaat aataatgatc ctattgtaag     300
atctagactt ttattcttta atctacgaat tattatgagt aacactgcaa gagagggaca     360
tagagctggt gctctcctca gtcttttatc actaccttct gcagctatga gtaatcacat     420
caaactagcc atgcattcac cagaagccag catagataga gtagaaataa cagggtttga     480
gaataattca ttccgagtta ttccagatgc tcgatcaact atgtccagag agaagtgct     540 ggccttcgaa gcattagctg aggacattcc tgatacccct aatcaccaaa ctccatttgt     600
aaataatgat gtggaagatg acatatttga tgaaacagag aaattcttgg atgtttgcta     660
tagtgtactt atgcaggcat ggataqtaac atgcaagtgc atgactgctc ctgatcaacc     720
accagtatca gtagcaaagc ggatggctaa atatcaacaa caagggagaa tcaatgctag     780
atatgtacta caacctgaag cacaaagact aattcagaat gccatccgca agtcaatggt     840
agtaaggcat ttcatgacct atgagcttca actttcacaa tcaagatctt tgctagcgaa     900
ccgttattat gccatggtgg gagacattgg caagtatatt gaacacagcg aatgggagg     960 gttttctta acacttaaat atggacttgg aacaagatgg cctacattgg ctcttgcagc    1020
attctctggg gaactccaga aattaaaggc tctcatgcta cattatcaga gtctaggacc    1080
catggccaag tacatggctc tattagaatc accaaagctg atggattttg tcccatctga    1140
atatccatta gtttatagct atgcaatggg tattggaact gtccttgata caaacatgag    1200
aaactatgca tatggtagat catatctaaa tccacaatat tttcagctag gggtagaaac    1260
```

```
agcaaggaaa cagcaaggag ctgttgacaa caggacagca gaggacctcg gcatgactgc    1320
tgcagataaa gcagacctca ctgcaaccat atcaaagcta tctttatccc aattacctag    1380
gggtagacaa ccaatatccg acccatttgc tggagcaaat gacagagaaa caggaggaca    1440
agcaactgat acacctgtgt ataacttcaa tccaatcaat aatcggaggt atgcaactta    1500
tgacagtgat agtgaggaca gaattgacaa cgatcaagat caggctatca gagagaacag    1560
aggagaacct ggacaaccaa acaaccagac aagcgaaaac cagcagagac tcaatctccc    1620
tgtaccgcaa agaacatcag gtatgagtag tgaagagttc aacattcaa tgaatcagta     1680 catccgtgct atgcatgagc aatacagagg ctcccaggat gatgatgcca atgatgccac    1740
agatgggaat gacatttcac ttgagctagt tggagatttt gattcctaac tctcactttc    1800
acataaccag acatacacat ccacaccacc cagagacata gctaccatcc acacactcac    1860
ccagacaaat caaactagat tcaaatcatt cggaaacaat tctcctagaa tttaagaaaa    1920
aaacataggc ccggacgggt tagagatccg gtgctcgtct gtggccagac aacctccaca    1980
ccagagccac acaatcatgg ccgaggaacc aacatacacc actgagcaag ttgatgaatt    2040
aatccatgct ggactaggaa cagtagattt cttcctatct agacccatag atgctcagtc    2100
ttctttaggt aaaggcagca tcccaccagg tgtcacggct gttctaacca atgcagcaga    2160
ggcaaaatcc aaaccagttg ctgctggtcc agtaaaaccc agacgaaga aagtgatcag      2220 caataccact ccatacacta ttgcagacaa catcccacct gagaagctac cgatcaacac    2280 tccaatacc aatccattac ttccactggc acgccctcac ggaaagatga cagacattga    2340
cattgtcact gggaacatta cagaaggatc atacaaaggt gtggagcttg ccaaattagg    2400
gaagcaaaca ctactcacaa ggttcacctc gaatgagcca gtctcctcag ctggatccgc    2460
ccaagacccc aactttaaga ggggggagc taatagagaa agagcaagag gcaaccatag    2520
gagagaatgg agtattgcat gggtcggaga tcaggtcaaa gtcttcgagt ggtgtaatcc    2580
caggtgtgcc ccagtcacgg cttcagctcg caagttcacc tgcacatgtg gatcctgccc    2640
cagcatctgc ggagaatgtg aaggagatca ttgagctctt aaaagggctt gatcttcgcc    2700
ttcagactgt agaagggaaa gtagataaaa ttcttgcaac ctctgcaact ataatcaatc    2760
ttaaaaatga aatgactagt cttaaggcga gcgttgcaac tgtggaaggt atgataacaa    2820
caattaaaat catggatccc agtacaccaa ccaatgtccc tgtagaggag atcagaaaga    2880
gtttacacaa tgttccagta gtaattgctg gtccgactag tggaggcttc acagccgaag    2940 gcagtgcat gatttcaatg gatgaactag ctaggcctac actctcatca acaaaaaaga    3000
tcacacgaaa gcctgaatcc aagaaagatt taacaggcat aaaactaacc ctgatgcagc    3060
ttgcaaatga ctgcatctcg cgtccagata ccaagactga gtttgtgact aagattcaag    3120
cagcaaccac agaatcacag ctcaacgaaa tcaaacggtc aataatacgc tctgcaatat    3180 aaaatgcgt gcaatcacac aagagacatt caacatgcat ccgatcaaga tccaaactcc    3240
ttccatccga aaacacactc accactgtca acaccaagaa acaactacag ccgaaccatg    3300
ctcaaccaaa agacccaaac aacatctcaa atcgacagaa ggctagacat gataaattta    3360
ataaaaaatt aaaagaagtt aagtaaaatt taaagaacac aatagagaaa acctaggtcc    3420
gaaagcttgc ctttcagaca gatcccaaaa tcatagttca aacttcaaac acagcagcag    3480
acatgcctat aatatcatta ccagcagatc caacttcacc cagtcaatcc cttactccgt    3540
ttccaataca acttgatacc aaagatggca aggcaggga actccttaaa cagattagaa    3600
```

```
ttaggtatct aaatgaacct aactctcgtc ataccaat aactttcatc aatacgtatg   3660
gatttgttta tgctcgagac acttcaggag gcattcacag cgagatcagc agtgacctag  3720
ctgcagggtc cataacggca tgcatgatga cactaggtcc tggtccaaat attcagaatg  3780
caaatctagt gctaagatcc ctgaatgaat tctacgtaaa agtcaagaag acatcaagcc  3840
agagggagga agcagtgttt gaattagtta acattccaac cttattgaga gaacatgctc  3900
tttgcaaacg caaacgtta gtatgctctg cagaaaaatt cctcaagaac ccatcaaagc    3960
tacaagctgg atttgaatat gtatacatcc aactttttgt ctccattaca tactcaccac  4020
gaaatctgaa ttaccaagtt gccagaccta tccttaagtt cagatcacgc tttgtgtata  4080
gcattcattt ggaattaatc ctgagattgc tatgcaaatc tgactcccct ttgatgaaat  4140
cttataatgc agatcgaaca ggtcgaggat gcctcgcatc agtctggatc cacgtatgta  4200
acattctgaa aaacaaaagc atcaagcaac aaggcagaga atcatatttc atagctaagt  4260
gcatgagtat gcagctgcag gtgtccattg cagatctttg ggaccaaca atcataatta   4320
aatcattggg tcacatcccc aagactgcac ttccttttt cagcaaagac gggattgcct   4380
gtcatccact acaagatgtt tcccctactc tgacaaaatc actgtggtca gtgggatgtg  4440
agatagaatc tgccaagttg atacttcaag aatctgatat taatgagcta atgggccacc  4500
aggacttgat tactgataag attgccatta gatcaggtca acggacattt gagaggtcca  4560
aattcagccc attcaaaaaa tacgcatcaa ttccaaactt agaagccatc aactgaatgc  4620
tccagcatct aggaatagaa caacaactaa gtcataccat tattgaccat acaataatca  4680
acaattttag ccaactgatt actaagatat tatcataggt ccgaactgat caatctaaca  4740
aaaaaactaa acattcaata ataaatcaaa gttcaggcca aattatccag ccatgcatca  4800
cctgcatcca atgatagtat gcattttgt tatgtacact ggaattgtag gttcagatgc    4860
cattgctgga gatcaactcc tcaatgtagg ggtcattcaa tcaaagataa gatcactcat  4920
gtactacact gatggtggcg ctagctttat tgttgtaaaa ttactaccca atcttccccc  4980
aagcaatgga acatgcaaca tcaccagtct agatgcatat aatgttaccc tatttaagtt  5040
gctaacaccc ctgattgaga acctgagcaa aatttctgct gttacagata ccaaaccccg  5100
ccgagaacga tttgcaggag tcgttattgg gcttgctgca ctaggagtag ctacagctgc  5160
acaaataacc gcagctgtag caatagtaaa agccaatgca aatgctgctg cgataaacaa  5220
tcttgcatct tcaattcaat ccaccaacaa ggcagtatcc gatgtgataa ctgcatcaag  5280
aacaattgca accgcagttc aagcgattca ggatcacatc aatggagcca ttgtcaacgg  5340
gataacatct gcatcatgcc gtgcccatga tgcactaatt gggtcaatat taaatttgta  5400
tctcactgag cttactacaa tatttcataa tcaaataaca aaccctgcgc tgacaccact  5460
ttccatccaa gctttaagaa tcctcctcgg tagcaccttg ccaattgtca ttgaatccaa  5520
actcaacaca aaactcaaca cagcagagct gctcagttcc ggactgttaa ctggtcaaat  5580
aatttccatt tccccaatgt acatgcaaat gctaattcaa atcaatgttc cgacatttat  5640
aatgcaaccc ggtgcgaagg taattgatct aattgctatc tctgcaaacc ataaattaca  5700
agaagtagtt gtacaagttc ctaatagaat tctagaatat gcaaatgaac tacaaaacta  5760
cccagccaat gattgtgtcg tgacaccaaa ctctgtattt tgtagataca atgagggttc  5820
cccgatccct gaatcacaat atcaatgctt aagggggaat cttaattctt gcactttac   5880
ccctattatc gggaactttc tcaagcgatt cgcatttgcc aatggtgtgc tctatgccaa  5940
ctgcaaatct tgctatgta agtgtgccga ccctcccat gttgtgtctc aagatgacaa    6000
```

```
ccaaggcatc agcataattg atattaagag gtgctctgag atgatgcttg acactttttc   6060
atttaggatc acatctacat tcaatgctac atacgtgaca gacttctcaa tgattaatgc   6120
aaatattgta catctaagtc ctctagactt gtcaaatcaa atcaattcaa taaacaaatc   6180
tcttaaaagt gctgaggatt ggattgcaga tagcaacttc ttcgctaatc aagccagaac   6240
agccaagaca ctttattcac taagtgcaat cgcattaata ctatcagtga ttactttggt   6300
tgttgtggga ttgctgattg cctacatcat caagctggtt tctcaaatcc atcaattcag   6360
agcactagct gctacaacaa tgttccacag ggagaatcct gccgtctttt ccaagaacaa   6420
tcatggaaac atatatggga tatcttaaga attctatcat aagtccatat atgtccatga   6480
ttgaccttta agagccaacc tccaatgatt atccgttaaa ttcagatata acaattcaaa   6540
aatcaatatt aagcctccag ataccaatga atatgaatat atctcttaga aaacttgatt   6600
attatgtgat aacatagtac aatttaagaa aaaacctaaa ataagcacga acccttaagg   6660
tgtcgtaacg tctcgtgacg ccgggttcag ttcaaacatc gaccccctgac ccaattcaat   6720
acccatttc ataaaggaac acagtataat ttaatcataa aagacctcaa aatctgatac   6780
agcttaatcc actcaacata taattataag actaataata atggaagatt acagcaatct   6840
atctcttaaa tcaattccta aaaggacatg tagaatcatt ttccgaactg ccacaattct   6900
tggcatatgc acattaattg tgctatgttc aagtattctt catgagataa ttcatcttga   6960
tgtttcctct ggtcttatga attctgatga gtcacagcaa ggcattattc agcctatcat   7020
agaatcatta aaatcattga ttgctttggc caaccagatt ctatataatg ttgcaatagt   7080
aattcctctt aaaattgaca gtatcgaaac tgtaatactc tctgctttaa aagatatgca   7140
caccgggagt atgtccaatg ccaactgcac gccaggaaat ctgcttctgc atgatgcagc   7200
atacatcaat ggaataaaca aattccttgt acttgaatca tacaatggga cgcctaaata   7260
tggacctctc ctaaatatac ccagctttat cccctcagca acatctcccc atgggtgtac   7320
tagaatacca tcattttcac tcatcaagac ccattggtgt tacactcaca atgtaatgct   7380
tggagattgt cttgatttca cggcatctaa ccagtattta tcaatgggga taatacaaca   7440
atctgctgca gggtttccaa ttttcaggac tatgaaaacc atttacctaa gtgatggaat   7500
caatcgcaaa agctgttcag tcactgctat accaggaggt tgtgtcttgt attgctatgt   7560
agctacaagg tctgaaaaag aagattatgc cacgactgat ctagctgaac tgagacttgc   7620
tttctattat tataatgata cctttattga aagagtcata tctcttccaa atacaacagg   7680
gcagtgggcc acaatcaacc ctgcagtcgg aagcgggatc tatcatctag gctttatctt   7740
atttcctgta tatggtggtc tcataaatgg gactacttct tacaatgagc agtcctcacg   7800
ctattttatc ccaaaacatc ccaacataac ttgtgccggt aactccagca acaggctgc   7860
aatagcacgg agttcctatg tcatccgtta tcactcaaac aggttaattc agagtgctgt   7920
tcttatttgt ccattgtctg acatgcatac agaagagtgt aatctagtta tgtttaacaa   7980
ttcccaagtc atgatgggtg cagaaggtag gctctatgtt attggtaata atttgtatta   8040
ttatcaacgc agttcctctt ggtggtctgc atcgctcttt tacaggatca atacagattt   8100
ttctaaagga attcctccga tcattgaggc tcaatgggta ccgtcctatc aagttcctcg   8160
tcctggagtc atgccatgca atgcaacaag tttttgccct gctaattgca tcacaggggt   8220
gtacgcagat gtgtggccgc ttaatgatcc agaactcatg tcacgtaatg ctctgaaccc   8280
caactatcga tttgctggag cctttctcaa aaatgagtcc aaccgaacta atcccacatt   8340
```

```
ctacactgca tcggctaact ccctcttaaa tactaccgga ttcaacaaca ccaatcacaa   8400
agcagcatat acatcttcaa cctgctttaa aaacactgga acccaaaaaa tttattgttt   8460
aataataatt gaaatgggct catctctttt aggggagttc caaataatac cattttaag    8520
ggaactaatg ctttaatcct attgaatgaa gactccagat tcaagaataa ttggaaggct   8580
ctttatttta tgcgatagtt atacgttttg gctgtattag aatgctatag cattctgctg   8640
tttttcccat atggaaaaat ccttcaacac caacttaggt tcaattttct catcatttac   8700
tgttgtaatt caatcttact aaagttattc tgatatttaa gaaaaaataa tctttatata   8760
atgtaacaat actactaaga ttataatata ggccagaatg gcggcctctt ctgagatact   8820
ccttcctgaa gtccatttga actcaccaat agtcaaacac aaactcatat actacttatt   8880
actagggcac ttcccgcatg atcttgacat ttctgaaata agccccttc acaataatga    8940
ttgggatcag attgccagag aagaatccaa tcttgctgaa cgactcggag tagctaaatc   9000
tgaattaatt aaacgtgtgc ccgcatttag agcaaccaga tggcgtagtc atgcagccgt   9060
ccttatatgg ccttcttgta taccattcct tgttaaattc ctaccccatt ctaagcttca   9120
accaatagaa caatggtaca agttgatcaa tgcttcatgc aatactatat ctgactcaat   9180
tgatagatgt atggagaata tttctattaa gcttactggg aaaaacaatc tattctctcg   9240
atccagagga actgcaggcg caggtaaaaa cagtaaaatc accctcaatg atatccaatc   9300
tatttgggaa tcaaacaaat ggcagcctaa tgtatcttta tggcttacaa ttaaatacca   9360
aatgcgacaa cttataatgc atcaaagttc tcgtcagcca actgatttag ttcacattgt   9420
tgacacacga tctggtctaa tagttatcac ccctgaactt gttatttgct ttgatcggtt   9480
gaataatgtt ttaatgtatt ttacatttga gatgacttta atggtaagtg acatgtttga   9540
gggacggatg aatgttgccg cgctctgcac tattagtcat tacttatcac cactagggcc   9600
aaggatagat agattgtttt ctattgtaga tgaattagca caactattgg gtgacactgt   9660
atataaaatt attgcatctc ttgaatcttt agtatatggg tgtctacaac ttaaagatcc   9720
agtggttgaa ttaacaggat catttcattc ctttattacg caagagatta tagatatcct   9780
aattgggtca aaagcccttg ataaggatga atcaataact gtcactacac aattgctaga   9840
tatattttcc aacctttctc cagatttaat cgctgagatg ttgtgtctca tgagactttg   9900
gggtcatccc actcttactg ctgcgcaagc tgcaggtaaa gtgagagaat ctatgtgtgc   9960
aggtaagtta cttgatttcc ctacaataat gaaaactctt gctttttcc acacaatttt   10020
aatcaatggt tatcgtagaa agaagaatgg aatgtggcct ccacttatac ttcctaaaaa   10080
tgcatcaaaa agcttaatag agtttcaaca tgataatgct gaaatatctt atgagtatac   10140
actcaagcat tggaaagaaa tctctctcat agaatttaga aagtgctttg actttgatcc   10200
tggtgaggag ctaagcattt ttatgaaaga caaggcaata agtgctccaa aaagtgattg   10260
gatgagtgta ttccgtagaa gtctaataaa acaacgacat cagagacatc atattcctat   10320
gcccaatcca tttaacagac gtctattact caatttctta gaagatgaca gttttgatcc   10380
agttgctgag cttcaatatg ttaccagtgg tgaatatctc cgagatgaca cattttgtgc   10440
atcttactca ttaaaagaga agaaataaa accagatgga aggatatttg ctaagcttac   10500
taatagaatg cggtcttgtc aagtaattgc ggaagcaatt cttgcaaatc acgcaggtac   10560
tctaatgaag gaaaacggag ttgtcttgaa tcaattatct ctgactaaat cattgcttac   10620
tatgagtcaa attggcataa tatcagaaaa agcaaagaga tatacccgag ataacatctc   10680
atctcaaggt ttccatacaa tcaagactga ctcaaaaaat aagaagaaaa gcaaaattgc   10740
```

```
atcatcatac ctcacagatc ctgatgatac atttgaactt agtgcatgtt ttataactac      10800
tgatcttgct aaatactgtc ttcaatggag atatcagacc ataatccatt ttgctcgaac      10860
attaaacaga atgtatggag ttccacattt atttgaatgg attcatcttc gtttgattag      10920
atctacatta tatgttggtg atccattcaa tcctcctgcc acaactgatg ccttcgatct      10980
agataaagta ttaaatggtg atatctttat agtctctccc aagggaggta ttgaaggcct      11040
atgtcagaaa atgtggacaa tgatctctat ttctgtgatc atcctttctt cagccgaatc      11100
caaaacaaga gtaatgagca tggttcaagg agataatcag gcgattgcag ttacaacaag      11160
agttcctaga tcattgccta gtgttcagaa aaaggagtta gcctacgcag caagcaagtt      11220
attctttgaa agacttaggg caaataatta tggtttgggt catcaactaa aggctcaaga      11280
gactataata agttccacgt tcttcatata tagtaaacgg gtattctatc aaggacgtat      11340
actaacacag gcacttaaaa atgctagcaa gttatgtctt actgcagatg tattaggtga      11400
atgtactcag gcttcctgct caaattctgc tactacaatc atgagattaa cagaaaatgg      11460
ggttgagaaa gatacatgtt ataagcttaa tatttatcaa tctattcgtc aactcacata      11520
tgatctaata tttccccaat actccatacc aggtgaaaca ataagtgaaa ttttcttaca      11580
gcatccaaga ttaatctcac gtattgttct gctcccttca cagctaggtg gtcttaatta      11640
cctcgcatgt agcagattat ttaaccgcaa tatcggagat cccccttggta cagccgtggc      11700 agacctcaag aggttaatta aatgtggtgc tcttgaatca tggatactgt acaatttact      11760
ggcaagaaaa ccagggaaag gttcatgggc cactttagca gccgatccat actcattgaa      11820
tcaagaatat ctttatcctc ctactactat acttaaaaga catactcaaa atactttaat      11880
ggagatatgt cggaatccta tgttaaaggg agttttttaca gataatgcaa agaggagga      11940 aaatctcctt gcaaaatttc ttcttgatcg tgatatagta ttgccaagag tcgcacacat      12000
tataatagat caatccagca ttggaaggaa gaaacagata caagggtttt ttgacaccac      12060
aaggaccata atgagacgat catttgagat caaaccactc tcaactaaga agacactttc      12120
agtcatagaa tataatacta attatttatc ttataactac cctgtcatac ttaatccttt      12180
acctattcct ggatatttaa attatattac tgaccaaact tgcagtattg atatatctag      12240
aagtttaaga aaattatcat ggtcttcttt attgaatgga agaactttag aaggattaga      12300
aactccagat ccaattgaag ttgtcaatgg ttccttgatt gtaggtacag agattgtga      12360 cttttgtatg cagggtgacg ataaattcac ttggttcttt ttacctatgg ggataattat      12420
tgatggaaat cctgaaacta atccacccat cagagttcca tacattgggt ctagaacaga      12480
ggaaagaaga gttgcatcaa tggcatatat taaaggtgcc acacacagtt gaaggctgc      12540 tcttagaggc gcaggggtat acatttgggc attcggagat acagtagtga actggaatga      12600
tgcacttgat atcgcaaata ctagggttaa gatatcccta gagcaacttc agactcttac      12660
acctcttcct acatctgcaa acattacaca tcgtttagat gatggagcca caacacttaa      12720
attcactcca gctagttcct atgcattttc tagttatact catatatcaa atgatcaaca      12780
atatttagaa atagatcaga gagtagtcga ttccaatatt attttatcaac aattaatgat      12840 aacagggctt gggatcattg agacctacca taacccacct atcaggacct ctacacagga      12900
aatcaccctc catttgcaca ctagctcatc ttgttgtgtt agaagtgtag atggttgcct      12960
tatatgtgag agcaatggag aggttcctca gatcactgtt ccctacacta attcatttgt      13020
atatgatcct gatccactag cagattatga gattgcacat ctagattatc tctcctacca      13080
```

```
agctaaaatt ggaagtacag attactactc acttactgat aaaattgatc tattggcaca   13140
tttaactgca aaacaaatga taaactcaat aattgggtta gatgaaacag tatcaattgt   13200
caatgatgcg gttattctat ctgattatac taataactgg attagtgaat gttcttatac   13260
taagatagat ttagttttta aattaatggc atggaatttc cttcttgagc ttgcattcca   13320
gatgtactac ctaagaatat catcttggac aaatatattt gactatactt acatgacttt   13380
acgcaggata cccggaactg ctctaaataa tattgcagct actattagcc acccaaaatt   13440
attaagacgt gcaatgaatc ttgatattat cactcctata catgcaccgt atttggcttc   13500
attagattat gtcaaattaa gtattgatgc aattcagtgg ggggttaaac aagttcttgc   13560
tgatttatca aatggaattg atcttgaaat cttgattctt tcagaggatt caatggaaat   13620
tagtgatagg gcaatgaatc tcattgctag aaaactaact ctccttgcac ttgttaaagg   13680
tgagaactat acatttccaa aaattaaagg gatgccacca gaggaaaagt gtttagtctt   13740
aactgaatac ctagcaatgt gttatcagaa tactccaccac ttagatccag atcttcaaaa   13800
gtatttatat aatctaacta atccaaaatt gactgcattt cccagtaaca acttctactt   13860
aacaaggaaa atccttaatc aaattagaga atcagacgaa ggacaatata ttatcacctc   13920
atattatgaa tccttcgaac aattagaaac agatataatt cttcactcta ctttaactgc   13980
tccttatgat aattcagaaa ctctaacaaa gtttgattta tcccttgaca tctttccaca   14040
tccagaatct ctcgagaaat atcctcttcc agttgatcat gactctcaat ctgcaatttc   14100
aacactaatt ccaggccctc cctctcatca tgtattacga ccactaggag tgtcatctac   14160
agcttggtat aaagggataa gttattgcag atacctggaa acgcaaaaga tacagactgg   14220
tgatcatctt tatttagctg aaggaagcgg tgcttcaatg tcacttctag aactcctatt   14280
tccaggagat actgtctatt ataatagtct ttttagtagt ggagagaatc ctccacagag   14340
aaattatgct cctcttccaa ctcaatttgt acagagtgtt ccatataaat tgtggcaagc   14400
tgatcttgct gatgatagta acttaataaa agatttttgtc ccattatgga atggaaacgg   14460
agcagttaca gacttatcga caaaggatgc agttgcattc ataatacata agtaggagc   14520 ggagaaagca tcccttgttc atatagatct cgaatcgact gctaatataa atcagcaaac   14580
tctgtccaga tcccagattc attcgttaat tatagcaact actgttctta agaggggtgg   14640
gatattagtt tacaaaacat catggcttcc gttttctagg tttagtcaac tagcaagcct   14700
actttggtgc ttttttgacc ggatccatct aatacgtagt agttattctg atcctcacag   14760
tcatgaggtt tatcttgtat gtagacttgc tgcggatttt agaactatcg gtttcagtgc   14820
agctctagta actgctacta ctcttcacaa tgacggattc acaacaatac atcctgatgt   14880
tgtttgtagt tattggcaac accatcttga gaatgttggg agagtcgaaa agtaattga   14940 tgagatactt gatggtttag ccaccaactt cttcgcagga gataatgggc ttattctaag   15000
atgtggagga actcccagct ctagaaaatg gttagagatt gatcagttag catcatttga   15060
ttcagttcaa gatgctctag tgacacttat caccatacac ctaaaggaaa ttatagaagt   15120
gcagtcatca catacagagg attatacatc tctcctttc acaccttata atattggtgc   15180
agcagggaaa gtaagaacta tcatcaaatt aattctagaa cgatctttaa tgtatacagt   15240
ccgaaattgg ttagttttac ccagttccat ccgggattcc gtacgacaag atctagagtt   15300
agggtcattt agattaatgt ctatttttaag tgaacagaca tttcttaaaa agacacccac   15360
caaaaaatac ttacttgatc agcttacaag gacatatata tcaaccttct ttaattctca   15420
ctcagtcctc cccctccacc gtccatatca aaaacaaata tggaaagcct taggtagtgt   15480
```

```
aatatattgt tcggagacgg ttgatatacc tctaattaga gacattcaga tagaagatat    15540
taatgatttt gaagatatcg agaggggtat cgatggcgaa gaattatgac aacagtgatt    15600
ataagaactc atgatagttt tatttaagaa aaacatattg attttcccct tggt          15654
```

<210> SEQ ID NO 53
<211> LENGTH: 1655
<212> TYPE: DNA
<213> ORGANISM: Human parainfluenza virus 2

<400> SEQUENCE: 53

```
atgcatcacc tgcatccaat gatagtatgc attttgtta tgtacactgg aattgtaggt      60
tcagatgcca ttgctggaga tcaactcctc aatgtagggg tcattcaatc aaagataaga    120
tcactcatgt actacactga tggtggcgct agctttattg ttgtaaaatt actacccaat    180
cttcccccaa gcaatggaac atgcaacatc accagtctag atgcatataa tgttacccta    240
tttaagttgc taacacccct gattgagaac ctgagcaaaa tttctgctgt tacagatacc    300
aaaccccgcc gagaacgatt tgcaggagtc gttattgggc ttgctgcact aggagtagct    360
acagctgcac aaataaccgc agctgtagca atagtaaaag ccaatgcaaa tgctgctgcg    420
ataaacaatc ttgcatcttc aattcaatcc accaacaagg cagtatccga tgtgataact    480
gcatcaagaa caattgcaac cgcagttcaa gcgattcagg atcacatcaa tggagccatt    540
gtcaacggga taacatctgc atcatgccgt gcccatgatg cactaattgg gtcaatatta    600
aatttgtatc tcactgagct tactacaata tttcataatc aaataacaaa ccctgcgctg    660
acaccacttt ccatccaagc tttaagaatc ctcctcggta gcaccttgcc aattgtcatt    720
gaatccaaac tcaacacaaa actcaacaca gcagagctgc tcagttccgg actgttaact    780
ggtcaaataa tttccatttc cccaatgtac atgcaaatgc taattcaaat caatgttccg    840
acatttataa tgcaacccgg tgcgaaggta attgatctaa ttgctatctc tgcaaaccat    900
aaattacaag aagtagttgt acaagttcct aatagaattc tagaatatgc aaatgaacta    960
caaaactacc cagccaatga ttgtgtcgtg acaccaaact ctgtattttg tagatacaat   1020
gagggttccc cgatccctga atcacaatat caatgcttaa gggggaatct taattcttgc   1080
acttttaccc ctattatcgg gaactttctc aagcgattcg catttgccaa tggtgtgctc   1140
tatgccaact gcaaatcttt gctatgtaag tgtgccgacc ctccccatgt tgtgtctcaa   1200
gatgacaacc aaggcatcag cataattgat attaagaggt gctctgagat gatgcttgac   1260 acttttttcat ttaggatcac atctacattc aatgctacat acgtgacaga cttctcaatg   1320
attaatgcaa atattgtaca tctaagtcct ctagacttgt caaatcaaat caattcaata   1380
aacaaatctc ttaaaagtgc tgaggattgg attgcagata gcaacttctt cgctaatcaa   1440
gccagaacag ccaagacact ttattcacta agtgcaatcg cattaatact atcagtgatt   1500
actttggttg ttgtgggatt gctgattgcc tacatcatca agctggtttc tcaaatccat   1560
caattcagag cactagctgc tacaacaatg ttccacaggg agaatcctgc cgtcttttcc   1620
aagaacaatc atggaaacat atatgggata tctta                             1655
```

<210> SEQ ID NO 54
<211> LENGTH: 552
<212> TYPE: PRT
<213> ORGANISM: Human parainfluenza virus 2
<220> FEATURE:
<221> NAME/KEY: misc_feature
<222> LOCATION: (552)..(552)

<223> OTHER INFORMATION: Xaa can be any naturally occurring amino acid

<400> SEQUENCE: 54

```
Met His His Leu His Pro Met Ile Val Cys Ile Phe Val Met Tyr Thr
1               5                   10                  15
Gly Ile Val Gly Ser Asp Ala Ile Ala Gly Asp Gln Leu Leu Asn Val
            20                  25                  30
Gly Val Ile Gln Ser Lys Ile Arg Ser Leu Met Tyr Tyr Thr Asp Gly
        35                  40                  45
Gly Ala Ser Phe Ile Val Val Lys Leu Leu Pro Asn Leu Pro Pro Ser
    50                  55                  60
Asn Gly Thr Cys Asn Ile Thr Ser Leu Asp Ala Tyr Asn Val Thr Leu
65                  70                  75                  80
Phe Lys Leu Leu Thr Pro Leu Ile Glu Asn Leu Ser Lys Ile Ser Ala
                85                  90                  95
Val Thr Asp Thr Lys Pro Arg Arg Glu Arg Phe Ala Gly Val Val Ile
            100                 105                 110
Gly Leu Ala Ala Leu Gly Val Ala Thr Ala Ala Gln Ile Thr Ala Ala
        115                 120                 125
Val Ala Ile Val Lys Ala Asn Ala Asn Ala Ala Ala Ile Asn Asn Leu
    130                 135                 140
Ala Ser Ser Ile Gln Ser Thr Asn Lys Ala Val Ser Asp Val Ile Thr
145                 150                 155                 160
Ala Ser Arg Thr Ile Ala Thr Ala Val Gln Ala Ile Gln Asp His Ile
                165                 170                 175
Asn Gly Ala Ile Val Asn Gly Ile Thr Ser Ala Ser Cys Arg Ala His
            180                 185                 190
Asp Ala Leu Ile Gly Ser Ile Leu Asn Leu Tyr Leu Thr Glu Leu Thr
        195                 200                 205
Thr Ile Phe His Asn Gln Ile Thr Asn Pro Ala Leu Thr Pro Leu Ser
    210                 215                 220
Ile Gln Ala Leu Arg Ile Leu Leu Gly Ser Thr Leu Pro Ile Val Ile
225                 230                 235                 240
Glu Ser Lys Leu Asn Thr Lys Leu Asn Thr Ala Glu Leu Leu Ser Ser
                245                 250                 255
Gly Leu Leu Thr Gly Gln Ile Ile Ser Ile Ser Pro Met Tyr Met Gln
            260                 265                 270
Met Leu Ile Gln Ile Asn Val Pro Thr Phe Ile Met Gln Pro Gly Ala
        275                 280                 285
Lys Val Ile Asp Leu Ile Ala Ile Ser Ala Asn His Lys Leu Gln Glu
    290                 295                 300
Val Val Val Gln Val Pro Asn Arg Ile Leu Glu Tyr Ala Asn Glu Leu
305                 310                 315                 320
Gln Asn Tyr Pro Ala Asn Asp Cys Val Val Thr Pro Asn Ser Val Phe
                325                 330                 335
Cys Arg Tyr Asn Glu Gly Ser Pro Ile Pro Glu Ser Gln Tyr Gln Cys
            340                 345                 350
Leu Arg Gly Asn Leu Asn Ser Cys Thr Phe Thr Pro Ile Ile Gly Asn
        355                 360                 365
Phe Leu Lys Arg Phe Ala Phe Ala Asn Gly Val Leu Tyr Ala Asn Cys
    370                 375                 380
Lys Ser Leu Leu Cys Lys Cys Ala Asp Pro Pro His Val Val Ser Gln
385                 390                 395                 400
```

```
Asp Asp Asn Gln Gly Ile Ser Ile Ile Asp Ile Lys Arg Cys Ser Glu
                405                 410                 415

Met Met Leu Asp Thr Phe Ser Phe Arg Ile Thr Ser Thr Phe Asn Ala
            420                 425                 430

Thr Tyr Val Thr Asp Phe Ser Met Ile Asn Ala Asn Ile Val His Leu
        435                 440                 445

Ser Pro Leu Asp Leu Ser Asn Gln Ile Asn Ser Ile Asn Lys Ser Leu
    450                 455                 460

Lys Ser Ala Glu Asp Trp Ile Ala Asp Ser Asn Phe Phe Ala Asn Gln
465                 470                 475                 480

Ala Arg Thr Ala Lys Thr Leu Tyr Ser Leu Ser Ala Ile Ala Leu Ile
            485                 490                 495

Leu Ser Val Ile Thr Leu Val Val Val Gly Leu Leu Ile Ala Tyr Ile
            500                 505                 510

Ile Lys Leu Val Ser Gln Ile His Gln Phe Arg Ala Leu Ala Ala Thr
        515                 520                 525

Thr Met Phe His Arg Glu Asn Pro Ala Val Phe Ser Lys Asn Asn His
    530                 535                 540

Gly Asn Ile Tyr Gly Ile Ser Xaa
545                 550
```

<210> SEQ ID NO 55
<211> LENGTH: 1716
<212> TYPE: DNA
<213> ORGANISM: Human parainfluenza virus 2

<400> SEQUENCE: 55

```
atggaagatt acagcaatct atctcttaaa tcaattccta aaaggacatg tagaatcatt    60
ttccgaactg ccacaattct tggcatatgc acattaattg tgctatgttc aagtattctt   120
catgagataa ttcatcttga tgtttcctct ggtcttatga attctgatga gtcacagcaa   180
ggcattattc agcctatcat agaatcatta aaattcattga ttgctttggc caaccagatt   240
ctatataatg ttgcaatagt aattcctctt aaaattgaca gtatcgaaac tgtaatactc   300
tctgctttaa aagatatgca caccgggagt atgtccaatg ccaactgcac gccaggaaat   360
ctgcttctgc atgatgcagc atacatcaat ggaataaaca aattccttgt acttgaatca   420
tacaatggga cgcctaaata tggacctctc taaatatac ccagctttat ccctcagca    480
acatctcccc atgggtgtac tagaatacca tcattttcac tcatcaagac ccattggtgt   540
tacactcaca atgtaatgct tggagattgt cttgatttca ggcatctaa ccagtattta   600
tcaatgggga taatacaaca atctgctgca gggtttccaa ttttcaggac tatgaaaacc   660
attacctaa gtgatggaat caatcgcaaa agctgttcag tcactgctat accaggaggt   720
tgtgtcttgt attgctatgt agctacaagg tctgaaaaag aagattatgc cacgactgat   780
ctagctgaac tgagacttgc tttctattat tataatgata cctttattga agagtcata   840
tctcttccaa atacaacagg gcagtgggcc acaatcaacc ctgcagtcgg aagcgggatc   900
tatcatctag ctttatcttt attcctgta tatggtggtc tcataaatgg gactacttct   960
tacaatgagc agtcctcacg ctattttac ccaaaacatc ccaacataac ttgtgccggt  1020
aactccagca acaggctgc aatagcacgg agttcctatg tcatccgtta tcactcaaac  1080
aggttaattc agagtgctgt tcttatttgt ccattgtctg acatgcatac agaagagtgt  1140
aatctagtta tgtttaacaa ttcccaagtc atgatgggtg cagaaggtag gctctatgtt  1200
attggtaata atttgtatta ttatcaacgc agttcctctt ggtggtctgc atcgctcttt  1260
```

```
tacaggatca atacagattt ttctaaagga attcctccga tcattgaggc tcaatgggta   1320
ccgtcctatc aagttcctcg tcctggagtc atgccatgca atgcaacaag tttttgccct   1380
gctaattgca tcacaggggt gtacgcagat gtgtggccgc ttaatgatcc agaactcatg   1440
tcacgtaatg ctctgaaccc caactatcga tttgctggag cctttctcaa aaatgagtcc   1500
aaccgaacta atcccacatt ctacactgca tcggctaact ccctcttaaa tactaccgga   1560
ttcaacaaca ccaatcacaa agcagcatat acatcttcaa cctgctttaa aaacactgga   1620
acccaaaaaa tttattgttt aataataatt gaaatgggct catctctttt aggggagttc   1680
caaataatac catttttaag ggaactaatg ctttaa                             1716
```

<210> SEQ ID NO 56
<211> LENGTH: 571
<212> TYPE: PRT
<213> ORGANISM: Human parainfluenza virus 2

<400> SEQUENCE: 56

```
Met Glu Asp Tyr Ser Asn Leu Ser Leu Lys Ser Ile Pro Lys Arg Thr
1               5                   10                  15

Cys Arg Ile Ile Phe Arg Thr Ala Thr Ile Leu Gly Ile Cys Thr Leu
            20                  25                  30

Ile Val Leu Cys Ser Ser Ile Leu His Glu Ile Ile His Leu Asp Val
        35                  40                  45

Ser Ser Gly Leu Met Asn Ser Asp Glu Ser Gln Gln Gly Ile Ile Gln
    50                  55                  60

Pro Ile Ile Glu Ser Leu Lys Ser Leu Ile Ala Leu Ala Asn Gln Ile
65                  70                  75                  80

Leu Tyr Asn Val Ala Ile Val Ile Pro Leu Lys Ile Asp Ser Ile Glu
                85                  90                  95

Thr Val Ile Leu Ser Ala Leu Lys Asp Met His Thr Gly Ser Met Ser
            100                 105                 110

Asn Ala Asn Cys Thr Pro Gly Asn Leu Leu Leu His Asp Ala Ala Tyr
        115                 120                 125

Ile Asn Gly Ile Asn Lys Phe Leu Val Leu Glu Ser Tyr Asn Gly Thr
    130                 135                 140

Pro Lys Tyr Gly Pro Leu Leu Asn Ile Pro Ser Phe Ile Pro Ser Ala
145                 150                 155                 160

Thr Ser Pro His Gly Cys Thr Arg Ile Pro Ser Phe Ser Leu Ile Lys
                165                 170                 175

Thr His Trp Cys Tyr Thr His Asn Val Met Leu Gly Asp Cys Leu Asp
            180                 185                 190

Phe Thr Ala Ser Asn Gln Tyr Leu Ser Met Gly Ile Ile Gln Gln Ser
        195                 200                 205

Ala Ala Gly Phe Pro Ile Phe Arg Thr Met Lys Thr Ile Tyr Leu Ser
    210                 215                 220

Asp Gly Ile Asn Arg Lys Ser Cys Ser Val Thr Ala Ile Pro Gly Gly
225                 230                 235                 240

Cys Val Leu Tyr Cys Tyr Val Ala Thr Arg Ser Glu Lys Glu Asp Tyr
                245                 250                 255

Ala Thr Thr Asp Leu Ala Glu Leu Arg Leu Ala Phe Tyr Tyr Tyr Asn
            260                 265                 270

Asp Thr Phe Ile Glu Arg Val Ile Ser Leu Pro Asn Thr Thr Gly Gln
        275                 280                 285
```

Trp Ala Thr Ile Asn Pro Ala Val Gly Ser Gly Ile Tyr His Leu Gly
            290                 295                 300

Phe Ile Leu Phe Pro Val Tyr Gly Gly Leu Ile Asn Gly Thr Thr Ser
305                 310                 315                 320

Tyr Asn Glu Gln Ser Ser Arg Tyr Phe Ile Pro Lys His Pro Asn Ile
                325                 330                 335

Thr Cys Ala Gly Asn Ser Ser Lys Gln Ala Ala Ile Ala Arg Ser Ser
                340                 345                 350

Tyr Val Ile Arg Tyr His Ser Asn Arg Leu Ile Gln Ser Ala Val Leu
                355                 360                 365

Ile Cys Pro Leu Ser Asp Met His Thr Glu Glu Cys Asn Leu Val Met
370                 375                 380

Phe Asn Asn Ser Gln Val Met Met Gly Ala Glu Gly Arg Leu Tyr Val
385                 390                 395                 400

Ile Gly Asn Asn Leu Tyr Tyr Gln Arg Ser Ser Trp Trp Ser
                405                 410                 415

Ala Ser Leu Phe Tyr Arg Ile Asn Thr Asp Phe Ser Lys Gly Ile Pro
                420                 425                 430

Pro Ile Ile Glu Ala Gln Trp Val Pro Ser Tyr Gln Val Pro Arg Pro
                435                 440                 445

Gly Val Met Pro Cys Asn Ala Thr Ser Phe Cys Pro Ala Asn Cys Ile
450                 455                 460

Thr Gly Val Tyr Ala Asp Val Trp Pro Leu Asn Asp Pro Glu Leu Met
465                 470                 475                 480

Ser Arg Asn Ala Leu Asn Pro Asn Tyr Arg Phe Ala Gly Ala Phe Leu
                485                 490                 495

Lys Asn Glu Ser Asn Arg Thr Asn Pro Thr Phe Tyr Thr Ala Ser Ala
                500                 505                 510

Asn Ser Leu Leu Asn Thr Thr Gly Phe Asn Asn Thr Asn His Lys Ala
                515                 520                 525

Ala Tyr Thr Ser Ser Thr Cys Phe Lys Asn Thr Gly Thr Gln Lys Ile
                530                 535                 540

Tyr Cys Leu Ile Ile Ile Glu Met Gly Ser Ser Leu Leu Gly Glu Phe
545                 550                 555                 560

Gln Ile Ile Pro Phe Leu Arg Glu Leu Met Leu
                565                 570

<210> SEQ ID NO 57
<211> LENGTH: 180
<212> TYPE: DNA
<213> ORGANISM: Human parainfluenza virus 2

<400> SEQUENCE: 57
tttaagttgc taacgcccct gattgagaac ctgagcaaaa tttctgctgt tacagatacc        60 aaacccgcc gagaacgatt tgcaggagtc gttattgggc ttgctgcact aggagtagct       120
acagctgcac aaataaccgc agctgtagca atagtaaaag ccaatgcaaa tgctgctgcg       180

<210> SEQ ID NO 58
<211> LENGTH: 180
<212> TYPE: DNA
<213> ORGANISM: Human parainfluenza virus 2

<400> SEQUENCE: 58
tttaagttgc taacgcccct gattgagaac ctgagcaaaa tttctgctgt tacagatacc        60 aaacccgcc gagaacgatt tgcaggagtc gttattgggc ttgctgcact aggagtagct       120
acagctgcac aaataaccgc agctgtagca atagtaaaag ccaatgcaaa tgctgctgcg 180

<210> SEQ ID NO 59
<211> LENGTH: 180
<212> TYPE: DNA
<213> ORGANISM: Human parainfluenza virus 2

<400> SEQUENCE: 59
tttaagttgc taacgcccct gattgagaac ctgagcaaaa tttctgctgt tacagatacc 60
aaaccccgcc gagaacgatt tgcaggagtc gttattgggc ttgctgcact aggagtagct 120
acagctgcac aaataaccgc agctgtagca atagtaaaag ccaatgcaaa tgctgctgcg 180

<210> SEQ ID NO 60
<211> LENGTH: 180
<212> TYPE: DNA
<213> ORGANISM: Human parainfluenza virus 2

<400> SEQUENCE: 60
tttaagttgc taacacccct gattgagaac ctgagcaaaa tttccgctgt tacagatacc 60
aaaccccgcc gagaacgatt tgcaggggtc gttattgggc ttgctgcact aggagtagct 120
acagctgcac aaataaccgc agctgtagca atagtgaaag ccaatgcaaa tgctgctgcg 180

<210> SEQ ID NO 61
<211> LENGTH: 180
<212> TYPE: DNA
<213> ORGANISM: Human parainfluenza virus 2

<400> SEQUENCE: 61
tttaagttgc taacgcccct gattgagaac ctgagcaaaa tttctgctgt tacagatacc 60
aaaccccgcc gagaacgatt tgcaggagtc gttattgggc ttgctgcact aggagtagct 120
acagctgcac aaataaccgc agctgtagca atagtaaaag ccaatgcaaa tgctgctgcg 180

<210> SEQ ID NO 62
<211> LENGTH: 137
<212> TYPE: DNA
<213> ORGANISM: Human parainfluenza virus 2

<400> SEQUENCE: 62
ctgattgaga acctgagcaa aatttctgct gttacagata ccaaaccccg ccgagaacga 60
tttgcaggag tcgttattgg gcttgctgca ctaggagtag ctacagctgc acaaataacc 120
gcagctgtag caatagt 137

<210> SEQ ID NO 63
<211> LENGTH: 137
<212> TYPE: DNA
<213> ORGANISM: Human parainfluenza virus 2

<400> SEQUENCE: 63
ctgattgaga acctgagcaa aatttctgct gttacagata ccaaaccccg ccgagaacga 60
tttgcaggag tcgttattgg gcttgctgca ctaggagtag ctacagctgc acaaataacc 120
gcagctgtag caatagt 137

<210> SEQ ID NO 64
<211> LENGTH: 137
<212> TYPE: DNA
<213> ORGANISM: Human parainfluenza virus 2

<400> SEQUENCE: 64
ctgattgaga acctgagcaa aatttctgct gttacagata ccaaaccccg ccgagaacga    60
tttgcaggag tcgttattgg gcttgctgca ctaggagtag ctacagctgc acaaataacc   120
gcagctgtag caatagt                                                 137

<210> SEQ ID NO 65
<211> LENGTH: 137
<212> TYPE: DNA
<213> ORGANISM: Human parainfluenza virus 2

<400> SEQUENCE: 65
ctgattgaga acctgagcaa aatttccgct gttacagata ccaaaccccg ccgagaacga    60
tttgcagggg tcgttattgg gcttgctgca ctaggagtag ctacagctgc acaaataacc   120
gcagctgtag caatagt                                                 137

<210> SEQ ID NO 66
<211> LENGTH: 137
<212> TYPE: DNA
<213> ORGANISM: Human parainfluenza virus 2

<400> SEQUENCE: 66
ctgattgaga acctgagcaa aatttctgct gttacagata ccaaaccccg ccgagaacga    60
tttgcaggag tcgttattgg gcttgctgca ctaggagtag ctacagctgc acaaataacc   120
gcagctgtag caatagt                                                 137

<210> SEQ ID NO 67
<211> LENGTH: 210
<212> TYPE: DNA
<213> ORGANISM: Human parainfluenza virus 2

<400> SEQUENCE: 67
ccagattcta tataatgttg caatagtaat tcctcttaaa attgacagta tcgaaactgt    60
aatactctct gctttaaaag atatgcacac cgggagtatg tccaatgcca actgcacgcc   120
aggaaatcta cttctgcatg atgcagcata catcaatgga ataaacaaat tccttgtact   180
tgaatcatac aatgggacgc ctaaatatgg                                   210

<210> SEQ ID NO 68
<211> LENGTH: 210
<212> TYPE: DNA
<213> ORGANISM: Human parainfluenza virus 2

<400> SEQUENCE: 68
ccagattcta tataatgttg caatagtaat tcctcttaaa attgacagta tcgaaactgt    60
aatactctct gctttaaaag atatgcacac cgggagtatg tccaatgcca actgcacgcc   120
aggaaatcta cttctgcatg atgcagcata catcaatgga ataaacaaat tccttgtact   180
tgaatcatac aatgggacgc ctaaatatgg                                   210

<210> SEQ ID NO 69
<211> LENGTH: 210
<212> TYPE: DNA
<213> ORGANISM: Human parainfluenza virus 2

<400> SEQUENCE: 69
ccagattcta tataatgttg caataataat tcctcttaaa attgacagta tcgaaactgt    60
aatactctct gctttaaaag atatgcacac cgggagtatg tccaatgcca actgcacgcc   120

```
aggaaatcta cttctgcatg atgcagcata catcaatgga ataaacaaat tccttgtact    180
tgaatcatac aatgggacgc ctaaatatgg                                     210

<210> SEQ ID NO 70
<211> LENGTH: 210
<212> TYPE: DNA
<213> ORGANISM: Human parainfluenza virus 2

<400> SEQUENCE: 70
ccagattcta tataatgttg caataataat tcctcttaaa attgacagta tcgaaactgt     60
aatactctct gctttaaaag atatgcacac cgggagtatg tccaatgcca actgcacgcc    120
aggaaatttg cttctgcatg atgcagcata catcaatgga ataaacaaat tccttgtacc    180
tgaatcatac aatgggacgc ctaaatatgg                                     210

<210> SEQ ID NO 71
<211> LENGTH: 180
<212> TYPE: DNA
<213> ORGANISM: Human parainfluenza virus 2

<400> SEQUENCE: 71
ctatataatg ttgcaatagt aattcctctt aaaattgaca gtatcgaaac tgtaatactc     60
tctgctttaa aagatatgca caccgggagt atgtccaatg ccaactgcac gccaggaaat    120
ctacttctgc atgatgcagc atacatcaat ggaataaaca aattccttgt acttgaatca    180

<210> SEQ ID NO 72
<211> LENGTH: 180
<212> TYPE: DNA
<213> ORGANISM: Human parainfluenza virus 2

<400> SEQUENCE: 72
ctatataatg ttgcaatagt aattcctctt aaaattgaca gtatcgaaac tgtaatactc     60
tctgctttaa aagatatgca caccgggagt atgtccaatg ccaactgcac gccaggaaat    120
ctacttctgc atgatgcagc atacatcaat ggaataaaca aattccttgt acttgaatca    180

<210> SEQ ID NO 73
<211> LENGTH: 180
<212> TYPE: DNA
<213> ORGANISM: Human parainfluenza virus 2

<400> SEQUENCE: 73
ctatataatg ttgcaataat aattcctctt aaaattgaca gtatcgaaac tgtaatactc     60
tctgctttaa aagatatgca caccgggagt atgtccaatg ccaactgcac gccaggaaat    120
ctacttctgc atgatgcagc atacatcaat ggaataaaca aattccttgt acttgaatca    180

<210> SEQ ID NO 74
<211> LENGTH: 180
<212> TYPE: DNA
<213> ORGANISM: Human parainfluenza virus 2

<400> SEQUENCE: 74
ctatataatg ttgcaataat aattcctctt aaaattgaca gtatcgaaac tgtaatactc     60
tctgctttaa aagatatgca caccgggagt atgtccaatg ccaactgcac gccaggaaat    120
ttgcttctgc atgatgcagc atacatcaat ggaataaaca aattccttgt acctgaatca    180

<210> SEQ ID NO 75
```

```
<211> LENGTH: 180
<212> TYPE: DNA
<213> ORGANISM: Human parainfluenza virus 2

<400> SEQUENCE: 75
tacaatgagc agtcctcacg ctattttatc ccaaaacatc ccaacataac ttgtgccggt      60
aactccagca acaggctgc aatagcacgg agttcctatg tcatccgtta tcactcaaac     120
aggttaattc agagtgctgt tcttatttgt ccattgtctg acatgcacac agaagagtgt    180

<210> SEQ ID NO 76
<211> LENGTH: 180
<212> TYPE: DNA
<213> ORGANISM: Human parainfluenza virus 2

<400> SEQUENCE: 76
tacaatgagc agtcctcacg ctattttatc ccaaaacatc ccaacataac ttgtgccggt      60
aactccagca acaggctgc aatagcacgg agttcctatg tcatccgtta tcactcaaac     120
aggttaattc agagtgctgt tcttatttgt ccattgtctg acatgcacac agaagagtgt    180

<210> SEQ ID NO 77
<211> LENGTH: 180
<212> TYPE: DNA
<213> ORGANISM: Human parainfluenza virus 2

<400> SEQUENCE: 77
tacaatgagc agtcctcacg ctattttatc ccaaaacatc ccaacataac ttgtgccggt      60
aactccagca acaggctgc aatagcacgg agttcctatg tcatccgtta tcactcaaac     120
aggttaattc agagtgctgt tcttatttgt ccattgtctg acatgcacac agaagagtgt    180

<210> SEQ ID NO 78
<211> LENGTH: 180
<212> TYPE: DNA
<213> ORGANISM: Human parainfluenza virus 2

<400> SEQUENCE: 78
tacaatgagc agtcctcacg ctattttatc ccaaaacatc ccaacataac ttgtgccggt      60
aactccagca acaggctgc aatagcacgg aattcttatg tcatccgtta tcactcaaac     120
aggttaattc agagtgctgt tcttatttgt ccattgtctg acatgcacac agaagagtgt    180

<210> SEQ ID NO 79
<211> LENGTH: 180
<212> TYPE: DNA
<213> ORGANISM: Human parainfluenza virus 2

<400> SEQUENCE: 79
gctaattgca tcacaggggt gtacgcagat gtgtggccgc ttaatgatcc agaactcatg      60
tcacgtaatg ctctgaaccc caactatcga tttgctggag cctttctcaa aaatgagtcc    120
aaccgaacta atcccacatt ctacactgca tcgtctaact ccctcttaaa tactaccgga    180

<210> SEQ ID NO 80
<211> LENGTH: 180
<212> TYPE: DNA
<213> ORGANISM: Human parainfluenza virus 2

<400> SEQUENCE: 80
gctaattgca tcacaggggt gtacgcagat gtgtggccgc ttaatgatcc agaactcatg      60
tcacgtaatg ctctgaaccc caactatcga tttgctggag cctttctcaa aaatgagtcc    120
```

```
aaccgaacta atcccacatt ctacactgca tcgtctaact ccctcttaaa tactaccgga      180
```

<210> SEQ ID NO 81
<211> LENGTH: 180
<212> TYPE: DNA
<213> ORGANISM: Human parainfluenza virus 2

<400> SEQUENCE: 81

```
gctaattgca tcacaggggt gtacgcagat gtgtggccgc ttaatgatcc agaactcatg      60
tcacgtaatg ctctgaaccc caactatcga tttgctggag cctttctcaa aaatgagtcc     120
aaccgaacta atcccacatt ctacactgca tcgtctaact ccctcttaaa tactaccgga    180
```

<210> SEQ ID NO 82
<211> LENGTH: 180
<212> TYPE: DNA
<213> ORGANISM: Human parainfluenza virus 2

<400> SEQUENCE: 82
gctaattgca tcacaggggt gtacgcagat gtgtggccgc ttaatgatcc agaactcatg 60
tcacgtaatg ctctgaaccc caactatcga tttgctggag cctttctcaa aaatgagtcc 120
aaccgaacta atcccacatt ttacactgca tcggctaact ccctcttaaa tactaccgga 180

<210> SEQ ID NO 83
<211> LENGTH: 208
<212> TYPE: DNA
<213> ORGANISM: Human parainfluenza virus 2

<400> SEQUENCE: 83
atcgatttgc tggagccttt ctcaaaaatg agtccaaccg aactaatccc acattctaca 60
ctgcatcgtc taactccctc ttaaatacta ccggattcaa caaaaccaat cacaaagcag 120
catatacatc ttcaacctgc tttaaaaaca ctggaaccca aaaaatttat tgtttaataa 180
taattgaaat gggctcatct cttttagg 208

<210> SEQ ID NO 84
<211> LENGTH: 208
<212> TYPE: DNA
<213> ORGANISM: Human parainfluenza virus 2

<400> SEQUENCE: 84
atcgatttgc tggagccttt ctcaaaaatg agtccaaccg aactaatccc acattctaca 60
ctgcatcgtc taactccctc ttaaatacta ccggattcaa caaaaccaat cacaaagcag 120
catatacatc ttcaacctgc tttaaaaata ctggaaccca aaaaatttat tgtttaataa 180
taattgaaat gggctcatct cttttagg 208

<210> SEQ ID NO 85
<211> LENGTH: 208
<212> TYPE: DNA
<213> ORGANISM: Human parainfluenza virus 2

<400> SEQUENCE: 85
atcgatttgc tggagccttt ctcaaaaatg agtccaaccg aactaatccc acattctaca 60
ctgcatcgtc taactccctc ttaaatacta ccggattcaa caaaaccaat cacaaagcag 120
catatacatc ttcaacctgc tttaaaaata ctggaaccca aaaaatttat tgtttaataa 180
taattgaaat gggctcatct cttttagg 208

```
<210> SEQ ID NO 86
<211> LENGTH: 208
<212> TYPE: DNA
<213> ORGANISM: Human parainfluenza virus 2

<400> SEQUENCE: 86
atcgatttgc tggagccttt ctcaaaaatg agtccaaccg aactaatccc acattttaca      60
ctgcatcggc taactccctc ttaaatacta ccggattcaa caacaccaat cacaaagcag     120
catatacatc ttcaacctgc tttaaaaaca ctggaaacca aaaaatttat tgtttaataa     180
taattgaaat gggctcatct cttttagg                                        208

<210> SEQ ID NO 87
<211> LENGTH: 18
<212> TYPE: DNA
<213> ORGANISM: Human parainfluenza virus 2

<400> SEQUENCE: 87
ctgattgaga acctgagc                                                    18

<210> SEQ ID NO 88
<211> LENGTH: 20
<212> TYPE: DNA
<213> ORGANISM: Human parainfluenza virus 2

<400> SEQUENCE: 88
actattgcta cagctgcggt                                                  20

<210> SEQ ID NO 89
<211> LENGTH: 24
<212> TYPE: DNA
<213> ORGANISM: Human parainfluenza virus 2

<400> SEQUENCE: 89
caggagtcgt tatgggcttt gctg                                             24

<210> SEQ ID NO 90
<211> LENGTH: 27
<212> TYPE: DNA
<213> ORGANISM: Human parainfluenza virus 2

<400> SEQUENCE: 90
agtcgttatt gggcttgctg cactagg                                          27

<210> SEQ ID NO 91
<211> LENGTH: 21
<212> TYPE: DNA
<213> ORGANISM: Human parainfluenza virus 2

<400> SEQUENCE: 91
ccagattctg tacaatgttg c                                                21

<210> SEQ ID NO 92
<211> LENGTH: 21
<212> TYPE: DNA
<213> ORGANISM: Human parainfluenza virus 2

<400> SEQUENCE: 92
ccatatttag gcgtcccatt g                                                21

<210> SEQ ID NO 93
<211> LENGTH: 28
```

```
<212> TYPE: DNA
<213> ORGANISM: Human parainfluenza virus 2

<400> SEQUENCE: 93
tgcacaccgg gagtatgtcc aatgccaa                                          28

<210> SEQ ID NO 94
<211> LENGTH: 27
<212> TYPE: DNA
<213> ORGANISM: Human parainfluenza virus 2

<400> SEQUENCE: 94
tccaatgcca actgcacgcc aggaaat                                           27

<210> SEQ ID NO 95
<211> LENGTH: 20
<212> TYPE: DNA
<213> ORGANISM: Human parainfluenza virus 2

<400> SEQUENCE: 95
atcgatttgc tggagccttt                                                   20

<210> SEQ ID NO 96
<211> LENGTH: 23
<212> TYPE: DNA
<213> ORGANISM: Human parainfluenza virus 2

<400> SEQUENCE: 96
cctaaaagag atgagcccat ttc                                               23

<210> SEQ ID NO 97
<211> LENGTH: 23
<212> TYPE: DNA
<213> ORGANISM: Human parainfluenza virus 2

<400> SEQUENCE: 97
ctacactgca tcgtctaact ccc                                               23

<210> SEQ ID NO 98
<211> LENGTH: 24
<212> TYPE: DNA
<213> ORGANISM: Human parainfluenza virus 2

<400> SEQUENCE: 98
cactgcatcg tctaactccc tctt                                              24

<210> SEQ ID NO 99
<211> LENGTH: 16
<212> TYPE: DNA
<213> ORGANISM: Human parainfluenza virus 2

<400> SEQUENCE: 99
taagttgcta acgccc                                                       16

<210> SEQ ID NO 100
<211> LENGTH: 17
<212> TYPE: DNA
<213> ORGANISM: Human parainfluenza virus 2

<400> SEQUENCE: 100
gagcaaaatt tctgctg                                                      17

<210> SEQ ID NO 101
```

```
<210> SEQ ID NO 101
<211> LENGTH: 15
<212> TYPE: DNA
<213> ORGANISM: Human parainfluenza virus 2

<400> SEQUENCE: 101
gagtcgttat tgggc                                                     15

<210> SEQ ID NO 102
<211> LENGTH: 16
<212> TYPE: DNA
<213> ORGANISM: Human parainfluenza virus 2

<400> SEQUENCE: 102
gctgcacaaa taaccg                                                    16

<210> SEQ ID NO 103
<211> LENGTH: 20
<212> TYPE: DNA
<213> ORGANISM: Human parainfluenza virus 2

<400> SEQUENCE: 103
gtaaaagcca atgcaaatgc                                                20

<210> SEQ ID NO 104
<211> LENGTH: 14
<212> TYPE: DNA
<213> ORGANISM: Human parainfluenza virus 2

<400> SEQUENCE: 104
ggcttgctgc acta                                                      14

<210> SEQ ID NO 105
<211> LENGTH: 15
<212> TYPE: DNA
<213> ORGANISM: Human parainfluenza virus 2

<400> SEQUENCE: 105
agatatgcac accgg                                                     15

<210> SEQ ID NO 106
<211> LENGTH: 15
<212> TYPE: DNA
<213> ORGANISM: Human parainfluenza virus 2

<400> SEQUENCE: 106
gcacaccggg agtat                                                     15

<210> SEQ ID NO 107
<211> LENGTH: 15
<212> TYPE: DNA
<213> ORGANISM: Human parainfluenza virus 2

<400> SEQUENCE: 107
atgccaactg cacgc                                                     15

<210> SEQ ID NO 108
<211> LENGTH: 15
<212> TYPE: DNA
<213> ORGANISM: Human parainfluenza virus 2

<400> SEQUENCE: 108
ccttgtactt gaatc                                                     15
```

```
<210> SEQ ID NO 109
<211> LENGTH: 13
<212> TYPE: DNA
<213> ORGANISM: Human parainfluenza virus 2

<400> SEQUENCE: 109
aactgcacgc cag                                                        13

<210> SEQ ID NO 110
<211> LENGTH: 15
<212> TYPE: DNA
<213> ORGANISM: Human parainfluenza virus 2

<400> SEQUENCE: 110
tacaatgagc agtcc                                                      15

<210> SEQ ID NO 111
<211> LENGTH: 19
<212> TYPE: DNA
<213> ORGANISM: Human parainfluenza virus 2

<400> SEQUENCE: 111
gcaaacaggc tgcaatagc                                                  19

<210> SEQ ID NO 112
<211> LENGTH: 17
<212> TYPE: DNA
<213> ORGANISM: Human parainfluenza virus 2

<400> SEQUENCE: 112
gtcatccgtt atcactc                                                    17

<210> SEQ ID NO 113
<211> LENGTH: 14
<212> TYPE: DNA
<213> ORGANISM: Human parainfluenza virus 2

<400> SEQUENCE: 113
cacacagaag agtg                                                       14

<210> SEQ ID NO 114
<211> LENGTH: 17
<212> TYPE: DNA
<213> ORGANISM: Human parainfluenza virus 2

<400> SEQUENCE: 114
catcgtctaa ctccctc                                                    17

<210> SEQ ID NO 115
<211> LENGTH: 14
<212> TYPE: DNA
<213> ORGANISM: Human parainfluenza virus 2

<400> SEQUENCE: 115
cacgtaatgc tctg                                                       14

<210> SEQ ID NO 116
<211> LENGTH: 16
<212> TYPE: DNA
<213> ORGANISM: Human parainfluenza virus 2

<400> SEQUENCE: 116
tgatccagaa ctcatg                                                     16
```

```
<210> SEQ ID NO 117
<211> LENGTH: 19
<212> TYPE: DNA
<213> ORGANISM: Human parainfluenza virus 2

<400> SEQUENCE: 117
ccgaactaat cccacattc                                                19

<210> SEQ ID NO 118
<211> LENGTH: 6
<212> TYPE: PRT
<213> ORGANISM: Human parainfluenza virus 2

<400> SEQUENCE: 118

Lys Thr Arg Gln Lys Arg
1               5
```

The invention claimed is:

1. A kit for diagnosis of a respiratory disease or infection, comprising:
a first primer, the nucleotide sequence of which is a DNA sequence consisting of the first 14-30 nucleotides at the 5' end of the sequence selected from the group consisting of SEQ ID NOs: 62-66;
a second primer, the nucleotide sequence of which is a DNA sequence consisting of the sequence that is complementary to the last 14-30 nucleotides at the 3' end of the selected sequence,
wherein said first primer and said second primer form a primer pair, which amplifies nucleic acid from each of the five HPIV-2 viruses deposited at Collection Nationale de Cultures de Microorganismes, accession numbers I-3761, I-3762, I-3763, I-3764 and I-3765; and
a first probe, which can be used in real-time amplification with said primer pair, wherein the nucleotide sequence of said first probe is a DNA sequence comprising the nucleotide sequence of SEQ ID NO: 90 or the complementary sequence thereof, and wherein said first probe detects each of said five deposited HPIV-2 viruses, without detecting the Greer, Toshiba and V98 isolates.

2. The kit of claim 1, wherein the last five nucleotides at the 3' end of each of said first and second primers do not include more than two G and/or C bases.

3. The kit of claim 1, wherein the nucleotide sequence of said first primer consists of the first 18-23 nucleotides at the 5' end of the selected sequence, and the nucleotide sequence of said second primer consists of the sequence that is complementary to the last 18-23 nucleotides at the 3' end of the selected sequence.

4. The kit of claim 1, wherein said first primer comprises the nucleotide sequence of SEQ ID NO: 87 and said second primer comprises the nucleotide sequence of SEQ ID NO: 88.

5. The kit of claim 1, wherein the nucleotide sequence of said first primer consists of the sequence of SEQ ID NO: 87 and the nucleotide sequence of said second primer consists of the sequence of SEQ ID NO: 88.

6. The kit of claim 1, wherein the sequence of said first probe, which hybridizes to each of said five deposited HPIV-2 viruses, without hybridizing to the Greer, Toshiba and V98 isolates, consists of at most 30 nucleotides.

7. The kit of claim 1, wherein the nucleotide sequence of said first probe consists of the sequence of SEQ ID NO: 90 or the complementary sequence thereof, or consists of the sequence of SEQ ID NO: 90 or the complementary sequence thereof linked to at least one nucleotide arm.

8. The kit of claim 1, wherein said first probe is labeled with at least one detection marker selected from the group consisting of radioactive markers, fluorescent markers and enzymatic markers.

9. The kit of claim 1, wherein said first probe is labeled with a fluorescent marker and a quencher.

10. The kit of claim 1, wherein said first primer, second primer and first probe are configured to perform a RT-PCR real-time amplification under the following amplification conditions:

at least one cycle of:
- 50° C. for 2 min,
- 60° C. for 30 min, and
- 95° C. for 10 min, followed by 25 to 40 cycles of:
- 95° C. to 97° C. for 15 seconds, and
- 55° C. to 70° C. for 1 min.

11. The kit of claim 1, further comprising a second probe, wherein said second probe detects each of the Greer, Toshiba and V98 isolates.

12. The kit of claim 8, wherein said second probe does not detect the V94 isolate.

13. The kit of claim 1, further comprising oligonucleotides capable of detecting HPIV-1, HPIV-3 or HPIV-4.

14. The kit of claim 1, further comprising oligonucleotides capable of detecting microorganisms involved in at least one disease or infection selected from the group consisting of pneumonia, bronchiolitis and influenza.

15. An isolated DNA obtainable by amplification from a HPIV-2 virus selected from the HPIV-2 viruses deposited at Collection Nationale de Cultures de Microorganismes, accession numbers I-3761, I-3762, I-3763, I-3764 and I-3765, using the primer pair of SEQ ID NOs: 87 and 88.

16. The isolated DNA of claim 15, which consists of the sequence selected from the group consisting of SEQ ID NOs: 62-66.

17. An amplification composition comprising the isolated DNA of claim 15 and at least one polymerase.

18. A kit for the diagnosis of a respiratory disease or infection, comprising the primer pair of SEQ ID NOs: 87 and 88, and at least one probe, which can be used in real-time amplification with said primer pair, wherein the nucleotide sequence of said at least one probe is a DNA sequence comprising the sequence of SEQ ID NO: 90 or the complementary sequence thereof, and wherein said probe detects each of the five HPIV-2 viruses deposited at Collection Nationale de Cultures de Microorganismes, accession numbers I-3761, I-3762, I-3763, I-3764 and I-3765, without detecting the Greer, Toshiba and V98 isolates.

* * * * *